(12) United States Patent
Buggy et al.

(10) Patent No.: US 10,004,746 B2
(45) Date of Patent: *Jun. 26, 2018

(54) USE OF INHIBITORS OF BRUTON'S TYROSINE KINASE (BTK)

(71) Applicant: Pharmacyclics LLC, Sunnyvale, CA (US)

(72) Inventors: Joseph J. Buggy, Mountain View, CA (US); Laurence Elias, Berkeley, CA (US); Gwen Fyfe, San Francisco, CA (US); Eric Hedrick, Summit, NJ (US); David J. Loury, Incline Village, NV (US); Tarak D. Mody, Sunnyvale, CA (US)

(73) Assignee: Pharmacyclics LLC, Sunnyvale, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/659,803

(22) Filed: Jul. 26, 2017

(65) Prior Publication Data

US 2018/0015091 A1  Jan. 18, 2018

Related U.S. Application Data

(63) Continuation of application No. 14/091,196, filed on Nov. 26, 2013, now Pat. No. 9,801,881, which is a continuation of application No. 13/869,700, filed on Apr. 24, 2013, now abandoned, which is a continuation of application No. 13/153,317, filed on Jun. 3, 2011, now abandoned.

(60) Provisional application No. 61/472,138, filed on Apr. 5, 2011, provisional application No. 61/419,764, filed on Dec. 3, 2010, provisional application No. 61/351,655, filed on Jun. 4, 2010, provisional application No. 61/351,793, filed on Jun. 4, 2010, provisional application No. 61/351,762, filed on Jun. 4, 2010, provisional application No. 61/351,130, filed on Jun. 3, 2010.

(51) Int. Cl.

| | |
|---|---|
| A61K 31/519 | (2006.01) |
| A61K 31/195 | (2006.01) |
| A61K 31/337 | (2006.01) |
| A61K 31/4184 | (2006.01) |
| A61K 31/436 | (2006.01) |
| A61K 31/437 | (2006.01) |
| A61K 31/454 | (2006.01) |
| A61K 31/4745 | (2006.01) |
| A61K 31/475 | (2006.01) |
| A61K 31/573 | (2006.01) |
| A61K 31/606 | (2006.01) |
| A61K 31/664 | (2006.01) |
| A61K 31/704 | (2006.01) |
| C07D 487/04 | (2006.01) |
| A61K 39/395 | (2006.01) |
| A61K 9/06 | (2006.01) |
| A61K 31/7076 | (2006.01) |
| A61K 31/7032 | (2006.01) |
| A61K 31/69 | (2006.01) |
| A61K 31/675 | (2006.01) |

(52) U.S. Cl.
CPC .............. *A61K 31/519* (2013.01); *A61K 9/06* (2013.01); *A61K 31/195* (2013.01); *A61K 31/337* (2013.01); *A61K 31/4184* (2013.01); *A61K 31/436* (2013.01); *A61K 31/437* (2013.01); *A61K 31/454* (2013.01); *A61K 31/475* (2013.01); *A61K 31/4745* (2013.01); *A61K 31/573* (2013.01); *A61K 31/606* (2013.01); *A61K 31/664* (2013.01); *A61K 31/675* (2013.01); *A61K 31/69* (2013.01); *A61K 31/704* (2013.01); *A61K 31/7032* (2013.01); *A61K 31/7076* (2013.01); *A61K 39/395* (2013.01); *C07D 487/04* (2013.01)

(58) Field of Classification Search
CPC .............. A61K 31/519; A61K 31/7076; A61K 31/704; A61K 31/7032; A61K 31/69; A61K 31/675; A61K 31/664; A61K 31/606; A61K 31/573; A61K 31/475; A61K 31/4745; A61K 31/454; A61K 31/437; A61K 31/436; A61K 31/4184; A61K 31/337; A61K 31/195; A61K 9/06; C07D 487/04

See application file for complete search history.

(56) References Cited

U.S. PATENT DOCUMENTS

| | | |
|---|---|---|
| 3,547,119 A | 12/1970 | Farb |
| 4,311,137 A | 1/1982 | Gerard |

(Continued)

FOREIGN PATENT DOCUMENTS

| | | |
|---|---|---|
| CA | 2663116 A1 | 4/2008 |
| CA | 2847852 A1 | 4/2008 |

(Continued)

OTHER PUBLICATIONS

PubChem CID 134780, "Pomalidomide."

(Continued)

*Primary Examiner* — Umamaheswari Ramachandran
(74) *Attorney, Agent, or Firm* — Foley Hoag LLP; Hathaway P. Russell; Lucas P. Watkins

(57) ABSTRACT

Disclosed herein are methods for treating a cancer comprising: a. administering a Btk inhibitor to a subject sufficient to result in an increase or appearance in the blood of a subpopulation of lymphocytes defined by immunophenotyping; b. determining the expression profile of one or more biomarkers from one or more subpopulation of lymphocytes; and c. administering a second agent based on the determined expression profile.

30 Claims, 39 Drawing Sheets

(56) References Cited

U.S. PATENT DOCUMENTS

| | | |
|---|---|---|
| 4,360,019 A | 11/1982 | Portner et al. |
| 4,487,603 A | 12/1984 | Harris |
| 4,531,937 A | 7/1985 | Yates |
| 4,683,202 A | 7/1987 | Mullis |
| 4,692,147 A | 9/1987 | Duggan |
| 4,725,852 A | 2/1988 | Gamblin et al. |
| 4,755,173 A | 7/1988 | Konopka et al. |
| 4,843,155 A | 6/1989 | Chomczynski |
| 5,033,252 A | 7/1991 | Carter |
| 5,052,558 A | 10/1991 | Carter |
| 5,323,907 A | 6/1994 | Kalvelage |
| 5,384,261 A | 1/1995 | Winkler et al. |
| 5,397,787 A | 3/1995 | Buzzetti et al. |
| 5,445,934 A | 8/1995 | Fodor et al. |
| 5,593,997 A | 1/1997 | Dow et al. |
| 5,643,207 A | 7/1997 | Rise |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,770,722 A | 6/1998 | Lockhart et al. |
| 5,789,162 A | 8/1998 | Dower et al. |
| 5,800,992 A | 9/1998 | Fodor et al. |
| 5,807,876 A | 9/1998 | Armistead et al. |
| 5,820,589 A | 10/1998 | Torgerson et al. |
| 5,854,033 A | 12/1998 | Lizardi |
| 5,856,174 A | 1/1999 | Lipshutz et al. |
| 5,874,219 A | 2/1999 | Rava et al. |
| 5,922,591 A | 7/1999 | Anderson et al. |
| 6,001,839 A | 12/1999 | Calderwood et al. |
| 6,017,328 A | 1/2000 | Fischell et al. |
| 6,020,135 A | 2/2000 | Levine et al. |
| 6,033,860 A | 3/2000 | Lockhart et al. |
| 6,040,138 A | 3/2000 | Lockhart et al. |
| 6,040,193 A | 3/2000 | Winkler et al. |
| 6,054,472 A | 4/2000 | Armistead et al. |
| 6,160,010 A | 12/2000 | Uckun et al. |
| 6,198,966 B1 | 3/2001 | Heruth |
| 6,221,900 B1 | 4/2001 | Uckun et al. |
| 6,303,652 B1 | 10/2001 | Uckun et al. |
| 6,306,897 B1 | 10/2001 | Uckun et al. |
| 6,326,469 B1 | 12/2001 | Ullrich et al. |
| 6,344,316 B1 | 2/2002 | Lockhart et al. |
| 6,344,465 B1 | 2/2002 | Armistead et al. |
| 6,498,178 B2 | 12/2002 | Stamos et al. |
| 6,506,769 B2 | 1/2003 | Snow et al. |
| 6,660,744 B1 | 12/2003 | Hirst et al. |
| 6,673,333 B1 | 1/2004 | Meade et al. |
| 6,753,348 B2 | 6/2004 | Uckun et al. |
| 6,770,639 B2 | 8/2004 | Snow et al. |
| 6,824,768 B2 | 11/2004 | Stalgis et al. |
| 6,893,636 B2 | 5/2005 | Anderson et al. |
| 6,921,763 B2 | 7/2005 | Hirst et al. |
| 6,950,493 B2 | 9/2005 | Besson |
| 7,083,784 B2 | 8/2006 | Dall'Acqua et al. |
| 7,116,749 B2 | 10/2006 | Besson |
| 7,138,420 B2 | 11/2006 | Bentzien et al. |
| 7,332,497 B2 | 2/2008 | Hirst et al. |
| 7,514,444 B2 | 4/2009 | Honigberg et al. |
| 7,547,689 B2 | 6/2009 | Sessler et al. |
| 7,599,542 B2 | 10/2009 | Brockway et al. |
| 7,700,075 B2 | 4/2010 | Weichert et al. |
| 7,718,662 B1 | 5/2010 | Chen et al. |
| 7,732,454 B2 | 6/2010 | Verner |
| 7,741,330 B1 | 6/2010 | Chen et al. |
| 7,825,118 B2 | 11/2010 | Honigberg et al. |
| 7,960,396 B2 | 6/2011 | Honigberg et al. |
| 8,008,309 B2 | 8/2011 | Honigberg et al. |
| 8,058,249 B2 | 11/2011 | Krieg et al. |
| 8,088,781 B2 | 1/2012 | Honigberg et al. |
| 8,158,786 B2 | 4/2012 | Honigberg et al. |
| 8,232,280 B2 | 7/2012 | Honigberg et al. |
| 8,236,812 B2 | 8/2012 | Honigberg et al. |
| 8,306,897 B2 | 11/2012 | Yolles |
| 8,377,946 B1 | 2/2013 | Chen et al. |
| 8,399,470 B2 | 3/2013 | Honigberg et al. |
| 8,476,284 B2 | 7/2013 | Honigberg et al. |
| 8,497,277 B2 | 7/2013 | Honigberg et al. |
| 8,501,724 B1 | 8/2013 | Chen et al. |
| 8,501,751 B2 | 8/2013 | Honigberg et al. |
| 8,552,010 B2 | 10/2013 | Honigberg et al. |
| 8,557,803 B2 | 10/2013 | Yamamoto et al. |
| 8,563,563 B2 | 10/2013 | Honigberg et al. |
| 8,568,653 B2 | 10/2013 | Thillen et al. |
| 8,633,311 B2 | 1/2014 | Bommer et al. |
| 8,642,604 B2 | 2/2014 | Knight et al. |
| 8,658,653 B2 | 2/2014 | Honigberg et al. |
| 8,691,546 B2 | 4/2014 | Honigberg et al. |
| 8,697,711 B2 | 4/2014 | Honigberg et al. |
| 8,703,780 B2 | 4/2014 | Honigberg et al. |
| 8,735,403 B2 | 5/2014 | Honigberg et al. |
| 8,735,404 B2 | 5/2014 | Honigberg et al. |
| 8,741,908 B2 | 6/2014 | Honigberg et al. |
| 8,748,438 B2 | 6/2014 | Honigberg et al. |
| 8,748,439 B2 | 6/2014 | Honigberg et al. |
| 8,754,090 B2 | 6/2014 | Buggy et al. |
| 8,754,091 B2 | 6/2014 | Honigberg et al. |
| 8,759,516 B2 | 6/2014 | Honigberg et al. |
| 8,809,273 B2 | 8/2014 | Honigberg et al. |
| 8,877,202 B2 | 11/2014 | Govindan et al. |
| 8,883,435 B2 | 11/2014 | Honigberg et al. |
| 8,883,803 B2 | 11/2014 | Honigberg et al. |
| 8,940,750 B2 | 1/2015 | Honigberg et al. |
| 8,952,015 B2 | 2/2015 | Honigberg et al. |
| 8,957,079 B2 | 2/2015 | Honigberg et al. |
| 8,975,266 B2 | 3/2015 | Honigberg et al. |
| 8,987,233 B2 | 3/2015 | Pan et al. |
| 8,999,999 B2 | 4/2015 | Buggy et al. |
| 9,012,463 B2 | 4/2015 | Chen et al. |
| 9,079,908 B2 | 7/2015 | Honigberg et al. |
| 9,107,924 B2 | 8/2015 | Buggy et al. |
| 9,117,924 B2 | 8/2015 | Kitagawa et al. |
| 9,125,889 B2 | 9/2015 | Buggy et al. |
| 9,127,012 B2 | 9/2015 | Honigberg et al. |
| 9,133,198 B2 | 9/2015 | Honigberg et al. |
| 9,133,201 B2 | 9/2015 | Honigberg et al. |
| 9,133,202 B2 | 9/2015 | Honigberg et al. |
| 9,139,591 B2 | 9/2015 | Honigberg et al. |
| 9,181,257 B2 | 11/2015 | Honigberg et al. |
| 9,181,263 B2 | 11/2015 | Honigberg et al. |
| 9,193,735 B2 | 11/2015 | Honigberg et al. |
| 9,206,189 B2 | 12/2015 | Honigberg et al. |
| 9,212,185 B2 | 12/2015 | Honigberg et al. |
| 9,266,893 B2 | 2/2016 | Honigberg et al. |
| 9,273,051 B2 | 3/2016 | Chen et al. |
| 9,278,100 B2 | 3/2016 | Honigberg et al. |
| 9,296,753 B2 | 3/2016 | Smyth et al. |
| 9,409,911 B2 | 8/2016 | Honigberg et al. |
| 9,415,050 B2 | 8/2016 | Chen et al. |
| 9,540,382 B2 | 1/2017 | Purro et al. |
| 9,540,385 B2 | 1/2017 | Chen et al. |
| 9,556,182 B2 | 1/2017 | Honigberg et al. |
| 9,670,205 B2 | 6/2017 | Aktoudianakis et al. |
| 9,717,731 B2 | 8/2017 | Buggy et al. |
| 9,730,938 B2 | 8/2017 | Kuo et al. |
| 9,801,881 B2 | 10/2017 | Buggy et al. |
| 9,801,883 B2 | 10/2017 | Buggy et al. |
| 9,814,721 B2 | 11/2017 | Buggy et al. |
| 9,885,086 B2 | 2/2018 | Byrd et al. |
| 2002/0004584 A1 | 1/2002 | Laughlin |
| 2002/0016460 A1 | 2/2002 | Snow et al. |
| 2002/0127203 A1 | 9/2002 | Albrecht |
| 2002/0155505 A1 | 10/2002 | Wells et al. |
| 2003/0013118 A1 | 1/2003 | Edge et al. |
| 2003/0013125 A1 | 1/2003 | Braisted et al. |
| 2003/0035833 A1 | 2/2003 | He |
| 2003/0040461 A1 | 2/2003 | McAtee |
| 2003/0103938 A1 | 6/2003 | Jinquan et al. |
| 2003/0118078 A1 | 6/2003 | Carlson et al. |
| 2003/0125235 A1 | 7/2003 | Foxwell |
| 2004/0006083 A1 | 1/2004 | Hirst et al. |
| 2004/0136954 A1 | 7/2004 | Grusby et al. |
| 2004/0241651 A1 | 12/2004 | Olek et al. |
| 2004/0264627 A1 | 12/2004 | Besson |

(56) References Cited

U.S. PATENT DOCUMENTS

| | | |
|---|---|---|
| 2005/0008640 A1 | 1/2005 | Waegell et al. |
| 2005/0064464 A1 | 3/2005 | Punnonen et al. |
| 2005/0084905 A1 | 4/2005 | Prescott et al. |
| 2005/0090499 A1 | 4/2005 | Currie et al. |
| 2005/0101604 A1 | 5/2005 | Currie et al. |
| 2005/0152983 A1 | 7/2005 | Ashraf et al. |
| 2005/0153990 A1 | 7/2005 | Watkins |
| 2005/0196851 A1 | 9/2005 | Uckun |
| 2005/0209255 A1 | 9/2005 | Jimenez et al. |
| 2005/0220265 A1 | 10/2005 | Besson |
| 2006/0079494 A1 | 4/2006 | Santi et al. |
| 2006/0167090 A1 | 7/2006 | Uckun et al. |
| 2006/0178367 A1 | 8/2006 | Currie et al. |
| 2006/0211112 A1 | 9/2006 | Harris et al. |
| 2006/0292181 A1 | 12/2006 | Brayden |
| 2007/0032457 A1 | 2/2007 | Blatt |
| 2007/0065449 A1 | 3/2007 | Verschraegen |
| 2007/0105136 A1 | 5/2007 | Staudt et al. |
| 2007/0122417 A1 | 5/2007 | Holt et al. |
| 2007/0281907 A1 | 12/2007 | Watkins |
| 2007/0293499 A1 | 12/2007 | Flynn et al. |
| 2008/0076921 A1 | 3/2008 | Honigberg et al. |
| 2008/0108636 A1 | 5/2008 | Honigberg et al. |
| 2008/0139582 A1 | 6/2008 | Honigberg et al. |
| 2008/0146555 A1 | 6/2008 | Caligiuri et al. |
| 2008/0153877 A1 | 6/2008 | Adimoolam et al. |
| 2008/0214501 A1 | 9/2008 | Pan et al. |
| 2009/0010911 A1 | 1/2009 | Andreotti et al. |
| 2009/0039734 A1 | 2/2009 | Takahashi et al. |
| 2009/0047353 A1 | 2/2009 | O'Hagan |
| 2009/0074787 A1 | 3/2009 | Gomez-Navarro et al. |
| 2009/0098137 A1 | 4/2009 | Burke et al. |
| 2009/0105209 A1 | 4/2009 | Dewdney et al. |
| 2009/0149389 A1 | 6/2009 | Panitch et al. |
| 2009/0181987 A1 | 7/2009 | Honigberg et al. |
| 2009/0186898 A1 | 7/2009 | Dewdney et al. |
| 2009/0197853 A1 | 8/2009 | Magda |
| 2009/0297551 A1 | 12/2009 | Sattentau et al. |
| 2009/0317836 A1 | 12/2009 | Kuhn et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0041677 A1 | 2/2010 | Honigberg et al. |
| 2010/0069458 A1 | 3/2010 | Atadja et al. |
| 2010/0087482 A1 | 4/2010 | Haber et al. |
| 2010/0143301 A1 | 6/2010 | Desai et al. |
| 2010/0158866 A1 | 6/2010 | Zhu |
| 2010/0185419 A1 | 7/2010 | Singh et al. |
| 2010/0189711 A1 | 7/2010 | Dranoff et al. |
| 2010/0222325 A1 | 9/2010 | Berthel et al. |
| 2010/0254905 A1 | 10/2010 | Honigberg et al. |
| 2010/0266589 A1 | 10/2010 | Hedrick et al. |
| 2010/0324050 A1 | 12/2010 | Honigberg et al. |
| 2011/0039868 A1 | 2/2011 | Honigberg et al. |
| 2011/0059854 A1 | 3/2011 | Gordon et al. |
| 2011/0086866 A1 | 4/2011 | Chen et al. |
| 2011/0124628 A1 | 5/2011 | Bruncko et al. |
| 2011/0125628 A1 | 5/2011 | Marchegiani |
| 2011/0152240 A1 | 6/2011 | Haddach et al. |
| 2011/0177011 A1 | 7/2011 | Currie et al. |
| 2011/0184001 A1 | 7/2011 | Honigberg et al. |
| 2011/0209230 A1 | 8/2011 | Korman et al. |
| 2011/0224235 A1 | 9/2011 | Honigberg et al. |
| 2011/0244465 A1 | 10/2011 | Harvey et al. |
| 2011/0281322 A1 | 11/2011 | Honigberg et al. |
| 2011/0281850 A1 | 11/2011 | Flynn et al. |
| 2011/0288032 A1 | 11/2011 | Ganji |
| 2011/0306599 A1 | 12/2011 | Inoue et al. |
| 2012/0039850 A1 | 2/2012 | McNair et al. |
| 2012/0065201 A1 | 3/2012 | Honigberg et al. |
| 2012/0071497 A1 | 3/2012 | Buggy et al. |
| 2012/0087915 A1 | 4/2012 | Buggy et al. |
| 2012/0088912 A1 | 4/2012 | Honigberg et al. |
| 2012/0095026 A1 | 4/2012 | Honigberg et al. |
| 2012/0100138 A1 | 4/2012 | Buggy et al. |
| 2012/0101113 A1 | 4/2012 | Honigberg et al. |
| 2012/0101114 A1 | 4/2012 | Honigberg et al. |
| 2012/0108547 A1 | 5/2012 | Jankowski et al. |
| 2012/0108612 A1 | 5/2012 | Honigberg et al. |
| 2012/0115889 A1 | 5/2012 | Honigberg et al. |
| 2012/0122894 A1 | 5/2012 | Honigberg et al. |
| 2012/0129821 A1 | 5/2012 | Honigberg et al. |
| 2012/0129853 A1 | 5/2012 | Elmore et al. |
| 2012/0129873 A1 | 5/2012 | Honigberg et al. |
| 2012/0135944 A1 | 5/2012 | Honigberg et al. |
| 2012/0165328 A1 | 6/2012 | Honigberg et al. |
| 2012/0178753 A1 | 7/2012 | Honigberg et al. |
| 2012/0183535 A1 | 7/2012 | Buggy et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0214826 A1 | 8/2012 | Honigberg et al. |
| 2012/0219522 A1 | 8/2012 | Xi |
| 2012/0252821 A1 | 10/2012 | Honigberg et al. |
| 2012/0252822 A1 | 10/2012 | Honigberg et al. |
| 2012/0277225 A1 | 11/2012 | Honigberg et al. |
| 2012/0277254 A1 | 11/2012 | Honigberg et al. |
| 2012/0277255 A1 | 11/2012 | Honigberg et al. |
| 2012/0283276 A1 | 11/2012 | Honigberg et al. |
| 2012/0283277 A1 | 11/2012 | Honigberg et al. |
| 2012/0296089 A1 | 11/2012 | Honigberg et al. |
| 2012/0329130 A1 | 12/2012 | Honigberg et al. |
| 2013/0005745 A1 | 1/2013 | Honigberg et al. |
| 2013/0005746 A1 | 1/2013 | Honigberg et al. |
| 2013/0012525 A1 | 1/2013 | Honigberg et al. |
| 2013/0018060 A1 | 1/2013 | Honigberg et al. |
| 2013/0029984 A1 | 1/2013 | Castro et al. |
| 2013/0035334 A1 | 2/2013 | Honigberg et al. |
| 2013/0041013 A1 | 2/2013 | Lavitrano et al. |
| 2013/0041014 A1 | 2/2013 | Lavitrano et al. |
| 2013/0079327 A1 | 3/2013 | Yamamoto et al. |
| 2013/0172314 A1 | 7/2013 | Chen et al. |
| 2013/0184223 A1 | 7/2013 | Land et al. |
| 2013/0184342 A1 | 7/2013 | Mills et al. |
| 2013/0195852 A1 | 8/2013 | Buggy et al. |
| 2013/0202611 A1 | 8/2013 | Buggy et al. |
| 2013/0217880 A1 | 8/2013 | Yamamoto et al. |
| 2013/0231328 A1 | 9/2013 | Harriman et al. |
| 2013/0273030 A1 | 10/2013 | Buggy et al. |
| 2013/0310402 A1 | 11/2013 | Buggy et al. |
| 2013/0338172 A1 | 12/2013 | Smyth et al. |
| 2014/0016306 A1 | 1/2014 | de Blois |
| 2014/0018414 A1 | 1/2014 | Brosnan |
| 2014/0039185 A1 | 2/2014 | Honigberg et al. |
| 2014/0057907 A1 | 2/2014 | Honigberg et al. |
| 2014/0079690 A1 | 3/2014 | Buggy et al. |
| 2014/0080844 A1 | 3/2014 | Chen et al. |
| 2014/0128413 A1 | 5/2014 | Honigberg et al. |
| 2014/0128414 A1 | 5/2014 | Honigberg et al. |
| 2014/0134265 A1 | 5/2014 | Buggy et al. |
| 2014/0135347 A1 | 5/2014 | Honigberg et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0171453 A1 | 6/2014 | Honigberg et al. |
| 2014/0187564 A1 | 7/2014 | Honigberg et al. |
| 2014/0187565 A1 | 7/2014 | Honigberg et al. |
| 2014/0194417 A1 | 7/2014 | Greenwood et al. |
| 2014/0194446 A1 | 7/2014 | Buggy et al. |
| 2014/0206681 A1 | 7/2014 | Kim et al. |
| 2014/0212485 A1 | 7/2014 | Honigberg et al. |
| 2014/0243355 A1 | 8/2014 | Honigberg et al. |
| 2014/0249215 A1 | 9/2014 | Pimont-Garro et al. |
| 2014/0275125 A1 | 9/2014 | Honigberg et al. |
| 2014/0303191 A1 | 10/2014 | Buggy et al. |
| 2014/0336203 A1 | 11/2014 | Smyth et al. |
| 2014/0336206 A1 | 11/2014 | Honigberg et al. |
| 2014/0371241 A1 | 12/2014 | Buggy et al. |
| 2014/0377258 A1 | 12/2014 | Stern et al. |
| 2014/0378446 A1 | 12/2014 | Chen et al. |
| 2015/0018336 A1 | 1/2015 | Chen et al. |
| 2015/0031710 A1 | 1/2015 | Buggy et al. |
| 2015/0031711 A1 | 1/2015 | Buggy et al. |
| 2015/0038518 A1 | 2/2015 | Balasubramanian |

(56) References Cited

U.S. PATENT DOCUMENTS

| | | |
|---|---|---|
| 2015/0044217 A1 | 2/2015 | Chen et al. |
| 2015/0072988 A1 | 3/2015 | Carducci et al. |
| 2015/0105409 A1 | 4/2015 | Quayle et al. |
| 2015/0118222 A1 | 4/2015 | Levy et al. |
| 2015/0133661 A1 | 5/2015 | Honigberg et al. |
| 2015/0140036 A1 | 5/2015 | Mannick et al. |
| 2015/0152115 A1 | 6/2015 | Honigberg et al. |
| 2015/0158871 A1 | 6/2015 | Purro et al. |
| 2015/0184249 A1 | 7/2015 | Chang et al. |
| 2015/0210769 A1 | 7/2015 | Freeman et al. |
| 2015/0238490 A1 | 8/2015 | Burger |
| 2015/0239897 A1 | 8/2015 | Chen et al. |
| 2015/0265618 A1 | 9/2015 | Honigberg et al. |
| 2015/0267261 A1 | 9/2015 | Byrd et al. |
| 2015/0306103 A1 | 10/2015 | Honigberg et al. |
| 2015/0306106 A1 | 10/2015 | Honigberg et al. |
| 2015/0307500 A1 | 10/2015 | Honigberg et al. |
| 2016/0000792 A1 | 1/2016 | Buggy et al. |
| 2016/0009714 A1 | 1/2016 | Sun et al. |
| 2016/0022683 A1 | 1/2016 | Fardis et al. |
| 2016/0032404 A1 | 2/2016 | Schweighofer et al. |
| 2016/0101128 A1 | 4/2016 | Wang et al. |
| 2016/0108045 A1 | 4/2016 | Andres et al. |
| 2016/0108123 A1 | 4/2016 | Freeman et al. |
| 2016/0159905 A1 | 6/2016 | Abdiche et al. |
| 2016/0175312 A1 | 6/2016 | Buggy et al. |
| 2016/0243033 A1 | 8/2016 | Buggy et al. |
| 2016/0287592 A1 | 10/2016 | Chang et al. |
| 2016/0324859 A1 | 11/2016 | Buggy et al. |
| 2017/0035762 A1 | 2/2017 | Buggy et al. |
| 2017/0071962 A1 | 3/2017 | Lannutti et al. |
| 2017/0209462 A1 | 7/2017 | Bilotti et al. |
| 2017/0209574 A1 | 7/2017 | Cao et al. |
| 2017/0266186 A1 | 9/2017 | Buggy et al. |
| 2017/0360796 A1 | 12/2017 | Jaglowski |

FOREIGN PATENT DOCUMENTS

| | | |
|---|---|---|
| CN | 101610676 A | 12/2009 |
| CN | 101626758 A | 1/2010 |
| CN | 103923084 A | 7/2014 |
| CN | 106336413 A | 1/2017 |
| CN | 106474143 A | 3/2017 |
| EP | 1038392 A1 | 9/2000 |
| EP | 1046399 A1 | 10/2000 |
| EP | 1240899 A2 | 9/2002 |
| EP | 1132393 B1 | 4/2003 |
| EP | 1473039 A1 | 11/2004 |
| EP | 2201840 A1 | 6/2010 |
| EP | 2220116 A1 | 8/2010 |
| JP | H01167840 A | 7/1989 |
| JP | 2003509428 A | 3/2003 |
| JP | 2004/518615 A | 6/2004 |
| JP | 2004531513 A | 10/2004 |
| JP | 2005/089352 A | 4/2005 |
| JP | 2007520559 A | 7/2007 |
| JP | 2010526768 A | 8/2010 |
| JP | 2011/508749 A | 3/2011 |
| JP | 4934197 B2 | 5/2012 |
| JP | 2013507448 A | 3/2013 |
| JP | 5717109 B2 | 5/2015 |
| JP | 5841998 B2 | 1/2016 |
| WO | WO-1994/014436 A1 | 7/1994 |
| WO | WO-1997/028161 A1 | 8/1997 |
| WO | WO-1997/040028 A1 | 10/1997 |
| WO | WO-1997/049706 A1 | 12/1997 |
| WO | WO-1998/040381 A1 | 9/1998 |
| WO | WO-1998/041525 A1 | 9/1998 |
| WO | WO-1999/054286 A2 | 10/1999 |
| WO | WO-2000/000823 A1 | 1/2000 |
| WO | WO-2000/056331 A1 | 9/2000 |
| WO | WO-2000/56737 A2 | 9/2000 |
| WO | WO-2001/019829 A2 | 3/2001 |
| WO | WO-2001/019829 A3 | 3/2001 |
| WO | WO 2001/25238 A2 | 4/2001 |
| WO | WO-0129058 A1 | 4/2001 |
| WO | WO-2001/041754 A2 | 6/2001 |
| WO | WO-2001/044258 A1 | 6/2001 |
| WO | WO-2002/38797 A2 | 5/2002 |
| WO | WO-2002/076986 A1 | 10/2002 |
| WO | WO-2002/080926 A1 | 10/2002 |
| WO | WO-02078731 A1 | 10/2002 |
| WO | WO-2003/000187 A2 | 1/2003 |
| WO | WO-2003/004053 A1 | 1/2003 |
| WO | WO-2003/013540 A1 | 2/2003 |
| WO | WO-2003/046200 A2 | 6/2003 |
| WO | WO-2003/097645 A1 | 11/2003 |
| WO | WO-2004/060319 A2 | 7/2004 |
| WO | WO-2004/074290 A1 | 9/2004 |
| WO | WO-2004/096253 A1 | 11/2004 |
| WO | WO-2004/100868 A2 | 11/2004 |
| WO | WO-2004/100868 A3 | 11/2004 |
| WO | WO-2005/000197 A2 | 1/2005 |
| WO | WO-2005/005429 A1 | 1/2005 |
| WO | WO-2005/014599 A1 | 2/2005 |
| WO | WO-2005/037836 A2 | 4/2005 |
| WO | WO-2005/037843 A1 | 4/2005 |
| WO | WO-2005/060956 A1 | 7/2005 |
| WO | WO-2005/074603 A2 | 8/2005 |
| WO | WO-2006/002871 A1 | 1/2006 |
| WO | WO-2006/012422 A1 | 2/2006 |
| WO | WO-2006/036527 A1 | 4/2006 |
| WO | WO-2006/036788 A2 | 4/2006 |
| WO | WO-2006/036941 A2 | 4/2006 |
| WO | WO-2006/050946 A1 | 5/2006 |
| WO | WO-2006/053121 A2 | 5/2006 |
| WO | WO-2006/071017 A1 | 7/2006 |
| WO | WO-2006/099075 A2 | 9/2006 |
| WO | WO-2006/124462 A2 | 11/2006 |
| WO | WO-2007/002325 A1 | 1/2007 |
| WO | WO-2007/058832 A2 | 5/2007 |
| WO | WO-2007/087068 A2 | 8/2007 |
| WO | WO-2007/136790 A2 | 11/2007 |
| WO | WO-2008/039218 A2 | 4/2008 |
| WO | WO-2008/054827 A2 | 5/2008 |
| WO | WO-2008/063727 A2 | 5/2008 |
| WO | WO-2008069881 A2 | 6/2008 |
| WO | WO-2008/108636 A1 | 9/2008 |
| WO | WO-2008/121742 A2 | 10/2008 |
| WO | WO-2008/124138 A1 | 10/2008 |
| WO | WO-2008127659 A2 | 10/2008 |
| WO | WO-2008/138578 A2 | 11/2008 |
| WO | WO-2009/051822 A1 | 4/2009 |
| WO | WO-2009/118523 A1 | 10/2009 |
| WO | WO-2009/140853 A1 | 11/2009 |
| WO | WO-2009/149179 A2 | 12/2009 |
| WO | WO-2009/158571 A1 | 12/2009 |
| WO | WO-2010/009342 A2 | 1/2010 |
| WO | WO-2010/009342 A3 | 1/2010 |
| WO | WO-2010/034670 A2 | 4/2010 |
| WO | WO-2010/065824 A2 | 6/2010 |
| WO | WO-2010/065898 A2 | 6/2010 |
| WO | WO-2010/069809 A1 | 6/2010 |
| WO | WO-2010/093843 A2 | 8/2010 |
| WO | WO-2010/126960 A1 | 11/2010 |
| WO | WO-2011/034907 A2 | 3/2011 |
| WO | WO-2011/046771 A1 | 4/2011 |
| WO | WO-2011046964 A2 | 4/2011 |
| WO | WO-2011/068560 A1 | 6/2011 |
| WO | WO-2011/133609 A2 | 10/2011 |
| WO | WO-2011/152351 A1 | 12/2011 |
| WO | WO-2011/153514 A1 | 12/2011 |
| WO | WO-2011/160206 A1 | 12/2011 |
| WO | WO-2011/162515 A2 | 12/2011 |
| WO | WO-2012/001090 A1 | 1/2012 |
| WO | WO-2012/021444 A1 | 2/2012 |
| WO | WO-2012/158764 A1 | 11/2012 |
| WO | WO-2013/010868 A1 | 1/2013 |
| WO | WO-2013/036994 A1 | 3/2013 |
| WO | WO-2013/059738 A2 | 4/2013 |
| WO | WO-2013/085893 A1 | 6/2013 |
| WO | WO-2013/184572 A1 | 12/2013 |
| WO | WO-2014/004707 A1 | 1/2014 |
| WO | WO-2014/018567 A1 | 1/2014 |

(56) References Cited

FOREIGN PATENT DOCUMENTS

| WO | WO-2014004376 A2 | 1/2014 |
|---|---|---|
| WO | WO-2014/071205 A1 | 5/2014 |
| WO | WO-2014/071231 A1 | 5/2014 |
| WO | WO-2014/135669 A1 | 9/2014 |
| WO | WO-2014/159745 A1 | 10/2014 |
| WO | WO-2014/168975 A1 | 10/2014 |
| WO | WO-2014/194254 A1 | 12/2014 |
| WO | WO-2015/013579 A1 | 1/2015 |
| WO | WO-2015/018522 A1 | 2/2015 |
| WO | WO-2015/048689 A1 | 4/2015 |
| WO | WO-2015/084892 A1 | 6/2015 |
| WO | WO-2015/127234 A1 | 8/2015 |
| WO | WO-2015/149105 A1 | 10/2015 |
| WO | WO-2015/181747 A1 | 12/2015 |
| WO | WO-2016/54555 A2 | 4/2016 |
| WO | WO-2016/054627 A1 | 4/2016 |
| WO | WO-2016/141092 A1 | 9/2016 |
| WO | WO-2016/161347 A1 | 10/2016 |

OTHER PUBLICATIONS

PubChem CID 24821094, "Ibrutinib."
Supplementary Partial European Search Report for European Application No. 15764524.3 dated Oct. 4, 2017.
Cuneo et al., "Modern Treatment in Chronic Lymphocytic Leukemia: Impact on Survival and Efficacy in High-risk Subgroups," Cancer Med-US, 3(3): 555-564 (2014).
Ramsay et al., "Chronic Lymphocytic Leukaemia—The Role of the Microenvironment Pathogenesis and Therapy," Brit J Haematol, 162(1): 15-24 (2013).
Jordan et al., "Tamoxifen: A Most Unlikely Pioneering Medicine," Nature Reviews: Drug Discovery, 2: 205 (2003).
Pathology and Clinical Medicine 2003, 21(2), 159-165, English abstract only.
Supplementary European Search Report for Application No. EP 14855030 dated Nov. 7, 2017.
Abraham, J., "Leukemia," Demos Medical Publishing: New York (2011).
ACS 2015 (http://www.cancer.org/cancer/non-hodgkinlymphoma/detailedguide/non-hodgkin-lymphoma-types-of-non-hodgkinlymphoma).
Adimoolam et al. HDAC inhibitor PCI-24761 decreases RAD51 expression and inhibits homologous recombination. PNAS 104 (49):1 9482-19487 (2007).
Advani et al. Effect of Btk inhibitor PCI-32765 monotherapy on responses in patients with relapsed aggressive NHL: Evidence of antitumor activity from a phase I study. J. Clin. Oncol., 2010 ASCO Annual Meeting Proceedings (Post-Meeting Edition), 28(15 Supp):8012 (2010).
Advani et al., "The Btk inhibitor PCI-32765 is highly active and well tolerated in patients (PTS) with relapsed/refractory B cell malignancies: final results from a phase I study," Ann Oncol, 22(Supp 4):abstract 153 (2011).
Advani, R.H., et al., 2013, "Bruton tyrosine kinase inhibitor Ibrutinib (PCI-32765) ha significant activity in patients with relapsed/refractory B-cell malignancies", Journal of Clinical Oncology, vol. 31, No. 1 ,pp. 88-94.
Agathocleous et al. Preliminary Results of a Phase I/II Study of Weekly or Twice Weekly Bortezomib in Combination with Rituximab, in Patients with Follicular Lymphoma, Mantle Cell Lymphoma and Waldenstrom's Macroglobulinaemia. Blood (ASH Annual Meeting Abstracts) 110:Abstract 2559 (2007).
Agency for Toxic Substances and Disease Registry, Public Health Assessment Guidance Manual, (2005).
Ahn et al. Michael acceptors as a tool for anticancer drug design. Current Pharmaceutical Design 2(3):247-262 (1996).
Almo et al., Considerations for combined immune checkpoint modulation and radiation treatment, Radiat Res, 182(2): 230-238 (2014).
American Cancer Society Melanoma Guidelines (Last Revised Feb. 1, 2016), p. 37.
Anderson. The process of structure-based drug design. Chem and Biol 10:787-797 (2003).
Anonymous: "Ibrutinib/Rituximab combination leads to high response rate among patient with CLL," The Asco Post (2013).
Anonymous: "NCT01217749 on Apr. 16, 2012: Clinical Trials.gov Archive," Apr. 16, 2012 (Apr. 16, 2012), XP055260251, Retrieved from the Internet: URL:https://clinicaltrials.gov/archive/NCT01217749/2012_04_16.
Ansell, "Two targets for the price of one," Blood 122(15): 2529-2531 (Oct. 10, 2013).
Apsel et al. Targeted Polypharmacology: Discovery of Dual Inhibitors of Tyrosine and Phosphoinositide Kinases. Nature Chem. Bio., 4(11):691-699 (2008).
Arkin et al. HER-2-directed, small-molecule antagonists. Curr Opin Investig Drugs. 2008;9(12)1264-1276. (saved on H drive and filesite).
Arnold et al. Pyrrolo[2,3-d]pyrimidines Containing an Extended 5-Substituent as Potent and Selective Inhibitors of Ick 1. Bioorg. Med. Chem. Ltrs. 10:2167-2170 (2000).
Asrani et al. The HER2- and heregulin β1 (HRG)-inducible TNFR superfamily member Fn14 promotes HRG-driven breast cancer cell migration, invasion, and MMP9 expression. Mol Cancer Res. Apr. 2013;11(4):393-404. doi: 10.1158/1541-7786.MCR-12-0542. Epub Feb. 1, 2013.
Atsukawa et al, "Ribavirin downmodulates inducible costimulator on Cd4+ T cells and their interleukin-10 secretino to assist in hepatitis C virus clearance," J Gastoenterology and Hepatology 27:823-831 (2012).
Axelrod, et al., "Combinatorial Drug Screening Identified Synergistic Co-Targeting of Bruton's Tyrosine Kinase and the Proteasome in Mantle Cell Lymphoma," Leukemia, 28(2): 407-410 (Feb. 1, 2014).
Baghdadi et al., "The impact of the TIM gene family on tumor immunity and immunosuppression," Cell Mol Immunol, 11(1): 41-48 (2014).
Balakrishnan et al. "AT-101 induces apoptosis in CLL B cells and overcomes stromal cell-mediated Mcl-1 induction and drug resistance," Blood, Oct. 3, 2008 (Oct. 3, 2008), vol. 113, No. 1, pp. 149-153.
Balasubramanian et al., "Identification of MicroRNA Markers of Sensitivity to the Novel Bruton's Tyrosine Kinase (BTK) Inhibitor PCI-32765 in Non-Hodgkin's Lymphoma," Blood, 112(11): 1155-1156 (2008).
Banker et al. Modern Pharmaceutics, 3ed., Marcel Dekker, New York 1996, p. 596.
Barany, "Genetic Disease Detection and DNA Amplification Using Cloned Thermostable Ligase," Proc. Natl. Acad. Sci. USA, 88:189-193 (1991).
Baselga. Targeting tyrosine kinases in cancer: the second wave. Science 312(5777):1175-1178 (2006).
Bauzon et al., "Armed therapeutic viruses—a disruptive therapy on the horizon of cancer immunotherapy," Front Immunol, 5: 74 (2014).
Bhagat et al., "Abstract 2570: IMO-8400, a Selective Antagonist of TLRs 7, 8 and 9, Inhibits MYD88 L265P Mutation-driven Signaling and Cell Survival: A Potential Novel Approach for Treatment of B-cell Lymphomas Harboring MYd88 L265P Mutation," Cancer Res, 74: 2570 Abstract (2014).
Bhalla et al. PCI-24781 induces caspase and reactive oxygen species-dependent apoptosis through NF-kappaB mechanisms and is synergistic with bortezomib in lymphoma cells. Clin Cancer Res 15:3354-3365 (2009).
Biocompare, "Th1 and Th2 Balance, Regulation, and Involvement in Disease," http://www.biocompare.com/Application-Notes/43518-Th1-And-Th1-Balance-Reg ulation-And-Involvement-In-Disease (Apr. 24, 2006).
Biospace, Dec. 8, 2009, pharmacyclics, Inc. (PCYC) announces presentation of interim results from phase I trial of its first-in-human btk inhibitor PCI-32765.
Bowen et al., "Adaptive Immune Responses in Acute and Chronic Hepatitis C Virus Infection," Nature 436(7053):946-852 (2005).

(56) References Cited

OTHER PUBLICATIONS

Brahmer et al., "Safety and activity of anti-PD-L1 antibody in patients with advanced cancer," N Engl J Med, 366(26): 2455-2465 (2012).
Brown et al. Phase Ib trial of AVL-292, a covalent inhibitor of Bruton's tyrosine kinase (Btk), in chronic lymphocytic leukemia (CLL) and B-non-Hodgkin lymphoma (B-NHL). J Clin. Oncol. 30(suppl):abstract 8032 (2012); [online][retrieved on Oct. 4, 2012] Retrieved from the Internet: < http://www.asco.ong/ASCOv2/Meetings/Abstracts?&vmview=abst_detail_view&confID=114&abstractID=98841>.
Brown et al., "PCI-32765, the first BTK (Bruton's Tyrosine Kinase) inhibitor in clinical trials," Cur Hematol Malig Rep, 8(1): 1-6 (2013).
Browning. B cells move to centre stage: novel opportunities for autoimmune disease treatment. Nature Reviews/Drug Discovery 5:564-576 (Jul. 2006).
Burchat et al. Pyrazolo[3,4-d]pyrimidines Containing an Extended 3-Substituent as Potent Inhibitors of Lck—a Selectivity Insight. Bioorg. Med. Chem. Ltrs. 12:1687-1690 (2002).
Burger et al. CXCR4 antagonists: targeting the microenvironment in leukemia and other cancers, Leukemia 23:43-52 (2009).
Burger et al. High-Level Expression of the T-Cell Chemokines CCL3 and CCL4 by Chronic Lymphocytic Leukemia B Cells in Nurselike Cell Cocultures and After BCR Stimulation. Blood 113(13):3050-3058 (2008).
Burger et al. The Btk Inhibitor Inbrutinib (PCI-32765) in Combination with Rituximab Is Well Tollerated and Displays Profound Activity in High-Risk Chronic Lyphocytic Leukemia (CLL) Patients. Blood (ASH Annual Meeing Abstracts).120:Abstract 187 (2012).
Burger et al., "Ibrutinib as Initial Therapy for Patients with Chronic Lymphocytic Leukemia," New Engl J Med, 373(25): 2425-2437 (2015).
Burger J.A., "The Bruton's Tyrosine Kinase Inhibitor, PCI-32765, Is Well Tolerated and Demonstrates Promising Clinical Activity in Chronic Lymphocytic Leukemia (CLL) and Small Lymphocytic Lymphoma (SLL): An Update on Ongoing Phase 1 Studies," Blood, Nov. 19, 2010, vol. 116 (21), p. 57.
Burger. Targeting the microenvironment in chronic lymphocytic leukemia is changing the therapeutic landscape. Curr. Opin. Oncol. 24(6):643-649 (Epub Sep. 6, 2012/Nov. 2012).
Byrd et al. Entering the era of targeted therapy for chronic lymphocytic leukemia: impact on the practicing clinician. J. Clinical Oncology (Jul. 21, 2014) (pii: JCO.2014.55.8262).
Byrd et al. Targeting BTK with Ibrutinib in relapsed chronic lymphocytic leukemia, NEJM 369(1):32-42 (Jul. 4, 2013).
Byrd J.C., et al., "Three-year follow-up of treatment-naïve and previously treated patients with CLL and SLL receiving single-agent ibrutinib", Blood, Apr. 16, 2015, vol. 125 (16), pp. 2497-2506.
Callahan et al., "At the bedside: CTLA-4- and PD-1-blocking antibodies in cancer immunotherapy," J Leukoc Biol, 94(1): 41-53 (2013).
Calpe et al., "ZAP-70 Enhances Migration of Malignant B Lymphocytes Toward CCL21 by Inducing CCR7 Expression via IgM-ERK1/2 Activation," Blood, 118(16): 4401-4410 (2011).
Cannon. Chapter Nineteen in Burger's Medicinal Chemistry and Drug Discovery, Fifth Edition, vol. I: Principles and Practice, Wiley-Interscience 1995, pp. 783-802.
Carmi et al. Clinical perspectives for irreversible tyrosine kinase inhibitors in cancer. Biochem. Pharmacol. (Epub Aug. 4, 2012) 84(11):1388-1399 (Dec. 2012).
Carrle et al. Current Strategies of Chemotherapy in Osteosarcoma. International Orthopaedics 30:445-451 (2006).
Celgene Corporation: "Pomalyst (pomalidomide) capsules for oral use", Feb. 1, 2013 (Feb. 1, 2013), XP002764262, Retrieved from the Internet: URL:http://www.accessdata.fda.gov/drugsatf da docs/label/2013/204026lbl.pdf [retrieved on Nov. 15, 2016].
Ceribelli, M et al. Blockade of oncogenic IKB kinase activity in diffuse large B-celllymphom by bromodomain and extraterminal domain protein inhibitors. Proceedings of the National Academy of Sciences. Published online: Jul. 21, 2014. vol. 111. No. 31. pp. 11365-11370.
Chang et al. Egress of CD19+CD5+ cells into peripheral blood following treatment with the Bruton tyrosine kinase inhibitor inbrutinib in mantel cell lymphoma patients. Blood, 122:2412-2424 (2013).
Chang et al., "PCI-45292, a novel Btk inhibitor with optimized pharmaceutical properties, demonstrates potent activities in rodent models of arthritis," ACR/ARHP Scientific Meeting, Poster #286 (2010).
Chang et al., "The Bruton tyrosine kinase inhibitor PCI-32765 ameliorates autoimmune arthritis by inhibition of multiple effector cells," Arhtritis Res Ther, 13:R115 (2011).
Chang et al., "Use of tumor genomic profiling to reveal mechanisms of resistance to the BTK inhibitor ibrutinib in chronic lumphocytic leukemia (CLL)," J Clin Oncol, 2013 ASCO Annual Meeting Abstracts, 31 (15): Abstract 7014 (2013).
Chaturvedi et al. "Mutant IDH1 promotes leukemogenesis in vivo and can be specifically targeted in human AML," Blood, Aug. 16, 2013 (Aug. 16, 2013), vol. 122, No. 16, pp. 2877-2887.
Chavez et al. Ibrutinib: An Evidence-Based Review of its Potential in the Treatment of Advanced Chronic Lymphocytic Leukemia. Core Evidence 8:37-45 (2013).
Chen et al. "Pim kinase inhibitor, SGI-1776, induces apoptosis in chronic lymphocytic leukemia cells," Blood, Sep. 4, 2009 (Sep. 4, 2009), vol. 114, No. 19, pp. 4150-4157.
Chen et al. SYK-dependent tonic B-cell receptor signaling is a rational treatment target in diffuse large B-cell lymphoma. Blood 111(4):2230-2237 (2008) [E-pub Nov. 15, 2007].
Chiron et al., "Cell-Cycle Reprogramming for PI3K Inhibition Overrides a Relapse-Specific C481S BTK Mutation Revealed by Longitudinal Functional Genomics in Mantle Cell Lymphoma," Cancer Discov, 4(9): 1022-1035 (2014).
Choi et al., "Inhibitors of B-cell receptor signaling for patients with B-cell malignancies," Cancer J, 18(5):404-410 (2012).
Chothia et al., "Canonical Structures for the Hypervariable Regions of Immunoglobulins," J. Mol. Biol., 196(4):901-917 (1987).
Clark et al., "The Role of Ribavirin in Direct Acting Antiviral Drug Regimens for Chronic Hepatitis C," Liver Int. 32(01):103-107 (2012).
Clinical.Trials.gov: "Study of Ibrutinib in Combination With Pomalidomide and Dexamethasone in Subjects With Relapsed I Refractory Multiple Myeloma", Nov. 9, 2016 (Nov. 9, 2016), Retrieved from the Internet: URL:https://clinicaltrials.gov/ct2/show/NCT02548962 [retrieved on Nov. 10, 2016].
Co-pending U.S. Appl. No. 14/855,270, filed Sep. 15, 2015.
Cohen et al. Structural Bioinformatics-Based Design of Selective, Irreversible Kinase Inhibitors. Science 308:1318-1321 (May 27, 2005).
Combination treatment of the Bruton's tyrosine kinase inhibitor ibrutinib and cartilzomib in patients with relapsed or relapsed and refractory multiple myeloma: initial results from a multicenter phase 1/2b study. NCT01962792 (2015).
Cui et al., "MicroRNA-155 Influences B-Cell Receptor Signaling and Associates with Aggressive Disease in Chronic Lymphocytic Leukemia," Blood, 124(4): 546-554 (2014).
Cummings et al., "Critical Role for Phosphoinositide 3-Kinase Gamma in Parasite Invasion and Disease Progression of Cutaneous Leishmaniasis," PNAS USA, 109:1251-1256 (2012).
Czuczman et al. Rituximab in combination with fludarabine chemotherapy in low-grade or follicular lymphoma. J. Clin. Oncol. 23(4):694-704 (Feb. 1, 2005).
D'Cruz et al. Novel Bruton's tyrosine kinase inhibitors currently in development. OncoTargets and Therapy 6:161-176 (2013).
Dana-Farber Cancer Institute. A Phase II Study of Ibrutinib Plus FCR in Previously Untreated, Younger Patients With Chronic Lymphocytic Leukemia (iFCR). In: ClinicalTrials.gov [Internet]. Bethesda (MD): National Library of Medicine (US). Sep. 23, 2014 [cited Feb. 5, 2015] Available from: https://clinicaltrial.gov/ct2/show/NCT02251548?term=NCT02251548 NLM Identifier: NCT02251548.

(56) References Cited

OTHER PUBLICATIONS

Dana-Farber Cancer Institute. Ibrutinib (PCI-32765) in Waldenstrom's Macroglobulinemia. In: ClinicalTrials.gov [Internet]. Bethesda (MD): National Library of Medicine (US). May 17, 2012—[cited Nov. 22, 2013]. Available from: http://clinicaltrials.gov/ct2/show/NCT01614821 NLM Identifier: NCT01614821.
Dasmahapatra, et al., "The Bruton Tyrosine Kinase (BTK) Inhibitor PCI-32765 Synergistically Increases Proteasome Inhibitor Activity in Diffuse large-B cell lymphoma (DLBCL) and Mantle Cell lymphoma (MCL) Cells Sensitive or Resistant to Bortezomib," British Journal of Haematology, 161(1): 43-56 (Jan. 30, 2013).
Davids et al. Targeting the B Cell Receptor Pathway in Chronic Lymphocytic Leukemia. Leuk. Lymphoma (Epub May 23, 2012), 53(12):2362-2370 (Dec. 2012).
Davids et al., "The BCL-2-specific BH3-mimetic ABT-199 (GDC-0199) is active and well-tolerated in patients with relapsed non-Hodgkin lymphoma: interim results of a phase I study," Blood, 120(21): Abstract No. 304 (2012).
Davis et al., "Chronic active B-cell receptor signalling in diffuse large B-cell lymphoma," Nature, 463(7277):88-92 (2010).
Delgado, Md et al. Myc Roles in Hematopoiesis and Leukemia. Genes & Cancer. 2010. vol. 1. No. 6. pp. 605-616; abstract; p. 609,Jeft column, 3rd paragraph; p. 610, righ column, 2nd paragraph; p. 612, middle column, 3rd paragraph, right column, 1st paragraph.
Deng et al., "New Strategies in the Treatment of Mantle Cell Lymphoma," Clin Cancer Res, 18(13): 3499-3508 (2012).
Desiderio. Role of Btk in B cell development and signaling. Curr. Op. in Immunology 1997, 9:534-540.
Devos et al., "The Bruton's tyrosine kinase (BTK) inhibitor, ibrutinib (PCI-32765), has preferential activity in the activated B cell-like (ABC) subtype of relapsed/refractory (RR) DLBCL: interim phase 2 results," Haematologica 98(s1):490 (2013).
Dias et al. Ibrutinib: A New Frontier in the Treatment of Chronic Lymphocytic Leukemia by Bruton's Tyrosine Kinase Inhibition. Cardiovascular & Hematological Agents in Medicinal Chemistry 11:265-271 (2013).
Dixon, "Evaluation of the CASP2 docking section," Proteins, Suppl 1: 198-204 (1997).
Dohner et al., "Genomic Aberrations and Survival in Chronic Lymphocytic Leukemia," The New England Journal of Medicine, pp. 1910-1916 (2000).
Dolganiuc et al., "T Cells with Regulatory Activity in Hepatitis C Virus Infection: What We Know and What We Don't," J Leukoc Biol. 84(3): 614-622 (2008).
Dorwald, F.Z., "Side Reactions in Organic Synthesis," Wiley:VCH, Weinheim p. IX of Preface, Wiley-VCH Verlag GmbH & C KGaA (2005).
Dubovsky et al, "Ibrutinib Is an Irreversible Molecular Inhibitor of Interleukin-2 Inducible Kinase: Expanding Therapeutic Potential and Modulating a th1 Selective Pressure in CD4 T-Cells," 54th ASH Annual Meeting and Exposition, Blood, 120:775 (2012).
Dubovsky et al., "Epigenetic Repolarization of T Lymphocytes from Chronic Lymphocytic Leukemia Patients Using 5-aza-2'-deoxycylidine," Leukemia Research 35:1193-1199 (2011).
Dubovsky et al., "Ibrutinib is an irreversible molecular inhibitor of ITK driving a Th1-selective pressure in T lymphocytes," Blood, 122(15): 2539-2549 (2013).
Dubovsky et al., "Restoring the Functional Immunogenicity of Chronic Lymphocytic Leukemia Using Epigenetic Modifiers," Leukemia Research 35(3):394-404 (2011).
Dy et al. Understanding, recognizing, and managing toxicities of targeted anticancer therapies. CA: a cancer Journal for clinicians. 63(4):249-279 (Epub May 2013).
EA200901313 Notification of Office Action dated Oct. 31, 2011.
EA201000599 Search Report dated Nov. 15, 2010.
Edwards. BTK inhibition in myeloma: targeting the seed and the soil. Blood 120(9):1757-1759 (Aug. 2012).
Elias et al. BTK Inhibitor Ibrutinib Inhibits Breast Cancer Growth by Inhibiting ErbB Kinases. Mol Cancer Ther. 2013;12:0258. (not available on pubmed).
Emens et al., "Breast cancer immunobiology driving immunotherapy: vaccines and immune checkpoint blockade," Expert Rev Anticancer Ther, 12(12): 1597-1611 (2012).
EP 06850039 Supplemental Search Report dated Feb. 9, 2010.
EP 06850386.1 Search Report and Written Opinion dated Sep. 10, 2010.
EP 08744513 Supplementary Search Report dated Mar. 11, 2010.
EP 08744513.6 Examination Report dated Jan. 16, 2013.
EP 09798770.5 Search Report and Written Opinion dated Oct. 28, 2011.
EP 10155834.4 Search Report dated May 19, 2010.
EP 10823966 Supplementary European Search Report dated Oct. 17, 2011.
EP 10823966.6 Written Opinion dated Dec. 6, 2011.
EP 12151943.3 Examination Report dated Feb. 5, 2013.
EP 12151943.3 Search Report and Written Opinion dated Mar. 13, 2012.
EP 12166295.1 Search Report and Written Opinion dated Nov. 6, 2012.
EP 12166296.9 Search Report and Written Opinion dated Nov. 8, 2012.
EP 12166298.5 Search Report and Written Opinion dated Nov. 7, 2012.
EP 12166300.9 Search Report and Written Opinion dated Oct. 31, 2012.
EP 12166301.7 Search Report and Written Opinion dated Nov. 6, 2012.
EP 12166302.5 Search Report and Written Opinion dated Nov. 6, 2012.
EP 12166305.8 Examination Report dated Dec. 3, 2013.
EP 12166305.8 Search Report and Written Opinion dated Nov. 6, 2012.
EP 12166306.6 Search Report and Written Opinion dated Nov. 8, 2012.
EP 12172840.6 Search Report and Written Opinion dated Dec. 12, 2012.
EP 12172841.4 Search Report and Written Opinion dated Jan. 2, 2013.
EP 12172842.2 Extended Search Report dated May 14, 2013.
EP 12172842.2 Partial Search Report dated Jan. 24, 2013.
EP 12172843.0 Search Report and Written Opinion dated Jan. 18, 2013.
European Search Report for Application No. EP 13166272 dated Sep. 4, 2013.
European Search Report for Application No. EP 15170739 dated Oct. 29, 2015.
Expert Scientific Group on Phase One Clinical Trials. Final Report. Nov. 2006, pp. C1, C35-C38.
Ezell S.A., et al., "Synergistic Induction of Apoptosis by Combination of BTK and Dual mTORC1/2 Inhibitors in Diffuse Large B Cell Lymphoma," Oncotarget, 2014, vol. 5 (13), pp. 4990-5001.
Fabian et al. A small molecule-kinase interaction map for clinical kinase inhibitors. Nature Biotechnology, 23(3): 329-336 (2005).
Fallahi et al., "Cytokines and HCV-Related Disorders," Clinical and Developmental Immunology. 2012. Article IDs 468102. 10 pgs.
Federal Register, vol. 66, No. 4, pp. 1099-1111, Jan. 5, 2001.
Fedorak et al. A novel colon-specific steroid prodrug enhances sodium chloride absorption in rat colitis. Am. J. Physiol. 269:G210-218 (1995).
Ferrajoli et al., "Prognostic Value of Mir-155 in Individuals with Monoclonal B-Cell Lymphocytosis and Patients with B Chronic Lymphocytic Leukemai," Blood, 122(11): 1891-1899 (2013).
Fisher et al. Prolonged disease-free survival in Hodgkin's disease with MOPP reinduction after first relapse. Ann. Intern. Med., 90(5):761-763 (1979).
Flynn et al., "Maintenance of TH1 HCV-Specific Responses in Individuals with Acute HCV who Achieve Sustained Virological Clearance After Treatment," Centre for Biomedical Research. Doi: 10.111/jgh.12265 (no date available).
Fontan et al., "Targeting Lymphomas Through MALT1 Inhibition," Oncotarget, 3(12): 1493-1494 (2012).

(56) References Cited

OTHER PUBLICATIONS

Fonte et al., "In vitro sensitivity of CLL cells to fludarabine may be modulated by the stimulation of Toll-like receptors," Clin Cancer Res 19:367-379 (2013).
Fowell et al., "Impaired NFATc Translocation and Failure of Th2 Development in Itk-Deficient CD4+ T Cells," Immunity 11:399-409 (1999).
Fowler et al. The Btk Inhibitor, PCI-32765, Induces Durable Responses with Minimal Toxicity in Patients with Relapsed/Refractory B-Cell Malignancies: Results From a Phase 1 Study. Blood (ASH Annual Meeting) 116 (21), p. 425:Abstract 964 (2010).
Fowler et al., "The Bruton's tyrosine kinase inhibitor ibrutinib (PCI-32765) is active and tolerated in relapsed follicular lymphoma," 54th American Society of Hematology Annual Meeting and Exposition, Abstract 156 (2012).
Friedberg et al. Inhibition of Syk with fostamatinib disodium has significant clinical activity in non-Hodgkin lymphoma and chronic lymphocytic leukemia. Blood 115(13):2578-2585 (2010) [E-pub Nov. 17, 2009].
Fritsche et al., "National Academy of Clinical Biochemistry Guidelines for the Use of Tumor Markers in Bladder Cancer," NACB: Practice Guidelines and Recommendations for Use of Tumor Markers in the Clinic Bladder Cancer (3H)1. (Oct. 30, 2013). http://www.aacc.org/SiteCollectionDocuments/NACB/LMPG/tumor/chp3h_bladder.pdf.
Fruman. Xid-like Phenotypes: A B Cell Signalosome Takes Shape. Immunity 13:1-3 (Jul. 2000).
Fujimoto et al., "Peripheral Pulmonary Carcinomas Evaluated with Dynamic MR Imaging: Correlation with Tumor Vascularity and Prognosis," Radiology, 227:786-793 (2003).
Fundamental Immunology p. 242 (William E. Paul, M.D. ed., 3d ed; 1993)].
Gad et al., "Distinct Immunoregulatory Cytokine Pattern in Egyptian Patients with Occult Hepatitis C Infection and Unexplained Persistently Elevated Liver Transaminases," Asian J. Transfus Sci. 6(1): 24-28 (2012).
Galli et al., "Evoking durable anti-cancer responses with blocking antibodies to PD-1 and PD-L1," Transl Cancer Res, 1(4): 287-289 (2012).
Gazitt et al. Differential mobilization of CD34+ Cells and lymphoma cells in non-Hodgkin's lymphoma patients mobilized with different growth factors, J of Hematotherapy & Stem Cell Research 10:167-176 (2001).
Ghia. Ibrutinib: better combined with other drugs? Lancet 15:1043-1044 (2014).
Giuliani. Multiple myeloma bone disease: pathophysiology of osteoblast inhibition. Blood (Epub Aug. 17, 2006) 108(13):3992-3996 (2006).
Glassman et al., "The value of fluorescence in situ hybridization in the diagnosis and prognosis of chronic lymphocytic leukemia," Cancer Genet Cytogen, 158:88-91 (2005).
Goding et al., "Combination of adoptive cell transfer, anti-PD-L1 and anti-LAG-3 antibodies for the treatment of recurrent tumors," OncoImmunology 2(8): e25050 (2013).
Goggins, "Markers of Pancreatic Cancer: Working Toward Early Detection," Clin. Cancer Res. 17(4):635-7 (2011).
Gold. To make antibodies or not:signaling by the B-cell antigen receptor. Trends in Pharmacological Sciences, 23(7):316-324 (Jul. 2002).
Gomez-Rodriguez et al, "Tec Family Kinases Itk and Rlk/Txk in T Lymphocytes Cross-Regulation of Cytokine Production and T-Cell Fates," FEBS Journal 278(12):1980-1989 (2011).
Gordon et al. Somatic hypermutation of the B cell receptor genes B29 (Igb, CD79b) and mb1 (Iga, CD79a). PNAS 100(7):4126-4131 (2003).
Grabinski N., et al., "Ibrutinib (ImbruvicaTM) Potently Inhibits ErbB Receptor Phosphorylation and Cell Viability of Erbb2-Positive Breast Cancer Cells," Investigational New Drugs, Aug. 2014, vol. 32 (6), pp. 1096-1104.
Gresheck et al. Molecular Target Class Is Predictive of In vitro Response Profile. Cancer Res. 70:3677-3686 (2010).
Grosso et al., CTLA-4 blockade in tumor models: an overview of preclinical and translational research, Cancer Immun, 13:5 (2013).
Grzywnowicz et al., "Expression of programmed death 1 ligand in different compartments of chronic lymphocytic leukemia," PLoS One, 7(4):e35178, pp. 1-8 (2012).
Guatelli et al., "Isothermal, in Vitro Amplification of Nucleic Acids by a Multienzyme Reaction Modeled After Retroviral Replication," Proc. Natl. Acad. Sci. USA, 87(5):1874-1678 (1990).
Guinn et al., "miR-155 expression is associated with chemoimmunotherapy outcome and is modulated by Bruton's tyrosine kinase inhibition with Ibrutinib," Leukemia 29(5): 1210-1213 (2015).
Guo, "Molecular Characteristic of CTA056, a Novel Interleukin-2-Inducible T-Cell Kinase Inhibitor that Selectively Target Malignat T Cell and Modulate Oncomirs," Molecular Pharmacology 82:938-947 (Aug. 2012).
Gupta et al., "Inhibition of Histone Deacetylase Overcomes Rapamycin-mediated Resistance in Diffuse Large B-cell Lymphoma by Inhibiting Akt Signaling Through MTOC2," Blood, 114: 2926-2935 (2009).
Gura. Systems for Identifiying New Drugs Are Often Faulty. Science 278(5340):1041-1042 (1997).
Hagemeister. Rituximab for the treatment of non-Hodgkin's lymphoma and chronic lymphocytic leukaemia. Drugs 70(3):261-272 (2010).
Hahtola et al., "Th1 Response and Cytotoxicity Genes are Down-Regulated in Cutaneous T-Cell Lymphoma," Clin Cancer Res. 12(16):4812-4821 (2006).
Hantschel et al. Systemic profiling and novel targets of the Bcr-Abl kinase inhibitors imatinib, nilotinib, and dasatinib. Blood 110 (11, Part 2):207B (2007) & 49th Annual Meeting of the American-Society-of-Hematology:Atlanta, Ga, USA; Dec. 8-11, 2007.
Hantschel et al. The Btk Tyrosine Kinase is a Major Target of the Bcr-Ab1 Inhibitor Dasatinib. PNAS 104(33):13283-13288 (2007).
Hata et al. Bruton's tyrosine kinase-mediated Interleukin-2 gene activation in mast cells. J. Biol. Chem. 273(18): 10979-10987 (1998).
Herman et al. "Ibrutinib inhibits BCR and NF-KB signaling and reduces tumor proliferation in tissue-resident cells of patients with CLL," Blood. Mar. 21, 2014 (Mar. 21, 2014), vol. 123, pp. 3286-3295.
Herman et al. Bruton tyrosine kinase represents a promising therapeutic target for treatment of chronic lymphocytic leukemia and is effectively targeted by PCI-32765. Blood (Epub Mar. 21, 2011), 117(23):6287-6296 (Jun. 2011).
Hiddeman et al. Rituximab Plus Chemotherapy in Follicular and Mantle Cell Lymphomas, Seminars in Oncology 30(1)Suppl.2:16-20 (Feb. 2003).
Hiddeman et al., "Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German low-grade lymphoma study group," Blood, 106(12):3725-32 (2005).
Higuchi et al. Pro-drugs as Novel Delivery Systems, vol. 14 of the A.C.S. Symposium Series (1975).
Hochhaus et al. A selective HPLC/RIA for dexamethasone and its prodrug dexamethasone-21-sulphobenzoate sodium in biological fluids. Biomed. Chrom., 6:283-286 (1992).
Honigberg et al. Targeting Btk in lymphoma: PCI-32765 inhibits tumor growth in mouse lymphoma models and a fluorescent analog of PCI-32765 is an active-site probe that enables assessment of Btk inhibition in vivo. ASH Annual Meeting Abstracts 1592. 110(11): 475A (2007).
Honigberg et al. The Bruton tyrosine kinase inhibitor PCI-32765 blocks B-cell activation and is efficacious in models of autoimmune disease and B-cell malignancy. PNAS USA 107:13075-13080 (2010).
Horning et al., The natural history of initially untreated low-grade non-Hodgkin's lymphomas, (1984) N. Engl. J. Med. 311:1471-1475.

(56) References Cited

OTHER PUBLICATIONS

Horwood et al. Bruton's Tyrosine Kinase Is Required for Lipopolysaccharide-induced Tumor Necrosis Factor α Production. J. Exp. Med. 197(12):1603-1611 (Jun. 2003).
http://www.uspto.gov/web/offices/pac/dapp/1pecba.htm#7, last accessed Feb. 16, 2011.
Huhn et al. Rituximab therapy of patients with B-cell chronic lymphocytic leukemia. Blood 98(5):1326-1331 (Sep. 1, 2001).
Hurrell et al. The in vitro influences of epidermal growth factor and heregulin-β1 on the efficacy of trastuzumab used in Her-2 positive breast adenocarcinoma. Cancer Cell Int. Oct. 11, 2013;13(1):97. doi: 10.1186/1475-2867-13-97.
IDW00201201693 Office Action dated Apr. 20, 2015.
Igietseme et al., "Suppression of Endogenous IL-10 Gene Expression in Dendritic Cells Enhances Antigen Presentation for Specific Th1 Induction: Potential for Cellular Vaccine Development," J Immunol, 164: 4212-4219 (2000).
Inhibitory effects of the BTK inhibitor, ibrutinib, on HER2-amplified breast cancer growth, cell cycle progression, and clonogenicity—Poster.
International Preliminary Report on Patentability for Application No. PCT/US15/21871, dated Sep. 29, 2016, 10 pages.
International Preliminary Report on Patentability for International Application No. PCT/US2012/061208 dated Feb. 25, 2013.
International Preliminary Report on Patentability for International Application No. PCT/US2014/068237 dated Jun. 16, 2016.
International Preliminary Report on Patentability for PCT/US2013/068132 dated May 5, 2015.
International Preliminary Report published Oct. 30, 2007 on Patentability for PCT/IB2005/002350, filed Apr. 28, 2005.
International Search Report and Written Opinion for International Application No. PCT/US2014/068237 dated Feb. 27, 2015.
International Search Report and Written Opinion for International Patent Application No. PCT/US15/61091 dated Mar. 11, 2016.
International Search Report and Written Opinion for International Patent Application No. PCT/US16/15697 dated Apr. 22, 2016.
International Search Report and Written Opinion for International Patent Application No. PCT/US16/41550 dated Nov. 15, 2016.
International Search Report and Written Opinion for International Patent Application No. PCT/US16/63085 dated May 22, 2017.
International Search Report and Written Opinion for International Patent Application No. PCT/US2014/058132 dated Jan. 14, 2015.
International Search Report and Written Opinion for International Patent Application No. PCT/US2015/051034 dated Dec. 18, 2015.
International Search Report for International Application No. PCT/US15/41841 dated Oct. 29, 2015.
International Search Report for International Application No. PCT/US2015/067504 dated Mar. 4, 2016.
International Search Report for International Application No. PCT/US2016/025673 dated Jun. 23, 2016.
International Search Report published Jan. 25, 2007 for PCT/IB2005/002350, filed Apr. 28, 2005.
Iqbal et al., on pp. 2-4 (Molecular Biology International, 2014, Article ID 852748, 9 pages.
Iriyama et al. "Clinical significance of genetic mutations of CD79B, CARD11, MYD88, and EZH2 genes in diffuse large B-cell-lymphoma patients," Dec. 10, 2011 (Dec. 10, 2011), 53rd ASH Annual Meeting, Abstract 2633, available at https://ash.confex.com/ash/2011/webprogram/Paper36650.html.
Iwaki et al. Btk Plays a Crucial Role in the Amplification of FceRI-mediated Mast Cell Activation by Kit. J. Biol. Chem. 280(48):40261-40270 (Dec. 2, 2005).
Jaffe. The 2008 WHO classification of lymphomas: implications for clinical practice and translational research. Hematology 1:523-531 (2009).
Jaglowski et al., "A Phase Ib/II Study Evaluating Activity and Tolerability of BTK Inhibitor PCI-32765 and Ofatumumab in Patients with Chronic Lymphocytic Leukemia/Small Lymphocytic Lymphoma (CLL/SLL) and related Diseases," J Clin Oncol, 30: Abstract 6508 (2012).
Jak et al., "CD40 Stimulation Sensitizes CLL Cells to Lysosomal Cell Death Induction by Type II Anti-CD20 mAb GA101," Blood, 118(19): 5178-5188 (2011).
Janssen Biotech, Inc. An open label treatment use protocol for ibrutinib in subjects with relapsed or refractory mantel cell lymphoma. In: ClinicalTrials.gov [Internet]. Bethesda (MD): National Library of Medicine (US). Apr. 6, 2013—[cited Nov. 22, 2013]. Available from: http://clinicaltrials.gov/ct2/show/NCT01833039 NLM Identifier: NCT01833039.
Janssen Pharmaceutical K.K. A study to evaluate the Bruton's tyrosine kinase (Btk) inhibitor PCI-32765 in patients with recurrent mature B-cell neoplasms. In: ClinicalTrials.gov [Internet]. Bethesda (MD): National Library of Medicine (US). Oct. 9, 2012—[cited Nov. 22, 2012]. Available from: http://clinicaltrials.gov/ct2/show/NCT01704963 NLM Identifier: NCT01704963.
Janssen Pharmaceutical K.K. Study of the Bruton's Tyrosine Kinase (BTK) Inhibitor Ibrutinib in Participants With Relapsed or Refractory Mantle Cell Lymphoma. In: ClinicalTrials.gov [Internet]. Bethesda (MD): National Library of Medicine (US). Jun. 19, 2014—[cited Feb. 5, 2015] Available from: https://clinicaltrial.gov/ct2/show/NCT02169180?term=NCT02169180 NLM Identifier: NCT02169180.
Janssen Research & Development, LLC. A Study to Evaluate the Effects of Ibrutinib on Cardiac Repolarization in Healthy Participants. In: ClinicalTrials.gov [Internet]. Bethesda (MD): National Library of Medicine (US). Oct. 20, 2014 [cited Feb. 5, 2015] Available from: https://clinicaltrial.gov/ct2/show/NCT02271438?term=NCT02271438 NLM Identifier: NCT02271438.
Janssen Research & Development, LLC. Pharmacokinetic and Pharmacodynamic Study to Evaluate Safety and Efficacy of the Combination of Ibrutinib With Nivolumab in Participants With Hematologic Malignancies. In: ClinicalTrials.gov [Internet]. Bethesda (MD): National Library of Medicine (US). Dec. 30, 2014 [cited Feb. 5, 2015] Available from: https://clinicaltrial.gov/ct2/show/NCT02329847?term=NCT02329847 NLM Identifier: NCT02329847.
Janssen Research and Development, LLC. A long-term extension study of PCI-32765 (Ibrutinib). In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01804686 NLM Identifier: NCT01804686.
Janssen Research and Development, LLC. A pharmacokinetic study in healthy participants to assess the pharmacokinetics and safety of a supratherapeutic dose of PCI-32765 (Ibrutinib) capsule and solution formulations administered with food. In: ClinicalTrials.gov [Internet]. Bethesda (MD): National Library of Medicine (US). Aug. 19, 2013—[cited Nov. 22, 2013]. Available from: http://clinicaltrials.gov/ct2/show/NCT01969266 NLM Identifier: NCT01969266.
Janssen Research and Development, LLC. A study combining Ibrutinib with rituximab, cyclophosphamide, doxorubicin, vincristine, and prednisone in patients with CD20-positive B-cell non Hodgkin lymphoma. In: ClinicalTrials.gov [Internet]. Bethesda (MD): National Library of Medicine (US). Mar. 30, 2012—[cited Nov. 22, 2013]. Available from: http://clinicaltrials.gov/ct2/show/NCT01569750 NLM Identifier: NCT01569750.
Janssen Research and Development, LLC. A study of ibrutinib in combination with bendamustine and rituximab in patients with relapsed or refractory chronic lymphocytic leukemia or small lymphocytic lymphoma. In: ClinicalTrials.gov [Internet]. Bethesda (MD): National Library of Medicine (US). May 15, 2012—[cited Nov. 22, 2013]. Available from: http://clinicaltrials.gov/ct2/show/NCT01611090 NLM Identifier: NCT01611090.
Janssen Research and Development, LLC. A study of PCI-32765 (Ibrutinib) in combination with either bendamustine and rituximab or rituximab, cyclophosphamide, doxorubicin, vincristine, and prednisone in patients with previously treated indolent non-Hodgkin lymphoma. In: ClinicalTrials.gov [Internet]. Bethesda (MD): National Library of Medicine (US). Oct. 28, 2013—[cited Nov. 22, 2013]. Available from: http://clinicaltrials.gov/ct2/show/NCT01974440 NLM Identifier: NCT01974440.

(56) References Cited

OTHER PUBLICATIONS

Janssen Research and Development, LLC. A study of PCI-32765 (Ibrutinib) in patients with refractory follicular lymphoma. In: ClinicalTrials.gov [Internet]. Bethesda (MD): National Library of Medicine (US). Jan. 25, 2013—[cited Nov. 22, 2013]. Available from: http://clinicaltrials.gov/ct2/show/NCT01779791 NLM Identifier: NCT01779791.

Janssen Research and Development, LLC. A study of the Bruton's tyrosine kinase inhibitor ibrutinib given in combination with bendamustine and rituximab in patients with newly diagnosed mantel cell lymphoma. In: ClinicalTrials.gov [Internet]. Bethesda (MD): National Library of Medicine (US). Jan. 24, 2013—[cited Nov. 22, 2013]. Available from: http://clinicaltrials.gov/ct2/show/NCT01776840 NLM Identifier: NCT01776840.

Janssen Research and Development, LLC. A study of the Bruton's tyrosine kinase inhibitor PCI-32765 (Ibrutinib) versus rituximab in patients with relapsed or refractory chronic lymphocytic leukemia/small lymphocytic lymphoma. In: ClinicalTrials.gov [Internet]. Bethesda (MD): National Library of Medicine (US). Oct. 25, 2013—[cited Nov. 22, 2013]. Available from: http://clinicaltrials.gov/ct2/show/NCT01973387 NLM Identifier: NCT01973387.

Janssen Research and Development, LLC. A study on the Bruton's tyrosine kinase inhibitor, PCI-32765 (Ibrutinib), in combination with rituximab, cyclophosphamide, doxorubicin, vincristine, and prednisone in patients with newly diagnosed non-germinal center B-cell subtype of diffuse large B-cell lymphoma. In: ClinicalTrials.gov [Internet]. Bethesda (MD): National Library of Medicine (US). May 14, 2013—[cited Nov. 22, 2013]. Available from: http://clinicaltrials.gov/ct2/show/NCT01855750 NLM Identifier: NCT01855750.

Janssen Research and Development, LLC. A study to assess the absolute bioavailability of Oral PCI-32765 and the effect of grapefruit juice on the bioavailability of PCI-32765 in healthy participants. In: ClinicalTrials.gov [Internet]. Bethesda (MD): National Library of Medicine (US). May 28, 2013—[cited Nov. 22, 2013]. Available from: http://clinicaltrials.gov/ct2/show/study/NCT01866033 NLM Identifier: NCT01866033.

Janssen Research and Development, LLC. A study to assess the effect of ketoconazole on the pharmacokinetics of ibrutinib in healthy participants. In: ClinicalTrials.gov [Internet]. Bethesda (MD): National Library of Medicine (US). Jun. 18, 2012—[cited Nov. 22, 2013]. Available from: http://clinicaltrials.gov/ct2/show/NCT01626651 NLM Identifier: NCT01626651.

Janssen Research and Development, LLC. A study to assess the effect of rifampin on the pharmacokinetics of PCI-32765 in healthy participants. In: ClinicalTrials.gov [Internet]. Bethesda (MD): National Library of Medicine (US). Jan. 4, 2013—[cited Nov. 22, 2013]. Available from: http://clinicaltrials.gov/ct2/show/NCT01763021 NLM Identifier: NCT01763021.

Janssen Research and Development, LLC. A study to determine the absorption, metabolism, and routes of excretion of (14C) radiolabeled ibrutinib in healthy male participants. In: ClinicalTrials.gov [Internet]. Bethesda (MD): National Library of Medicine (US). Aug. 9, 2012—[cited Nov. 22, 2013]. Available from: http://clinicaltrials.gov/ct2/show/NCT01674322 NLM Identifier: NCT01674322.

Janssen Research and Development, LLC. A study to determine the effect of food on the pharmacokinetics of PCI-32765. In: ClinicalTrials.gov [Internet]. Bethesda (MD): National Library of Medicine (US). Mar. 4, 2013—[cited Nov. 22, 2013]. Available from: http://clinicaltrials.gov/ct2/show/NCT01820936 NLM Identifier: NCT01820936.

Janssen Research and Development, LLC. A study to evaluate the efficacy and safety of ibrutinib, in patients with mantel cell lymphoma who progress after bortezomib therapy. In: ClinicalTrials.gov [Internet]. Bethesda (MD): National Library of Medicine (US). May 14, 2012—[cited Nov. 22, 2013]. Available from: http://clinicaltrials.gov/ct2/show/NCT01599949 NLM Identifier: NCT01599949.

Janssen Research and Development, LLC. A study to evaluate the pharmacokinetics of PCI-32765 in participants with varying degrees of hepatic impairment. In: ClinicalTrials.gov [Internet]. Bethesda (MD): National Library of Medicine (US). Jan. 9, 2013—[cited Nov. 22, 2013]. Available from: http://clinicaltrials.gov/ct2/show/NCT01767948 NLM Identifier: NCT01767948.

Janssen Research and Development, LLC. Study of ibrutinib (a Bruton's tyrosine kinase inhibitor), versus temsirolimus in patients with relapsed or refractory mantel cell lymphoma who have received at least one prior therapy. In: ClinicalTrials.gov [Internet]. Bethesda (MD): National Library of Medicine (US). Jul. 18, 2012—[cited Nov. 22, 2013]. Available from: http://clinicaltrials.gov/ct2/show/NCT01646021 NLM Identifier: NCT01646021.

Jefferies et al., "Bruton's tyrosine kinase is a toll/interleukin-1 receptor domain-binding protein that participates in nuclear factor kB activation by toll-like receptor 4," J Biol Chem, 278:26258-64 (2003).

Kabat et al., "Sequences of Proteins of Immunological Interest," NIH Publ. No. 91-3242, 1:647-669 (1991).

Kamb. What's wrong with our cancer models? Nature Reviews Drug Discovery 4:161-165 (2005).

Kang et al., "Dynamic Analysis of Th1/Th2 Cytokine Concentration During Antiretroviral Therapy of HIV-1/HCV Co-Infected Patients," MCS Infectious Diseases 12:102-112 (2012).

Karanjawala et al., "New Markers of Pancreatic Cancer Identified Through Differential Gene Expression Analyses: Claudin 18 and Annexin A8," Am J. Surg. Pathol. 32(2)188-196 (2008).

Kathawala et al., "Masitinib Antagonizes ATP-Binding Cassette Subfamily C Member 10-Mediated Paclitaxel Resistance: A Preclinical Study," Mol Cancer Ther, 13(3): 714-723 (2014).

Kathawala et al., "The Small Molecule Tyrosine Kinase Inhibitor NVP-BHG712 Antagonizes ABCC10-mediated Paclitaxel Resistance: A Preclinical and Pharmacokinetic Study," Oncotarget, 6(1): 510-521 (2014).

Kaur et al., "Inhibitors of Interleukin-2 Inducible T-Cell Kinase as Potential Therapeutic Candidates for the Treatment of Various Inflammatory Disease Conditions," Eur J Pharm Sci 47(3):574-578 (2012).

Kawakami et al. Terreic acid, a quinone epoxide inhibitor of Bruton's tyrosine kinase. PNAS USA 96:2227-2232 (1999).

Kawakami et al., "Regulation of Dendritic Cell Maturation and Function by Bruton's Tyrosine Kinase via IL-10 and Stat3," Proc Natl Acad Sci USA, 103(1): 153-158 (2006).

Keeton et al. "AZD1208, a potent and selective pan-Pim kinase inhibitor, demonstrates efficacy in preclinical models of acute myeloid leukemia," Blood, Dec. 20, 2013 (Dec. 20, 2013), vol. 123, No. 6, pp. 905-913.

Khan et al., "Circulating Biomarkers and their Possible Role in Pathogenesis of Chronic Hepatits B and C Viral Infections," Ind J Clin Biochem 46(2):161-168 (2011).

Kim et al. HRG-β1-driven ErbB3 signaling induces epithelial-mesenchymal transition in breast cancer cells. BMC Cancer. Aug. 12, 2013;13:383. doi: 10.1186/1471-2407-13-383.

Ko. Everyone's Guide to Cancer Therapy: How Cancer is Diagnosed, treated and Managed Day to Day. 3 pgs. (2009).

Kola et al. Can the pharmaceutical industry reduce attrition rates? Nature Reviews Drug Discover 3:711-715 (2004).

Kong et al., "Opportunistic Autoimmune Disorders Potentiated by Immune-Checkpoint Inhibitors Anti-CTLA-4 and Anti-PD-1," Front Immunol, 5(206): 1-8 (2014).

Kono, "Current status of cancer immunotherapy," J Stem Cells Regen med, 10(1): 8-13 (2014).

Korade-Mirnics et al. Src kinase-mediated signaling in leukocytes. J. Leukoc. Bio., 68(5):603-613 (Nov. 2000).

Kozaki et al. Development of a Bruton's tyrosine kinase (Btk) inhibitor-ONO-WG-307, a potential treatment for B-cell malignancies. 53rd American Society of Hematology Annual Meeting and Exposition, San Diego, CA, Poster #857 (Dec. 10-13, 2011).

Kuglstatter et al. Insights into the conformational flexibility of Bruton's tyrosine kinase from multiple ligand complex structures. Protein Science 20(2):428-436 (2011) [E-pub Dec. 17, 2010].

Kuppers. Mechanisms of B-cell lymphoma pathogenesis. Nature Reviews/Cancer 5:251-262 (2005).

(56) References Cited

OTHER PUBLICATIONS

Kurosaki. Functional dissection of BCR signaling pathways. Curr. Op. Imm. 12:276-281 (2000).

Kushner et al. Pharmacological uses and perspective of heavy water and deuterated compounds. Canadian Journal of Physiology and Pharmacology 77(2):79-88 (1999).

Kwoh et al., "Transcription-based amplification system and detection of amplified human immunodeficiency virus type 1 with a bead-based sandwich hybridization format," Proc. Natl. Acad. Sci. USA, 86:1173-1177 (1989).

Kyi et al., "Checkpoint blocking antibodies in cancer immunotherapy," FEBS Letters, 588(2): 368-376 (2013).

Langhans et al., "Ribavirin Exerts Differential Effects on Function of Cd4+Th1, Th2, and Regulator T Cell Clones in Hepatitis C," PLOS One 7(7):e42094-42103 (2012).

Lapalombella et al., "Testrapanin CD37 Directly Mediates Transduction of Survival and Apoptotic Signals," Cancer Cell 21, 694-708 (2012).

Larsen et al., "Prodrug forms for the sulfonamide group. II. Water-soluble amino acid derivatives of N-methylsulfonamides as possible prodrugs," Int. J. Pharmaceutics. 47:103 (1988).

Larsen et al.Prodrug forms for the sulfonamide group. I. Evaluation of N-acyl derivatives, N-sulfonylaminides, N-sulfonylsulfilimines and sulfonylureas as possible prodrug derivatives. Int. J. Pharmaceutics 37:87-95 (1987).

Lau et al., "Mechanism of Action of Ribavirin in the Combination of Treatment of Chronic HCV Infection," Hepatology 35(5):1002-1009 (2002).

Le Tourneau et al. Dose Escalation Methods in Phase I Cancer Clinical Trials. J. Natl Cancer 101:708-720 (2009).

Leaf. Why Are We Losing the War on Cancer (And How to Win It). Health Admin. V. XVII, No. 1, pp. 172-183 (2005).

Lemery, "US Food and Drug Administration Approval: Ofatumumab for the Treatment of Patients with Chronic Lymphocytic Leukemia Refractory to Fludarabine and Alemtuzmab," Clinical Cancer Research pp. 4331-4338 (2010).

Lensink et al., "Docking and scoring protein complexes: CAPRI 3rd Edition," Proteins, 69(4): 704-718 (2007).

Leonard et al., "Selective CDK4/6 Inhibition with Tumor Responses by PD0332991 in Patients with Mantle Cell Lymphoma," Blood, 119(20): 4597-4607 (2012).

Lester et al., "Interleukin 2-Inducible T Cell Kinase (ITK) Facilitates Efficient Egress of HIV-1 by Coordinating Gag Distribution and Actin Organization," Virology 436 (1): 235-243 (2013).

Li et al. Activation of Bruton's Tyrosine Kinase (BTK) by a Point Mutation in its Pleckstrin Homology (PH) domain. Immunity 2:451-460 (1995).

Liao et al., "Interleukin-2 at the Crossroads of Effector Responses, Tolerance, and Immunotherapy," Immunity 38(1):13-25 (2013).

Lichtman. Battling the hematological malignancies: The 200 years' war. The Oncologist 13:126-138 (2008).

Lim et al. Asymmetric syntheses of fused bicyclic lactams. Journal of Organic chemistry 66(26):9056-9062 (2001).

Lin et al. Selective Itk inhibitors block T-cell activation and murine lung inflammation, Biochemistry 43:11056-11062 (2004).

Lin, "New Agents in Chronic Lymphocytic Leukemia," Curr Hematol Malig Rep, 5: 29-34 (2010).

Liu et al. Structural Basis for selective inhibition of Src family kinases by PPI. Chemistry and Biology 6:671-678, in particular table 1, p. 671 (1999).

Lizardi et al., "Exponential Amplification of Recombinant-RNA Hybridization Probes," Bio/Technology, 6:1197-1202 (1988).

Lo et al., "Itk Inhibitors: A Patent Review," Expert Opin. The Patents 20(4):459-469 (2010).

Lopez et al. Combining PCI-24781, a Novel Histone Deacetylase Inhibitor, with Chemotherapy for the Treatment of Soft Tissue Sarcoma. Clin Cancer Res 15:1774-1775, 3472-3483 (2009).

Lossos. Molecular Pathogenesis of Diffuse Large B-Cell Lymphoma. J. Clin. Oncol. 23(26):6351-6357 (Sep. 10, 2005).

Lou et al. Bruton's tyrosine kinase inhibitors: approaches to potent and selective inhibition, preclinical and clinical evaluation for inflammatory diseases and B cell malignancies. J Med Chem. May 24, 2012;55(10):4539-50 Publication Date (Web): Mar. 6, 2012.

Luban, "TRIM5 and the Regulation of HIV-1 Infectivity," Mol. Biol. Int. 2012:426840 (2012).

Luskova et al. Modulation of the Fce Receptor I Signaling by Tyrosine Kinase Inhibitors: Search for Therapeutic Targets of Inflammatory and Allergy Diseases. Curr. Pharmaceutical Design 10:1727-1737 (2004).

M.D. Anderson Cancer Center. A Phase I/II Study of Ibrutinib in Previously Treated Epidermal Growth Factor Receptor (EGFR) Mutant Non-Small Cell Lung Cancer. In: ClinicalTrials.gov [Internet]. Bethesda (MD): National Library of Medicine (US). Dec. 17, 2014 [cited Feb. 5, 2015] Available from: https://clinicaltrial.gov/ct2/show/NCT02321540?term=NCT02321540 NLM Identifier: NCT02321540.

M.D. Anderson Cancer Center. A Phase I/II Trial of PCI-32765 (BTK Inhibitor) in Combination With Carfilzomib in Relapse/Refractory Mantle Cell Lymphoma. In: ClinicalTrials.gov [Internet]. Bethesda (MD): National Library of Medicine (US). Oct. 16, 2014 [cited Feb. 5, 2015] Available from: https://clinicaltrial.gov/ct2/show/NCT02269085?term=NCT02269085 NLM Identifier: NCT02269085.

M.D. Anderson Cancer Center. Ibrutinib Post Stem Cell Transplantation (SCT) in Double-Hit B-Cell Lymphoma. In: ClinicalTrials.gov [Internet]. Bethesda (MD): National Library of Medicine (US). Oct. 21, 2014 [cited Feb. 5, 2015] Available from: https://clinicaltrial.gov/ct2/show/NCT02272666?term=NCT02272686 NLM Identifier: NCT02272686.

M.D. Anderson Cancer Center. Ibrutinib versus ibrutinib + rituximab (i vs iR) in patients with relapsed chronic lymphocytic leukemia (CLL). In: ClinicalTrials.gov [Internet]. Bethesda (MD): National Library of Medicine (US). Dec. 5, 2013—[cited Apr. 15, 2014]. Available from: http://clinicaltrials.gov/ct2/show/NCT02007044 NLM Identifier: NCT02007044.

M.D. Anderson Cancer Center. Phase 2 ibrutinib + rituximab in relapsed/refractory mantel cell lymphoma (R/R MCL). In: ClinicalTrials.gov [Internet]. Bethesda (MD): National Library of Medicine (US). Jun. 14, 2013—[cited Nov. 22, 2013]. Available from: http://clinicaltrials.gov/ct2/show/NCT01880567 NLM Identifier: NCT01880567.

M.D. Anderson Cancer Center. Phase 2 study of the combination of Bruton's tyrosine kinase inhibitor PCI-32765 and rituximab in high-risk chronic lymphocytic leukemia and small lymphocytic lymphoma patients. In: ClinicalTrials.gov [Internet]. Bethesda (MD): National Library of Medicine (US). Jan. 25, 2012—[cited Nov. 22, 2013]. Available from: http://clinicaltrials.gov/ct2/show/NCT01520519 NLM Identifier: NCT01520519.

M.D. Anderson Cancer Center. Pilot study to determine effects of the Btk inhibitor PCI-32765 on leukemia cell kinetics and trafficking, using heavy water labeling in subjects with CLL and SLL. In: ClinicalTrials.gov [Internet]. Bethesda (MD): National Library of Medicine (US). Dec. 13, 2012—[cited Nov. 22, 2013]. Available from: http://clinicaltrials.gov/ct2/show/NCT01752426 NLM Identifier: NCT01752426.

MacPartlin et al. Bruton's tyrosine kinase is not essential for Bcr-Abl-mediated transformation of lymphoid or myeloid cells. Leukemia 22:1354-1360 (2008).

Maddock et al, "Etiology of Ibrutinib Therapy Discontinuation and Outcomes in Patients With Chronic Lymphocytic Leukemia," JAMA Oncology, 1(1):80-87 (2015).

Maddocks et al. Ibrutinib in B-cell lymphomas. Current Treatment Options in Oncology 15:226-237 (2014) (Epub: Feb. 1, 2014).

Mahajan et al. Rational Design and Synthesis of a Novel Antileukemic Agent Targeting Bruton's Tyrosine Kinase (BTK), LFM-A13 [a-Cyano-β-Methyl-N-(2,5-Dibromophenyl)Propenamide]. J. of Biol. Chem. 274(14):9587-9599 (1999).

Mallis et al. Structural characterization of a proline-driven conformational switch within the Itk SH2 domain. Nat. Struct. Biol., 9(12):900-905 (2002).

(56) References Cited

OTHER PUBLICATIONS

Mangla et al., "Pleiotropic consequences of Bruton tyrosine kinase deficiency in myeloid lineages lead to poor inflammatory responses," Blood, 104(4):1191-1197 (2004).
Marcotte et al, Structures of human Bruton's tyrosine kinase in active and inactive conformations suggest a mechanism of activation for TEC family kinases., Protein Science. 2010, 19:429-439.
Marina et al. Biology and Therapeutic Advances for Pediatric Osteosarcoma. The Oncologist 9:422-441 (2004).
Martin et al. Novel therapeutic targets in mantle cell lymphoma. Expert Opin. in Therapeutic Targets 11:929-940 (2007).
Mathews, et al., "High-Throughput Combinatorial Screening Identifies Drugs that Cooperate with Ibrutinib to Kill Activated B-cell-like diffuse large B-cell lymphoma cells," Proceedings of the National Academy of Sciences, 111(6): 2349-2354 (Jan. 27, 2014).
McConathy et al. Stereochemistry in Drug Action. J Clinical Psychiatry. 5:70-73 (2003).
McDermott et al., PD-1 as a potential target in cancer therapy, Cancer Med, 2(5): 662-673 (2013).
McLeod et al., "A glucocorticoid prodrug facilitates normal mucosal function in rat colitis without adrenal suppression," Gastroenterol, 106:405-413 (1994).
Memorial Sloan-Kettering Cancer Center. Bruton's Tyrosine Kinase (BTK) Inhibitor, Ibrutinib, in Patients With Refractory/Recurrent Primary Central Nervous System Lymphoma (PCNSL) and Refractory/Recurrent Secondary Central Nervous System Lymphoma (SCNSL). In: ClinicalTrials.gov [Internet]. Bethesda (MD): National Library of Medicine (US). Dec. 9, 2014 [cited Feb. 5, 2015] Available from: https://clinicaltrial.gov/ct2/show/NCT02315326?term=NCT02315326 NLM Identifier: NCT02315326.
Mendel et al. In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res 9(1):327-337 (2003).
Merged Markush Service Search, Jun. 27, 2005.
Middendorp et al. Function of Bruton's Tyrosine Kinase during B Cell Development is Partially Independent of its Catalytic Activity. J Immunol 171:5988-5996 (2003).
Middendorp et al. Tumor Suppressor Function of Bruton Tyrosine Kinase is Independent of its catalytic activity. Blood 105(1):259-261 (2005).
Mishan-Eisenberg et al., "Differential Regulation of Th1/Th2 Cytokine Respones by Placental Protein 14," The Journal of Immunology 173(9):5524-5530 (2004).
Moingeon, "Strategies for Designing Vaccines Eliciting Th1 Responses in Humans," Journal of Biotechnology 98:189-198 (2002).
Monge et al., "Genetic factors and pathogenesis of waldenstrom's macroglobulinemia," Curr Oncol Rep, 15(5): 450-456 (2013).
Montero et al. Neuregulins and cancer Clin Cancer Res. Jun. 1, 2008;14(11):3237-41. doi: 10.1158/1078-0432.CCR-07-5133.
Morgan L., Leukemia, 8 (Special Issue), 2015.
Mossner et al., "Increasing the Efficacy of CD20 Antibody Therapy Through the Engineering of a New Type II Anti-CD20 Antibody with Enhanced Direct and Immune Effector Cell-Mediated B-cell Cytotoxicity," Blood, 115(22): 4393-4402 (2010).
Mukoyama et al., "Preparation of imidazol [1,5-a]pyrazine derivatives, pharmaceutical compositions containing them, and their uses for prevention or treatment of protein tyrosine kinase-related diseases," retrieved from STN Database Accession No. 2005:299462 Patent No. JP2005089352, Abstract (2005).
Murawski et al., "New Drugs for Aggressive B-cell and T-cell Lymphomas," The Lancet Oncology, 11(11): 1074-1085 (2010).
Myrmel et al., "The Hepatitis C Virus Enigma," APMIS 117:427-439 (2009).
Nagel et al. "Pharmacologic inhibition of MAL T1 protease by phenothiazines as a therapeutic approach for the treatment of aggressive ABC-DLBCL," Cancer Cell, Dec. 11, 2012 (Dec. 11, 2012), vol. 22, No. 6, pp. 825-837.
National Cancer Institute (NCI). A multicenter phase 2 study of the Bruton's tyrosine kinase inhibitor PCI-32765 for treatment of relapsed hairy cell leukemia. In: ClinicalTrials.gov [Internet]. Bethesda (MD): National Library of Medicine (US). Nov. 2, 2013—[cited Nov. 22, 2013]. Available from: http://clinicaltrials.gov/ct2/show/NCT01981512 NLM Identifier: NCT01981512.
National Cancer Institute (NCI). Ibrutinib and rituximab compared with fludarabine phosphate, cyclophosphamide, and rituximab in treating patients with untreated chronic lymphocytic leukemia or small lymphocytic lymphoma. In: ClinicalTrials.gov [Internet]. Bethesda (MD): National Library of Medicine (US). Jan. 27, 2014—[cited Apr. 15, 2014]. Available from: http://clinicaltrials.gov/ct2/show/NCT02048813 NLM Identifier: NCT02048813.
National Cancer Institute (NCI). Ibrutinib in treating patients with relapsed hairy cell leukemia. In: ClinicalTrials.gov [Internet]. Bethesda (MD): National Library of Medicine (US). Apr. 24, 2013—[cited Nov. 22, 2013]. Available from: http://clinicaltrials.gov/ct2/show/NCT01841723 NLM Identifier: NCT01641723.
National Cancer Institute (NCI). Ibrutinib in treating patients with relapsed or refractory follicular lymphoma. In: ClinicalTrials.gov [Internet]. Bethesda (MD): National Library of Medicine (US). May 6, 2013—[cited Nov. 22, 2013]. Available from: http://clinicaltrials.gov/ct2/show/NCT01849263 NLM Identifier: NCT01849263.
National Cancer Institute (NCI). Lenalidomide and ibrutinib in treating patients with relapsed or refractory B-Cell non-Hodgkin lymphoma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01955499 NLM Identifier: NCT01955499.
National Cancer Institute (NCI). Rituximab and bendamustine hydrochloride, rituximab and ibrutinib, or ibrutinib alone in treating older patients with previously untreated chronic lymphocytic leukemia. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886872 NLM Identifier: NCT01886872.
National Cancer Institute (NCI). Rituximab, lenalidomide, and ibrutinib in treating patients with previously untreated stage II-IV follicular lymphoma. In: ClinicalTrials.gov [Internet]. Bethesda (MD): National Library of Medicine (US). Apr. 9, 2013—[cited Nov. 22, 2013]. Available from: http://clinicaltrials.gov/ct2/show/NCT01829568 NLM Identifier: NCT01829568.
National Cancer Institute sponsored study of classifications of non-Hodgkin's lymphomas: summary and description of a working formulation for clinical usage. The Non-Hodgkin's Lymphoma Pathologic Classification Project., The Non-Hodgkin's Lymphoma Pathologic Classification Project, Cancer 49:2112-2135 (1982).
National Cancer Institute. Ibrutinib and Combination Chemotherapy in Treating Patients With Relapsed or Refractory Diffuse Large B-Cell Lymphoma. In: ClinicalTrials.gov [Internet]. Bethesda (MD): National Library of Medicine (US). Jul. 16, 2014 [cited Feb. 5, 2015] Available from: https://clinicaltrial.gov/ct2/show/NCT02219737?term=NCT02219737 NLM Identifier: NCT02219737.
National Cancer Institute. Ibrutinib and Palbociclib Isethionate in Treating Patients With Previously Treated Mantle Cell Lymphoma. In: ClinicalTrials.gov [Internet]. Bethesda (MD): National Library of Medicine (US). Jun. 9, 2014—[cited Feb. 5, 2015] Available from: https://clinicaltrial.gov/ct2/show/NCT02159755?term=NCT02159755 NLM Identifier: NCT02159755.
National Cancer Institute. Ibrutinib in Treating Patients With Relapsed or Refractory B-cell Acute Lymphoblastic Leukemia. In: ClinicalTrials.gov [Internet]. Bethesda (MD): National Library of Medicine (US). Apr. 30, 2014 [cited Feb. 5, 2015] Available from: https://clinicaltrial.gov/ct2/show/NCT02129062?term=NCT02129062 NLM Identifier: NCT02129062.
National Cancer Institute. Ibrutinib in Treating Relapsed or Refractory B-cell Non-Hodgkin Lymphoma in Patients With HIV infection. In: ClinicalTrials.gov [Internet]. Bethesda (MD): National

(56) References Cited

OTHER PUBLICATIONS

Library of Medicine (US). Apr. 7, 2014 [ cited Feb. 5, 2015]. Available from: https://clinicaltrial.gov/ct2/show/NCT02109224?term=NCT02109224. NLM Identifier: NCT02109224.
National Cancer Institute. Lenalidomide, Ibrutinib, and Rituximab in Treating Patients With Relapsed or Refractory Chronic Lymphocytic Leukemia or Small Lymphocytic Lymphoma. In: ClinicalTrials.gov [Internet]. Bethesda (MD): National Library of Medicine (US). May 30, 2014 [cited Feb. 15, 2015] Available from: https://clinicaltrial.gov/ct2/show/NCT02160015?term=NCT02160015 NLM Identifier: NCT02160015.
National Cancer Institute. Phase 1 Study of Ibrutinib and Immuno-Chemotherapy Using Dose-Adjusted-Temozolomide, Etoposide, Doxil, Dexamethasone, Ibrutinib,Rituximab (DA-TEDDI-R) in Primary CNS Lymphoma. In: ClinicalTrials.gov [Internet]. Bethesda (MD): National Library of Medicine (US). Jul. 29, 2014 [cited Feb. 5, 2015] Available from: https://clinicaltrial.gov/ct2/show/NCT02203526?term=NCT02203526 NLM Identifier: NCT02203526.
National Center Institute (NCI). Lenalidomide and Ibrutinib in treating patients with relapsed or refractory chronic lymphocytic leukemia or small lymphocytic lymphoma. In: ClinicalTrials.gov [Internet]. Bethesda (MD): National Library of Medicine (US). Jun. 24, 2013—[cited Nov. 22, 2013]. Available from: http://clinicaltrials.gov/ct2/show/NCT01886859 NLM Identifier: NCT01886859.
National Heart, Lung, and Blood Institute (NHLBI). PCI-32765 for special cases of chronic lymphocytic leukemia or small lymphocytic lymphoma. In: ClinicalTrials.gov [Internet]. Bethesda (MD): National Library of Medicine (US). Dec. 22, 2011—[cited Nov. 22, 2013]. Available from: http://clinicaltrials.gov/ct2/show/NCT01500733 NLM Identifier: NCT01500733.
Neidle. Cancer Drug Design and Discovery. Elsevier/Academic Press. pp. 427-431 (2008).
Nicolaou et al., "Calicheamicineθ1: A Rationally Designed Molecule with Extremely Potent and Selective DNA Cleaving Properties and Apoptosis Inducing Activity," Angewandte Chemie International Edition in English 33:183-186 (1994).
Niiro et al. Regulation of B-Cell Fate by Antigen-Receptor Signals. Nature Reviews 2:945-956 (2002).
Nisitani et al. In situ detection of activated Bruton's tyrosine kinase in the Ig signaling complex by phosphopeptide-specific monoclonal antibodies. PNAS USA 96:2221-2226 (1999).
Nogrady (1985) Medicinal Chemistry A Biochemical Approach, Oxford University Press, New York, pp. 388-394.
Northwestern University. Ibrutinib After Intensive Induction in Treating Patients With Previously Untreated Mantle Cell Lymphoma. In: ClinicalTrials.gov [Internet]. Bethesda (MD): National Library of Medicine (US). Sep. 12, 2014 [cited 2-15 Feb. 5] Available from: https://clinicaltrial.gov/ct2/show/NCT02242097?term=NCT02242097 NLM Identifier: NCT02242097.
Notification of Transmittal of the International Search Report and the Written Opinion for the of the International Searching Authority, or the Declaration for Application No. PCT/US2016/049638, dated Nov. 30, 2016, 14, pages.
Noy et al., "Targeting Bruton Tyrosine Kinase with Ibrutinib in Relapsed/refractory Marginal Zone Lymphoma," Blood, 129(16): 2224-2232 (2017).
O'Brien et al. Combination of the Bruton's tyrosine kinase (BTK) inhibitor PCI-32765 with bendamustine (B)/rituximan® (BR) in patients (pts) with relapsed/refractory (R/R) chronic lymphocytic leukemia (CLL): Interm results of phase Ib/II study. J Clin Onc. 2012. Supp. Abstract 6515.
Ohio State University Comprehensive Cancer Center. PCI-32765 (Ibrutinib) in treating patients with relapsed or refractory chronic lymphocytic leukemia, small lymphocytic lymphoma, or B-cell prolymphocytic leukemia. In: ClinicalTrials.gov [Internet]. Bethesda (MD): National Library of Medicine (US). Apr. 23, 2012—[cited Nov. 22, 2013]. Available from: http://clinicaltrials.gov/ct2/show/NCT01589302 NLM Identifier: NCT01589302.
Ohio State University Comprehensive Cancer Center. Rituxan/Bendamustine/PCI-32765 in relapsed DLBCL, MCL, or indolent non-Hodgkin's lymphoma. In: ClinicalTrials.gov [Internet]. Bethesda (MD): National Library of Medicine (US). Nov. 1, 2011— [cited Feb. 6, 2014]. Available from: http://clinicaltrials.gov/ct2/show/NCT01479842 NLM Identifier: NCT01479842.
Oligino et al. Targeting B cells for the treatment of rheumatoid arthritis. Arthritis Res. Ther., 5(Suppl.4):S7-S11 (2002).
Ott et al., "CTLA-4 and PD-1/PD-L1 blockade: new immunotherapeutic modalities with durable clinical benefit in melanoma patients," Clin Cancer Res, 19(19): 5300-5309 (2013).
Ou. Second-generation irreversible epidermal growth factor receptor (EGFR) tyrosine kinase inhibitors (TKIs): A better mousetrap? A review of the clinical evidence. Crit Rev Onc/Hemat. 2012;83(3):407-421.
Pagel et al., "Induction of apoptosis using inhibitors of lysophosphatidic acid acyltransferase-beta and anti-CD20 monoclonal antibodies for treatment of human non-Hodgkin's lymphomas," Clin Cancer Res, 11(13):4857-4866 (2005).
Pan et al., "Discovery of selective irreversible inhibitors for Bruton's tyrosine kinase," ChemMedChem, 2:58-61 (2007).
Pan, Z. et al., "Discovery of Selectable Irreversible Inhibitors for Brutons Tyrosine Kinase," ChemMedChem, 1:1-5 (2006).
Paul G Richardson et al: "Pomalidomide alone or in combination with low-dose dexamethasone in relapsed and refractory multiple myeloma: a randomized phase 2 study", Mar. 20, 2014 (Mar. 20, 2014), DOI: 1 0.1182/blood—Retrieved from the Internet: URL:http://www.bloodjournal.org/content/bloodjournal/123/12/1826. fu II. pdf retrieved on Nov. 11, 2016].
PCT/US06/49626 Search Report dated Apr. 9, 2008.
PCT/US08/058528 Search Report and Written Opinion dated Sep. 30, 2008.
PCT/US09/50897 IPER and Written Opinion dated Jan. 27, 2011.
PCT/US09/50897 Search Report dated Mar. 15, 2010.
PCT/US2006/49626 International Preliminary Report on Patentability Search Report dated Mar. 24, 2009.
PCT/US2008/058528 International Preliminary Report on Patentability Search Report dated Sep. 29, 2009.
PCT/US2010/52377 International Search Report and Written Opinion dated Jun. 29, 2011.
PCT/US2011/039190 International Preliminary Report on Patentability Search Report dated Dec. 4, 2012.
PCT/US2011/039190 International Search Report and Written Opinion dated Feb. 23, 2012.
PCT/US2013/043888 International Search Report and Written Opinion dated Sep. 23, 2013.
PCT/US2013/051741 International Preliminary Report on Patentability dated Jan. 27, 2015.
PCT/US2013/051741 International Search Report and Written Opinion dated Jan. 7, 2014.
PCT/US2013/068132 International Search Report and Written Opinion dated Jan. 29, 2014.
PCT/US2014/024966 International Preliminary Report on Patentability dated Sep. 15, 2015.
PCT/US2014/024966 International Search Report and Written Opinion dated Aug. 27, 2014.
PCT/US2014/033378 International Search Report and Written Opinion dated Aug. 26, 2014.
PCT/US2014/062278 International Search Report and Written Opinion dated Jan. 29, 2015.
PCT/U52015/040214 International Search Report and Written Opinion dated dated Dec. 21, 2015.
PCT/US2015/043300 International search report and written opinion dated Nov. 9, 2015.
PCT/US2015/044095 International search report and written opinion dated Nov. 20, 2015.
PCT/US2015/16895 International Search Report and Written Opinion dated May 22, 2015.
PCT/US2015/21871 International Search Report and Written Opinion dated Jul. 8, 2015.

(56) References Cited

OTHER PUBLICATIONS

PCT/US2015/35665 International Search Report and Written Opinion dated Sep. 21, 2015.
Perry et al., "Biological prognostic markers in diffuse large B-cell lymphoma," Cancer Control, 19(3): 214-226 (2012).
Peterson et al. Prolonged single-agent versus combination chemotherapy in indolent follicular lymphomas: a study of the cancer and leukemia group. Br. J. Clin. Oncol., 21(1):5-15 (Jan. 1, 2003).
Pharmacyclics, "Executive Summary: Bruton's Tyrosine Kinase (Btk) Inhibitor Programs for Oncology and Autoimmune Diseases," pp. 1-6 (Jan. 2010).
Pharmacyclics, Inc. A Multi-Center Study of Ibrutinib in Combination With Obinutuzumab Versus Chlorambucil in Combination With Obinutuzumab in Patients With Treatment naïve CLL or SLL. In: ClinicalTrials.gov [Internet]. Bethesda (MD): National Library of Medicine (US). Oct. 1, 2014 [cited Feb. 5, 2015] Available from: https://clinicaltrial.gov/ct2/show/NCT02264574?term=NCT02264574 NLM Identifier: NCT02264574.
Pharmacyclics, Inc. A multicenter phase 2 study of PCI-32765 (Ibrutinib) in patients with relapsed or refractory chronic lymphocytic leukemia (CLL) or small lymphocytic lymphoma (SLL) with 17p deletion. In: ClinicalTrials.gov [Internet]. Bethesda (MD): National Library of Medicine (US). Dec. 3, 2012—[cited Nov. 22, 2013]. Available from: http://clinicaltrials.gov/ct2/show/NCT01744691 NLM Identifier: NCT01744691.
Pharmacyclics, Inc. A multicenter, open-label, phase 3 study of the Bruton's tyrosine kinase inhibitor PCI-32765 versus chlorambucil in patients 65 years or older with treatment-naive chronic lymphocytic leukemia or small lymphocytic lymphoma (RESONATE-2). In: ClinicalTrials.gov [Internet]. Bethesda (MD): National Library of Medicine (US). Oct. 29, 2012—[cited Nov. 22, 2013]. Available from: http://clinicaltrials.gov/ct2/show/NCT01722487 NLM Identifier: NCT01722487.
Pharmacyclics, Inc. A phase 3 study of ibrutinib (PCI-32765) versus ofatumumab in patients with relapsed or refractory chronic lymphocytic leukemia (RESONATE). In: ClinicalTrials.gov [Internet]. Bethesda (MD): National Library of Medicine (US). Apr. 11, 2012—[cited Nov. 22, 2013]. Available from: http://clinicaltrials.gov/ct2/show/NCT01578707 NLM Identifier: NCT01578707.
Pharmacyclics, Inc. An open-label extension study in patients 65 years or older with chronic lymphocytic leukemia (CLL) or small lymphocytic lymphoma (SLL) who participated in study PCYC-115-CA (PCI-32765 versus chlorambucil). In: ClinicalTrials.gov [Internet]. Bethesda (MD): National Library of Medicine (US). Nov. 2, 2012—[cited Nov. 22, 2013]. Available from: http://clinicaltrials.gov/ct2/show/NCT01724346 NLM Identifier: NCT01724346.
Pharmacyclics, Inc. Efficacy and safety study of PCI-32765 combined with ofatumumab in CLL (PCYC-1109-CA). In: ClinicalTrials.gov [Internet]. Bethesda (MD): National Library of Medicine (US). Oct. 7, 2010—[cited Nov. 22, 2013]. Available from: http://clinicaltrials.gov/ct2/show/NCT01217749 NLM Identifier: NCT01217749.
Pharmacyclics, Inc. Ibrutinib and Lenalidomide With Dose Adjusted EPOCH-R in Subjects With Relapsed/Refractory Diffuse Large B-cell Lymphoma. In: ClinicalTrials.gov [Internet]. Bethesda (MD): National Library of Medicine (US). May 12, 2014 [cited Feb. 5, 2015] Available from: https://clinicaltrial.gov/ct2/show/NCT02142049?term=NCT02142049 NLM Identifier: NCT02142049.
Pharmacyclics, Inc. Ibrutinib in combination with lenalidomide, with and without rituximab in participants with relapsed or refractory diffuse large B-cell lymphoma. in: ClinicalTrials.gov [Internet]. Bethesda (MD): National Library of Medicine (US). Feb. 10, 2014—[cited Apr. 15, 2014]. Available from: http://clinicaltrials.gov/ct2/show/NCT02077166 NLM Identifier: NCT02077166.
Pharmacyclics, Inc. Ibrutinib Wth Rituximab in Previously Treated Adults With Waldenstrom's Macroglobulinemia. In: ClinicalTrials.gov [Internet]. Bethesda (MD): National Library of Medicine (US). Jun. 9, 2014 [cited Feb. 5, 2015] Available from: https://clinicaltrial.gov/ct2/show/NCT02165397?term=NCT02165397 NLM Identifier: NCT02165397.
Pharmacyclics, Inc. Safety and efficacy of PCI-32765 in subjects with relapsed/refractory mantel cell lymphoma (MCL). In: ClinicalTrials.gov [Internet]. Bethesda (MD): National Library of Medicine (US). Oct. 18, 2010—[cited Nov. 22, 2013]. Available from: http://clinicaltrials.gov/ct2/show/NCT01236391 NLM Identifier: NCT01236391.
Pharmacyclics, Inc. Safety and efficacy study of Bruton's tyrosine kinase inhibitor in subjects with relapsed or refractory diffuse large B-cell lymphoma. In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01325701 NLM Identifier: NCT01325701.
Pharmacyclics, Inc. Safety and tolerability study of PCI-32765 combined with fludarabine/cyclophosphamide/rituximab (FCR) and bendamustine/rituximab (BR) in chronic lymphocytic leukemia (CLL). In: ClinicalTrials.gov [Internet]. Bethesda (MD): National Library of Medicine (US). Feb. 2, 2011—[cited Nov. 22, 2013]. Available from: http://clinicaltrials.gov/ct2/show/NCT01292135 NLM Identifier: NCT01292135.
Pharmacyclics, Inc. Safety and tolerability study of PCI-32765 in B Cell lymphoma and chronic lymphocytic leukemia. In: ClinicalTrials.gov [Internet]. Bethesda (MD): National Library of Medicine (US). Apr. 19, 2010—[cited Nov. 25, 2013]. Available from: http://clinicaltrials.gov/ct2/show/NCT01109069 NLM Identifier: NCT01109069.
Pharmacyclics, Inc. Safety of PCI-32765 in chronic lymphocytic leukemia. In: ClinicalTrials.gov [Internet]. Bethesda (MD): National Library of Medicine (US). Apr. 13, 2010—[cited Nov. 22, 2013]. Available from: http://clinicaltrials.gov/ct2/show/NCT01105247 NLM Identifier: NCT01105247.
Pharmacyclics, Inc. Study of the Bruton's tyrosine kinase inhibitor in combination with carfilzomib (Kyprolis), in subjects with relapsed or relapsed and refractory multiple myeloma. In: ClinicalTrials.gov [Internet]. Bethesda (MD): National Library of Medicine (US). Sep. 27, 2013—[cited Nov. 22, 2013]. Available from: http://clinicaltrials.gov/ct2/show/NCT01962792 NLM Identifier: NCT01962792.
Pharmacyclics, Inc. Study of the Bruton's tyrosine kinase inhibitor in combination with rituximab in previously untreated subjects with follicular lymphoma. In: ClinicalTrials.gov [Internet]. Bethesda (MD): National Library of Medicine (US). Oct. 24, 2013—[cited Nov. 22, 2013]. Available from: http://clinicaltrials.gov/ct2/show/NCT01980654 NLM Identifier: NCT01980654.
Pharmacyclics, Inc. Study of the Bruton's Tyrosine Kinase Inhibitor in Subjects With Chronic Graft Versus Host Disease. In: ClinicalTrials.gov [Internet]. Bethesda (MD): National Library of Medicine (US). Jul. 11, 2014 [cited Feb. 5, 2015] Available from: https://clinicaltrial.gov/ct2/show/NCT02195869?term=NCT02195869 NLM Identifier: NCT02195869.
Pharmacyclics, Inc. Study of the Bruton's tyrosine kinase inhibitor in subjects with relapsed or relapsed and refractory multiple myeloma. In: ClinicalTrials.gov [Internet]. Bethesda (MD): National Library of Medicine (US). Nov. 18, 2011—[cited Nov. 22, 2013]. Available from: http://clinicaltrials.gov/ct2/show/NCT01478581 NLM Identifier: NCT01478581.
Pharmacyclics, Inc. Study of the Bruton's tyrosine kinase inhibitor in subjects with relapsed/refractory marginal zone lymphoma. In: ClinicalTrials.gov [Internet]. Bethesda (MD): National Library of Medicine (US). Oct. 29, 2013—[cited Nov. 22, 2013]. Available from: http://clinicaltrials.gov/ct2/show/NCT01980628 NLM Identifier: NCT01980628.
Pharmacyclics, Inc. Study of the safety and tolerability of PCI-32765 in patients with recurrent B cell lymphoma (PCYC-04753). In: ClinicalTrials.gov [Internet]. Bethesda (MD): National Library of Medicine (US). Feb. 20, 2009—[cited Nov. 22, 2013]. Available from: http://clinicaltrials.gov/ct2/show/NCT00849654 NLM Identifier: NCT00849654.
Pharmacyclics: Pharmacyclics initiates phase 1 clinical trial of novel oral Btk inhibitor for refractory B-cell non-Hodgkin's lym-

(56) References Cited

OTHER PUBLICATIONS phoma. The American Association of Cancer Research (AACR) 100th Annual Meeting in Denver, CO (Apr. 13, 2009).
Picci, P. et al., "Osteosarcoma (osteogenic sarcoma)," Orphanet J Rare Dis, 2(6):1-4 (2007).
Pileri et al. Mantle Cell Lymphoma. Haematologica 94(11):1488-1492 (2009).
Pollyea D.A., et al., "A Phase I Dose Escalation Study of the Btk Inhibitor PCI-32765 in Replace and Refractory B Cell Non-Hodgkin Lymphoma and Use of a Novel Fluorescent Probe Pharmacodynamic Assay," Blood, 2009, vol. 114, Abstract 3713 (published online Oct. 5, 2015).
Pollyea et al., "A phase I dose escalation study of the Btk inhibitor PCI-32765 in relapsed and refractory B cell non-Hodgkin lymphoma and use of a novel fluorescent probe pharmacodynamic assay," 51st ASH Annual Meeting and Exposition, Poster Abstract #3713 (2009).
Pollyea et al., "A Phase I Dose Escalation Study of the BTK Inhibitor PCI-32765 in Relapsed and Refractory B Cell Non-Hodgkin Lymphoma," ASH Meeting Poster Abstracts (2009).
Ponader et al. The Bruton tyrosine kinase inhibitor PCI-32765 thwarts chronic lymphocytic leukemia cell survival and tissue homing in vitro and in vivo. Blood (Epub Dec. 16, 2011), 119(5):1182-1189 (Feb. 2012).
Powers et al. Irreversible Inhibitors of Serine, Cysteine, and Threonine Proteases. Chem. Rev., 102(12):4639-4750 (2002).
Prakash et al. Chicken sarcoma to human cancers: a lesson in molecular therapeutics. The Ochsner Journal, 7(2):61-64 (Jan. 1, 2007).
Prenata et al., "Separation on the basis of size: Gel permeation chromatography," Protein Purification Methods: A Practical Approach, (Harris & Angal Eds.) IRL Press 1989 293-306.
PRNewsire "U.S. FDA grants regular (full) approval for IMBRUVICA for two indications," Jul. 28, 2014.
PRNewswire, "Pharmacyclics, Inc. announces presentation of interim results from phase I trial of its first-in-human Btk inhibitor PCI-32765," Dec. 7, 2009.
PRNewswire, "Update on preclinical finding and development timeline for PCI-45292," Mar. 2, 2011.
Quek et al. A role for Bruton's tyrosine kinase (Btk) in platelet activation by collagen. Curr. Biol. 8(20):1137-1140 (1998).
Rabin et al. Absolute Lymphocyte Counts Refine MRD-Based Risk Stratification in Pediatric ALL. Blood (Ash Annual Meeting Abstracts) 114:Abstract 1593 (2009).
Ramsay, "Immune checkpoint blockade immunotherapy to activate anti-tumour T-cell immunity," Br J Haematol, 162(3): 313-325 (2013).
Rao et al. Inhibition of invasion, angiogenesis, tumor growth, and metastasis by adenovirus-mediated transfer of antisense uPAR and MMP-9 in non-small cell lung cancer cells. Mol Cancer Ther 4(9):1399-1408 (2005).
Rastetter et al. Rituximab: expanding role in therapy for lymphomas and autoimmune diseases. Ann. Rev. Med 55:477-503 (2004).
Raval et al., "Tumor immunology and cancer immunotherapy: summary of the 2013 SITC primer," J Immunother Cancer, 2:14 (2014).
Readinger et al., "Selective Targeting of ITK Blocks Multiple Steps of HIV Replication," PNAS USA 105(18):6684-6689 (2008).
Ritter et al. Osteosarcoma. Ann. Oncol. 21(Supplement 7):320-325 (2010).
Robak et al. A Targeted Therapy for Protein and Lipid Kinases in Chronic Lymphocytic Leukemia. Curr. Med. Chem. (Epub Jul. 24, 2012), 19(31):5294-5318 (2012).
Robak et al. Tyrosine kinase inhibitors as potential drugs for B-cell lymphoid malignancies and autoimmune disorders. Expert Opin. Investig. Drugs (Epub May 22, 2012), 21(7):921-947 (Jul. 2012).
Roberts, Jr. et al. Trends in the Risks and Benefits to Patients With Cancer Participating in Phase 1 Clinical Trials. JAMA 292(17):2130-2140 (2004).

Rohle et al. "An inhibitor of mutant IDH1 delays growth and promotes differentiation of glioma cells," Science, Apr. 4, 2013 (Apr. 4, 2013), vol. 340, No. 6132, pp. 626-630.
Rooij et al. "The Clinically active BTK inhibitor PCI-32765 targets B-cell receptor-and chemokine-controlled adhesion and migration in chronic lymphocytic leukemia," Blood, Mar. 15, 2012, vol. 119, No. 11, pp. 2590-2594.
Rosenquist et al., Prognostic markers and their clinical applicability in chronic lymphocytic leukemia: where do we stand? Leuk Lymphoma, 54(11): 2351-2361 (2013).
Rozali et al., "Programmed death ligand 2 in cancer-induced immune suppression," Clin Dev Immunol, Article ID: 656340 (2012).
Rummel et al., "Bendamustine plus rituximab is effective and has a favorable toxicity profile in the treatment of mantle cell and low-grade non-Hodgkin's lymphoma," J Clinc Oncol, 23(15): 3383-3389 (2005).
Rushworth et al. BTK inhibitor ibrutinib is cytotoxic to myeloma and potently enhances bortezomib and lenalidomide activities through NF-κb. Cell Signal (Epub Sep. 11, 2012), 25(1):106-112 (Jan. 2013).
Rushworth et al. BTK inhibitor ibrutinib is cytotoxic to myeloma and potently enhances bortezomib and lenalidomide activities through NF-kB. Cell. Signal. Sep. 11, 2012. pii: S0898-6568(12)00250-1. doi: 10.1016/j.cellsig.2012.09.008. [Epub ahead of print].
Sada et al. Protein-Tyrosine Kinases and Adaptor Proteins in FceRI-Mediated Signaling in Mast Cells. Curr. Mol. Med. 3(1):85-94 (2003).
Sagiv-Barfi et al. Therapeutic anti-tumor immunity by checkpoint blockade is enhanced by ibrutinib, an inhibitor of both BTK and ITK. Proc. Natl. Acad. Sci. USA 112(9):E966-E972 (Mar. 2015).
Sahu et al., "ITK Inhibitors in Inflammation and Immune-Mediated Disorders," Curr Top Med Chem 9(8):690-703 (2009).
Saulnier et al., "An efficient method for the synthesis of guanidine prodrugs," Bioorganic and Medicinal Chemistry Letters, vol. 4, p. 1985-90 (1994).
Schaeffer et al. Tec family kinases in lymphocyte signaling and function. Curr. Op. Imm. 12:282-286 (2000).
Schiffner et al., "Development of Prophylactic Vaccines Against HIV-1," Retrovirology 10:72 (2013).
Schnute et al., "Bruton's tyrosine kinase (Btk)," Anti-Inflammatory Drug Discovery, Ed. J.I. Levin and S. Laufer, (2012), pp. 297-326.
Schwamb et al. B-cell receptor triggers drug sensitivity of primary CLL cells by controlling glucosylation of ceramides. Blood (Epub Aug. 27, 2012), 120(19):3978-3985 (Nov. 2012).
Science Daily Counting tumor cells in blood predicts treatment benefit in prostate cancer. (Jul. 7, 2008), http://www.sciencedaily.com/releases/2008/07/080706083142.htm , last accessed Jul. 23, 2013.
Science Daily, "Drug shows surprising efficacy as treatment for chronic leukemia, mantle cell lymphoma," (Jun. 19, 2013), http://www.sciencedaily.com/releases/2013/06/130619195217.htm, last accessed Jan. 15, 2016.
Science IP CAS Search, Mar. 16, 2006.
Science IP CAS Search, Sep. 5, 2006.
Scott et al., "Monoclonal Antibodies in Cancer Therapy," Cancer Immunity 12:14 (2012).
Search Report and Written Opinion for Singapore Application No. 11201401625T, dated Dec. 8, 2016, 27 pages.
SG201208724-3 Search Report and Written Opinion dated Mar. 17, 2015.
Shaffer et al. Lymphoid malignancies: the dark side of B-cell differentiation. Nature Reviews/Immunology 2:920-932 (2002).
Shah et al. Ibrutinib for the treatment of mantle cell lymphoma. Expert Rev. Hematol. 7(5):521-531 (2014) (Epub Aug. 27, 2014).
Shah et al., "Mantle Cell Lymphoma: A Clinically Heterogeneous Disease in Need of Tailored Approaches," Cancer Control, 19(3): 227-235 (2012).
Silverman. The Organic Chemistry of Drug Design and Drug Action, Academic Press, Inc., San Diego, pp. 352-401 (1992).
Singapore Patent Application No. 201006601-7 Written Opinion dated Aug. 19, 2013.

(56) References Cited

OTHER PUBLICATIONS

Singh et al., "Therapeutic vaccines as a promising treatment modality against prostate cancer: rationale and recent advances," Ther Adv Vaccines, 2(5): 137-148 (2014).
Sinkula et al. Rationale for design of biologically reversible drug derivatives: prodrugs. J. Pharm. Sci., 64:181-210 (1975).
Sivina et al. CCL3 (MIP-1a) Plasma Levels and the Risk for Disease Progression in Chronic Lymphocytic Leukemia. Blood 117(5):1662-1669 (2010).
Slupsky, "Does B cell receptor signaling in chronic lymphocytic leukaemia cells differ from that in other B cell types??" Scientifica (Cairo) 2014: 1-14 (2014).
Smaill et al., "Tyrosine kinase inhibitors. 15. 4-(phenylamino)quinazoline and 4-(phenylamino)pyrido[d]pyrimidine acrylamides as irreversible inhibitors of the ATP binding site of the epidermal growth factor receptor," J Med Chem, 42(10):1803-15 (1999).
Smith et al., "The Tec family of cytoplasmic tyrosine kinases: mammalian Btk, Bmx, Itk, Tec, Txk and homologs in other species," BioEssays, 23:436-46 (2001).
Smolen et al. Therapeutic Strategies for Rheumatoid Arthritis. Nature Reviews 2:473-488 (2003).
Sofian et al., "Serum Profile of T Helper 1 and T Helper 2 Cytokines in Hepatities C Virus Infected Patients," Hepat Mon. 12(12):e6156 (2012).
Specialty Pharmacy Times, "MedCart Specialty Pharmacy: Preparing for the Next Advancements in Hepatitis C Therapy," (Dec. 18, 2012) http://www.specialtypharmacytimes.com/publications/specialty-pharmacy-times/2012/December-2012/MedCart-Specialty-Pharmacy-Preparing-for-the-Next-Advancements-in-Hepatitis-C-Therapy.
Spurrell et al., "Adaptive immunity in cancer immunology and therapeutics," Ecancermedicalscience, 2(8): 441 (2014).
Srivastava et al., "Update on benefit of immunotherapy and targeted therapy in melanoma: the changing landscape," Cancer Manag Res, 6: 279-289 (2014).
Stanford School of Medicine, "Precursor B Lymphoblastic Lymphoma," pp. 1-7 (2005).
Stead et al. Concise synthesis of (+/−)-Cytisine via lithiation of N-Boc-bispidine. Organic Letters 7(20):4459-4462 (2005).
STN Registry No. 936563-96-1. Ibrutinib. Retrieved from STN Registry Jul. 27, 2015. 1 pg.
Strimbu et al. What are biomarkers? Curr Opin HIV AIDS 5(6):463-466 (2010.
Supplementary European Search Report for Application No. EP 11790524 dated Sep. 25, 2013.
Supplementary European Search Report for Application No. EP 14855030.4 dated Jul. 5, 2017.
Supplementary European Search Report for Application No. EP14774808, dated Oct. 24, 2016, 9 pages.
Supplementary European Search Report for Application No. EP14782886, dated Feb. 8, 2017, 16 pages.
Supplementary European Search Report for EP13850097 dated Mar. 31, 2016.
Supplementary Partial European Search Report for Application No. EP14782886 dated Nov. 4, 2016, 11 pages.
Suzuki et al., "Skewed Th1 Responses Caused by Excessive Expression of Txk, a Member of the Tec Family of Tyrosine Kinases, in Patients with Behcet's Disease," Clinical Medicine & Research 4(2):147-151 (2006).
Tai et al., "Bruton's Tyrosine Kinase: Oncotarget in Myeloma," Oncotarget, 3(9): 913-914 (2012).
Taiwan Search Report for TW104125847dated Jun. 13, 2016.
Takahashi at at. Serum CCL3 and CCL4 Levels Function As Novel Prognostic Markers in Diffuse Large B Cell Lymphoma [online]. 54th ASH Annual Meeting and Exposition. [retrieved on Apr. 21, 2015], Abstract 2709. Retrieved from the Internet: https://ash.confex.com/ash/2012/webprogram/Paper53900.html.
Takayama et al., "Mammalian and Viral IL-10 Enhance C-C Chemokine Receptor 5 but Down-Regulate C-C Chemokine Receptor 7 Expression by Myeloid Dendritic Cells: Impact on Chemotactic Responses and In Vivo Homing Ability," J Immunol, 166: 7136-7143 (2001).
Tame, "Scoring functions: a view from the bench," J Comput Aided Mol Des, 13(2): 99-108 (1999).
Teta et al., "Exercise is Medicine: Using Exercise to Manipulate TH1 and TH2 Immune Function," http://www.freelibrary.com/_/print/PrintArticle.aspx?id=202661767 (2009).
TG Therapeutics, Inc. Ublituximab + ibrutinib in select B-cell malignancies. In: ClinicalTrials.gov [Internet]. Bethesda (MD): National Library of Medicine (US). Dec. 11, 2013—[cited Apr. 15, 2014]. Available from: http://clinicaltrials.gov/ct2/show/NCT02013128 NLM Identifier: NCT02013128.
The Lymphoma Academic Research Organisation. Bruton's tyrosine kinase (BTK) inhibition in B-cell lymphomas (BIBLOS). In: ClinicalTrials.gov [Internet]. Bethesda (MD): National Library of Medicine (US). Jan. 31, 2014—[cited Apr. 15, 2014]. Available from: http://clinicaltrials.gov/ct2/show/NCT02055924 NLM Identifier: NCT02055924.
Theil. Structure-aided drug design's next generation. Nature Biotechnol 2:513-519 (2004).
Thimme et al., "Determinants of Viral Clearance and Persistence During Acute Hepatitis C Virus Infection," J Exp Med 194(10):1395-1406 (2001).
Thurn et al. (Future Oncol. Feb. 2011; 7(2): 263-2830.
Tinmouth et al. Fludarabine in alkylator-resistant follicular non-Hodgkin's lymphoma. Leuk. Lymphoma 41(1-2):137-145 (2001).
Toomer et al., "Autoimmunity as a double agent in tumor killing and cancer promotion," Front Immunol, 5: 116 (2014).
Tosti et al., "Anti-cytotoxic T lymphocyte antigen-4 antibodies in melanoma," Clin Cosmet Investig Dermatol, 6: 245-256 (2013).
Traxler et al., "Use of a pharmacophore model for the design of EGF-R tyrosine kinase inhibitors: 4-(phenylamino)pyrazolo[3,4-d]pyramidines," J Med Chem, 40(22):3601-16 (1997).
Trentin et al., "Homcostatic Chemokines Drive Migration of Malignant B Cells in Patients with non-Hodgkin Lymphomas," Blood, 104(2): 502-508 (2004).
Tsai et al., "Detection of Type 2-Like T-Helper Cells in Hepatitis C Virus Infection: Implications for Hepatitis C Virus Chronicity," Hepatology 25(2):449-458 (1997).
Tse et al., "ABT-263: A Potent and Orally Bioavailable Bcl-2 Family Inhibitor," Cancer Res 68:3421-3428 (2008).
Tufman et al., "Biological Markers in Lung Cancer: A Clinician's Perspective," Cancer Biomark 6(3-4):123-135 (2010).
Tykodi et al., "PD-1 as an emerging therapeutic target in renal cell carcinoma: current evidence," OncoTargets and Therapy, 7: 1349-1359 (2014).
Uckun et al. Bruton's Tyrosine Kinase (BTK) as a Dual-Function Regulator of Apoptosis. Biochem. Pharmacology 56:683-691 (1998).
Uckun et al. The Anti-leukemic Bruton's Tyrosin Kinase Inhibitor a-cyano-$\beta$-hydroxy-$\beta$-mehyl-N-(2,5-dibromophenyl)Propenamide (LFM-A13)Prevents Fatal Thromboembolism. Leuk. Lymphoma 44(9):1569-1577 (2003).
Uckun et al., "Bruton's tyrosine kinase as a molecular target in treatment of leukemias and lymphomas as well as inflammatory disorders and autoimmunity," Expert Opin Ther Pat, 20(11):1-14 (2010).
Uckun et al., "Btk as a mediator of radiation-induced apoptosis in DT-40 lymphoma B cells," Science, 273(5278):1096-100 (1996).
Uckun et al., "In vivo pharmacokinetic features, toxicity profile, and chemosensitizing activity of alpha-cyano-beta-hydroxy-beta-methyl-N-(2,5-dibromophenyl)propenamide (LFM-A13), a novel antileukemic agent targeting Bruton's tyrosine kinase," Clin Cancer Res, 6(5):1224-33 (2002).
University of California, San Diego. A Phase Ib/II Study of Ibrutinib in Combination With GA101—Obinutuzumab in Previously Untreated Chronic Lymphocytic Leukemia (CLL) Patients Over 65 Years of Age or With Comorbidities That Preclude the Use of Chemotherapy Based Treatment. In: ClinicalTrials.gov [Internet]. Bethesda (MD): National Library of Medicine (US). Oct. 30, 2014

(56) References Cited

OTHER PUBLICATIONS

[cited Feb. 5, 2015] Available from: https://clinicaltrial.gov/ct2/show/NCT02315768?term=NCT02315768 NLM Identifier: NCT02315768.
Vanneman et al., "Combining immunotherapy and targeted therapies in cancer treatment," Nat Rev Cancer, 12(4): 237-251 (2012).
Vargas et al., "Inhibitors of BTK and ITK: state of the new drugs for cancer, autoimmunity and inflammatory diseases," Scand J Immunol, 78(2): 130-139 (2013).
Vargova et al., "MYB transcriptionally regulates the miR-155 host gene in chronic lymphocytic leukemia," Blood 117(14): 3816-3825 (2011).
Vassilev et al. Bruton's Tyrosine Kinase as an Inhibitor of the Fas/CD95 Death-inducing Signaling Complex. J. Biol. Chem. 274(3):1646-1656 (1999).
Vassilev et al. Therapeutic Potential of Inhibiting Bruton's Tyrosine Kinase, (BTK). Current Pharmaceutical Design 10:1757-1766 (2004).
Vij Ravi et al: "Ibrutinib, Single Agent or in Combination with Dexamethasone, in Patients with Relapsed or Relapsed/Refractory Multiple Myeloma (MM): Preliminary Phase 2 Results", Blood, American Society of Hematology, US, vol. 124, No. 21, Dec. 1, 2014 (Dec. 1, 2014), ISSN: 0006-4971.
Villuendas et al., "Identification of Genes Involved in Imatinib Resistance in CML: A Gene-Expression Profiling Approach," Leukemia, 20(6): 1047-1054 (2006).
Vippagunta et al. Crystalline Solids, Advanced Drug Delivery Reviews, 48:3-26 (2001).
Vose. Mantle cell lymphoma: 2012 update on diagnosis, risk-stratification, and clinical management. Am. J. Hematol. 87(6):604-609 (Jun. 2012).
Walker et al., "Treg and CTLA-4: two intertwining pathways to immune tolerance," J Autoimmun, 45: 49-57 (2013).
Wang et al. "Ibrutinib and rituximab are an efficacious and safe combination in relapsed mantle cell lymphoma: preliminary results from a Phase II clinical trial," Oral Abstract Session 624, 56th ASH Annual Meeting and Exposition (Dec. 6-9, 2014).
Wang et al. Targeting BTK with ibrutinib in relapsed or refractory mantel-cell lymphoma. N Engl J Med 369(6):507-516 (Aug. 8, 2013).
Wanner et al., "Mammalian Target of Rapamycin Inhibition Includes Cell Cycle Arrest in Diffuse Large B Cell Lymphoma (DLBCL) Cells and Sensitises DLBCL Cells to RituXimab," British Journal of Haematology, 2006, vol. 134, pp. 475-484.
Ward et al., "Isoform-Specific Phosphoinositide 3-Kinase Inhibitors as Therapeutic Agents," Current Opinion in Pharmacology 3(4):426-434 (2003).
Watters, "Cancer Pharmacogenomics: Current and Future Application," Biochimica pp. 99-111 (2003).
Wilkinson et al. Selective tyrosine kinase inhibitors. Expert Opin. Emerging Drugs 5(3):287-297 (2000).
Wilson et al. "Targeting B cell receptor signaling with ibrutinib in diffuse large B cell lymphoma," Nat Med. Jul. 20, 2015 (Jul. 20, 2015), vol. 21, pp. 922-926. entire document.
Wilson et al., "The Bruton's tyrosine kinase (BTK) inhibitor, ibrutinib (PCI-32765), has preferential activity in the ABC subtype of relapsed/refractory de novo diffuse large B-cell lymphoma (DLBCL): interim results of a multicenter, open-label, phase 2 study," Blood 120:Abstract 686 (2012).
Winer et al. "PCI-32765: a novel Bruton's tyrosine kinase inhibitor for the treatment of lymphoma malignacies," Expert Opinion on Investigational Drugs, Mar. 2012, vol. 21, No. 3, pp. 355-361.
Witzens-Harig et al. Current treatment of mantle cell lymphoma: results of a national survey and consensus meeting. Ann Hematol. (Epub Aug. 29, 2012), 91(11):1765-1772 (Nov. 2012).
Witzig et al. Detection of myeloma cells in the peripheral blood by flow cytometry. Cytometry (Communications in Clinical Cytometry), 26:113-120 (1996).
Witzig et al. Lenalidomide oral monotherapy produces durable responses in relapsed or refractory indolent non-Hodgkin's lymphoma. J. Clin. Oncol. 27:5404-5409 (Epub Oct. 5, 2009).
Wolff. Burger's Medicinal Chemistry and Drug Discovery. 5th Ed. Part 1, pp. 975-977 (1995).
Woyach et al., "Bruton's Tyrosine Kinase (BTK) Function is Important to the Development and Expansion of Chronic Lymphocytic Leukemia (CLL)," Blood, 123(8): 1207-1213 (2014).
Woyach et al., "Outcome of patients with relapsed or refractory chronic lymphocytic leukemia treated with flavopiridol: impact of genetic features," Leukemia, 26:1442-1444 (2012).
Woyach et al., "Resistance Mechanisms for the Bruton's Tyrosine Kinase Inhibitor Ibrutinib," N Engl J Med, 370(24): 2286-2294 (2014).
Written Opinion published Oct. 28, 2007 for PCT/IB2005/002350, filed Apr. 28, 2005.
Wu et al., "Immunotherapies: the blockade of inhibitory signals," Int J Biol Sci, 8(10): 1420-1430 (2012).
Yamamoto et al. The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY61-3606) Blocks Antigen-Induced Airway Inflammation in Rodents. J. Pharma. and Exp. Therapeutics 306(3):1174-1181 (2003).
Yang et al. Tyrosine kinase inhibition in diffuse large B-cell lymphoma: molecular basis for antitumor activity and drug resistance of dasatinib. Leukemia 22(9):1755-1766 (2008) [E-pub Jul. 3, 2008].
Yang, et al., "Exploiting Synthetic Lethality for the Therapy of ABC Diffuse Large B Cell Lymphoma," Cancer Cell, 21(6): 723-737 (Jun. 1, 2012).
Yasuhiro et al., "ONO-WG-307, a novel, potent and selective inhibitor of Bruton's tyrosine kinase, in sustained inhibition of the Erk, Akt and PKD signaling pathways," 53rd American Society of Hematology Annual Meeting and Exposition, San Diego, CA, Poster #2021 (2011).
Yu et al., "Proteasome Inhibitors Block HIV-1 Replication by Affecting Both Cellular and Viral Targets," Biochem Biophys Res Commun. 385(1):100-105 (2009).
Yue et al., "Th1 and Th2 Cytokine Profiles Induced by Hepatitis C Virus F Protein in Peripheral Blood Mononuclear Cells from Chronic Hepatitis C Patients," Immunol Lett 152(2):89-95 (2013).
Zabel et al., "The Novel Chemokine Receptor CXCR7 Regulates Trans-endothelial Migration of Cancer Cells," Mol Cancer, 10(73): 1-8 (2011).
Zapata et al., "Engineering Linear F(ab')2 Fragments for Efficient Production in *Escherichia coli* and Enhanced Antiproliferative Activity," Protein Eng., 10:1057-1062 (1995).
Zent et al. The Treatment of Recurrent/Refractory chronic Lymphocytic Leukemia/Small Lymphocytic Lymphoma (CLL) With Everolimus Results in Clinical Responses and Mobilization of CLL Cells Into the Circulation. Cancer 116(9):2201-2207 (2010).
Zhang et al., "In vitro, in vivo and Ex vivo Characterization of Ibrutinib: A Potent Inhibitor of the Efflux Function of the Transporter MRP1," Brit J Pharmacol, 171: 5835-5857 (2014).
Zhao, et al., "Combination of Ibrutinib with ABT-199, a BCL-2 Pathway Inhibitor: Effective Therapeutic Strategy in a Novel Mantle Cell Lymphoma Cell Line Model," Blood, 122(21): 645 (2013).
Zhu et al., "Calpain inhibitor II induces caspase-dependent apoptosis in human acute lymphoblastic leukemia and non-Hodgkin's lymphoma cells as well as some solid tumor cells," Clin Cancer Res, 6:2456-63 (2000).
Zhu et al., "miR-181a/b significantly enhances drug sensitivity in chronic lymphocytic leukemia cells via targeting multiple anti-apoptosis genes," Carcinogenesis 33(7): 1294-1301 (2012).
Zigmond et al., "Ly6Chi Monocytes in the Inflamed Colon Give Rise to Proinflammatory Effector Cells and Migratory Antigen-Presenting Cells," Immunity, 37: 1-15 (2012).
Zitvogel et al., "Targeting PD-1/PD-L1 interactions for cancer immunotherapy," Oncoimmunology, 1(8):1223-1225, (2012).
Badoux et al., "Patients with Relapsed CLL and 17p Deletion by FISH Have Very Poor Survival Outcomes," Blood, 114: 1248 (2009).

(56) References Cited

OTHER PUBLICATIONS

Bam et al., "Role of Bruton's Tyrosine Kinase (BTK) in Growth and Metastasis of INA6 Myeloma Cells," Blood Cancer Journal, 4: 1-9 (2014).
Bartlett et al., "Ibrutinib Monotherapy in Relapsed/Refractory Follicular Lymphoma (FL): Preliminary Results of a Phase 2 Consortium (P2C) Trial," Blood, 124: 800 (2014).
Bernstein, "Polymorphism—A Perspective," Crystal Growth & Design, 11: 632-650 (2011).
Bischler et al., "A new method for the synthesis of isoquinolones," Ber, 26:1093-1908 (1893).
Blum et al., "Adult Burkitt Leukemia and Lymphoma," Blood, 104: 3009-3020 (2004).
Bohers et al., "Targetable Activating Mutations are Very Frequent in GCB and ABC Diffuse Large B-Cell Lymphoma," Genes, Chromosomes & Cancer, 53(2): 114-153 (2014).
Byrd et al., "Ibrutinib versus Ofatumumab in Previously Treated Chronic Lymphoid Leukemia," The New England Journal of Medicine, 371(3): 213-223 (2014).
Byrn et al., "Pharmaceutical Solids: A Strategic Approach to Regulatory Considerations," Pharmaceutical Research, 12: 945-954 (1995).
Calderwood et al., "Pyrrolo[2,3-d]pyrimidines Containing Diverse N-7 Substituents as Potent Inhibitors of Lcks," Bioorg Med Chem Lett, 12: 1683-1686 (2002).
Campàs et al., "Bcl-2 Inhibitors Induce Apoptosis in Chronic Lymphocytic Leukemia Cells," Exp Hematol, 34(12): 1663-1669 (2006).
Celgene, "Safety and Efficacy of Pomalidomide, Bortezomib and Low Dose Dexamethasone in Subjects with Relapsed or Refractory Multiple Myeloma (OPTIMISMM)." ClinicalTrials.gov [Internet]. Bethesda (MD): National Library of Medicine (US). Nov. 28, 2012. Available from: <https://clinicaltrials.gov/ct2/show/NCT01734928>. NLM Identifier: NCT01734928.
Cerchietti et al., "Inhibition of Analplastic Lymphoma Kinase (ALK) Activity Provides a Therapeutic Approach for CLTC-ALK-positive Human Diffuse Large B Cell Lymphomas," PLoS One, 6(4): e18436 (2011).
Cervantes-Gomez et al., "Pharmacological and Protein Profiling Suggests Venetoclax (ABT-199) as Optimal Partner with Ibrutinib in Chronic Lymphocytic Leukemia," Clinical Cancer Research, 21(16): 3705-3715 (2015).
Chen et al., "Abstract 4564: Inhibitory Effects of the BTK Inhibitor, Ibrutinib, on Her2 Amplified Breast Cancer Growth, Cell Cycle Progression and Clonogenicity," Cancer Res, 74(19): Abstract 4564 (2014).
Cheson et al., "Bendamustine: Rebirth of an Old Drug," J Clin Oncol, 27: 1492-1501 (2009).
Ciric et al., "Clonal Evolution in Waldenstrom macroglobulinemia Highlights Functional Role of B-Cell Receptor," Blood, 97: 312-232 (2001).
Corigliano et al., "Plant Hsp90 Proteins Interact with B-Cells and Stimulate Their Proliferation," PLoS One, 6(6): e21231 (2011).
Dana-Farber Cancer Institute, "Study of Ibrutinib in Patients with Symptomatic, Previously Untreated Waldenstrom's Macroglobulinemia, and Impact on Tumor Genomic Evolution Using Whole Genome Sequencing," In: ClinicalTrials.gov. National Library of Medicine (US). Nov. 13, 2015. NLM Identifier: NCT02604511.
Extended European Search Report for Application No. EP 15764524.3 dated Jan. 18, 2018.
FDA Guidelines: FDA's Guidance for Industry, "Estimating the Maximum Safe Starting Dose in Initial Clinical Trials for Therapeutics in Adult Healthy Volunteers," (Jul. 2005).
Fischer et al., "Bendamustine in Combination with Rituximab (BR) for Patients with Relapsed Chronic Lymphocytic Leukemia (CLL): A Multicenter Phase II Trials for the German CLL Study Group (GCLLSG)," Blood, 110: 3106 (2006).
Fodor et al., "The Mechanism of the Bischler☐ Napieralski Reaction," Angew Chem Int Ed Engl, 11:911-920 (1972).
Fry et al., "Specific Irreversible Inactivation of the Epidermal Growth Factor Receptor and erbB2, by a New Class of Tyrosine Kinase Inhibitor," Proc Natl Acad Sci, 95: 12022-12027 (1998).
Good et al., "Classification of non-hodgkin's Lymphoma," Hematol Oncol Clin N Am, 22: 781-805 (2008).
Gu et al., "Polymorph Screening: Influence of Solvent on the Rate of Solvent-Mediated Polymorphic Transformation," Journal of Pharmaceutical Sciences, 90(11): 1878-1890 (2001).
Gupta et al., "Elevated Serum IL-10 Levels in Diffuse Large B-cell Lymphoma: A Mechanism of Aberrant JAK2 Activation," Blood, 119(12): 2844-2853 (2012).
Hallek et al., "Continuing Medical Education Activity," Am J Hematol, 88(9): 803-816 (2013).
Hallek et al., "First-line treatment with fludarabine (F), cyclophosphamide (C), and Rituximab (R) (FCR) Improves Overall Survival (OS) in previously untreated patients (pts) with advanced chronic lymphocytic leukemia (CLL): Results of a Randomized Phase III Trial on behave of an International Group of Investigators and the German CLL Study Group [abstract No. 535]," Blood (ASH Annual Meeting Abstracts), 114 (2009).
Harris et al., "World Health Organization Classification of Neoplastic Diseases of the Hematopoietic and Lymphoid Tissue: Report of the Clinical Advisory Committee Hearing—Airlie house, Virginia, Nov. 1997," J Clin Oncol, 17(12): 3835-3849 (Dec. 1999).
Hauptrock et al., "Rituximab in the Treatment of non-Hodgkin's Lymphoma," Biologics: Targets & Therapy, 2(4): 619-633 (2008).
International Conference on Harmonisation of Technical Requirements for Registration of Pharmaceuticals for Human Use-Specifications: Test Procedures and Acceptance Criteria for New Drug Substances and New Drug Products: Chemistcal Substances (1999).
Kim et al., "CD79B and MYD88 Mutations in Diffuse Large B-Cell Lymphoma," Human Pathology, 45(3): 556-564 (2014).
Kuo et al., "Combination of Ibrutinib and ABT-199 in Diffuse Large B-Cell Lymphoma and Follicular Lymphoma," Molecular Cancer Therapeutics, 16(7): 1246-1256 (2017).
Medscape, "Ibrutinib." © Jun. 30, 2014. Available from: <https://web.archive.org/web/20140630074515/https://reference.medscape.com/drug/imbruvi>.
Medscape, "Pomalidomide." © Mar. 9, 2013. Available from: <https://web.archive.org/web/20130309203122/https://reference.medscape.com/drug/pomalyst-pomalidomide-999809>.
Mizuno et al., "Fas-induced Apoptosis in B Cells," Apoptosis, 8: 451 (2003).
Montserrat et al., "How I Treat Refractory CLL," Blood, 106: 1276-1284 (2006).
Morissette et al., "High-throughput Crystallization: Polymorphs, Salts, Co-Crystals and Solvates of Pharmaceutical Solids," Advanced Drug Delivery Review, 56: 275-300 (2004).
Morrison et al., "Small Lymphocytic Lymphoma," J Clin Oncol, 7(5): 598-606 (May 1989).
Nam, "Ibrutinib Effective as First-line Therapy for Waldenstrom Macroglobulinemia," Cancer Therapy Advisor (Dec. 5, 2017).
National Cancer Institute, "Pomalidomide plus Low-Dose Dexamethasone Improves Survival for Patients with Multiple Myeloma," Lancet Oncology, pp. 1 of 3 through 3 of 3 (Sep. 3, 2013).
Partial Supplementary European Search Report for EP Application No. 15828160.0 dated Feb. 19, 2018.
Scapin, "Structural Biology in Drug Design: Selective Protein Kinase Inhibitors," Drug Discovery Today, 7(11): 601-611 (2002).
Schaffer et al., "Identification of Potential Ibrutinib Combinations in Hematological Malignancies Using a Combination High-Throughput Screen," Leukemia & Lymphoma, 1-10 (2017).
Smaill et al., "Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J Med Chem, 43: 1380-1397 (2000).

(56) References Cited

OTHER PUBLICATIONS

Souers et al., "ABT-199, a Potent and Selective BCL-2 Inhibitor, Achieves Antitumor Activity While Sparing Platelets," Nature Medicine, 19(2): 202-208 (2013).
Stilgenbauer et al., "Genomic Aberrations, VH Mutation Status and Outcome After fludarabine and cyclophosphamide (FC) or FC plus Rituximab (FCR) in the CLL8 Trial [abstract No. 781]," Blood (ASH Meeting Abstracts), 112 (2008).
Tam et al., "De Novo Deletion 17p13.1 Chronic Lymphocytic Leukemia shows Significant Clinical Heterogeneity: the M.D. Anderson and Mayo Clinic Experience," Blood, 114(5): 957-964 (Jul. 30, 2009).
Tam et al., "Long-term Results of fludarabine, cyclophosphamide, and rituximab regimen as initial therapy of chronic lymphocytic leukemia," Blood, 112: 975-980 (2008).
TREANDA® label, revised Mar. 2008.
Treon et al., "2767 Ibrutinib is Highly Active as First Line Therapy in Symptomatic Waldenstrom's Macroglobulinemia," ASH 59th Annual Meeting & Exposition, Atlanta, GA (Dec. 9-12, 2017).
Treon et al., "A Prospective, Multicentre, Phase II Study of the Bruton's Tyrosine Kinase Inhibitor Ibrutinib in Patients with Relapsed and Refractory Waldenstrom's Macroglobulinemia," Hematol Oncol, 31(Suppl 1): 96-150, Jun. 17, 2013, Abstract #067.
Tsimberidou et al., "Chemoimmunotherapy May Overcome the Adverse Prognostic Significance of 11q Deletion in Previously Untreated Patients with Chronic Lymphocytic Leukemia," Cancer, 115: 373-380 (Jan. 2009).
Uckun et al., "Structure-Based Design of Novel Anticancer Agents," Curr Cancer Drug Targets, 1: 59 (2001).
Vose et al., "Phase II Study of Rituximab in Combination with CHOP Chemotherapy in Patients with Previously Untreated, Aggressive non-Hodgkin's Lymphoma," J Clin Oncol, 19: 389-397 (2001).
Wierda et al., "Chemoimmunotherapy with fludarabine, cyclophosphamide, and rituximab for relapsed and refractory chronic lymphocytic leukemia," J Clin Oncol, 23(18): 4070-4078 (Jun. 2005).
Wilson et al., "The Bruton's Tyrosine Kinase (BTK) Inhibitor, Ibrutinib (PCI-32765), has Preferential Activity in the ABC Subtype of Relapsed/Refractory De Novo Diffuse Large B-Cell Lymphoma (DLBCL): Interim Results of a Multicenter, Open-Label, Phase 2 Study," Blood, 120(21): Abstract 686 (Nov. 16, 2012).
Wohner et al., "Rituximab, cyclophosphamide, doxorubicin, vincristine, and prednisone (R-CHOP) for Treatment of Early-stage Gastic Diffuse Large B-Cell Lymphoma," Annals of Oncology, 15: 1086-1090 (Jul. 2004).

Pre-treatment with Btk inhibitor    Post-treatment with Btk inhibitor

US 10,004,746 B2

USE OF INHIBITORS OF BRUTON'S TYROSINE KINASE (BTK)

RELATED APPLICATIONS

This application is a continuation of U.S. application Ser. No. 14/091,196, filed Nov. 26, 2013; which is a continuation of U.S. application Ser. No. 13/869,700, filed Apr. 24, 2013; which is a continuation of U.S. application Ser. No. 13/153, 317, filed Jun. 3, 2011; which claims the benefit of priority from U.S. Provisional Patent Application No. 61/351,130, filed Jun. 3, 2010; U.S. Provisional Patent Application No. 61/351,655, filed Jun. 4, 2010; U.S. Provisional Patent Application No. 61/351,793, filed Jun. 4, 2010; U.S. Provisional Patent Application No. 61/351,762, filed Jun. 4, 2010; U.S. Provisional Patent Application No. 61/419,764, filed Dec. 3, 2010; and U.S. Provisional Patent Application No. 61/472,138, filed Apr. 5, 2011; all of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy is named 25922-819-307SEQ.txt and is 812 bytes in size.

BACKGROUND OF THE INVENTION

Bruton's tyrosine kinase (Btk), a member of the Tec family of non-receptor tyrosine kinases, is a key signaling enzyme expressed in all hematopoietic cells types except T lymphocytes and natural killer cells. Btk plays an essential role in the B-cell signaling pathway linking cell surface B-cell receptor (BCR) stimulation to downstream intracellular responses.

Btk is a key regulator of B-cell development, activation, signaling, and survival (Kurosaki, *Curr Op Imm*, 2000, 276-281; Schaeffer and Schwartzberg, *Curr Op Imm* 2000, 282-288). In addition, Btk plays a role in a number of other hematopoietic cell signaling pathways, e.g., Toll like receptor (TLR) and cytokine receptor-mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. See, e.g., C. A. Jeffries, et al., (2003), *Journal of Biological Chemistry* 278:26258-26264; N. J. Horwood, et al., (2003), *The Journal of Experimental Medicine* 197: 1603-1611; Iwaki et al. (2005), *Journal of Biological Chemistry* 280(48):40261-40270; Vassilev et al. (1999), *Journal of Biological Chemistry* 274(3):1646-1656, and Quek et al. (1998), *Current Biology* 8(20):1137-1140.

SUMMARY OF THE INVENTION

Disclosed herein, in certain embodiments, is a method for treating a hematological malignancy in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, the hematological malignancy is CLL. In some embodiments, the treating the hematological malignancy comprises managing the hematological malignancy. In some embodiments, the hematological malignancy is a B-cell malignancy. In some embodiments, the hematological malignancy is a leukemia, lymphoproliferative disorder, or myeloid. In some embodiments, the mobilized cells are myeloid cells or lymphoid cells. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time. In some embodiments, analyzing the mobilized plurality of cells comprises preparing a biomarker profile for a population of cells isolated from the plurality of cells, wherein the biomarker profile indicates the expression of a biomarker, the expression level of a biomarker, mutations in a biomarker, or the presence of a biomarker. In some embodiments, the biomarker is any cytogenetic, cell surface molecular or protein or RNA expression marker. In some embodiments, the biomarker is: ZAP70; t(14, 18); β-2 microglobulin; p53 mutational status; ATM mutational status; del(17)p; del(11)q; del(6)q; CD5; CD11c; CD19; CD20; CD22; CD25; CD38; CD103; CD138; secreted, surface or cytoplasmic immunoglobulin expression; $V_H$ mutational status; or a combination thereof. In some embodiments, the method further comprises providing a second cancer treatment regimen based on the biomarker profile. In some embodiments, the method further comprises not administering based on the biomarker profile. In some embodiments, the method further comprises predicting the efficacy of a treatment regimen based on the biomarker profile. In some embodiments, the hematological malignancy is a chronic lymphocytic leukemia (CLL), small lymphocytic lymphoma (SLL), high risk CLL, or a non-CLL/SLL lymphoma. In some embodiments, the hematological malignancy is follicular lymphoma, diffuse large B-cell lymphoma (DLBCL), mantle cell lymphoma, Waldenstrom's macroglobulinemia, multiple myeloma, marginal zone lymphoma, Burkitt's lymphoma, non-Burkitt high grade B cell lymphoma, or extranodal marginal zone B cell lymphoma. In some embodiments, the hematological malignancy is chronic myelogenous (or myeloid) leukemia, or acute lymphoblastic leukemia. In some embodiments, the hematological malignancy is relapsed or refractory diffuse large B-cell lymphoma (DLBCL), relapsed or refractory mantle cell lymphoma, relapsed or refractory follicular lymphoma, relapsed or refractory CLL; relapsed or refractory SLL; relapsed or refractory multiple myeloma. In some embodiments, the Btk inhibitor forms a covalent bond with a cysteine sidechain of a Bruton's tyrosine kinase, a Bruton's tyrosine kinase homolog, or a Btk tyrosine kinase cysteine homolog. In some embodiments, the irreversible Btk inhibitor is (R)-1-(3-(4-amino-3-(4-phenoxyphenyl)-1H-pyrazolo[3,4-d]pyrimidin-1-yl)piperidin-1-yl)prop-2-en-1-one. In some embodiments, the amount of the irreversible Btk inhibitor is from 300 mg/day up to, and including, 1000 mg/day. In some embodiments, the amount of the irreversible Btk inhibitor is from 420 mg/day up to, and including, 840 mg/day. In some embodiments, the amount of the irreversible Btk inhibitor is about 420 mg/day, about 560 mg/day, or about 840 mg/day. In some embodiments, the amount of the irreversible Btk inhibitor is about 420 mg/day. In some embodiments, the $AUC_{0-24}$ of the Btk inhibitor is between about 150 and about 3500 ng*h/mL. In some embodiments, the $AUC_{0-24}$ of the Btk inhibitor is between about 500 and about 1100 ng*h/mL. In some embodiments, the Btk inhibitor is administered orally. In some embodiments, the Btk inhibitor is administered once per day, twice per day, or three times per day. In some embodiments, the Btk inhibitor is administered until disease progression, unacceptable toxicity, or individual choice. In some embodiments, the Btk inhibitor is administered daily until disease progression, unacceptable toxicity, or individual choice. In some embodiments, the Btk inhibitor is administered every other day until disease progression, unacceptable toxicity, or individual choice. In some embodiments, the Btk inhibitor is a front line therapy, second line therapy, third line therapy, fourth line therapy, fifth line therapy, or sixth line therapy. In some embodiments, the Btk inhibitor treats a refractory hematological malignancy. In some embodiments, the Btk inhibitor is a maintenance therapy. In some embodiments, the second cancer treatment regimen comprises a chemotherapeutic agent, a steroid, an immunotherapeutic agent, a targeted therapy, or a combination thereof. In some embodiments, the second cancer treatment regimen comprises a B cell receptor pathway inhibitor. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the second cancer treatment regimen comprises an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof. In some embodiments, the second cancer treatment regimen comprises chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof. In some embodiments, the second cancer treatment regimen comprises cyclophosphamide, hydroxydaunorubicin, vincristine, and prednisone, and optionally, rituximab. In some embodiments, the second cancer treatment regimen comprises bendamustine, and rituximab. In some embodiments, the second cancer treatment regimen comprises fludarabine, cyclophosphamide, and rituximab. In some embodiments, the second cancer treatment regimen comprises cyclophosphamide, vincristine, and prednisone, and optionally, rituximab. In some embodiments, the second cancer treatment regimen comprises etoposide, doxorubicin, vinristine, cyclophosphamide, prednisolone, and optionally, rituximab. In some embodiments, the second cancer treatment regimen comprises dexamethasone and lenalidomide. In some embodiments, the inhibitor of Bruton's tyrosine kinase is a reversible inhibitor. In some embodiments, the inhibitor of Bruton's tyrosine kinase is an irreversible inhibitor. In some embodiments, the inhibitor of Bruton's tyrosine kinase forms a covalent bond with a cysteine sidechain of a Bruton's tyrosine kinase, a Bruton's tyrosine kinase homolog, or a Btk tyrosine kinase cysteine homolog. In some embodiments, the inhibitor of Bruton's tyrosine kinase has the structure of Formula (D):

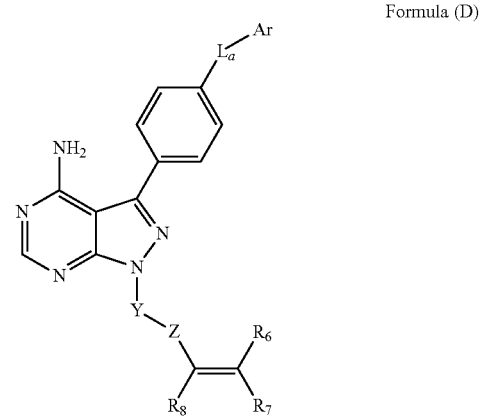

Formula (D)

wherein:
$L_a$ is $CH_2$, O, NH or S;
Ar is a substituted or unsubstituted aryl, or a substituted or unsubstituted heteroaryl;
Y is an optionally substituted group selected from among alkyl, heteroalkyl, cycloalkyl, heterocycloalkyl, aryl, and heteroaryl;
Z is C(=O), OC(=O), NHC(=O), C(=S), S(=O)$_x$, OS(=O)$_x$, NHS(=O)$_x$, where x is 1 or 2;
$R_7$ and $R_8$ are independently H; or
$R_7$ and $R_8$ taken together form a bond;
$R_6$ is H; and pharmaceutically active metabolites, or pharmaceutically acceptable solvates, pharmaceutically acceptable salts, or pharmaceutically acceptable prodrugs thereof. In some embodiments, the Bruton's tyrosine kinase inhibitor is (R)-1-(3-(4-amino-3-(4-phenoxyphenyl)-1H-pyrazolo[3,4-d]pyrimidin-1-yl)piperidin-1-yl)prop-2-en-1-one. In some embodiments, La is O. In some embodiments, Ar is phenyl. In some embodiments, Z is C(=O), NHC(=O), or S(=O)$_2$. In some embodiments, each of $R_7$ and $R_8$ is H. In some embodiments, Y is a 4-, 5-, 6-, or 7-membered cycloalkyl ring; or Y is a 4-, 5-, 6-, or 7-membered heterocycloalkyl ring.

Disclosed herein, in certain embodiments, is a method for treating relapsed or refractory non-Hodgkin's lymphoma in an individual in need thereof, comprising: administering to the individual a therapeutically-effective amount of (R)-1-(3-(4-amino-3-(4-phenoxyphenyl)-1H-pyrazolo[3,4-d]pyrimidin-1-yl)piperidin-1-yl)prop-2-en-1-one. In some embodiments, the non-Hodgkin's lymphoma is relapsed or refractory diffuse large B-cell lymphoma (DLBCL), relapsed or refractory mantle cell lymphoma, or relapsed or refractory follicular lymphoma. In some embodiments, the amount of (R)-1-(3-(4-amino-3-(4-phenoxyphenyl)-1H-pyrazolo[3,4-d]pyrimidin-1-yl)piperidin-1-yl)prop-2-en-1-one is from 300 mg/day up to, and including, 1000 mg/day. In some embodiments, the amount of (R)-1-(3-(4-amino-3-(4-phenoxyphenyl)-1H-pyrazolo[3,4-d]pyrimidin-1-yl)piperidin-1-yl)prop-2-en-1-one is from 420 mg/day up to, and including, 840 mg/day. In some embodiments, the amount of (R)-1-(3-(4-amino-3-(4-phenoxyphenyl)-1H-pyrazolo[3,4-d]pyrimidin-1-yl)piperidin-1-yl)prop-2-en-1-one is about 420 mg/day, about 560 mg/day, or about 840 mg/day. In some embodiments, the amount of the irreversible Btk inhibitor is about 420 mg/day. In some embodiments, the $AUC_{0-24}$ of the Btk inhibitor is between about 150 and about 3500 ng*h/mL. In some embodiments, the $AUC_{0-24}$ of the Btk inhibitor is between about 500 and about 1100 ng*h/mL. In some embodiments, (R)-1-(3-(4-amino-3-(4-phenoxyphenyl)-1H-pyrazolo[3,4-d]pyrimidin-1-yl)piperidin-1-yl)prop-2-en-1-one is administered orally. In some embodiments, (R)-1-(3-(4-amino-3-(4-phenoxyphenyl)-1H-pyrazolo[3,4-d]pyrimidin-1-yl)piperidin-1-yl)prop-2-en-1-one is administered once per day, twice per day, or three times per day. In some embodiments, (R)-1-(3-(4-amino-3-(4-phenoxyphenyl)-1H-pyrazolo[3,4-d]pyrimidin-1-yl)piperidin-1-yl)prop-2-en-1-one is administered until disease progression, unacceptable toxicity, or individual choice. In some embodiments, (R)-1-(3-(4-amino-3-(4-phenoxyphenyl)-1H-pyrazolo[3,4-d]pyrimidin-1-yl)piperidin-1-yl)prop-2-en-1-one is administered until disease progression, unacceptable toxicity, or individual choice. In some embodiments, (R)-1-(3-(4-amino-3-(4-phenoxyphenyl)-1H-pyrazolo[3,4-d]pyrimidin-1-yl)piperidin-1-yl)prop-2-en-1-one is administered daily until disease progression, unacceptable toxicity, or individual choice. In some embodiments, (R)-1-(3-(4-amino-3-(4-phenoxyphenyl)-1H-pyrazolo[3,4-d]pyrimidin-1-yl)piperidin-1-yl)prop-2-en-1-one is administered every other day until disease progression, unacceptable toxicity, or individual choice. In some embodiments, (R)-1-(3-(4-amino-3-(4-phenoxyphenyl)-1H-pyrazolo[3,4-d]pyrimidin-1-yl)piperidin-1-yl)prop-2-en-1-one is a second line therapy, third line therapy, fourth line therapy, fifth line therapy, or sixth line therapy. In some embodiments, the Btk inhibitor is a maintenance therapy. In some embodiments, the method further comprises administering a second cancer treatment regimen. In some embodiments, the second cancer treatment regimen is administered after mobilization of a plurality of lymphoid cells from the non-Hodgkin's lymphoma. In some embodiments, the second cancer treatment regimen is administered after lymphocytosis of a plurality of lymphoid cells from the non-Hodgkin's lymphoma. In some embodiments, the second cancer treatment regimen comprises a chemotherapeutic agent, a steroid, an immunotherapeutic agent, a targeted therapy, or a combination thereof. In some embodiments, the second cancer treatment regimen comprises a B cell receptor pathway inhibitor. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the second cancer treatment regimen comprises an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof. In some embodiments, the second cancer treatment regimen comprises chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof. In some embodiments, the second cancer treatment regimen comprises cyclophosphamide, hydroxydaunorubicin, vincristine, and prednisone, and optionally, rituximab. In some embodiments, the second cancer treatment regimen comprises bendamustine, and rituximab. In some embodiments, the second cancer treatment regimen comprises fludarabine, cyclophosphamide, and rituximab. In some embodiments, the second cancer treatment regimen comprises cyclophosphamide, vincristine, and prednisone, and optionally, rituximab. In some embodiments, the second cancer treatment regimen comprises etoposide, doxorubicin, vinristine, cyclophosphamide, prednisolone, and optionally, rituximab. In some embodiments, the second cancer treatment regimen comprises dexamethasone and lenalidomide.

Disclosed herein, in certain embodiments, is a method for treating diffuse large B-cell lymphoma, activated B cell-like subtype (ABC-DLBCL), in an individual in need thereof, comprising: administering to the individual an irreversible Btk inhibitor in an amount from 300 mg/day up to, and including, 1000 mg/day. In some embodiments, the method further comprises diagnosing the individual with diffuse large B-cell lymphoma, activated B cell-like subtype (ABC-DLBCL), by determining the gene sequence of one or more biomarkers in a plurality of lymphoid cells isolated from the diffuse large B-cell lymphoma. In some embodiments, the irreversible Btk inhibitor is (R)-1-(3-(4-amino-3-(4-phenoxyphenyl)-1H-pyrazolo[3,4-d]pyrimidin-1-yl)piperidin-1-yl)prop-2-en-1-one. In some embodiments, the ABC-DLBCL is characterized by a CD79B mutation. In some embodiments, the CD79B mutation is a mutation of the immunoreceptor tyrosine-based activation motif (ITAM) signaling module. In some embodiments, the CD79B mutation is a missense mutation of the first immunoreceptor tyrosine-based activation motif (ITAM) tyrosine. In some embodiments, the CD79B mutation increases surface BCR expression and attenuates Lyn kinase activity. In some embodiments, the ABC-DLBCL is characterized by a CD79A mutation. In some embodiments, the CD79A mutation is in the immunoreceptor tyrosine-based activation motif (ITAM) signaling module. In some embodiments, the CD79A mutation is a splice-donor-site mutation of the immunoreceptor tyrosine-based activation motif (ITAM) signaling module. In some embodiments, the CD79A mutation deletes the immunoreceptor tyrosine-based activation motif (ITAM) signaling module. In some embodiments, the ABC-DLBCL is characterized by a mutation in MyD88, A20, or a combination thereof. In some embodiments, the MyD88 mutation is the amino acid substitution L265P in the MYD88 Toll/IL-1 receptor (TIR) domain. In some embodiments, the amount of the irreversible Btk inhibitor is from 420 mg/day up to, and including, 840 mg/day. In some embodiments, the amount of the irreversible Btk inhibitor is about 420 mg/day, about 560 mg/day, or about 840 mg/day. In some embodiments, the amount of the irreversible Btk inhibitor is about 420 mg/day. In some embodiments, the $AUC_{0-24}$ of the Btk inhibitor is between about 150 and about 3500 ng*h/mL. In some embodiments, the $AUC_{0-24}$ of the Btk inhibitor is between about 500 and about 1100 ng*h/mL. In some embodiments, the irreversible Btk inhibitor is administered orally. In some embodiments, the irreversible Btk inhibitor is administered daily until disease progression, unacceptable toxicity, or individual choice. In some embodiments, the irreversible Btk inhibitor is administered every other day until disease progression, unacceptable toxicity, or individual choice. In some embodiments, the irreversible Btk inhibitor is a front line therapy, second line therapy, third line therapy, fourth line therapy, fifth line therapy, or sixth line therapy. In some embodiments, the irreversible Btk inhibitor treats a refractory hematological malignancy. In some embodiments, the irreversible Btk inhibitor is a maintenance therapy. In some embodiments, the method further comprises administering at least one additional cancer treatment regimen. In some embodiments, the additional cancer treatment regimen comprises a chemotherapeutic agent, an immunotherapeutic agent, a steroid, radiation therapy, a targeted therapy, or a combination thereof. In some embodiments, the second cancer treatment regimen comprises an antibody, B cell receptor signaling inhibitor, a PI3K inhibitor, an IAP inhibitor, an mTOR inhibitor, a radioimmunotherapeutic, in certain embodiments is a damaging agent, a proteosome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof.

Disclosed herein, in certain embodiments, is a method of determining a cancer treatment regimen for an individual with a hematological malignancy, comprising: (a) administering to the individual an amount of an irreversible Btk inhibitor sufficient to mobilize a plurality of cells from the malignancy; (b) analyzing the mobilized plurality of cells; and (c) selecting a cancer treatment regimen. In some embodiments, the cancer treatment regimen comprises a chemotherapeutic agent, a steroid, an immunotherapeutic agent, a targeted therapy, or a combination thereof. In some embodiments, the second cancer treatment regimen comprises a B cell receptor pathway inhibitor. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the cancer treatment regimen comprises a B cell receptor pathway inhibitor. In some embodiments, the cancer treatment regimen comprises a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the cancer treatment regimen comprises an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof. In some embodiments, the cancer treatment regimen comprises chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof. In some embodiments, the cancer treatment regimen comprises cyclophosphamide, hydroxydaunorubicin, vincristine, and prednisone, and optionally, rituximab. In some embodiments, the cancer treatment regimen comprises bendamustine, and rituximab. In some embodiments, the cancer treatment regimen comprises fludarabine, cyclophosphamide, and rituximab. In some embodiments, the cancer treatment regimen comprises cyclophosphamide, vincristine, and prednisone, and optionally, rituximab. In some embodiments, the cancer treatment regimen comprises etoposide, doxorubicin, vinristine, cyclophosphamide, prednisolone, and optionally, rituximab. In some embodiments, the cancer treatment regimen comprises dexamethasone and lenalidomide.

DETAILED DESCRIPTION OF THE INVENTION

Figure 1:
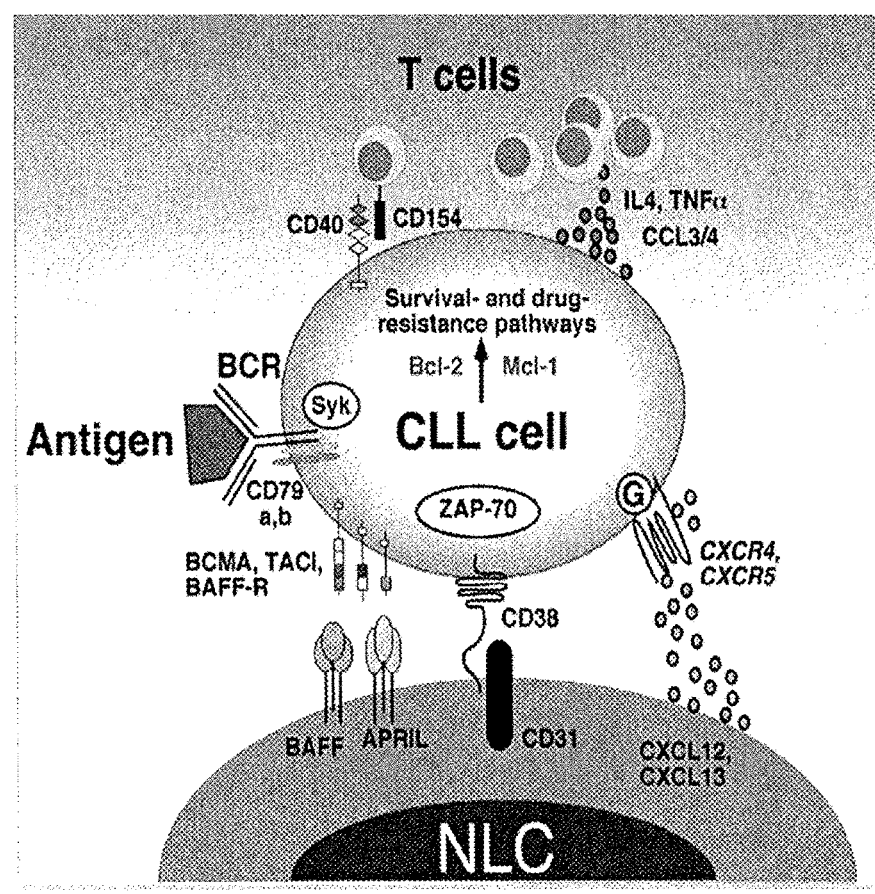
FIG. 1 depicts the role of Btk activity in a number of processes in a CLL cell that contribute to the pathogenesis of the disease
Figure 2:
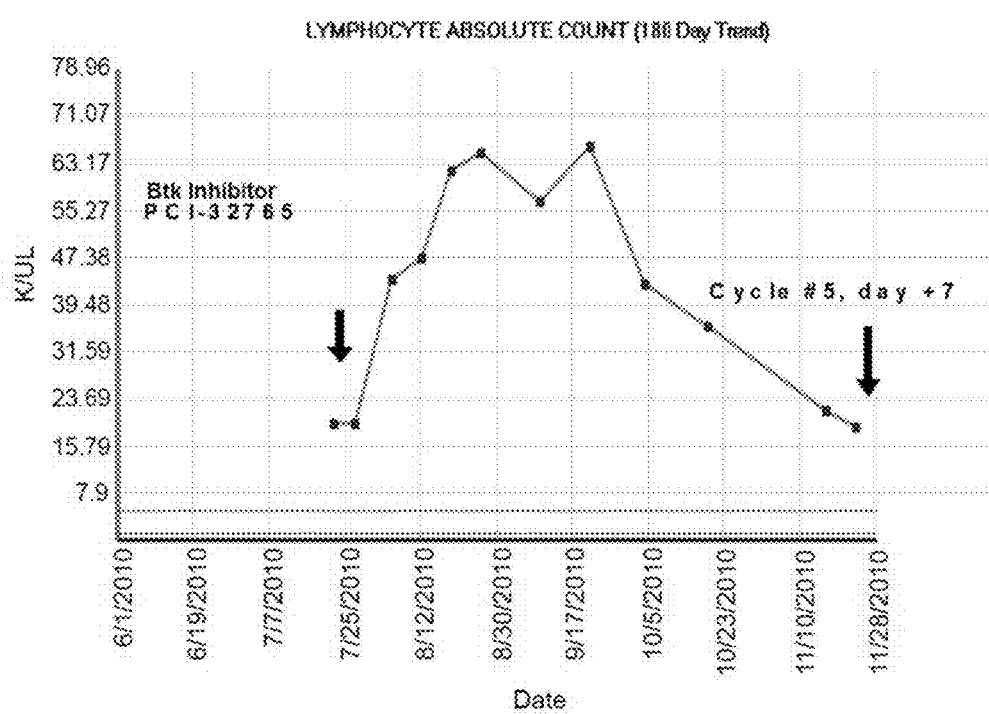
FIG. 2 presents the absolute lyphocyte count during the course of treatment with an irreversible Btk inhibitor for an individual with CLL.
Figure 3:
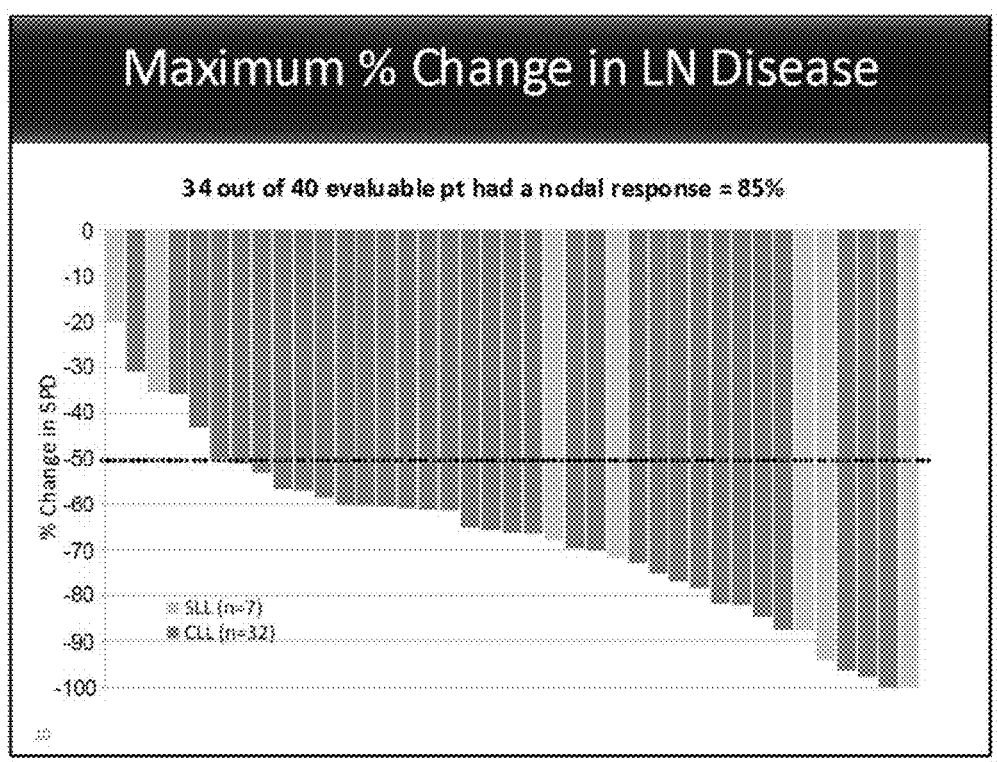
FIG. 3 presents change in the sum of the product of the diameters of lymph node (LN) in patients with CLL and SLL who are treated with an irreversible Btk inhibitor.
Figure 4:
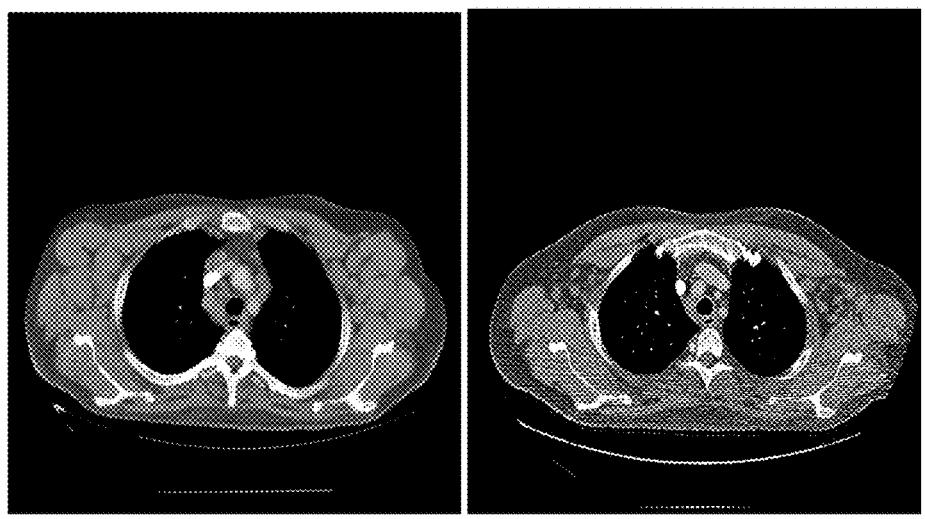
FIG. 4 depicts LN response in patient suffering from CLL. Left panel depicts LN prior to treatment with an irreversible Btk inhibitor and Right panel depicts LN post-treatment with an irreversible Btk inhibitor.

There is currently a need for methods of treating (including, diagnosing) hematological malignancies, including relapsed and refractory B cell malignancies, and ABC-DLBCL. The present application is based, in part, on the unexpected discovery that Btk inhibitors induce mobilization (or, in some cases, lymphocytosis) of lymphoid cells in solid hematological malignancies. Mobilization of the lymphoid cells increases their exposure to additional cancer treatment regimens and their availability for biomarker screening. The inventors have also found that Btk inhibitors are useful for treating relapsed and refractory malignancies and ABC-DLBCL.

Disclosed herein, in certain embodiments, is a method for treating a hematological malignancy in an individual in need thereof, comprising: (a) administering to the individual an amount of an irreversible Btk inhibitor sufficient to mobilize a plurality of cells from the malignancy; and (b) analyzing the mobilized plurality of cells. Disclosed herein, in certain embodiments, is a method for treating diffuse large B-cell lymphoma, activated B cell-like subtype (ABC-DLBCL), in an individual in need thereof, comprising: administering to the individual an irreversible Btk inhibitor in an amount from 300 mg/day up to, and including, 1000 mg/day. Further disclosed herein, in certain embodiments, is a method for treating relapsed or refractory non-Hodgkin's lymphoma in an individual in need thereof, comprising: administering to the individual a therapeutically-effective amount of (R)-1-(3-(4-amino-3-(4-phenoxyphenyl)-1H-pyrazolo[3,4-d]pyrimidin-1-yl)piperidin-1-yl)prop-2-en-1-one.

Certain Terminology

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, may be branched, straight chain, or cyclic. Depending on the structure, an alkyl group can be a monoradical or a diradical (i.e., an alkylene group). The alkyl group could also be a "lower alkyl" having 1 to 6 carbon atoms.

As used herein, $C_1$-$C_x$ includes $C_1$-$C_2$, $C_1$-$C_3$ ... $C_1$-$C_x$.

The "alkyl" moiety may have 1 to 10 carbon atoms (whenever it appears herein, a numerical range such as "1 to 10" refers to each integer in the given range; e.g., "1 to 10 carbon atoms" means that the alkyl group may have 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups can be substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

As used herein, the term "non-cyclic alkyl" refers to an alkyl that is not cyclic (i.e., a straight or branched chain containing at least one carbon atom). Non-cyclic alkyls can be fully saturated or can contain non-cyclic alkenes and/or alkynes. Non-cyclic alkyls can be optionally substituted.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which may be the same or different. The alkenyl moiety may be branched, straight chain, or cyclic (in which case, it would also be known as a "cycloalkenyl" group). Depending on the structure, an alkenyl group can be a monoradical or a diradical (i.e., an alkenylene group). Alkenyl groups can be optionally substituted. Non-limiting examples of an alkenyl group include —CH=CH$_2$, —C(CH$_3$)=CH$_2$, —CH=CHCH$_3$, —C(CH$_3$)=CHCH$_3$. Alkenylene groups include, but are not limited to, —CH=CH—, —C(CH$_3$)=CH—, —CH=CHCH$_2$—, —CH=CHCH$_2$CH$_2$— and —C(CH$_3$)=CHCH$_2$—. Alkenyl groups could have 2 to 10 carbons. The alkenyl group could also be a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which may be the same or different. The "R" portion of the alkynyl moiety may be branched, straight chain, or cyclic. Depending on the structure, an alkynyl group can be a monoradical or a diradical (i.e., an alkynylene group). Alkynyl groups can be optionally substituted. Non-limiting examples of an alkynyl group include, but are not limited to, —C≡CH, —C≡CCH$_3$, —C≡CCH$_2$CH$_3$, —C≡C—, and —C≡CCH$_2$—. Alkynyl groups can have 2 to 10 carbons. The alkynyl group could also be a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to a (alkenyl)O— group, where alkenyl is as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e a heteroatom). Heterocycle includes heteroaryl and heterocycloalkyl. Carbocycles and heterocycles can be optionally substituted.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

"Aralkyl" means an alkyl radical, as defined herein, substituted with an aryl group. Non-limiting aralkyl groups include, benzyl, phenethyl, and the like.

"Aralkenyl" means an alkenyl radical, as defined herein, substituted with an aryl group, as defined herein.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

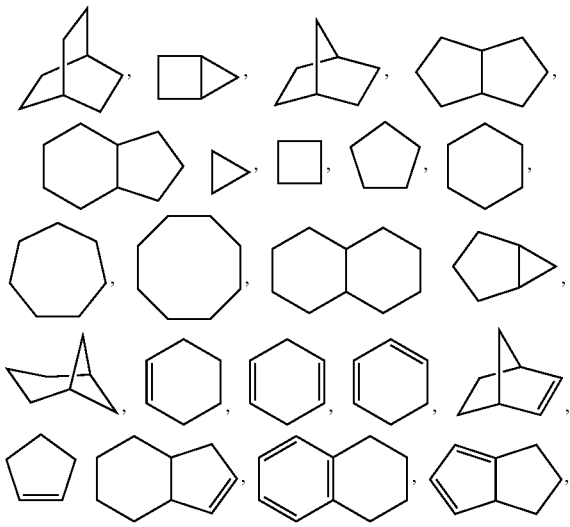

and the like. Depending on the structure, a cycloalkyl group can be a monoradical or a diradical (e.g., an cycloalkylene group). The cycloalkyl group could also be a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocyclic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

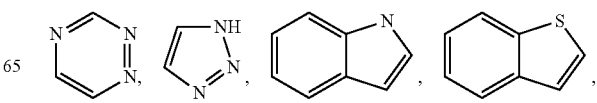

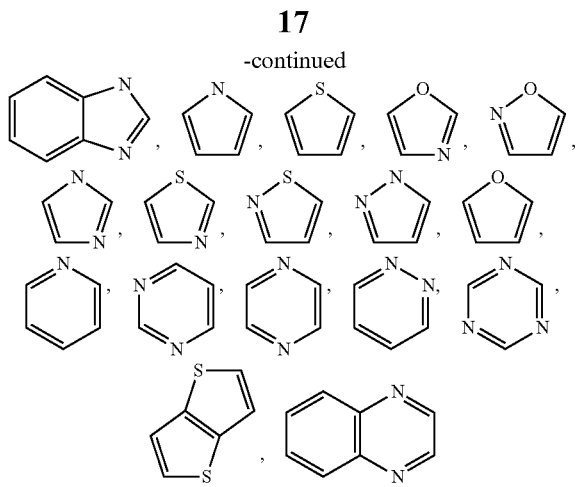

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

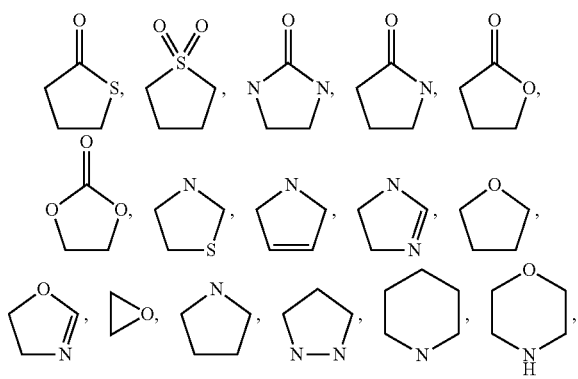

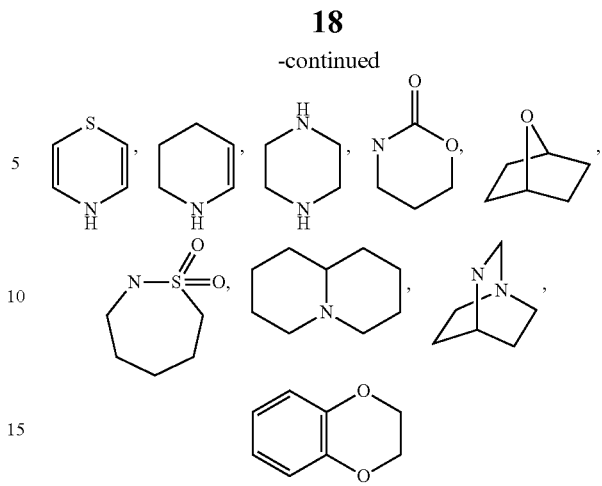

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo and iodo.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —$CF_3$, —$CH_2CF_3$, —$CF_2CF_3$, —$CH_2CH_2CF_3$ and the like.

As used herein, the terms "heteroalkyl" "heteroalkenyl" and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

An "isocyanato" group refers to a —NCO group.

An "isothiocyanato" group refers to a —NCS group.

The term "moiety" refers to a specific segment or functional group of a molecule. Chemical moieties are often recognized chemical entities embedded in or appended to a molecule.

A "sulfinyl" group refers to a —S(=O)—R.

A "sulfonyl" group refers to a —S(=O)$_2$—R.

A "thioalkoxy" or "alkylthio" group refers to a —S-alkyl group.

A "alkylthioalkyl" group refers to an alkyl group substituted with a —S-alkyl group.

As used herein, the term "O-carboxy" or "acyloxy" refers to a group of formula RC(=O)O—.

"Carboxy" means a —C(O)OH radical.

As used herein, the term "acetyl" refers to a group of formula —C(=O)CH$_3$.

"Acyl" refers to the group —C(O)R.

As used herein, the term "trihalomethanesulfonyl" refers to a group of formula X$_3$CS(=O)$_2$— where X is a halogen.

As used herein, the term "cyano" refers to a group of formula —CN.

"Cyanoalkyl" means an alkyl radical, as defined herein, substituted with at least one cyano group.

As used herein, the term "N-sulfonamido" or "sulfonylamino" refers to a group of formula RS(=O)$_2$NH—.

As used herein, the term "O-carbamyl" refers to a group of formula —OC(=O)NR$_2$.

As used herein, the term "N-carbamyl" refers to a group of formula ROC(=O)NH—.

As used herein, the term "O-thiocarbamyl" refers to a group of formula —OC(=S)NR2.

As used herein, the term "N-thiocarbamyl" refers to a group of formula ROC(=S)NH—.

As used herein, the term "C-amido" refers to a group of formula —C(=O)NR2.

"Aminocarbonyl" refers to a —CONH2 radical.

As used herein, the term "N-amido" refers to a group of formula RC(=O)NH—.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be L$_s$R$_s$, wherein each L$_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O) O—, -(substituted or unsubstituted C$_1$-C$_6$ alkyl), or -(substituted or unsubstituted C$_2$-C$_6$ alkenyl); and each R$_s$ is independently selected from H, (substituted or unsubstituted C$_1$-C$_4$alkyl), (substituted or unsubstituted C$_3$-C$_6$cycloalkyl), heteroaryl, or heteroalkyl. The protecting groups that may form the protective derivatives of the above substituents are known to those of skill in the art and may be found in references such as Greene and Wuts, above.

The term "Michael acceptor moiety" refers to a functional group that can participate in a Michael reaction, wherein a new covalent bond is formed between a portion of the Michael acceptor moiety and the donor moiety. The Michael acceptor moiety is an electrophile and the "donor moiety" is a nucleophile.

The term "nucleophile" or "nucleophilic" refers to an electron rich compound, or moiety thereof. An example of a nucleophile includes, but in no way is limited to, a cysteine residue of a molecule, such as, for example Cys 481 of Btk.

The term "electrophile", or "electrophilic" refers to an electron poor or electron deficient molecule, or moiety thereof. Examples of electrophiles include, but in no way are limited to, Micheal acceptor moieties.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

"B-cell lymphoproliferative disorders (BCLD) biomarkers", as used herein, refer to any biological molecule (found either in blood, other body fluids, or tissues) or any chromosomal abnormality that is a sign of a BCLD-related condition or disease.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The terms "cancer" and "cancerous" refer to or describe the physiological condition in mammals that is typically characterized by unregulated cell growth. Examples of cancer include, but are not limited to, B-cell lymphoproliferative disorders (BCLDs), such as lymphoma and leukemia, and solid tumors. By "B cell-related cancer" or "cancer of B-cell lineage" is intended any type of cancer in which the dysregulated or unregulated cell growth is associated with B cells.

By "refractory" in the context of a cancer is intended the particular cancer is resistant to, or non-responsive to, therapy with a particular therapeutic agent. A cancer can be refractory to therapy with a particular therapeutic agent either from the onset of treatment with the particular therapeutic agent (i.e., non-responsive to initial exposure to the therapeutic agent), or as a result of developing resistance to the therapeutic agent, either over the course of a first treatment period with the therapeutic agent or during a subsequent treatment period with the therapeutic agent.

By "agonist activity" is intended that a substance functions as an agonist. An agonist combines with a receptor on a cell and initiates a reaction or activity that is similar to or the same as that initiated by the receptor's natural ligand.

By "antagonist activity" is intended that the substance functions as an antagonist. An antagonist of Btk prevents or reduces induction of any of the responses mediated by Btk.

By "significant" agonist activity is intended an agonist activity of at least 30%, 35%, 40%, 45%, 50%, 60%, 70%, 75%, 80%, 85%, 90%, 95%, or 100% greater than the agonist activity induced by a neutral substance or negative control as measured in an assay of a B cell response. Preferably, "significant" agonist activity is an agonist activity that is at least 2-fold greater or at least 3-fold greater than the agonist activity induced by a neutral substance or negative control as measured in an assay of a B cell response. Thus, for example, where the B cell response of interest is B cell proliferation, "significant" agonist activity would be induction of a level of B cell proliferation that is at least 2-fold greater or at least 3-fold greater than the level of B cell proliferation induced by a neutral substance or negative control.

A substance "free of significant agonist activity" would exhibit an agonist activity of not more than about 25% greater than the agonist activity induced by a neutral substance or negative control, preferably not more than about 20% greater, 15% greater, 10% greater, 5% greater, 1% greater, 0.5% greater, or even not more than about 0.1% greater than the agonist activity induced by a neutral substance or negative control as measured in an assay of a B cell response.

In some embodiments, the Btk inhibitor therapeutic agent is an antagonist anti-Btk antibody. Such antibodies are free of significant agonist activity as noted above when bound to a Btk antigen in a human cell. In one embodiment of the invention, the antagonist anti-Btk antibody is free of significant agonist activity in one cellular response. In another embodiment of the invention, the antagonist anti-Btk antibody is free of significant agonist activity in assays of more than one cellular response (e.g., proliferation and differentiation, or proliferation, differentiation, and, for B cells, antibody production).

By "Btk-mediated signaling" it is intended any of the biological activities that are dependent on, either directly or indirection, the activity of Btk. Examples of Btk-mediated signaling are signals that lead to proliferation and survival of Btk-expressing cells, and stimulation of one or more Btk-signaling pathways within Btk-expressing cells.

A Btk "signaling pathway" or "signal transduction pathway" is intended to mean at least one biochemical reaction, or a group of biochemical reactions, that results from the activity of Btk, and which generates a signal that, when transmitted through the signal pathway, leads to activation of one or more downstream molecules in the signaling cascade. Signal transduction pathways involve a number of signal transduction molecules that lead to transmission of a signal from the cell-surface across the plasma membrane of a cell, and through one or more in a series of signal transduction molecules, through the cytoplasm of the cell, and in some instances, into the cell's nucleus. Of particular interest to the present invention are Btk signal transduction pathways which ultimately regulate (either enhance or inhibit) the activation of NF-κB via the NF-κB signaling pathway.

The methods of the present invention are directed to methods for treating cancer that, in certain embodiments, utilize antibodies for determining the expression or presence of certain BCLD biomarkers in these methods. The following terms and definitions apply to such antibodies.

Antibodies" and "immunoglobulins" (Igs) are glycoproteins having the same structural characteristics. The terms are used synonymously. In some instances the antigen specificity of the immunoglobulin may be known.

The term "antibody" is used in the broadest sense and covers fully assembled antibodies, antibody fragments that can bind antigen (e.g., Fab, F(ab')2, Fv, single chain antibodies, diabodies, antibody chimeras, hybrid antibodies, bispecific antibodies, humanized antibodies, and the like), and recombinant peptides comprising the forgoing.

The terms "monoclonal antibody" and "mAb" as used herein refer to an antibody obtained from a substantially homogeneous population of antibodies, i.e., the individual antibodies comprising the population are identical except for possible naturally occurring mutations that may be present in minor amounts.

Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies (see, Kabat et al. (1991) NIH PubL. No. 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

The term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) J. Mol. Biol., 196:901-917). "Framework" or "FR" residues are those variable domain residues other than the hypervariable region residues, as herein deemed.

"Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) Protein Eng. 10:1057-

1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H1}$) of the heavy chain. Fab fragments differ from Fab' fragments by the addition of a few residues at the carboxy terminus of the heavy chain Cm domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

The term "Bruton's tyrosine kinase (Btk)," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEEL-YSSARQ" (SEQ ID NO: 1)).

The terms "co-administration" or "combination therapy" and the like, as used herein, are meant to encompass administration of the selected therapeutic agents to a single patient, and are intended to include treatment regimens in which the agents are administered by the same or different route of administration or at the same or different time.

The term "effective amount," as used herein, refers to a sufficient amount of a Btk inhibitory agent or a Btk inhibitor compound being administered which will result in an increase or appearance in the blood of a subpopulation of lymphocytes (e.g., pharmaceutical debulking). For example, an "effective amount" for diagnostic and/or prognostic uses is the amount of the composition including a compound as disclosed herein required to provide a clinically significant decrease an increase or appearance in the blood of a subpopulation of lymphocytes without undue adverse side effects. An appropriate "effective amount" in any individual case may be determined using techniques, such as a dose escalation study.

The term "therapeutically effective amount," as used herein, refers to a sufficient amount of an agent or a compound being administered which will relieve to some extent one or more of the symptoms s B-cell lymphoproliferative disorder (BCLD). The result can be reduction and/or alleviation of the signs, symptoms, or causes of BCLD, or any other desired alteration of a biological system. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (A), Formula (B), Formula (C), or Formula (D), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350. See also the sequence alignments of tyrosine kinases (TK) published on the world wide web at kinase.com/human/kinome/phylogeny.html.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits", "inhibiting", or "inhibitor" of a kinase, as used herein, refer to inhibition of enzymatic phosphotransferase activity.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "selective binding compound" refers to a compound that selectively binds to any portion of one or more target proteins.

As used herein, the term "selectively binds" refers to the ability of a selective binding compound to bind to a target protein, such as, for example, Btk, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulator refers to modulating a target activity at least 10, 50, 100, 250, 500, 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, effects on particular biomarkers related to B-cell lymphoproliferative disorder pathology.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a disease or condition, or symptoms thereof; managing a disease or condition, or symptoms thereof; preventing additional symptoms; ameliorating or preventing the underlying metabolic causes of symptoms; inhibiting the disease or condition, e.g., arresting the development of the disease or condition; relieving the disease or condition; causing regression of the disease or condition, relieving a condition caused by the disease or condition; or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

Hematological Malignancies

Disclosed herein, in certain embodiments, is a method for treating a hematological malignancy in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, the hematological malignancy is CLL. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time. In some embodiments, the hematological malignancy is a chronic lymphocytic leukemia (CLL), small lymphocytic lymphoma (SLL), high risk CLL, or a non-CLL/SLL lymphoma. In some embodiments, the hematological malignancy is follicular lymphoma, diffuse large B-cell lymphoma (DLBCL), mantle cell lymphoma, Waldenstrom's macroglobulinemia, multiple myeloma, marginal zone lymphoma, Burkitt's lymphoma, non-Burkitt high grade B cell lymphoma, or extranodal marginal zone B cell lymphoma. In some embodiments, the hematological malignancy is acute or chronic myelogenous (or myeloid) leukemia, myelodysplastic syndrome, or acute lymphoblastic leukemia. In some embodiments, the hematological malignancy is relapsed or refractory diffuse large B-cell lymphoma (DLBCL), relapsed or refractory mantle cell lymphoma, relapsed or refractory follicular lymphoma, relapsed or refractory CLL; relapsed or refractory SLL; relapsed or refractory multiple myeloma. In some embodiments, the hematological malignancy is a hematological malignancy that is classified as high-risk. In some embodiments, the hematological malignancy is high risk CLL or high risk SLL.

B-cell lymphoproliferative disorders (BCLDs) are neoplasms of the blood and encompass, inter alia, non-Hodgkin lymphoma, multiple myeloma, and leukemia. BCLDs can originate either in the lymphatic tissues (as in the case of lymphoma) or in the bone marrow (as in the case of leukemia and myeloma), and they all are involved with the uncontrolled growth of lymphocytes or white blood cells. There are many subtypes of BCLD, e.g., chronic lymphocytic leukemia (CLL) and non-Hodgkin lymphoma (NHL). The disease course and treatment of BCLD is dependent on the BCLD subtype; however, even within each subtype the clinical presentation, morphologic appearance, and response to therapy is heterogeneous.

Malignant lymphomas are neoplastic transformations of cells that reside predominantly within lymphoid tissues. Two groups of malignant lymphomas are Hodgkin's lymphoma and non-Hodgkin's lymphoma (NHL). Both types of lymphomas infiltrate reticuloendothelial tissues. However, they differ in the neoplastic cell of origin, site of disease, presence of systemic symptoms, and response to treatment (Freedman et al., "Non-Hodgkin's Lymphomas" Chapter 134, Cancer Medicine, (an approved publication of the American Cancer Society, B.C. Decker Inc., Hamilton, Ontario, 2003).

Non-Hodgkin's Lymphomas

Disclosed herein, in certain embodiments, is a method for treating a non-Hodgkin's lymphoma in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, the hematological malignancy is CLL. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

Further disclosed herein, in certain embodiments, is a method for treating relapsed or refractory non-Hodgkin's lymphoma in an individual in need thereof, comprising: administering to the individual a therapeutically-effective amount of (R)-1-(3-(4-amino-3-(4-phenoxyphenyl)-1H-pyrazolo[3,4-d]pyrimidin-1-yl)piperidin-1-yl)prop-2-en-1-one. In some embodiments, the non-Hodgkin's lymphoma is relapsed or refractory diffuse large B-cell lymphoma (DLBCL), relapsed or refractory mantle cell lymphoma, or relapsed or refractory follicular lymphoma.

Non-Hodgkin lymphomas (NHL) are a diverse group of malignancies that are predominately of B-cell origin. NHL may develop in any organs associated with lymphatic system such as spleen, lymph nodes or tonsils and can occur at any age. NHL is often marked by enlarged lymph nodes, fever, and weight loss. NHL is classified as either B-cell or T-cell NHL. Lymphomas related to lymphoproliferative disorders following bone marrow or stem cell transplantation are usually B-cell NHL. In the Working Formulation classification scheme, NHL has been divided into low-, intermediate-, and high-grade categories by virtue of their natural histories (see "The Non-Hodgkin's Lymphoma Pathologic Classification Project," Cancer 49(1982):2112-2135). The low-grade lymphomas are indolent, with a median survival of 5 to 10 years (Horning and Rosenberg (1984) N. Engl. J. Med. 311:1471-1475). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

A non-limiting list of the B-cell NHL includes Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lympoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma. Additional non-Hodgkin's lymphomas are contemplated within the scope of the present invention and apparent to those of ordinary skill in the art.

DLBCL

Disclosed herein, in certain embodiments, is a method for treating a DLCBL in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

As used herein, the term "Diffuse large B-cell lymphoma (DLBCL)" refers to a neoplasm of the germinal center B lymphocytes with a diffuse growth pattern and a high-intermediate proliferation index. DLBCLs represent approximately 30% of all lymphomas and may present with several morphological variants including the centroblastic, immunoblastic, T-cell/histiocyte rich, anaplastic and plasmoblastic subtypes. Genetic tests have shown that there are different subtypes of DLBCL. These subtypes seem to have different outlooks (prognoses) and responses to treatment. DLBCL can affect any age group but occurs mostly in older people (the average age is mid-60s).

Disclosed herein, in certain embodiments, is a method for treating diffuse large B-cell lymphoma, activated B cell-like subtype (ABC-DLBCL), in an individual in need thereof, comprising: administering to the individual an irreversible Btk inhibitor in an amount from 300 mg/day up to, and including, 1000 mg/day. The ABC subtype of diffuse large B-cell lymphoma (ABC-DLBCL) is thought to arise from post germinal center B cells that are arrested during plasmatic differentiation. The ABC subtype of DLBCL (ABC-DLBCL) accounts for approximately 30% total DLBCL diagnoses. It is considered the least curable of the DLBCL molecular subtypes and, as such, patients diagnosed with the ABC-DLBCL typically display significantly reduced survival rates compared with individuals with other types of DLCBL. ABC-DLBCL is most commonly associated with chromosomal translocations deregulating the germinal center master regulator BCL6 and with mutations inactivating the PRDM1 gene, which encodes a transcriptional repressor required for plasma cell differentiation.

A particularly relevant signaling pathway in the pathogenesis of ABC-DLBCL is the one mediated by the nuclear factor (NF)-κB transcription complex. The NF-κB family comprises 5 members (p50, p52, p65, c-rel and RelB) that form homo- and heterodimers and function as transcriptional factors to mediate a variety of proliferation, apoptosis, inflammatory and immune responses and are critical for normal B-cell development and survival. NF-κB is widely used by eukaryotic cells as a regulator of genes that control cell proliferation and cell survival. As such, many different types of human tumors have misregulated NF-κB: that is, NF-κB is constitutively active. Active NF-κB turns on the expression of genes that keep the cell proliferating and protect the cell from conditions that would otherwise cause it to die via apoptosis.

The dependence of ABC DLBCLs on NF-kB depends on a signaling pathway upstream of IkB kinase comprised of CARD11, BCL10 and MALT1 (the CBM complex). Interference with the CBM pathway extinguishes NF-kB signaling in ABC DLBCL cells and induces apoptosis. The molecular basis for constitutive activity of the NF-kB pathway is a subject of current investigation but some somatic alterations to the genome of ABC DLBCLs clearly invoke this pathway. For example, somatic mutations of the coiled-coil domain of CARD11 in DLBCL render this signaling scaffold protein able to spontaneously nucleate protein-protein interaction with MALT1 and BCL10, causing IKK activity and NF-kB activation. Constitutive activity of the B cell receptor signaling pathway has been implicated in the activation of NF-kB in ABC DLBCLs with wild type CARD11, and this is associated with mutations within the cytoplasmic tails of the B cell receptor subunits CD79A and CD79B. Oncogenic activating mutations in the signaling adapter MYD88 activate NF-kB and synergize with B cell receptor signaling in sustaining the survival of ABC DLBCL cells. In addition, inactivating mutations in a negative regulator of the NF-kB pathway, A20, occur almost exclusively in ABC DLBCL.

Indeed, genetic alterations affecting multiple components of the NF-κB signaling pathway have been recently identified in more than 50% of ABC-DLBCL patients, where these lesions promote constitutive NF-κB activation, thereby contributing to lymphoma growth. These include mutations of CARD11 (~10% of the cases), a lymphocyte-specific cytoplasmic scaffolding protein that—together with MALT1 and BCL10—forms the BCR signalosome, which relays signals from antigen receptors to the downstream mediators of NF-κB activation. An even larger fraction of cases (~30%) carry biallelic genetic lesions inactivating the negative NF-κB regulator A20. Further, high levels of expression of NF-κB target genes have been observed in ABC-DLBCL tumor samples. See, e.g., U. Klein et al., (2008), *Nature Reviews Immunology* 8:22-23; R. E. Davis et al., (2001), *Journal of Experimental Medicine* 194:1861-1874; G. Lentz et al., (2008), *Science* 319:1676-1679; M. Compagno et al., (2009), *Nature* 459:712-721; and L. Srinivasan et al., (2009), *Cell* 139:573-586).

DLBCL cells of the ABC subtype, such as OCI-Ly10, have chronic active BCR signalling and are very sensitive to the Btk inhibitors described herein. The irreversible Btk inhibitors described herein potently and irreversibly inhibit the growth of OCI-Ly10 (EC50 continuous exposure=10 nM, EC50 1 hour pulse=50 nM). In addition, induction of apoptosis, as shown by capsase activation, Annexin-V flow cytometry and increase in sub-GO fraction is observed in OCILy10. Both sensitive and resistant cells express Btk at similar levels, and the active site of Btk is fully occupied by the inhibitor in both as shown using a fluorescently labeled affinity probe. OCI-Ly10 cells are shown to have chronically active BCR signalling to NF-kB which is dose dependently inhibited by the Btk inhibitors described herein. The activity of Btk inhibitors in the cell lines studied herein are also characterized by comparing signal transduction profiles (Btk, PLCγ, ERK, NF-kB, AKT), cytokine secretion profiles and mRNA expression profiles, both with and without BCR stimulation, and observed significant differences in these profiles that lead to clinical biomarkers that identify the most sensitive patient populations to Btk inhibitor treatment. See U.S. Pat. No. 7,711,492 and Staudt et al., *Nature*, Vol. 463, Jan. 7, 2010, pp. 88-92, the contents of which are incorporated by reference in their entirety.

Follicular Lymphoma

Disclosed herein, in certain embodiments, is a method for treating a follicular lymphoma in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

As used herein, the term "follicular lymphoma" refers to any of several types of non-Hodgkin's lymphoma in which the lymphomatous cells are clustered into nodules or follicles. The term follicular is used because the cells tend to grow in a circular, or nodular, pattern in lymph nodes. The average age for people with this lymphoma is about 60.

CLL/SLL

Disclosed herein, in certain embodiments, is a method for treating a CLL or SLL in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the CLL or SLL is high-risk. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

Chronic lymphocytic leukemia and small lymphocytic lymphoma (CLL/SLL) are commonly thought as the same disease with slightly different manifestations. Where the cancerous cells gather determines whether it is called CLL or SLL. When the cancer cells are primarily found in the lymph nodes, lima bean shaped structures of the lymphatic system (a system primarily of tiny vessels found in the body), it is called SLL. SLL accounts for about 5% to 10% of all lymphomas. When most of the cancer cells are in the bloodstream and the bone marrow, it is called CLL.

Both CLL and SLL are slow-growing diseases, although CLL, which is much more common, tends to grow slower. CLL and SLL are treated the same way. They are usually not considered curable with standard treatments, but depending on the stage and growth rate of the disease, most patients live longer than 10 years. Occasionally over time, these slow-growing lymphomas may transform into a more aggressive type of lymphoma.

Chronic lymphoid leukemia (CLL) is the most common type of leukemia. It is estimated that 100,760 people in the United States are living with or are in remission from CLL. Most (>75%) people newly diagnosed with CLL are over the age of 50. Currently CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes). Though CLL progresses slowly in most cases, it is considered generally incurable. Certain CLLs are classified as high-risk. As used herein, "high risk CLL" means CLL characterized by at least one of the following 1) 17p13-; 2) 11q22-; 3) unmutated IgVH together with ZAP-70+ and/or CD38+; or 4) trisomy 12.

CLL treatment is typically administered when the patient's clinical symptoms or blood counts indicate that the disease has progressed to a point where it may affect the patient's quality of life.

Small lymphocytic leukemia (SLL) is very similar to CLL described supra, and is also a cancer of B-cells. In SLL the abnormal lymphocytes mainly affect the lymph nodes. However, in CLL the abnormal cells mainly affect the blood and the bone marrow. The spleen may be affected in both conditions. SLL accounts for about 1 in 25 of all cases of non-Hodgkin lymphoma. It can occur at any time from young adulthood to old age, but is rare under the age of 50. SLL is considered an indolent lymphoma. This means that the disease progresses very slowly, and patients tend to live many years after diagnosis. However, most patients are diagnosed with advanced disease, and although SLL responds well to a variety of chemotherapy drugs, it is generally considered to be incurable. Although some cancers tend to occur more often in one gender or the other, cases and deaths due to SLL are evenly split between men and women. The average age at the time of diagnosis is 60 years.

Although SLL is indolent, it is persistently progressive. The usual pattern of this disease is one of high response rates to radiation therapy and/or chemotherapy, with a period of disease remission. This is followed months or years later by an inevitable relapse. Re-treatment leads to a response again, but again the disease will relapse. This means that although the short-term prognosis of SLL is quite good, over time, many patients develop fatal complications of recurrent disease. Considering the age of the individuals typically diagnosed with CLL and SLL, there is a need in the art for a simple and effective treatment of the disease with minimum side-effects that do not impede on the patient's quality of life. The instant invention fulfills this long standing need in the art.

Mantle Cell Lymphoma

Disclosed herein, in certain embodiments, is a method for treating a Mantle cell lymphoma in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

As used herein, the term, "Mantle cell lymphoma" refers to a subtype of B-cell lymphoma, due to CD5 positive antigen-naive pregerminal center B-cell within the mantle zone that surrounds normal germinal center follicles. MCL cells generally over-express cyclin D1 due to a t(11:14) chromosomal translocation in the DNA. More specifically, the translocation is at t(11;14)(q13;q32). Only about 5% of lymphomas are of this type. The cells are small to medium in size. Men are affected most often. The average age of patients is in the early 60s. The lymphoma is usually widespread when it is diagnosed, involving lymph nodes, bone marrow, and, very often, the spleen. Mantle cell lymphoma is not a very fast growing lymphoma, but is difficult to treat.

Marginal Zone B-Cell Lymphoma

Disclosed herein, in certain embodiments, is a method for treating a marginal zone B-cell lymphoma in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

As used herein, the term "marginal zone B-cell lymphoma" refers to a group of related B-cell neoplasms that involve the lymphoid tissues in the marginal zone, the patchy area outside the follicular mantle zone. Marginal zone lymphomas account for about 5% to 10% of lymphomas. The cells in these lymphomas look small under the microscope. There are 3 main types of marginal zone lymphomas including extranodal marginal zone B-cell lymphomas, nodal marginal zone B-cell lymphoma, and splenic marginal zone lymphoma.

MALT

Disclosed herein, in certain embodiments, is a method for treating a MALT in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

The term "mucosa-associated lymphoid tissue (MALT) lymphoma", as used herein, refers to extranodal manifestations of marginal-zone lymphomas. Most MALT lymphoma are a low grade, although a minority either manifest initially as intermediate-grade non-Hodgkin lymphoma (NHL) or evolve from the low-grade form. Most of the MALT lymphoma occur in the stomach, and roughly 70% of gastric MALT lymphoma are associated with *Helicobacter pylori* infection. Several cytogenetic abnormalities have been identified, the most common being trisomy 3 or t(11;18). Many of these other MALT lymphoma have also been linked to infections with bacteria or viruses. The average age of patients with MALT lymphoma is about 60.

Nodal Marginal Zone B-Cell Lymphoma

Disclosed herein, in certain embodiments, is a method for treating a nodal marginal zone B-cell lymphoma in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

The term "nodal marginal zone B-cell lymphoma" refers to an indolent B-cell lymphoma that is found mostly in the lymph nodes. The disease is rare and only accounts for 1% of all Non-Hodgkin's Lymphomas (NHL). It is most commonly diagnosed in older patients, with women more susceptible than men. The disease is classified as a marginal zone lymphoma because the mutation occurs in the marginal zone of the B-cells. Due to its confinement in the lymph nodes, this disease is also classified as nodal.

Splenic Marginal Zone B-Cell Lymphoma

Disclosed herein, in certain embodiments, is a method for treating a splenic marginal zone B-cell lymphoma in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

The term "splenic marginal zone B-cell lymphoma" refers to specific low-grade small B-cell lymphoma that is incorporated in the World Health Organization classification. Characteristic features are splenomegaly, moderate lymphocytosis with villous morphology, intrasinusoidal pattern of involvement of various organs, especially bone marrow, and relative indolent course. Tumor progression with increase of blastic forms and aggressive behavior are observed in a minority of patients. Molecular and cytogenetic studies have shown heterogeneous results probably because of the lack of standardized diagnostic criteria.

Burkitt Lymphoma

Disclosed herein, in certain embodiments, is a method for treating a Burkitt lymphoma in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

The term "Burkitt lymphoma" refers to a type of Non-Hodgkin Lymphoma (NHL) that commonly affects children. It is a highly aggressive type of B-cell lymphoma that often starts and involves body parts other than lymph nodes. In spite of its fast-growing nature, Burkitt's lymphoma is often curable with modern intensive therapies. There are two broad types of Burkitt's lymphoma—the sporadic and the endemic varieties:

Endemic Burkitt's lymphoma: The disease involves children much more than adults, and is related to Epstein Barr Virus (EBV) infection in 95% cases. It occurs primarily is equatorial Africa, where about half of all childhood cancers are Burkitt's lymphoma. It characteristically has a high chance of involving the jawbone, a rather distinctive feature that is rare in sporadic Burkitt's. It also commonly involves the abdomen.

Sporadic Burkitt's lymphoma: The type of Burkitt's lymphoma that affects the rest of the world, including Europe and the Americas is the sporadic type. Here too, it's mainly a disease in children. The link between Epstein Barr Virus (EBV) is not as strong as with the endemic variety, though direct evidence of EBV infection is present in one out of five patients. More than the involvement of lymph nodes, it is the abdomen that is notably affected in more than 90% of the children. Bone marrow involvement is more common than in the sporadic variety.

Waldenstrom Macroglobulinemia

Disclosed herein, in certain embodiments, is a method for treating a Waldenstrom macroglobulinemia in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

The term "Waldenstrom macroglobulinemia", also known as lymphoplasmacytic lymphoma, is cancer involving a subtype of white blood cells called lymphocytes. It is characterized by an uncontrolled clonal proliferation of terminally differentiated B lymphocytes. It is also characterized by the lymphoma cells making an antibody called immunoglobulin M (IgM). The IgM antibodies circulate in the blood in large amounts, and cause the liquid part of the blood to thicken, like syrup. This can lead to decreased blood flow to many organs, which can cause problems with vision (because of poor circulation in blood vessels in the back of the eyes) and neurological problems (such as headache, dizziness, and confusion) caused by poor blood flow within the brain. Other symptoms can include feeling tired and weak, and a tendency to bleed easily. The underlying etiology is not fully understood but a number of risk factors have been identified, including the locus 6p21.3 on chromosome 6. There is a 2- to 3-fold risk increase of developing WM in people with a personal history of autoimmune diseases with autoantibodies and particularly elevated risks associated with hepatitis, human immunodeficiency virus, and rickettsiosis.

Multiple Myeloma

Disclosed herein, in certain embodiments, is a method for treating a myeloma in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

Disclosed herein, in certain embodiments, is a method for treating a multiple myeloma in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

Multiple myeloma, also known as MM, myeloma, plasma cell myeloma, or as Kahler's disease (after Otto Kahler) is a cancer of the white blood cells known as plasma cells. A type of B cell, plasma cells are a crucial part of the immune system responsible for the production of antibodies in humans and other vertebrates. They are produced in the bone marrow and are transported through the lymphatic system.

Leukemia

Disclosed herein, in certain embodiments, is a method for treating a leukemia in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the concentration before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

Leukemia is a cancer of the blood or bone marrow characterized by an abnormal increase of blood cells, usually leukocytes (white blood cells). Leukemia is a broad term covering a spectrum of diseases. The first division is between its acute and chronic forms: (i) acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children; (ii) chronic leukemia is distinguished by the excessive build up of relatively mature, but still abnormal, white blood cells. Typically taking months or years to progress, the cells are produced at a much higher rate than normal cells, resulting in many abnormal white blood cells in the blood. Chronic leukemia mostly occurs in older people, but can theoretically occur in any age group. Additionally, the diseases are subdivided according to which kind of blood cell is affected. This split divides leukemias into lymphoblastic or lymphocytic leukemias and myeloid or myelogenous leukemias: (i) lymphoblastic or lymphocytic leukemias, the cancerous change takes place in a type of marrow cell that normally goes on to form lymphocytes, which are infection-fighting immune system cells; (ii) myeloid or myelogenous leukemias, the cancerous change takes place in a type of marrow cell that normally goes on to form red blood cells, some other types of white cells, and platelets.

Within these main categories, there are several subcategories including, but not limited to, Acute lymphoblastic leukemia (ALL), Acute myelogenous leukemia (AML), Chronic myelogenous leukemia (CIVIL), and Hairy cell leukemia (HCL).

Btk Inhibitors

Also presented herein are methods for treating a cancer such as by way of example only, a BCLD, in a subject wherein the subject has been treated with a dosing regimen of a Btk inhibitor. In the following description of irreversible Btk compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. In addition, nucleic acid and amino acid sequences for Btk (e.g., human Btk) are known in the art as disclosed in, e.g., U.S. Pat. No. 6,326,469. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

The Btk inhibitor compounds described herein are selective for Btk and kinases having a cysteine residue in an amino acid sequence position of the tyrosine kinase that is homologous to the amino acid sequence position of cysteine 481 in Btk. Generally, an irreversible inhibitor compound of Btk used in the methods described herein is identified or characterized in an in vitro assay, e.g., an acellular biochemical assay or a cellular functional assay. Such assays are useful to determine an in vitro $IC_{50}$ for an irreversible Btk inhibitor compound.

For example, an acellular kinase assay can be used to determine Btk activity after incubation of the kinase in the absence or presence of a range of concentrations of a candidate irreversible Btk inhibitor compound. If the candidate compound is in fact an irreversible Btk inhibitor, Btk kinase activity will not be recovered by repeat washing with inhibitor-free medium. See, e.g., J. B. Smaill, et al. (1999), J. Med. Chem. 42(10):1803-1815. Further, covalent complex formation between Btk and a candidate irreversible Btk inhibitor is a useful indicator of irreversible inhibition of Btk that can be readily determined by a number of methods known in the art (e.g., mass spectrometry). For example, some irreversible Btk-inhibitor compounds can form a covalent bond with Cys 481 of Btk (e.g., via a Michael reaction).

Cellular functional assays for Btk inhibition include measuring one or more cellular endpoints in response to stimulating a Btk-mediated pathway in a cell line (e.g., BCR activation in Ramos cells) in the absence or presence of a range of concentrations of a candidate irreversible Btk inhibitor compound. Useful endpoints for determining a response to BCR activation include, e.g., autophosphorylation of Btk, phosphorylation of a Btk target protein (e.g., PLC-γ), and cytoplasmic calcium flux.

High throughput assays for many acellular biochemical assays (e.g., kinase assays) and cellular functional assays (e.g., calcium flux) are well known to those of ordinary skill in the art. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of irreversible Btk compounds without undue effort.

In some embodiments, the Btk inhibitor is selected from the group consisting of a small organic molecule, a macromolecule, a peptide or a non-peptide.

In some embodiments, the Btk inhibitor provided herein is a reversible or irreversible inhibitor. In certain embodiments, the Btk inhibitor is an irreversible inhibitor.

In some embodiments, the irreversible Btk inhibitor forms a covalent bond with a cysteine sidechain of a Bruton's tyrosine kinase, a Bruton's tyrosine kinase homolog, or a Btk tyrosine kinase cysteine homolog.

Irreversible Btk inhibitor compounds can use for the manufacture of a medicament for treating any of the foregoing conditions (e.g., autoimmune diseases, inflammatory diseases, allergy disorders, B-cell proliferative disorders, or thromboembolic disorders).

In some embodiments, the irreversible Btk inhibitor compound used for the methods described herein inhibits Btk or a Btk homolog kinase activity with an in vitro $IC_{50}$ of less than 10 μM. (e.g., less than 1 μM, less than 0.5 μM, less than 0.4 μM, less than 0.3 μM, less than 0.1, less than 0.08 μM, less than 0.06 μM, less than 0.05 μM, less than 0.04 μM, less than 0.03 μM, less than less than 0.02 μM, less than 0.01, less than 0.008 μM, less than 0.006 μM, less than 0.005 μM, less than 0.004 μM, less than 0.003 μM, less than less than 0.002 μM, less than 0.001, less than 0.00099 μM, less than 0.00098 μM, less than 0.00097 μM, less than 0.00096 μM, less than 0.00095 μM, less than 0.00094 μM, less than 0.00093 μM, less than 0.00092, or less than 0.00090 μM).

In one embodiment, the irreversible Btk inhibitor compound selectively and irreversibly inhibits an activated form of its target tyrosine kinase (e.g., a phosphorylated form of the tyrosine kinase). For example, activated Btk is transphosphorylated at tyrosine 551. Thus, in these embodiments the irreversible Btk inhibitor inhibits the target kinase in cells only once the target kinase is activated by the signaling events.

In other embodiments, the Btk inhibitor used in the methods describe herein has the structure of any of Formula (A), Formula (B), Formula (C), Formula (D), Formula (E), or Formula (F). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by any of Formula (A), Formula (B), Formula (C), Formula (D), Formula (E), or Formula (F), are also provided.

Formula (A) is as follows:

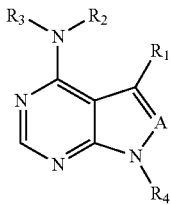

Formula (A)

wherein:

A is independently selected from N or $CR_5$;

$R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);

$R_2$ and $R_3$ are independently selected from H, lower alkyl and substituted lower alkyl;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

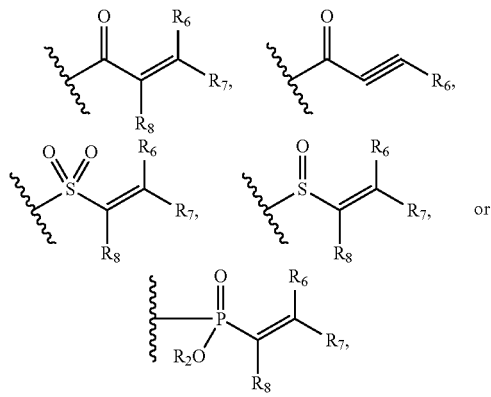

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

$R_5$ is H, halogen, -$L_6$-(substituted or unsubstituted $C_1$-$C_3$ alkyl), -$L_6$-(substituted or unsubstituted $C_2$-$C_4$ alkenyl), -$L_6$-(substituted or unsubstituted heteroaryl), or -$L_6$-(substituted or unsubstituted aryl), wherein $L_6$ is a bond, O, S, —S(=O), S(=O)$_2$, NH, C(O), —NHC(O)O, —OC(O)NH, —NHC(O), or —C(O)NH;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_9$ and $R_{10}$ can together form a 5-, 6-, 7-, or 8-membered heterocyclic ring; or each $R_{11}$ is independently selected from H, —S(=O)$_2$R$_8$, —S(=O)$_2$NH$_2$, —C(O)R$_8$, —CN, —NO$_2$, heteroaryl, or heteroalkyl; and pharmaceutically active metabolites, pharmaceutically acceptable solvates, pharmaceutically acceptable salts, or pharmaceutically acceptable prodrugs thereof.

In one aspect are compounds having the structure of Formula (A1):

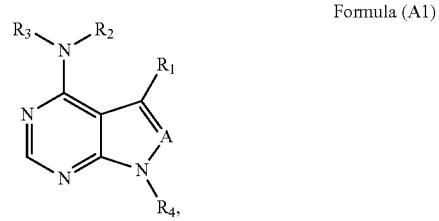

Formula (A1)

wherein

A is independently selected from N or $CR_5$;

$R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);

$R_2$ and $R_3$ are independently selected from H, lower alkyl and substituted lower alkyl;

$R_4$ is $L_3$-X-$L_4$-G, wherein, $L_3$ is optional, and when present is a bond, or an optionally substituted group selected from alkyl, heteroalkyl, aryl, heteroaryl, alkylaryl, alkylheteroaryl, or alkylheterocycloalkyl;

X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring, or an optionally substituted group selected from alkyl, heteroalkyl, aryl, heteroaryl, alkylaryl, alkylheteroaryl, or alkylheterocycloalkyl;

G is

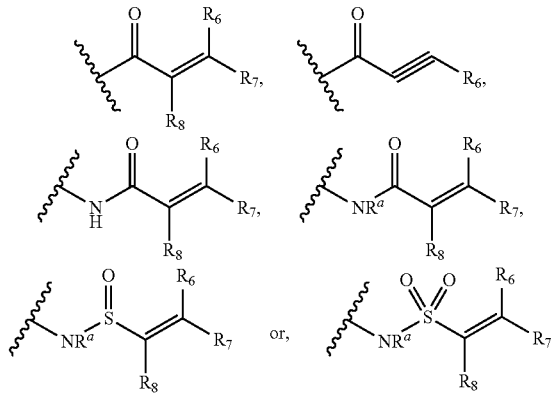

where $R^a$ is H, substituted or unsubstituted alkyl, substituted or unsubstituted cycloalkyl; and either $R_7$ and $R_8$ are H;

$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);

$R_6$ and $R_8$ are H;

$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$ cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or $R_6$ and $R_8$ taken together form a bond;

$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or $R_5$ is H, halogen, -$L_6$-(substituted or unsubstituted $C_1$-$C_3$ alkyl), -$L_6$-(substituted or unsubstituted $C_2$-$C_4$ alkenyl), -$L_6$-(substituted or unsubstituted heteroaryl), or -$L_6$-(substituted or unsubstituted aryl), wherein $L_6$ is a bond, O, S, —S(=O), S(=O)$_2$, NH, C(O), —NHC(O)O, —OC(O)NH, —NHC(O), or —C(O)NH;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_9$ and $R_{10}$ can together form a 5-, 6-, 7-, or 8-membered heterocyclic ring; or each $R_{11}$ is independently selected from H, —S(=O)$_2$R$_8$, —S(=O)$_2$NH$_2$, —C(O)R$_8$, —CN, —NO$_2$, heteroaryl, or heteroalkyl; and pharmaceutically active metabolites, pharmaceutically acceptable solvates, pharmaceutically acceptable salts, or pharmaceutically acceptable prodrugs thereof.

In another embodiment are provided pharmaceutically acceptable salts of compounds of Formula (A1). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (A1), including those in which the ester group is selected from a formate, acetate, propionate, butyrate, acrylate and ethylsuccinate.

In another embodiment are pharmaceutically acceptable carbamates of compounds of Formula (A1). In another embodiment are pharmaceutically acceptable N-acyl derivatives of compounds of Formula (A1). Examples of N-acyl groups include N-acetyl and N-ethoxycarbonyl groups.

In a further embodiment, the compound of Formula (A) has the following structure of Formula (B):

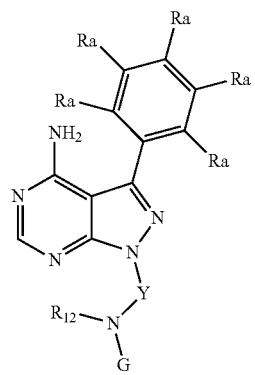

Formula (B)

wherein:

Y is alkyl or substituted alkyl, or a 4-, 5-, or 6-membered cycloalkyl ring;

each $R_a$ is independently H, halogen, —$CF_3$, —CN, —$NO_2$, OH, $NH_2$, -$L_a$-(substituted or unsubstituted alkyl), -$L_a$-(substituted or unsubstituted alkenyl), -$L_a$-(substituted or unsubstituted heteroaryl), or -$L_a$-(substituted or unsubstituted aryl), wherein $L_a$ is a bond, O, S, —S(=O), —S(=O)$_2$, NH, C(O), $CH_2$, —NHC(O)O, —NHC(O), or —C(O)NH;

G is

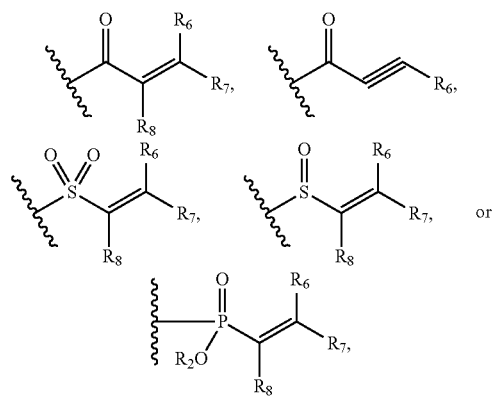

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

$R_{12}$ is H or lower alkyl; or

Y and $R_{12}$ taken together form a 4-, 5-, or 6-membered heterocyclic ring; and pharmaceutically acceptable active metabolites, pharmaceutically acceptable solvates, pharmaceutically acceptable salts, or pharmaceutically acceptable prodrugs thereof.

In further embodiments, G is selected from among

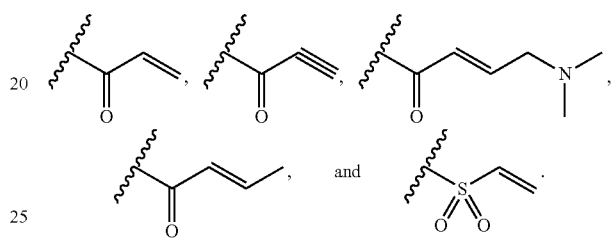

In further embodiments,

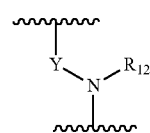

is selected from among

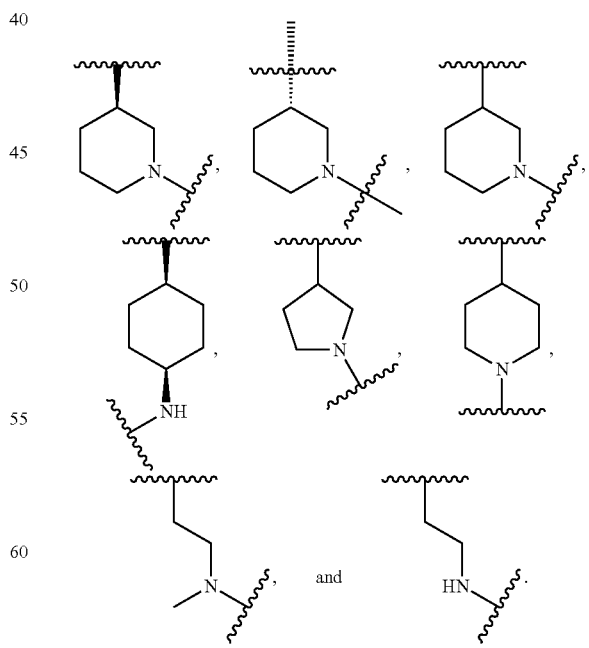

In a further embodiment, the compound of Formula (A1) has the following structure of Formula (B1):

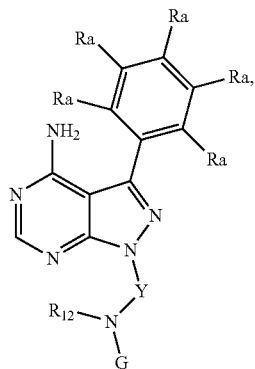

Formula (B1)

wherein:
Y is an optionally substituted group selected from among alkylene, heteroalkylene, arylene, heteroarylene, alkylenearylene, alkyleneheteroarylene, and alkyleneheterocycloalkylene;
each $R_a$ is independently H, halogen, —$CF_3$, —CN, —$NO_2$, OH, $NH_2$, -$L_a$-(substituted or unsubstituted alkyl), -$L_a$-(substituted or unsubstituted alkenyl), -$L_a$-(substituted or unsubstituted heteroaryl), or -$L_a$-(substituted or unsubstituted aryl), wherein $L_a$ is a bond, O, S, —S(=O), —S(=O)$_2$, NH, C(O), $CH_2$, —NHC(O)O, —NHC(O), or —C(O)NH;
G is

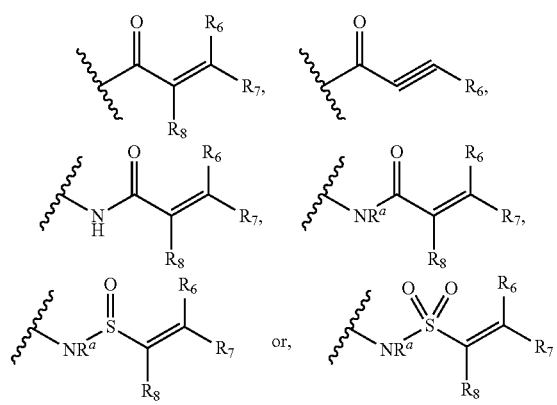

where $R^a$ is H, substituted or unsubstituted alkyl, substituted or unsubstituted cycloalkyl; and either
$R_7$ and $R_8$ are H;
$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);
$R_6$ and $R_8$ are H;
$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or
$R_6$ and $R_8$ taken together form a bond;
$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);
$R_{12}$ is H or lower alkyl; or
Y and $R_{12}$ taken together form a 4-, 5-, or 6-membered heterocyclic ring; and
pharmaceutically acceptable active metabolites, pharmaceutically acceptable solvates, pharmaceutically acceptable salts, or pharmaceutically acceptable prodrugs thereof.

In further embodiments, G is selected from among

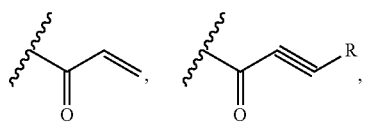

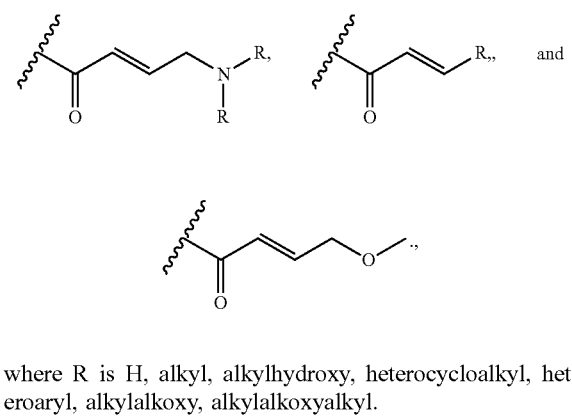

where R is H, alkyl, alkylhydroxy, heterocycloalkyl, heteroaryl, alkylalkoxy, alkylalkoxyalkyl.

In further embodiments,

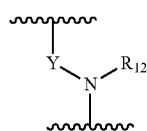

is selected from among

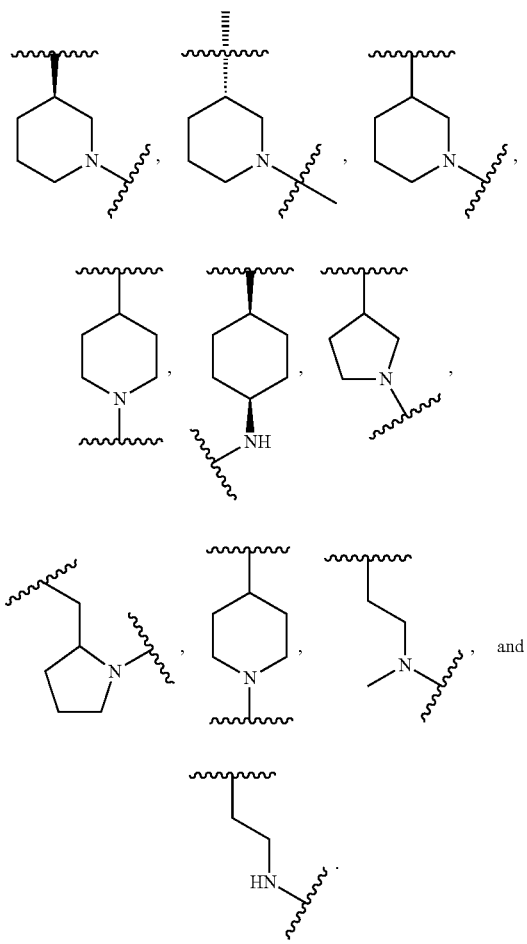

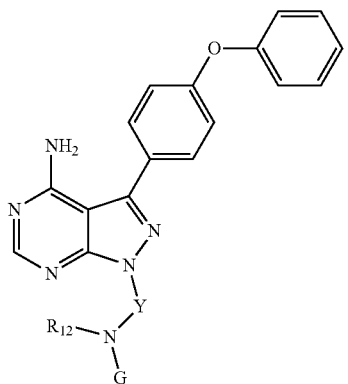

In a further embodiment, the compound of Formula (B) has the following structure of Formula (C):

Formula (C)

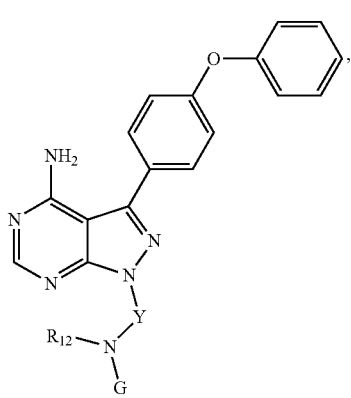

Y is alkyl or substituted alkyl, or a 4-, 5-, or 6-membered cycloalkyl ring;

$R_{12}$ is H or lower alkyl; or

Y and $R_{12}$ taken together form a 4-, 5-, or 6-membered heterocyclic ring;

G is

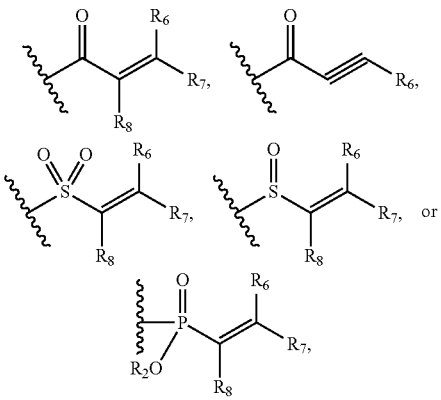

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl; and pharmaceutically acceptable active metabolites, pharmaceutically acceptable solvates, pharmaceutically acceptable salts, or pharmaceutically acceptable prodrugs thereof.

In further embodiment, the compound of Formula (B1) has the following structure of Formula (C1):

Formula (C1)

Y is an optionally substituted group selected from among alkyl, heteroalkyl, aryl, heteroaryl, alkylaryl, alkylheteroaryl, and alkylheterocycloalkyl;

$R_{12}$ is H or lower alkyl; or

Y and $R_{12}$ taken together form a 4-, 5-, or 6-membered heterocyclic ring;

G is

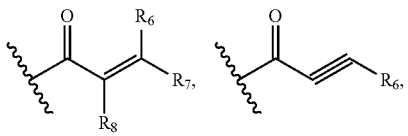

-continued

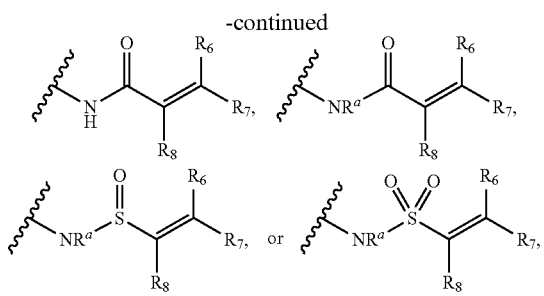

where $R^a$ is H, substituted or unsubstituted alkyl, substituted or unsubstituted cycloalkyl; and either $R_7$ and $R_8$ are H;
$R_6$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);

$R_6$ and $R_8$ are H;
$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or $R_6$ and $R_8$ taken together form a bond;
$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$ cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); and pharmaceutically acceptable active metabolites, pharmaceutically acceptable solvates, pharmaceutically acceptable salts, or pharmaceutically acceptable prodrugs thereof.

In a further or alternative embodiment, the "G" group of any of Formula (A1), Formula (B1), or Formula (C1) is any group that is used to tailor the physical and biological properties of the molecule. Such tailoring/modifications are achieved using groups which modulate Michael acceptor chemical reactivity, acidity, basicity, lipophilicity, solubility and other physical properties of the molecule. The physical and biological properties modulated by such modifications to G include, by way of example only, enhancing chemical reactivity of Michael acceptor group, solubility, in vivo absorption, and in vivo metabolism. In addition, in vivo metabolism includes, by way of example only, controlling in vivo PK properties, off-target activities, potential toxicities associated with cypP450 interactions, drug-drug interactions, and the like. Further, modifications to G allow for the tailoring of the in vivo efficacy of the compound through the modulation of, by way of example, specific and non-specific protein binding to plasma proteins and lipids and tissue distribution in vivo.

In another embodiment, provided herein is a compound of Formula (D). Formula (D) is as follows:

Formula (D)

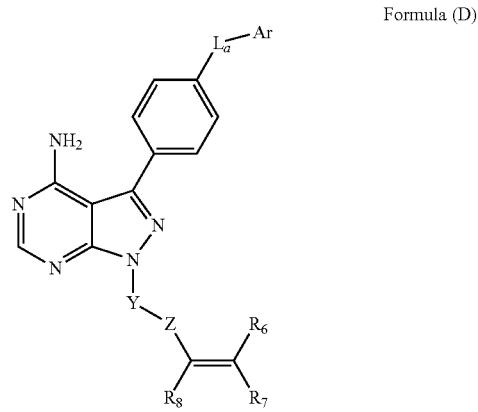

wherein:

$L_a$ is $CH_2$, O, NH or S;

Ar is a substituted or unsubstituted aryl, or a substituted or unsubstituted heteroaryl;

Y is an optionally substituted group selected from among alkyl, heteroalkyl, cycloalkyl, heterocycloalkyl, aryl, and heteroaryl;

Z is C(=O), OC(=O), NHC(=O), C(=S), S(=O)$_x$, OS(=O)$_x$, NHS(=O)$_x$, where x is 1 or 2;

$R_6$, $R_7$, and $R_8$ are each independently selected from among H, substituted or unsubstituted $C_1$-$C_4$alkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl, substituted or unsubstituted heteroaryl, substituted or unsubstituted $C_1$-$C_4$alkyl(aryl), substituted or unsubstituted $C_1$-$C_4$alkyl(heteroaryl), substituted or unsubstituted $C_1$-$C_4$alkyl($C_3$-$C_8$cycloalkyl), or substituted or unsubstituted $C_1$-$C_4$alkyl($C_2$-$C_8$heterocycloalkyl); or $R_7$ and $R_8$ taken together form a bond; and pharmaceutically active metabolites, or pharmaceutically acceptable solvates, pharmaceutically acceptable salts, or pharmaceutically acceptable prodrugs thereof.

In one embodiment are compounds having the structure of Formula (D1):

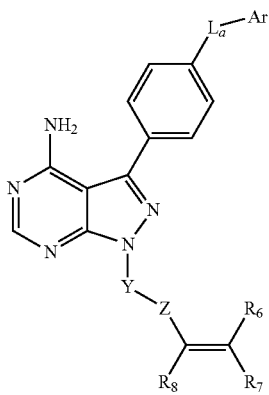

Formula (D1)

wherein
L$_a$ is CH$_2$, O, NH or S;
Ar is an optionally substituted aromatic carbocycle or an aromatic heterocycle;
Y is an optionally substituted group selected from among alkylene, heteroalkylene, arylene, heteroarylene, alkylenearylene, alkyleneheteroarylene, and alkyleneheterocycloalkylene, or combination thereof;
Z is C(=O), NHC(=O), NR$^a$C(=O), NR$^a$S(=O)$_x$, where x is 1 or 2, and R$^a$ is H, substituted or unsubstituted alkyl, substituted or unsubstituted cycloalkyl; and either
R$_7$ and R$_8$ are H;
 R$_6$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl);
R$_6$ and R$_8$ are H;
 R$_7$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl); or
R$_6$ and R$_8$ taken together form a bond;
 R$_7$ is H, substituted or unsubstituted C$_1$-C$_4$alkyl, substituted or unsubstituted C$_1$-C$_4$heteroalkyl, C$_1$-C$_8$alkylaminoalkyl, C$_1$-C$_8$hydroxyalkylaminoalkyl, C$_1$-C$_8$alkoxyalkylaminoalkyl, substituted or unsubstituted C$_3$-C$_6$cycloalkyl, substituted or unsubstituted C$_1$-C$_8$alkylC$_3$-C$_6$cycloalkyl, substituted or unsubstituted aryl, substituted or unsubstituted C$_2$-C$_8$heterocycloalkyl, substituted or unsubstituted heteroaryl, C$_1$-C$_4$alkyl(aryl), C$_1$-C$_4$alkyl(heteroaryl), C$_1$-C$_8$alkylethers, C$_1$-C$_8$alkylamides, or C$_1$-C$_4$alkyl(C$_2$-C$_8$heterocycloalkyl);
or combinations thereof; and
pharmaceutically active metabolites, or pharmaceutically acceptable solvates, pharmaceutically acceptable salts, or pharmaceutically acceptable prodrugs thereof.

In another embodiment are provided pharmaceutically acceptable salts of compounds of Formula (D1). By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is an cation, such as sodium, lithium, potassium, calcium, magnesium, ammonium, and quaternary ammonium (substituted with at least one organic moiety) cations.

In another embodiment are pharmaceutically acceptable esters of compounds of Formula (D1), including those in which the ester group is selected from a formate, acetate, propionate, butyrate, acrylate and ethylsuccinate.

In another embodiment are pharmaceutically acceptable carbamates of compounds of Formula (D1). In another embodiment are pharmaceutically acceptable N-acyl derivatives of compounds of Formula (D1). Examples of N-acyl groups include N-acetyl and N-ethoxycarbonyl groups.

In a further embodiment, L$_a$ is O.
In a further embodiment, Ar is phenyl.
In a further embodiment, Z is C(=O), NHC(=O), or NCH$_3$C(=O).
In a further embodiment, each of R$_1$, R$_2$, and R$_3$ is H.
In one embodiment is a compound of Formula (D1) wherein R$_6$, R$_7$, and R$_8$ are all H.
In another embodiment, R$_6$, R$_7$, and R$_8$ are not all H.
For any and all of the embodiments, substituents can be selected from among from a subset of the listed alternatives. For example, in some embodiments, L$_a$ is CH$_2$, O, or NH. In other embodiments, L$_a$ is O or NH. In yet other embodiments, L$_a$ is O.
In some embodiments, Ar is a substituted or unsubstituted aryl. In yet other embodiments, Ar is a 6-membered aryl. In some other embodiments, Ar is phenyl.
In some embodiments, x is 2. In yet other embodiments, Z is C(=O), OC(=O), NHC(=O), S(=O)$_x$, OS(=O)$_x$, or NHS(=O)$_x$. In some other embodiments, Z is C(=O), NHC(=O), or S(=O)$_2$.
In some embodiments, R$_7$ and R$_8$ are independently selected from among H, unsubstituted C$_1$-C$_4$ alkyl, substituted C$_1$-C$_4$alkyl, unsubstituted C$_1$-C$_4$heteroalkyl, and substituted C$_1$-C$_4$heteroalkyl; or R$_7$ and R$_8$ taken together form a bond. In yet other embodiments, each of R$_7$ and R$_8$ is H; or R$_7$ and R$_8$ taken together form a bond.

In some embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_2$alkyl-N($C_1$-$C_3$alkyl)$_2$, substituted or unsubstituted aryl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In some other embodiments, $R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_2$alkyl-N($C_1$-$C_3$alkyl)$_2$, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl). In yet other embodiments, $R_6$ is H, substituted or unsubstituted $C_1$-$C_4$alkyl, —CH$_2$—O—($C_1$-$C_3$alkyl), —CH$_2$—N($C_1$-$C_3$alkyl)$_2$, $C_1$-$C_4$alkyl(phenyl), or $C_1$-$C_4$alkyl(5- or 6-membered heteroaryl). In some embodiments, $R_6$ is H, substituted or unsubstituted $C_1$-$C_4$alkyl, —CH$_2$—O—($C_1$-$C_3$alkyl), —CH$_2$—N($C_1$-$C_3$alkyl)$_2$, $C_1$-$C_4$alkyl(phenyl), or $C_1$-$C_4$alkyl(5- or 6-membered heteroaryl containing 1 or 2 N atoms), or $C_1$-$C_4$alkyl(5- or 6-membered heterocycloalkyl containing 1 or 2 N atoms).

In some embodiments, Y is an optionally substituted group selected from among alkyl, heteroalkyl, cycloalkyl, and heterocycloalkyl. In other embodiments, Y is an optionally substituted group selected from among $C_1$-$C_6$alkyl, $C_1$-$C_6$heteroalkyl, 4-, 5-, 6- or 7-membered cycloalkyl, and 4-, 5-, 6- or 7-membered heterocycloalkyl. In yet other embodiments, Y is an optionally substituted group selected from among $C_1$-$C_6$alkyl, $C_1$-$C_6$heteroalkyl, 5-, or 6-membered cycloalkyl, and 5-, or 6-membered heterocycloalkyl containing 1 or 2 N atoms. In some other embodiments, Y is a 5-, or 6-membered cycloalkyl, or a 5-, or 6-membered heterocycloalkyl containing 1 or 2 N atoms.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In one embodiment the irreversible inhibitor of a kinase has the structure of Formula (E):

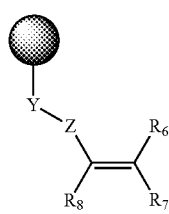

Formula (E)

wherein:
wherein

is a moiety that binds to the active site of a kinase, including a tyrosine kinase, further including a Btk kinase cysteine homolog;

Y is an optionally substituted group selected from among alkylene, heteroalkylene, arylene, heteroarylene, heterocycloalkylene, cycloalkylene, alkylenearylene, alkyleneheteroarylene, alkylenecycloalkylene, and alkyleneheterocycloalkylene;

Z is C(=O), OC(=O), NHC(=O), NCH$_3$C(=O), C(=S), S(=O)$_x$, OS(=O)$_x$, NHS(=O)$_x$, where x is 1 or 2;

$R_6$, $R_7$, and $R_8$ are each independently selected from among H, substituted or unsubstituted $C_1$-$C_4$alkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl, substituted or unsubstituted heteroaryl, substituted or unsubstituted $C_1$-$C_4$alkyl(aryl), substituted or unsubstituted $C_1$-$C_4$alkyl(heteroaryl), substituted or unsubstituted $C_1$-$C_4$alkyl($C_3$-$C_8$cycloalkyl), or substituted or unsubstituted $C_1$-$C_4$alkyl($C_2$-$C_8$heterocycloalkyl); or $R_7$ and $R_8$ taken together form a bond; and pharmaceutically active metabolites, or pharmaceutically acceptable solvates, pharmaceutically acceptable salts, or pharmaceutically acceptable prodrugs thereof.

In some embodiments,

is a substituted fused biaryl moiety selected from

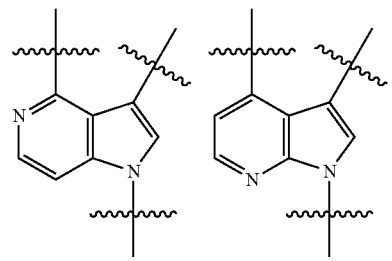

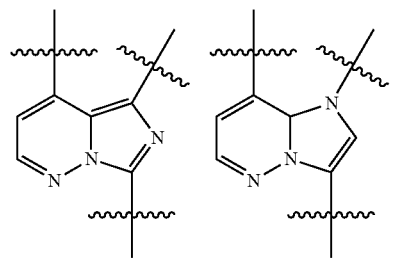

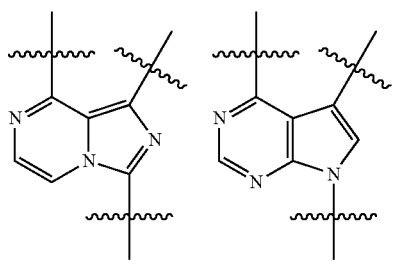

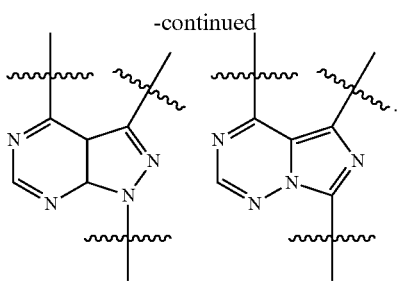

In one aspect, provided herein are compounds of Formula (F). Formula (F) is as follows:

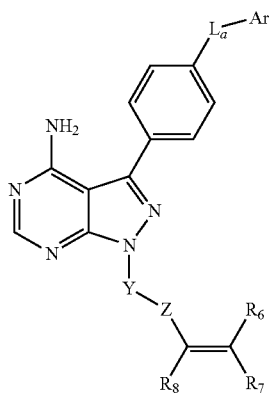

Formula (F)

wherein
$L_a$ is $CH_2$, O, NH or S;
Ar is a substituted or unsubstituted aryl, or a substituted or unsubstituted heteroaryl; and either
(a) Y is an optionally substituted group selected from among alkylene, heteroalkylene, arylene, heteroarylene, alkylenearylene, alkyleneheteroarylene, alkylenecycloalkylene and alkyleneheterocycloalkylene;
Z is C(=O), NHC(=O), $NR^aC$(=O), $NR^aS$(=O)$_x$, where x is 1 or 2, and $R^a$ is H, substituted or unsubstituted alkyl, substituted or unsubstituted cycloalkyl; and either
(i) $R_6$, $R_7$, and $R_8$ are each independently selected from among H, substituted or unsubstituted $C_1$-$C_4$alkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl, substituted or unsubstituted heteroaryl, substituted or unsubstituted $C_1$-$C_4$alkyl(aryl), substituted or unsubstituted $C_1$-$C_4$alkyl(heteroaryl), substituted or unsubstituted $C_1$-$C_4$alkyl($C_3$-$C_8$cycloalkyl), or substituted or unsubstituted $C_1$-$C_4$alkyl($C_2$-$C_8$heterocycloalkyl);
(ii) $R_6$ and $R_8$ are H;
$R_7$ is H, substituted or unsubstituted $C_1$-$C_4$alkyl, substituted or unsubstituted $C_1$-$C_4$heteroalkyl, $C_1$-$C_8$alkylaminoalkyl, $C_1$-$C_8$ hydroxyalkylaminoalkyl, $C_1$-$C_8$ alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or
(iii) $R_7$ and $R_8$ taken together form a bond;
$R_6$ is selected from among H, substituted or unsubstituted $C_1$-$C_4$alkyl, substituted or unsubstituted $C_1$-$C_4$heteroalkyl, substituted or unsubstituted $C_3$-$C_6$cycloalkyl, substituted or unsubstituted $C_2$-$C_6$heterocycloalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl, substituted or unsubstituted heteroaryl, substituted or unsubstituted $C_1$-$C_4$alkyl(aryl), substituted or unsubstituted $C_1$-$C_4$alkyl(heteroaryl), substituted or unsubstituted $C_1$-$C_4$alkyl($C_3$-$C_8$cycloalkyl), or substituted or unsubstituted $C_1$-$C_4$alkyl($C_2$-$C_8$heterocycloalkyl) or
(b) Y is an optionally substituted group selected from cycloalkylene or heterocycloalkylene;
Z is C(=O), NHC(=O), $NR^aC$(=O), $NR^aS$(=O)$_x$, where x is 1 or 2, and $R^a$ is H, substituted or unsubstituted alkyl, substituted or unsubstituted cycloalkyl; and either
(i) $R_7$ and $R_8$ are H;
$R_6$ is substituted or unsubstituted $C_1$-$C_4$alkyl, substituted or unsubstituted $C_1$-$C_4$heteroalkyl, $C_1$-$C_8$alkylaminoalkyl, $C_1$-$C_8$ hydroxyalkylaminoalkyl, $C_1$-$C_8$ alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl);
(ii) $R_6$ and $R_8$ are H;
$R_7$ is substituted or unsubstituted $C_1$-$C_4$alkyl, substituted or unsubstituted $C_1$-$C_4$heteroalkyl, $C_1$-$C_8$alkylaminoalkyl, $C_1$-$C_8$ hydroxyalkylaminoalkyl, $C_1$-$C_8$ alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); or
(iii) $R_7$ and $R_8$ taken together form a bond;
$R_6$ is substituted or unsubstituted $C_1$-$C_4$alkyl, substituted or unsubstituted $C_1$-$C_4$heteroalkyl, $C_1$-$C_8$alkylaminoalkyl, $C_1$-$C_8$hydroxyalkylaminoalkyl, $C_1$-$C_8$alkoxyalkylaminoalkyl, substituted or unsubstituted $C_3$-$C_6$cycloalkyl, substituted or unsubstituted $C_1$-$C_8$alkyl$C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_8$alkylethers, $C_1$-$C_8$alkylamides, or $C_1$-$C_4$alkyl($C_2$-$C_8$heterocycloalkyl); and pharmaceutically active metabolites, or pharmaceutically acceptable solvates, pharmaceutically acceptable salts, or pharmaceutically acceptable prodrugs thereof Further embodiments of compounds of Formula (A), Formula (B), Formula (C), Formula (D), include, but are not limited to, compounds selected from the group consisting of:

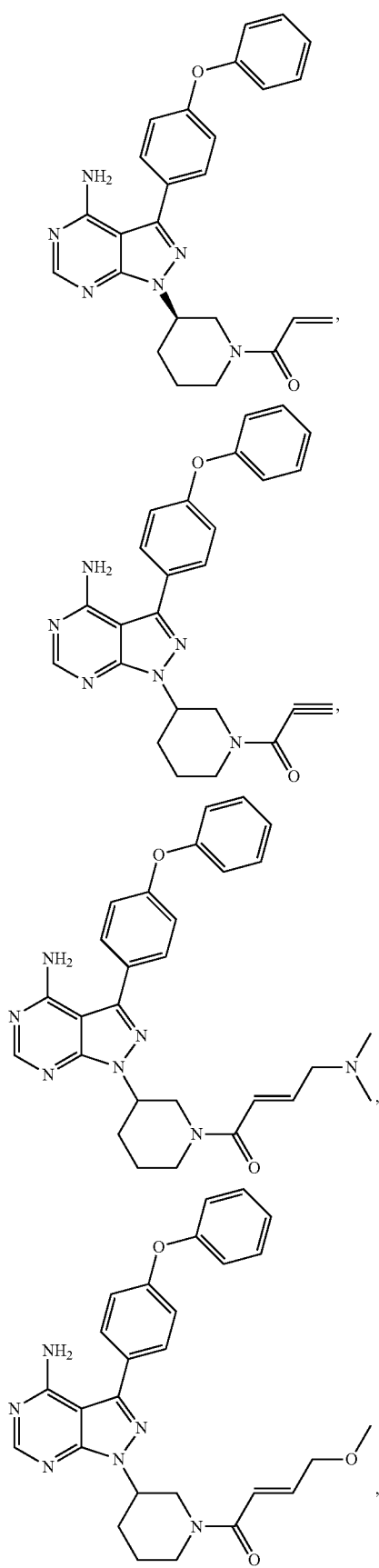
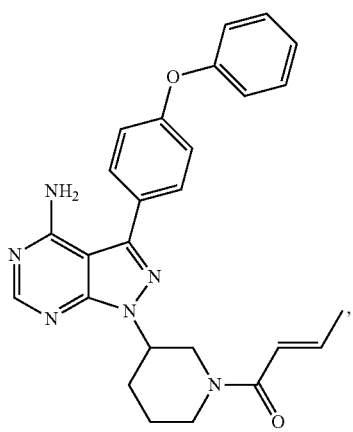
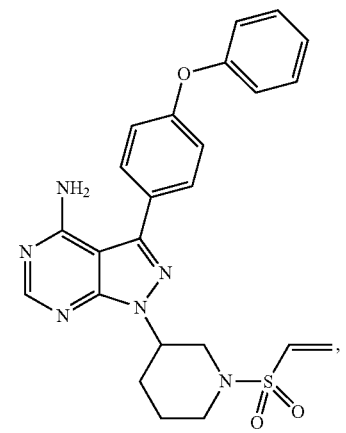
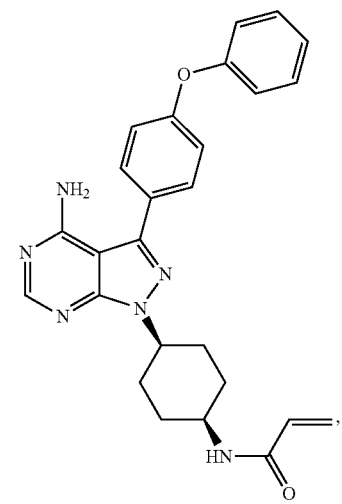

-continued
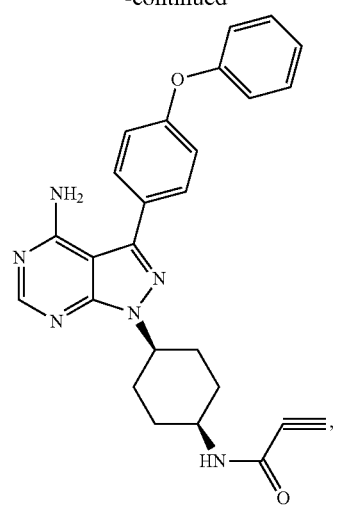
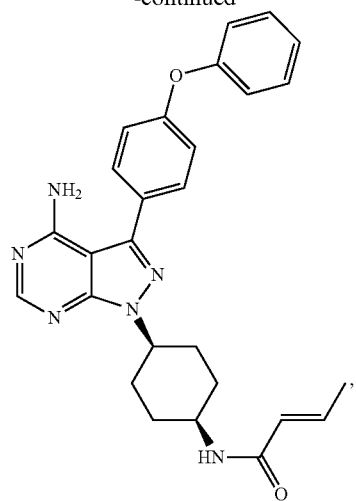
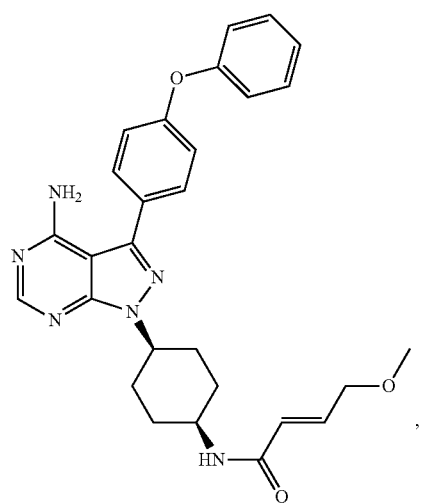
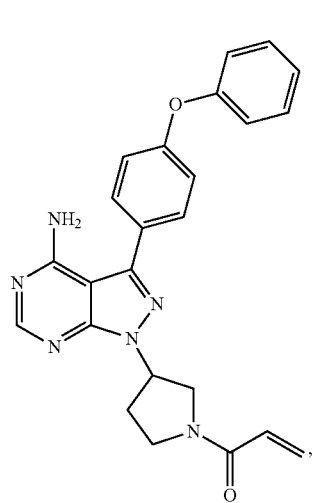

| 69 | 70 |
|---|---|
| -continued | -continued |
| 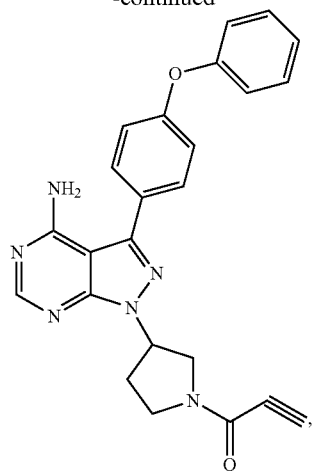 | 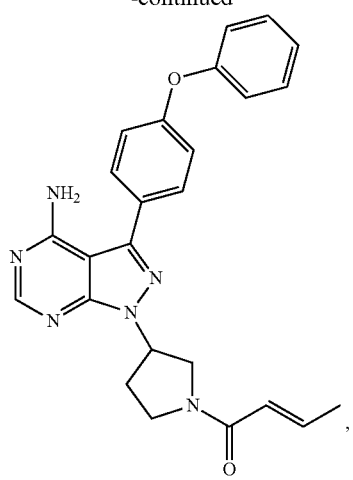 |
| 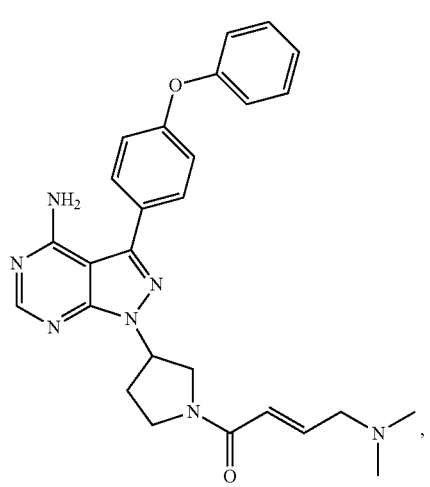 | 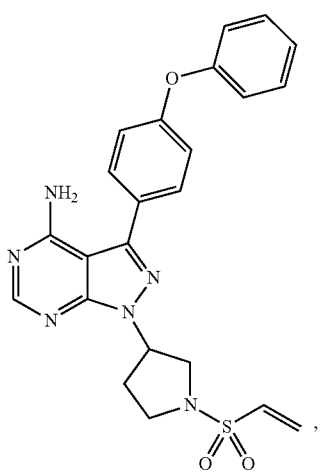 |
| 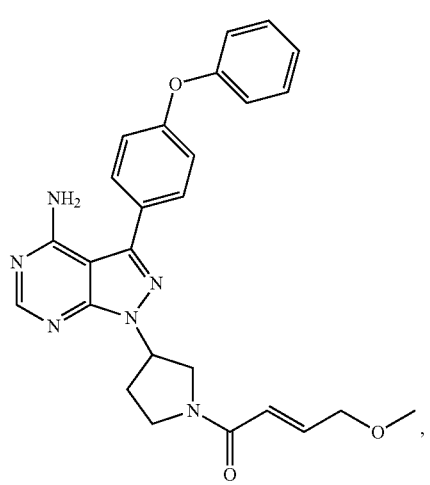 | 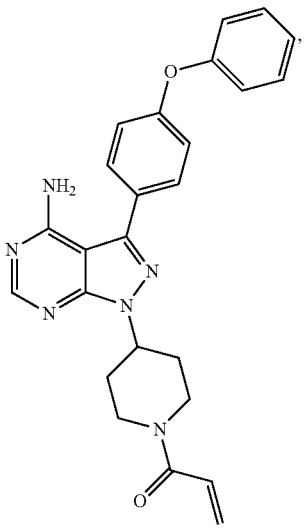 |

71
-continued
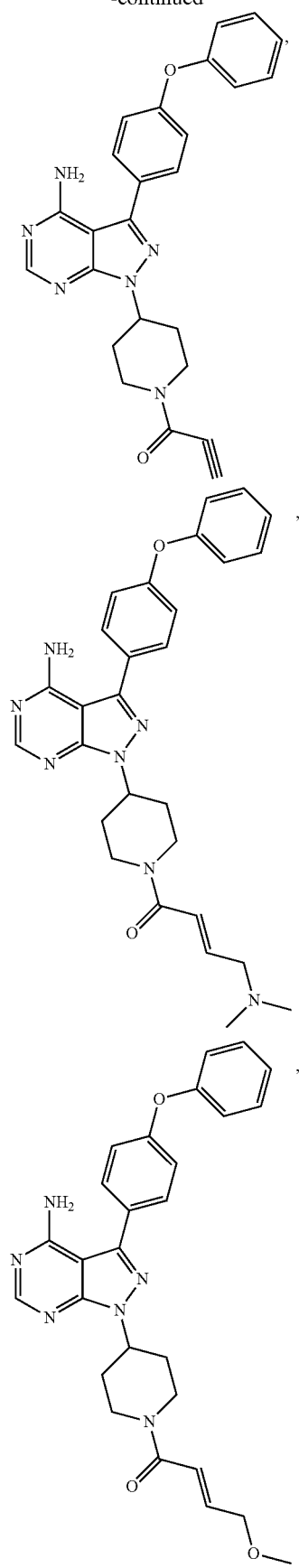
72
-continued
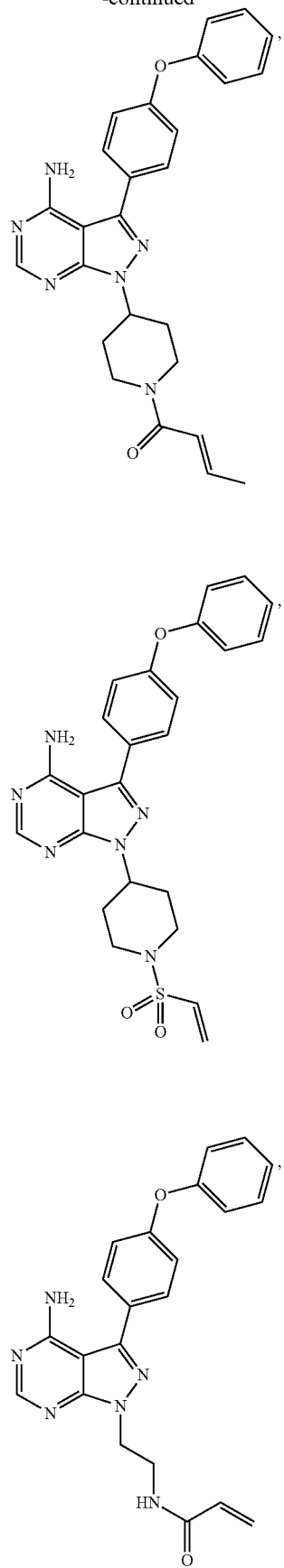

73
-continued
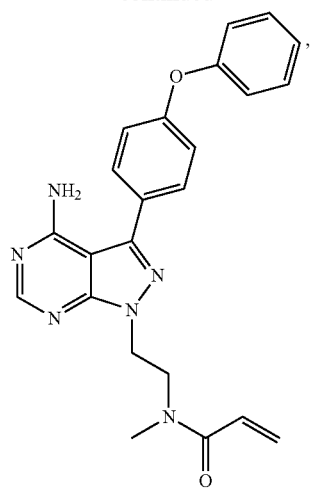
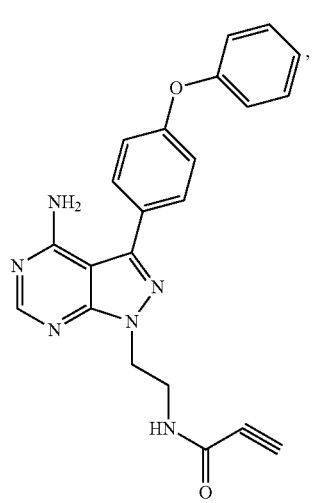
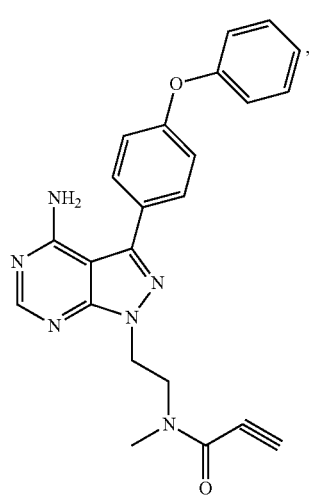
74
-continued
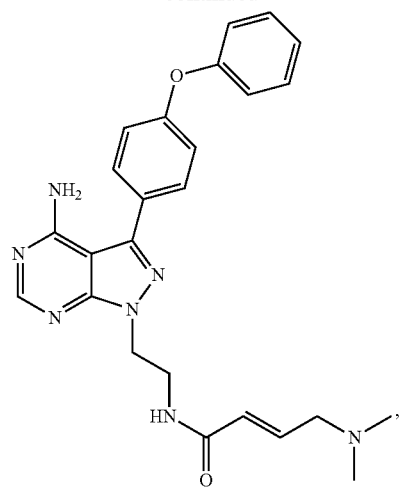
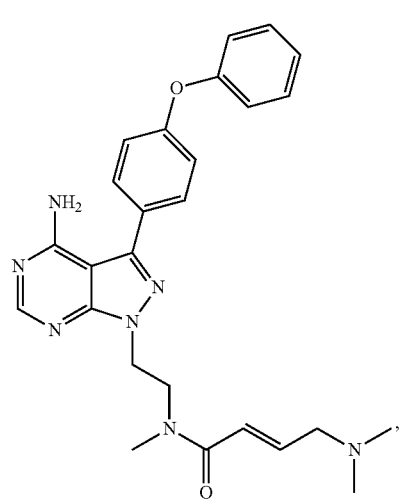
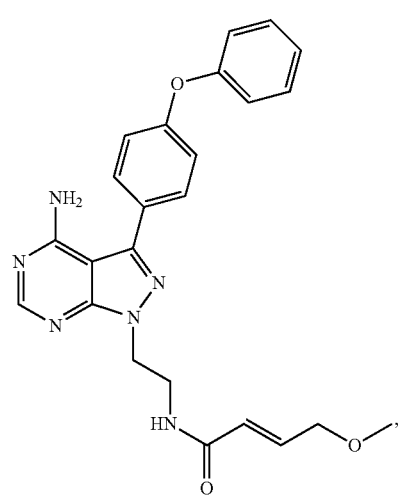

75
-continued
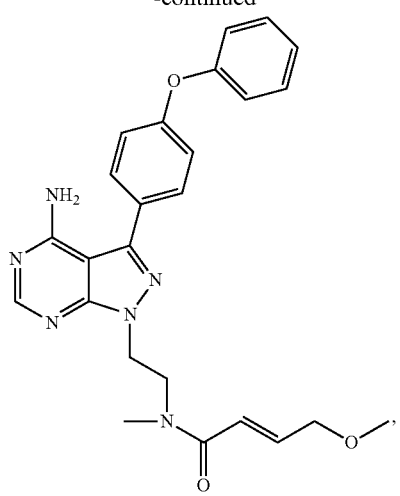
In still another embodiment, compounds provided herein are selected from among:
76
-continued
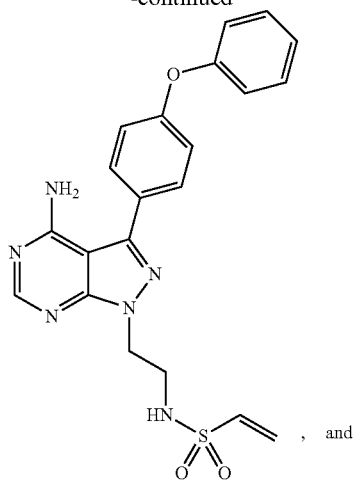
, and
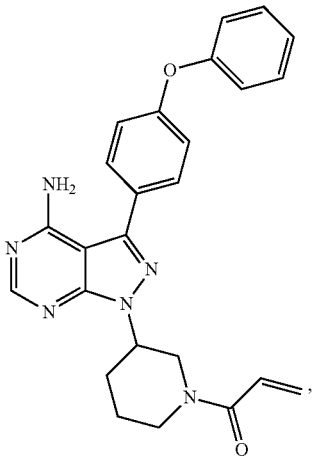
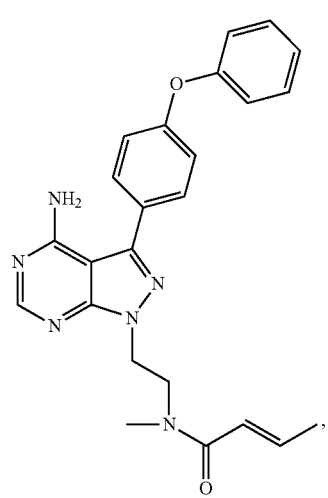

77
-continued
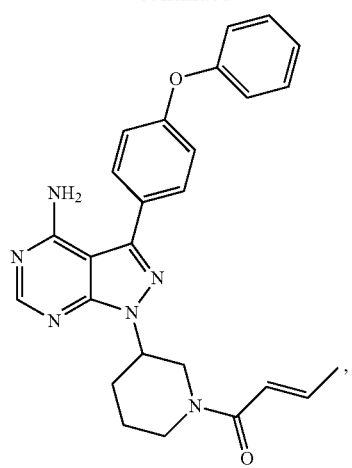
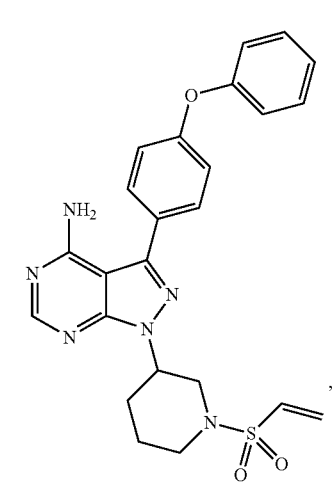
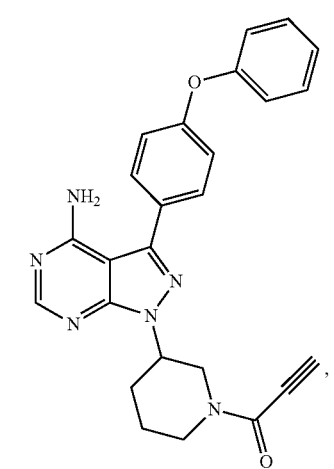
78
-continued
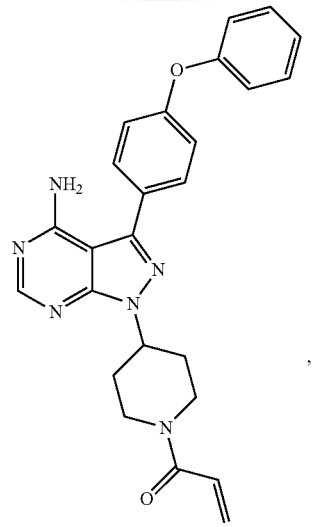
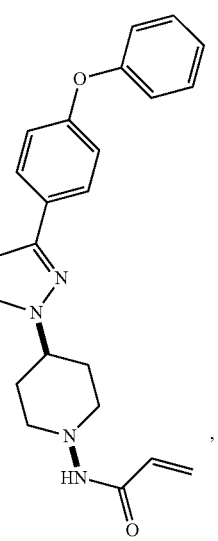
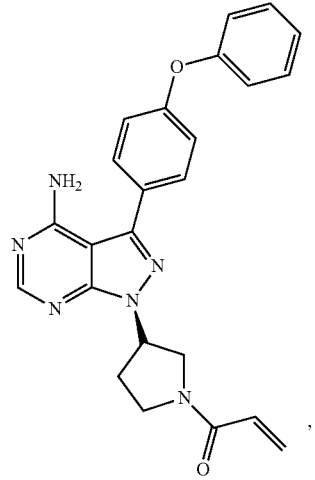

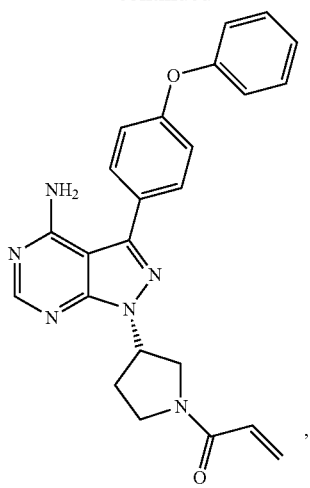

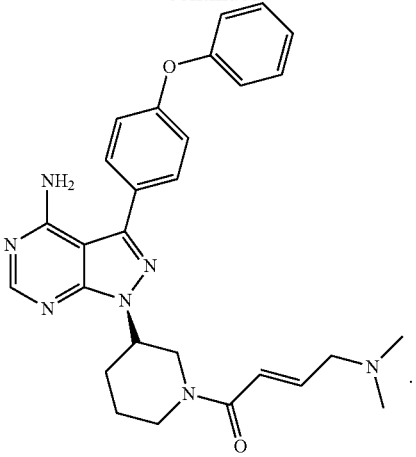

In one aspect, provided herein is a compound selected from among: 1-(3-(4-amino-3-(4-phenoxyphenyl)-1H-pyrazolo[3,4-d]pyrimidin-1-yl)piperidin-1-yl)prop-2-en-1-one (Compound 4); (E)-1-(3-(4-amino-3-(4-phenoxyphenyl)-1H-pyrazolo[3,4-d]pyrimidin-1-yl)piperidin-1-yl)but-2-en-1-one (Compound 5); 1-(3-(4-amino-3-(4-phenoxyphenyl)-1H-pyrazolo[3,4-d]pyrimidin-1-yl)piperidin-1-yl) sulfonylethene (Compound 6); 1-(3-(4-amino-3-(4-phenoxyphenyl)-1H-pyrazolo[3,4-d]pyrimidin-1-yl) piperidin-1-yl)prop-2-yn-1-one (Compound 8); 1-(4-(4-amino-3-(4-phenoxyphenyl)-1H-pyrazolo[3,4-d]pyrimidin-1-yl)piperidin-1-yl)prop-2-en-1-one (Compound 9); N-((1s,4s)-4-(4-amino-3-(4-phenoxyphenyl)-1H-pyrazolo[3,4-d]pyrimidin-1-yl)cyclohexyl)acrylamide (Compound 10); 1-((R)-3-(4-amino-3-(4-phenoxyphenyl)-1H-pyrazolo[3,4-d]pyrimidin-1-yl)pyrrolidin-1-yl)prop-2-en-1-one (Compound 11); 1-((S)-3-(4-amino-3-(4-phenoxyphenyl)-1H-pyrazolo[3,4-d]pyrimidin-1-yl)pyrrolidin-1-yl)prop-2-en-1-one (Compound 12); 1-((R)-3-(4-amino-3-(4-phenoxyphenyl)-1H-pyrazolo[3,4-d]pyrimidin-1-yl) piperidin-1-yl)prop-2-en-1-one (Compound 13); 1-((S)-3-(4-amino-3-(4-phenoxyphenyl)-1H-pyrazolo[3,4-d] pyrimidin-1-yl)piperidin-1-yl)prop-2-en-1-one (Compound 14); and (E)-1-(3-(4-amino-3-(4-phenoxyphenyl)-1H-pyrazolo[3,4-d]pyrimidin-1-yl)piperidin-1-yl)-4-(dimethylamino)but-2-en-1-one (Compound 15).

In some embodiments, the Btk inhibitor is (R)-1-(3-(4-amino-3-(4-phenoxyphenyl)-1H-pyrazolo[3,4-d]pyrimidin-1-yl)piperidin-1-yl)prop-2-en-1-one.

In one embodiment, the Btk inhibitor is α-cyano-β-hydroxy-β-methyl-N-(2,5-dibromophenyl)propenamide (LFM-A13), AVL-101, 4-tert-butyl-N-(3-(8-(phenylamino)imidazo[1,2-a]pyrazin-6-yl)phenyl)benzamide, 5-(3-amino-2-methylphenyl)-1-methyl-3-(4-(morpholine-4-carbonyl)phenylamino)pyrazin-2(1H)-one, N-(2-methyl-3-(4-methyl-6-(4-(morpholine-4-carbonyl)phenylamino)-5-oxo-4,5-dihydropyrazin-2-yl)phenyl)acetamide, 4-tert-butyl-N-(2-methyl-3-(4-methyl-6-(4-(morpholine-4-carbonyl)phenylamino)-5-oxo-4,5-dihydropyrazin-2-yl)phenyl)benzamide, 5-(3-(4-tert-butylbenzylamino)-2-methylphenyl)-1-methyl-3-(4-(morpholine-4-carbonyl)phenylamino)pyrazin-2(1H)-one, 5-(3-(3-tert-butylbenzylamino)-2-methylphenyl)-1-methyl-3-(4-(morpholine-4-carbonyl)phenylamino)pyrazin-2(1H)-one, 3-tert-butyl-N-(2-methyl-3-(4-methyl-6-(4-(morpholine-4-carbonyl)phenylamino)-5-oxo-4,5-dihydropyrazin-2-yl)phenyl)benzamide, 6-tert-butyl-N-(2-methyl-3-(4-methyl-6-

(4-(morpholine-4-carbonyl)phenylamino)-5-oxo-4,5-dihydropyrazin-2-yl)phenyl)nicotinamide, and terreic acid.

Throughout the specification, groups and substituents thereof can be chosen by one skilled in the field to provide stable moieties and compounds.

In certain embodiments, any of the Btk inhibitors and/or the second agent provided herein for the invention methods is included in a pharmaceutical composition comprising: i) a physiologically acceptable carrier, diluent, and/or excipient.

In some embodiments, the Btk inhibitor of the invention methods is administered at a dose of from about 1.25 mg/kg/day to about 12.5 mg/kg/day. In certain embodiments, the Btk inhibitor is administered at a dose selected from the group consisting of about 1.25 mg/kg/day, about 2.5 mg/kg/day, about 5 mg/kg/day, about 8.3 mg/kg/day, or about 12.5 mg/kg/day.

In some embodiments provide the biomarkers in accordance with the practice of the present invention is selected from ZAP-70, CD5, t(14;18), CD38, β-2 microglobulin, p53 mutational status, ATM mutational status, chromosome 17p deletion, chromosome 11q deletion, surface or cytoplasmic immunoglobulin, CD138, CD25, 6q deletion, CD19, CD20, CD22, CD11c, CD 103, chromosome 7q deletion, and $V_H$ mutational status.

In some embodiments, determining the expression or presence of one or more biomarkers from one or more subpopulation of lymphocytes is of a combination of biomarkers. In certain embodiments, the combination of biomarkers is CD19 and CD5 or CD20 and CD5.

In other embodiments, the second agent is administered at a dose of from about 1.25 mg/kg/day to about 12.5 mg/kg/day. In certain embodiments, the second agent is administered at a dose selected from the group consisting of about 1.25 mg/kg/day, about 2.5 mg/kg/day, about 5 mg/kg/day, about 8.3 mg/kg/day, or about 12.5 mg/kg/day. The dosage of the second agent is based on the determined expression or presence of one or more biomarkers from one or more subpopulation of lymphocytes. A person skilled in the art such as a physician can readily determine the suitable regimen (e.g. dosage of the second agent) based on the diagnostic results.

In other embodiments, the present invention provides methods for treating a cancer comprising determining the expression or presence of one or more biomarkers from one or more subpopulation of lymphocytes in a subject that has received a dose of a Btk inhibitor; and administering a second agent based on the determined expression profile.

In other embodiments, the present invention also provides methods for treating a cancer comprising administering a Btk inhibitor sufficient to result in an increase or appearance in the blood of a subpopulation of lymphocytes defined by immunophenotyping; and administering a second agent once the increase or appearance in the blood of the subpopulation of lymphocytes is determined.

In some embodiments, the subject is a human.

In some embodiments, the Btk inhibitors are orally administered.

In any of the aforementioned aspects are further embodiments in which administration is enteral, parenteral, or both, and wherein (a) the effective amount of the Btk inhibitor is systemically administered to the mammal; (b) the effective amount of the Btk inhibitor is administered orally to the mammal; (c) the effective amount of the Btk inhibitor is intravenously administered to the mammal; (d) the effective amount of the Btk inhibitor administered by inhalation; (e) the effective amount of the Btk inhibitor is administered by nasal administration; or (f) the effective amount of the Btk inhibitor is administered by injection to the mammal; (g) the effective amount of the Btk inhibitor is administered topically (dermal) to the mammal; (h) the effective amount of the Btk inhibitor is administered by ophthalmic administration; or (i) the effective amount of the Btk inhibitor is administered rectally to the mammal.

In any of the aforementioned aspects are further embodiments comprising single administrations of the effective amount of the Btk inhibitor, including further embodiments in which (i) the Btk inhibitor is administered once; (ii) the Btk inhibitor is administered to the mammal multiple times over the span of one day; (iii) continually; or (iv) continuously.

In any of the aforementioned aspects are further embodiments comprising multiple administrations of the effective amount of the Btk inhibitor, including further embodiments in which (i) the Btk inhibitor is administered in a single dose; (ii) the time between multiple administrations is every 6 hours; (iii) the Btk inhibitor is administered to the mammal every 8 hours. In further or alternative embodiments, the method comprises a drug holiday, wherein the administration of the Btk inhibitor is temporarily suspended or the dose of the Btk inhibitor being administered is temporarily reduced; at the end of the drug holiday, dosing of the Btk inhibitor is resumed. The length of the drug holiday can vary from 2 days to 1 year.

In any of the aforementioned aspects are further embodiments in which administration is enteral, parenteral, or both, and wherein (a) the effective amount of the second agent is systemically administered to the mammal; (b) the effective amount of the second agent is administered orally to the mammal; (c) the effective amount of the second agent is intravenously administered to the mammal; (d) the effective amount of the second agent administered by inhalation; (e) the effective amount of the second agent is administered by nasal administration; or (f) the effective amount of the second agent is administered by injection to the mammal; (g) the effective amount of the second agent is administered topically (dermal) to the mammal; (h) the effective amount of the second agent is administered by ophthalmic administration; or (i) the effective amount of the second agent is administered rectally to the mammal.

In any of the aforementioned aspects are further embodiments comprising single administrations of the effective amount of second agent, including further embodiments in which (i) the second agent is administered once; (ii) the second agent is administered to the mammal multiple times over the span of one day; (iii) continually; or (iv) continuously.

In any of the aforementioned aspects are further embodiments comprising multiple administrations of the effective amount of the second agent, including further embodiments in which (i) the second agent is administered in a single dose; (ii) the time between multiple administrations is every 6 hours; (iii) the second agent is administered to the mammal every 8 hours. In further or alternative embodiments, the method comprises a drug holiday, wherein the administration of the second agent is temporarily suspended or the dose of the second agent being administered is temporarily reduced; at the end of the drug holiday, dosing of the second agent is resumed. The length of the drug holiday can vary from 2 days to 1 year.

In any of the aforementioned aspects the second agent is selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

Preparation of Compounds

Compounds of Formula D may be synthesized using standard synthetic techniques known to those of skill in the art or using methods known in the art in combination with methods described herein. In additions, solvents, temperatures and other reaction conditions presented herein may vary according to those of skill in the art. As a further guide the following synthetic methods may also be utilized.

The reactions can be employed in a linear sequence to provide the compounds described herein or they may be used to synthesize fragments which are subsequently joined by the methods described herein and/or known in the art.

Formation of Covalent Linkages by Reaction of an Electrophile with a Nucleophile The compounds described herein can be modified using various electrophiles or nucleophiles to form new functional groups or substituents. Table 1 entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 1

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |

TABLE 1-continued

Examples of Covalent Linkages and Precursors Thereof

| Covalent Linkage Product | Electrophile | Nucleophile |
| --- | --- | --- |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |
| Alkyl thiol | α,β-unsaturated ester | thiols |
| Alkyl ethers | α,β-unsaturated ester | alcohols |
| Alkyl amines | α,β-unsaturated ester | amines |
| Alkyl thiol | Vinyl sulfone | thiols |
| Alkyl ethers | Vinyl sulfone | alcohols |
| Alkyl amines | Vinyl sulfone | amines |
| Vinyl sulfide | Propargyl amide | thiol |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

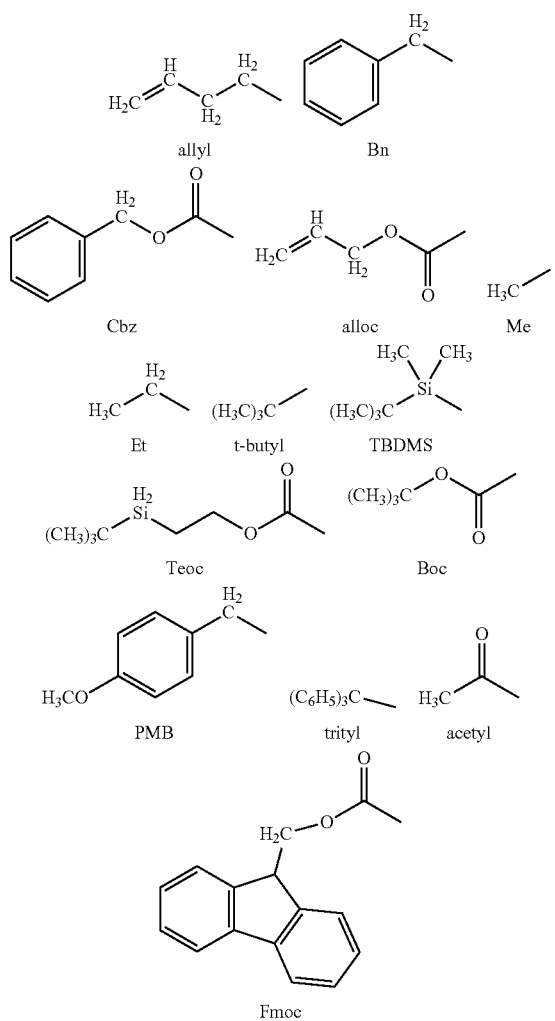

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

Further Forms of Compounds

The compounds described herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of Formula D in unoxidized form can be prepared from N-oxides of compounds of Formula D by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.,* 269:G210-218 (1995); McLoed et al., *Gastroenterol,* 106:405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems,* Vol. 14 of the A.C.S. Symposium Series; and Edward B. Roche, *Bioreversible Carriers in Drug Design,* American Pharmaceutical Association and Pergamon Press, 1987, all incorporated herein in their entirety.

Sites on the aromatic ring portion of compounds of Formula D can be susceptible to various metabolic reactions, therefore incorporation of appropriate substituents on the aromatic ring structures, such as, by way of example only, halogens can reduce, minimize or eliminate this metabolic pathway.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2H$, $^3H$, $^{13}C$, $^{14}C$, $^{15}N$, $^{18}O$, $^{17}O$, $^{35}S$, $^{18}F$, $^{36}Cl$ respectively. Certain isotopically-labeled compounds described herein, for example those into which radioactive isotopes such as $^3H$ and $^{14}C$ are incorporated, are useful in drug and/or substrate tissue distribution assays. Further, substitution with isotopes such as deuterium, i.e., $^2H$, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed) by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

Cancer Treatment Regimens

Disclosed herein, in certain embodiments, is a method for treating a hematological malignancy in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises measuring the peripheral blood concentration of the mobilized plurality of cells. In some embodiments, the method further comprises administering a second cancer treatment regimen after the peripheral blood concentration of the mobilized plurality of cells increases as compared to the concentration before administration of the Btk inhibitor. In some embodiments, administering the second cancer treatment regimen occurs after a subsequent decrease in peripheral blood concentration of the mobilized plurality of cells. In some embodiments, analyzing the mobilized plurality of cells comprises measuring the duration of an increase in the peripheral blood concentration of the mobilized plurality of cells as compared to the concentration before administration of the Btk inhibitor. In some embodiments, the method further comprises administering a second cancer treatment regimen after the peripheral blood concentration of the mobilized plurality of cells has increased for a predetermined length of time. In some embodiments, analyzing the mobilized plurality of cells comprises counting the number of mobilized plurality of cells in the peripheral blood. In some embodiments, the method further comprises administering a second cancer treatment regimen after the number of mobilized plurality of cells in the peripheral blood increases as compared to the number before administration of the Btk inhibitor. In some embodiments, administering the second cancer treatment regimen occurs after a subsequent decrease in the number of mobilized plurality of cells in the peripheral blood. In some embodiments, analyzing the mobilized plurality of cells comprises measuring the duration of an increase in the number of mobilized plurality of cells in the peripheral blood as compared to the number before administration of the Btk inhibitor. In some embodiments, the method further comprises administering a second cancer treatment regimen after the number of mobilized plurality of cells in the peripheral blood has increased for a predetermined length of time.

In some embodiments, administering a Btk inhibitor before a second cancer treatment regimen reduces immune-mediated reactions to the second cancer treatment regimen. In some embodiments, administering a Btk inhibitor before ofatumumab reduces immune-mediated reactions to ofatumumab.

In some embodiments, the second cancer treatment regimen comprises a chemotherapeutic agent, a steroid, an immunotherapeutic agent, a targeted therapy, or a combination thereof. In some embodiments, the second cancer treatment regimen comprises a B cell receptor pathway inhibitor. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the second cancer treatment regimen comprises an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof.

In some embodiments, the second cancer treatment regimen comprises chlorambucil, ifosfamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In some embodiments, the second cancer treatment regimen comprises cyclophosphamide, hydroxydaunorubicin, vincristine, and prednisone, and optionally, rituximab.

In some embodiments, the second cancer treatment regimen comprises bendamustine, and rituximab.

In some embodiments, the second cancer treatment regimen comprises fludarabine, cyclophosphamide, and rituximab.

In some embodiments, the second cancer treatment regimen comprises cyclophosphamide, vincristine, and prednisone, and optionally, rituximab.

In some embodiments, the second cancer treatment regimen comprises etoposide, doxorubicin, vinristine, cyclophosphamide, prednisolone, and optionally, rituximab.

In some embodiments, the second cancer treatment regimen comprises dexamethasone and lenalidomide.

Additional cancer treatment regimens include Nitrogen Mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; Other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; Vinca Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfin; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane.

Additional cancer treatment regimens include interferons, interleukins, Tumor Necrosis Factors, Growth Factors, or the like.

Additional cancer treatment regimens include Immunostimulants such as for example ancestim, filgrastim, lenograstim, molgramostim, pegfilgrastim, sargramostim; Interferons such as for example interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, peginterferon alfa-2b; Interleukins such as for example aldesleukin, oprelvekin; Other Immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; Other Immunosuppressants such as for example azathioprine, lenalidomide, methotrexate, thalidomide.

Additional cancer treatment regimens include Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

Additional cancer treatment regimens include Monoclonal Antibodies such as for example alemtuzumab, bevacizumab, catumaxomab, cetuximab, edrecolomab, gemtuzumab, ofatumumab, panitumumab, rituximab, trastuzumab, Immunosuppressants, eculizumab, efalizumab, muromab-CD3, natalizumab; TNF alpha Inhibitors such as for example adalimumab, afelimomab, certolizumab pegol, golimumab, infliximab, Interleukin Inhibitors, basiliximab, canakinumab, daclizumab, mepolizumab, tocilizumab, ustekinumab, Radiopharmaceuticals, ibritumomab tiuxetan, tositumomab; Others Monoclonal Antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

Additional cancer treatment regimens include agents that affect the tumor micro-enviroment such as cellular signaling network (e.g. phosphatidylinositol 3-kinase (PI3K) signaling pathway, signaling from the B-cell receptor and the IgE receptor). In some embodiments, the second agent is a PI3K signaling inhibitor or a syc kinase inhibitor. In one embodiment, the syk inhibitor is R788. In another embodiment is a PKCγ inhibitor such as by way of example only, enzastaurin.

Examples of agents that affect the tumor micro-environment include PI3K signaling inhibitor, syc kinase inhibitor, Protein Kinase Inhibitors such as for example dasatinib, erlotinib, everolimus, gefitinib, imatinib, lapatinib, nilotinib, pazonanib, sorafenib, sunitinib, temsirolimus; Other Angiogenesis Inhibitors such as for example GT-111, JI-101, R1530; Other Kinase Inhibitors such as for example AC220, AC480, ACE-041, AMG 900, AP24534, Arry-614, AT7519, AT9283, AV-951, axitinib, AZD1152, AZD7762, AZD8055, AZD8931, bafetinib, BAY 73-4506, BGJ398, BGT226, BI 811283, BI6727, BIM 1120, BMW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, RO5185426, SAR103168, SCH 727965, SGI-1176, SGX523, SNS-314, TAK-593, TAK-901, TKI258, TLN-232, TTP607, XL147, XL228, XL281RO5126766, XL418, XL765.

Further examples of anti-cancer agents for use in combination with a Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a Btk inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rlL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a Btk inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides;

insulin-such as for example growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of alkylating agents that can be employed in combination a Btk inhibitor compound include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of anti-cancer agents which act by arresting cells in the G2-M phases due to stabilized microtubules and which can be used in combination with a Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCI), AC-7700 (Ajinomoto, also known as AVE-8062, AVE-8062A, CS-39-L-Ser.HCI, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Biomarkers

Disclosed herein, in certain embodiments, is a method for treating a hematological malignancy in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, analyzing the mobilized plurality of cells comprises preparing a biomarker profile for a population of cells isolated from the plurality of cells. In some embodiments, the biomarker expression profile is used to diagnose, determine a prognosis, or create a predictive profile of a hematological malignancy. In some embodiments, the biomarker profile indicates the expression of a biomarker, the expression level of a biomarker, mutations in a biomarker, or the presence of a biomarker. In some embodiments, the biomarker is any cytogenetic, cell surface molecular or protein or RNA expression marker. In some embodiments, the biomarker is: ZAP70; t(14,18); β-2 microglobulin; p53 mutational status; ATM mutational status; del(17)p; del(11)q; del(6)q; CD5; CD11c; CD19; CD20; CD22; CD25; CD38; CD103; CD138; secreted, surface or cytoplasmic immunoglobulin expression; $V_H$ mutational status; or a combination thereof. In some embodiments, the method further comprises providing a second cancer treatment regimen based on the biomarker profile. In some embodiments, the method further comprises not administering based on the biomarker profile. In some embodiments, the method further comprises predicting the efficacy of a treatment regimen based on the biomarker profile.

In certain embodiments, the methods comprise diagnosing, determining a prognosis, or creating a predictive profile of a hematological malignancy based upon the expression or presence of certain biomarkers. In other embodiments, the methods further comprise stratifying patient populations based upon the expression or presence of certain biomarkers in the affected lymphocytes. In still other embodiments, the methods further comprise determining a therapeutic regimen for the subject based upon the expression or presence of certain biomarkers in the affected lymphocytes. In yet other embodiments, the methods further comprise predicting a response to therapy in a subject based upon the expression or presence of certain biomarkers in the affected lymphocytes.

In certain aspects, provided herein are methods of diagnosing, determining a prognosis, or creating a predictive profile of a hematological malignancy in a subject comprising: (a) administering a Btk inhibitor to the subject sufficient to result in an increase or appearance in the blood of a subpopulation of lymphocytes; and (b) determining the expression or presence of one or more biomarkers from one or more subpopulation of lymphocytes; wherein the expression or presence of one or more biomarkers is used to diagnose the hematological malignancy, determine the prognosis of the hematological malignancy, or create a predictive profile of the hematological malignancy. In one embodiment, the increase or appearance in the blood of a subpopulation of lymphocytes is determined by immunophenotyping. In another embodiment, the increase or appearance in the blood of a subpopulation of lymphocytes is determined by fluorescent activated cell sorting (FACS).

In other aspects, provided herein are methods of stratifying a patient population having a hematological malignancy comprising: (a) administering a Btk inhibitor to the subject sufficient to result in an increase or appearance in the blood of a subpopulation of lymphocytes; and (b) determining the expression or presence of one or more biomarkers from one or more subpopulation of lymphocytes; wherein the expression or presence of one or more biomarkers is used to stratify patients for treatment of the hematological malignancy. In one embodiment, the increase or appearance in the blood of a subpopulation of lymphocytes is determined by immunophenotyping. In another embodiment, the increase or appearance in the blood of a subpopulation of lymphocytes is determined by fluorescent activated cell sorting (FACS).

In still other aspects, provided herein are methods of determining a therapeutic regimen in a subject having a hematological malignancy comprising: (a) administering a Btk inhibitor to the subject sufficient to result in an increase or appearance in the blood of a subpopulation of lymphocytes; and (b) determining the expression or presence of one or more biomarkers from one or more subpopulation of lymphocytes; wherein the expression or presence of one or more biomarkers is used to determine the therapeutic regimen for the treatment of the hematological malignancy. In one embodiment, the increase or appearance in the blood of a subpopulation of lymphocytes is determined by immunophenotyping. In another embodiment, the increase or appearance in the blood of a subpopulation of lymphocytes is determined by fluorescent activated cell sorting (FACS).

In yet other aspects, provided herein are methods of predicting a response to therapy in a subject having a hematological malignancy comprising: (a) administering a Btk inhibitor to the subject sufficient to result in an increase or appearance in the blood of a subpopulation of lymphocytes; and (b) determining the expression or presence of one or more biomarkers from one or more subpopulation of lymphocytes; wherein the expression or presence of one or more biomarkers is used to predict the subject's response to therapy for the hematological malignancy. In one embodiment, the increase or appearance in the blood of a subpopulation of lymphocytes is determined by immunophenotyping. In another embodiment, the increase or appearance in the blood of a subpopulation of lymphocytes is determined by fluorescent activated cell sorting (FACS).

In certain aspects, provided herein are methods of diagnosing, determining a prognosis, or creating a predictive profile of a hematological malignancy in a subject comprising determining the expression or presence of one or more biomarkers from one or more subpopulation of lymphocytes in a subject that has received a dose of a Btk inhibitor wherein the expression or presence of one or more biomarkers is used to diagnose the hematological malignancy, determine the prognosis of the hematological malignancy, or create a predictive profile of the hematological malignancy. In one embodiment, the dose of Btk inhibitor is sufficient to result in an increase or appearance in the blood of a subpopulation of lymphocytes defined by immunophenotyping. In another embodiment, the determining the expression or presence of one or more biomarkers from one or more subpopulation of lymphocytes further comprises isolating, detecting or measuring one or more type of lymphocyte. In still another embodiment, the Btk inhibitor is a reversible or irreversible inhibitor.

In other aspects, provided herein are methods of stratifying a patient population having a hematological malignancy comprising determining the expression or presence of one or more biomarkers from one or more subpopulation of lymphocytes in a subject that has received a dose of a Btk inhibitor wherein the expression or presence of one or more biomarkers is used to stratify patients for treatment of the hematological malignancy. In one embodiment, the dose of Btk inhibitor is sufficient to result in an increase or appearance in the blood of a subpopulation of lymphocytes defined by immunophenotyping. In another embodiment, the determining the expression or presence of one or more biomarkers from one or more subpopulation of lymphocytes further comprises isolating, detecting or measuring one or more type of lymphocyte. In still another embodiment, the Btk inhibitor is a reversible or irreversible inhibitor.

In still other aspects, provided herein are methods of determining the therapeutic regimen in a subject having a hematological malignancy comprising determining the expression or presence of one or more biomarkers from one or more subpopulation of lymphocytes in a subject that has received a dose of a Btk inhibitor wherein the expression or presence of one or more biomarkers is used to determine the therapeutic regimen for the treatment of the hematological malignancy. In one embodiment, the dose of Btk inhibitor is sufficient to result in an increase or appearance in the blood of a subpopulation of lymphocytes defined by immunophenotyping. In another embodiment, the determining the expression or presence of one or more biomarkers from one or more subpopulation of lymphocytes further comprises isolating, detecting or measuring one or more type of lymphocyte. In still another embodiment, the Btk inhibitor is a reversible or irreversible inhibitor.

In yet other aspects, provided herein are methods of predicting a response to therapy in a subject having a hematological malignancy comprising determining the expression or presence of one or more biomarkers from one or more circulating lymphocytes in a subject that has received a dose of a Btk inhibitor wherein the expression or presence of one or more biomarkers is used to predict the subject's response to therapy for the hematological malignancy. In one embodiment, the dose of Btk inhibitor is sufficient to result in an increase or appearance in the blood of a subpopulation of lymphocytes defined by immunophenotyping. In another embodiment, the determining the expression or presence of one or more biomarkers from one or more subpopulation of lymphocytes further comprises isolating, detecting or measuring one or more type of lymphocyte. In still another embodiment, the Btk inhibitor is a reversible or irreversible inhibitor.

As contemplated herein, any biomarker related to hematological malignancies are in some embodiments utilized in the present methods. These biomarkers include any biological molecule (found either in blood, other body fluids, or tissues) or any chromosomal abnormality that is a sign of a hematological malignancy. In certain embodiments, the biomarkers include, but are not limited to, TdT, CD5, CD11c, CD19, CD20, CD22, CD79a, CD15, CD30, CD38, CD138, CD103, CD25, ZAP-70, p53 mutational status, ATM mutational status, mutational status of IgVH, chromosome 17 deletions (del 17p), chromosome 6 deletions (del 6q), chromosome 7 deletions (del 7q), chromosome 11 deletions (del 11q), trisomy 12, chromosome 13 deletions (del 13 q), t(11:14) chromosomal translocation, t(14:18) chromosomal translocation, CD10, CD23, beta-2 microglobulin, bcl-2 expression, CD9, presence of *Helicobacter pylori*, CD154/CD40, Akt, NF-κB, WNT, Mtor, ERK, MAPK, and Src tyrosine kinase expression. In certain embodiments, the biomarkers include ZAP-70, CD5, t(14;18), CD38, β-2 microglobulin, p53 mutational status, ATM mutational status, chromosome 17p deletion, chromosome 11q deletion, surface or cytoplasmic immunoglobulin, CD138, CD25, 6q deletion, CD19, CD20, CD22, CD11c, CD 103, chromosome 7q deletion, $V_H$ mutational status, or a combination thereof.

In certain embodiments, subpopulations of patients having a hematological malignancy cancer or pre- that would benefit from a known treatment regimen are identified by screening candidate subjects for one or more clinically useful biomarkers known in the art. Any clinically useful prognostic marker known to those of skill in the art can be used. In some embodiments, the subpopulation includes patients having chronic lymphocytic leukemia (CLL), and the clinically useful prognostic markers of particular interest include, but are not limited to, ZAP-70, CD38, .beta.2 microglobulin, and cytogenetic markers, for example, p53 mutational status, ATM mutational status, chromosome deletions, such as the chromosome 17p deletion and the chromosome 11q deletion, all of which are clinically useful prognostic markers for this disease.

ZAP-70 is a tyrosine kinase that associates with the zeta subunit of the T cell antigen receptor (TCR) and plays a pivotal role in T cell activation and development (Chan et al. (1992) Cell 71:649-662). ZAP-70 undergoes tyrosine phosphorylation and is essential in mediating signal transduction following TCR stimulation. Overexpression or constitutive activation of tyrosine kinases has been demonstrated to be involved in a number of malignancies including leukemias and several types of solid tumors. For example, increased ZAP-70 RNA expression levels are a prognostic marker of chronic lymphocytic leukemia (CLL) (Rosenwald et al. (2001) J. Exp. Med. 194:1639-1647). ZAP-70 is expressed in T-cells and natural killer cells, but is not known to be expressed in normal B-cells. However, ZAP-70 is expressed at high levels in the B-cells of chronic lymphocytic leukemia/small lymphocytic lymphoma (CLL/SLL) patients, and more particularly in the subset of CLL patients who tend to have the more aggressive clinical course that is found in CLL/SLL patients with unmutated Ig genes (Wiestner et al. (2003) Blood 101: 4944-4951; U.S. Patent Application Publication No. 20030203416). Because of the correlation between ZAP-70 expression levels and Ig gene mutation status, ZAP-70 can be used as a prognostic indicator to identify those patients likely to have severe disease (high ZAP-70, unmutated Ig genes), and who are therefore candidates for aggressive therapy.

CD38 is a signal transduction molecule as well as an ectoenzyme catalyzing the synthesis and degradation of cyclic ADP ribose (cADPR). CD38 expression is present at high levels in bone marrow precursor B cells, is downregulated in resting normal B cells, and then is re-expressed in terminally differentiated plasma cells (Campana et al. (2000) Chem. Immunol. 75:169-188). CD38 is a reliable prognostic indicator in B-CLL, with the expression of CD38 generally indicating a less favorable outcome (D'Arena et al. (2001) Leuk. Lymphoma 42:109; Del Poeta et al. (2001) Blood 98:2633; Durig et al. (2002) Leukemia 16:30; Ibrahim et al. (2001) Blood 98:181; Deaglio et al. (2003) Blood 102:2146-2155). The unfavorable clinical indications that CD38 expression has been associated with include an advanced stage of disease, poor responsiveness to chemotherapy, a shorter time before initial treatment is required, and a shorter survival time (Deaglio et al. (2003) Blood 102:2146-2155). Initially, a strong correlation between CD38 expression and IgV gene mutation was observed, with patients having unmutated V genes displaying higher percentages of CD38.sup.+ B-CLL cells than those with mutated V genes (Damle et al. (1999) Blood 94:1840-1847). However, subsequent studies have indicated that CD38 expression does not always correlate with the rearrangement of the IgV genes (Hamblin et al. (2002) Blood 99:1023; Thunberg et al. (2001) Blood 97:1892).

p53 is a nuclear phosphoprotein that acts as a tumor suppressor. Wild-type p53 is involved in regulating cell growth and division. p53 binds to DNA, stimulating the production of a protein (p21) that interacts with a cell division-stimulating protein (cdk2). When p21 is bound to cdk2, the cell is blocked from entering the next stage of cell division. Mutant p53 is incapable of binding DNA effectively, thus preventing p21 from acting as the stop signal for cell division, resulting in uncontrolled cell division, and tumor formation. p53 also regulates the induction of programmed cell death (apoptosis) in response to DNA damage, cell stress or the aberrant expression of some oncogenes. Expression of wild type p53 in some cancer cell lines has been shown to restore growth suppression control (Casey et al. (1991) Oncogene 6:1791-1797; Takahashi et al. (1992) Cancer Res. 52:734-736). Mutations in p53 are found in most tumor types, including tumors of the colon, breast, lung, ovary, bladder, and many other organs. p53 mutations have been found to be associated with Burkitt's lymphoma, L3-type B-cell acute lymphoblastic leukemia, B-cell chronic lymphocytic leukemia (Gaidano et al. (1991) Proc. Natl. Acad. Sci. U.S.A. 88:5413-5417). p53 abnormalities have also been found associated with B-cell prolymphocytic leukemia (Lens et al. (1997) Blood 89:2015-2023). The gene for p53 is located on the short arm of chromosome 17 at 17p13.105-p12.

B-2-microglobulin is an extracellular protein that is non-covalently associated with the .alpha. chain of the class I major histocompatibility complex (MHC). It is detectable in the serum, and is an adverse prognostic indicator in CLL (Keating et al. (1998) Blood 86:606a) and Hodgkin's lymphoma (Chronowski et al. (2002) Cancer 95:2534-2538). It is clinically used for lymphoproliferative diseases including leukemia, lymphoma, and multiple myeloma, where serum β-2-microglobulin levels are related to tumor cell load, prognosis, and disease activity (Bataille et al. (1983) Br. J. Haematol. 55:439-447; Aviles et al. (1992) Rev. Invest. Clin. 44:215-220). P2 microglobulin is also useful in staging myeloma patients (Pasqualetti et al. (1991) Eur. J. Cancer 27:1123-1126).

Cytogenetic aberrations may also be used as markers to create a predictive profile of a hematological malignancy. For example, chromosome abnormalities are found in a large percentage of CLL patients and are helpful in predicting the course of CLL. For example, a 17p deletion is indicative of aggressive disease progression. In addition, CLL patients with a chromosome 17p deletion or mutation in p53, or both, are known to respond poorly to chemotherapeutics and rituximab. Allelic loss on chromosome 17p may be also be a useful prognostic marker in colorectal cancer, where patients with a 17p deletion are associated with an increased tendency of disease dissemination in colorectal cancer (Khine et al. (1994) Cancer 73:28-35).

Deletions of the long arm of chromosome 11 (11q) are one of the most frequent structural chromosome aberrations in various types of lymphoproliferative disorders. CLL patients with chromosome 11q deletion and possibly ATM mutations have a poor survival compared to patients without either this defect or the 17p deletion. Furthermore, an 11q deletion is often accompanied by extensive lymph node involvement (Dohner et al. (1997) Blood 89:2516-2522). This deletion also identifies patients who are at high risk for disease persistence after high-dose therapy and autologous transplantation.

The ataxia telangiectasia mutated (ATA4) gene is a tumor suppressor gene that is involved in cell cycle arrest, apoptosis, and repair of DNA double-strand breaks. It is found on chromosome 11. ATMmutations are associated with increased risk for breast cancer among women with a family history of breast cancer (Chenevix-Trench et al. (2002) J. Natl. Cancer Inst. 94:205-215; Thorstenson et al. (2003) Cancer Res. 63:3325-3333) and/or early-onset breast cancers (Izatt et al. (1999) Genes Chromosomes Cancer 26:286-294; Teraoka et al. (2001) Cancer 92:479-487). There is also a high frequency of association of rhabdomyosarcoma with ATM gene mutation/deletion (Zhang et al. (2003) Cancer Biol. Ther. 1:87-91).

Methods for detecting chromosomal abnormalities in a patient are well known in the art (see, for example, Cuneo et al. (1999) Blood 93:1372-1380; Dohner et al. (1997) Blood 89:2516-2522). Methods to measure mutated proteins, such as ATM, are well known in the art (see, for example, Butch et al. (2004) Clin. Chem. 50: 2302-2308).

Thus, the biomarkers that are evaluated in the methods described herein include the cell survival and apoptotic proteins described supra, and proteins involved in hematological malignancy-related signaling pathways. Determining the expression or presence can be at the protein or nucleic acid level. Thus, the biomarkers include these proteins and the genes encoding these proteins. Where detection is at the protein level, the biomarker protein comprises the full-length polypeptide or any detectable fragment thereof, and can include variants of these protein sequences. Similarly, where detection is at the nucleotide level, the biomarker nucleic acid includes DNA comprising the full-length coding sequence, a fragment of the full-length coding sequence, variants of these sequences, for example naturally occurring variants or splice-variants, or the complement of such a sequence. Biomarker nucleic acids also include RNA, for example, mRNA, comprising the full-length sequence encoding the biomarker protein of interest, a fragment of the full-length RNA sequence of interest, or variants of these sequences. Biomarker proteins and biomarker nucleic acids also include variants of these sequences. By "fragment" is intended a portion of the polynucleotide or a portion of the amino acid sequence and hence protein encoded thereby. Polynucleotides that are fragments of a biomarker nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention. "Variant" is intended to mean substantially similar sequences. Generally, variants of a particular biomarker of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that biomarker as determined by sequence alignment programs known in the art.

As provided above, any method known in the art can be used in the methods for determining the expression or presence of biomarker described herein. Circulating levels of biomarkers in a blood sample obtained from a candidate subject, can be measured, for example, by ELISA, radioimmunoassay (MA), electrochemiluminescence (ECL), Western blot, multiplexing technologies, or other similar methods. Cell surface expression of biomarkers can be measured, for example, by flow cytometry, immunohistochemistry, Western Blot, immunoprecipitation, magnetic bead selection, and quantification of cells expressing either of these cell surface markers. Biomarker RNA expression levels could be measured by RT-PCR, Qt-PCR, microarray, Northern blot, or other similar technologies.

As previously noted, determining the expression or presence of the biomarker of interest at the protein or nucleotide level can be accomplished using any detection method known to those of skill in the art. By "detecting expression" or "detecting the level of" is intended determining the expression level or presence of a biomarker protein or gene in the biological sample. Thus, "detecting expression" encompasses instances where a biomarker is determined not to be expressed, not to be detectably expressed, expressed at a low level, expressed at a normal level, or overexpressed.

In certain aspects of the method provided herein, the one or more subpopulation of lymphocytes are isolated, detected or measured. In certain embodiments, the one or more subpopulation of lymphocytes are isolated, detected or measured using immunophenotyping techniques. In other embodiments, the one or more subpopulation of lymphocytes are isolated, detected or measured using fluorescence activated cell sorting (FACS) techniques.

In certain embodiments of the methods provided herein, the one or more biomarkers comprises ZAP-70, CD5, t(14; 18), CD38, β-2 microglobulin, p53 mutational status, ATM mutational status, chromosome 17p deletion, chromosome 11q deletion, surface or cytoplasmic immunoglobulin, CD138, CD25, 6q deletion, CD19, CD20, CD22, CD11c, CD 103, chromosome 7q deletion, VH mutational status, or a combination thereof.

In certain aspects, the methods described herein, the determining step requires determining the expression or presence of a combination of biomarkers. In certain embodiment, the combination of biomarkers is CD19 and CD5 or CD20 and CD5.

In certain aspects, the expression or presence of these various biomarkers and any clinically useful prognostic markers in a biological sample can be detected at the protein or nucleic acid level, using, for example, immunohistochemistry techniques or nucleic acid-based techniques such as in situ hybridization and RT-PCR. In one embodiments, the expression or presence of one or more biomarkers is carried out by a means for nucleic acid amplification, a means for nucleic acid sequencing, a means utilizing a nucleic acid microarray (DNA and RNA), or a means for in situ hybridization using specifically labeled probes.

In other embodiments, the determining the expression or presence of one or more biomarkers is carried out through gel electrophoresis. In one embodiment, the determination is carried out through transfer to a membrane and hybridization with a specific probe.

In other embodiments, the determining the expression or presence of one or more biomarkers carried out by a diagnostic imaging technique.

In still other embodiments, the determining the expression or presence of one or more biomarkers carried out by a detectable solid substrate. In one embodiment, the detectable solid substrate is paramagnetic nanoparticles functionalized with antibodies.

In another aspect, provided herein are methods for detecting or measuring residual lymphoma following a course of treatment in order to guide continuing or discontinuing treatment or changing from one therapeutic regimen to another comprising determining the expression or presence of one or more biomarkers from one or more subpopulation of lymphocytes in a subject wherein the course of treatment is treatment with a Btk inhibitor.

Methods for detecting expression of the biomarkers described herein, and optionally cytokine markers, within the test and control biological samples comprise any methods that determine the quantity or the presence of these markers either at the nucleic acid or protein level. Such methods are well known in the art and include but are not limited to western blots, northern blots, ELISA, immunoprecipitation, immunofluorescence, flow cytometry, immunohistochemistry, nucleic acid hybridization techniques, nucleic acid reverse transcription methods, and nucleic acid amplification methods. In particular embodiments, expression of a biomarker is detected on a protein level using, for example, antibodies that are directed against specific biomarker proteins. These antibodies can be used in various methods such as Western blot, ELISA, multiplexing technologies, immunoprecipitation, or immunohistochemistry techniques. In some embodiments, detection of cytokine markers is accomplished by electrochemiluminescence (ECL).

Any means for specifically identifying and quantifying a biomarker (for example, biomarker, a biomarker of cell survival or proliferation, a biomarker of apoptosis, a biomarker of a Btk-mediated signaling pathway) in the biological sample of a candidate subject is contemplated. Thus, in some embodiments, expression level of a biomarker protein of interest in a biological sample is detected by means of a binding protein capable of interacting specifically with that biomarker protein or a biologically active variant thereof. Preferably, labeled antibodies, binding portions thereof, or other binding partners may be used. The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The antibodies for detection of a biomarker protein may be monoclonal or polyclonal in origin, or may be synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols can be found in numerous texts in the art (see, for example, Ausubel et al., eds. (1995) Current Protocols in Molecular Biology) (Greene Publishing and Wiley-Interscience, NY)); Coligan et al., eds. (1994) Current Protocols in Immunology (John Wiley & Sons, Inc., New York, N.Y.).

The choice of marker used to label the antibodies will vary depending upon the application. However, the choice of the marker is readily determinable to one skilled in the art. These labeled antibodies may be used in immunoassays as well as in histological applications to detect the presence of any biomarker or protein of interest. The labeled antibodies may be polyclonal or monoclonal. Further, the antibodies for use in detecting a protein of interest may be labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that can serve as detectable labels include, for example, I-131, I-123, I-125, Y-90, Re-188, Re-186, At-211, Cu-67, Bi-212, and Pd-109. Examples of enzymes that can serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Examples of suitable ligand-receptor pairs are biotin-avidin or biotin-streptavidin, and antibody-antigen.

In certain embodiments, expression or presence of one or more biomarkers or other proteins of interest within a biological sample, for example, a sample of bodily fluid, is determined by radioimmunoassays or enzyme-linked immunoassays (ELISAs), competitive binding enzyme-linked immunoassays, dot blot (see, for example, Promega Protocols and Applications Guide ($2^{nd}$ ed.; Promega Corporation (1991), Western blot (see, for example, Sambrook et al. (1989) Molecular Cloning, A Laboratory Manual, Vol. 3, Chapter 18 (Cold Spring Harbor Laboratory Press, Plainview, N.Y.), chromatography, preferably high performance liquid chromatography (HPLC), or other assays known in the art. Thus, the detection assays can involve steps such as, but not limited to, immunoblotting, immunodiffusion, immunoelectrophoresis, or immunoprecipitation.

In certain other embodiments, the methods of the invention are useful for identifying and treating hematological malignancies, including those listed above, that are refractory to (i.e., resistant to, or have become resistant to) first-line oncotherapeutic treatments.

The expression or presence of one or more of the biomarkers described herein may also be determined at the nucleic acid level. Nucleic acid-based techniques for assessing expression are well known in the art and include, for example, determining the level of biomarker mRNA in a biological sample. Many expression detection methods use isolated RNA. Any RNA isolation technique that does not select against the isolation of mRNA can be utilized for the purification of RNA (see, e.g., Ausubel et al., ed. (1987-1999) Current Protocols in Molecular Biology (John Wiley & Sons, New York). Additionally, large numbers of tissue samples can readily be processed using techniques well known to those of skill in the art, such as, for example, the single-step RNA isolation process disclosed in U.S. Pat. No. 4,843,155.

Thus, in some embodiments, the detection of a biomarker or other protein of interest is assayed at the nucleic acid level using nucleic acid probes. The term "nucleic acid probe" refers to any molecule that is capable of selectively binding to a specifically intended target nucleic acid molecule, for example, a nucleotide transcript. Probes can be synthesized by one of skill in the art, or derived from appropriate biological preparations. Probes may be specifically designed to be labeled, for example, with a radioactive label, a fluorescent label, an enzyme, a chemiluminescent tag, a colorimetric tag, or other labels or tags that are discussed above or that are known in the art. Examples of molecules that can be utilized as probes include, but are not limited to, RNA and DNA.

For example, isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker, biomarker described herein above. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan can readily adapt known mRNA detection methods for use in detecting the level of mRNA encoding the biomarkers or other proteins of interest.

An alternative method for determining the level of a mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad.

Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan® System).

Expression levels of an RNA of interest may be monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression may also comprise using nucleic acid probes in solution.

In one embodiment of the invention, microarrays are used to determine expression or presence of one or more biomarkers. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation of an all-inclusive device. See, for example, U.S. Pat. Nos. 5,856,174 and 5,922,591, herein incorporated by reference.

Pharmaceutical Compositions/Formulations

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

A pharmaceutical composition, as used herein, refers to a mixture of a compound described herein, such as, for example, compounds of Formula D or the second agent, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of any of Formula D and the second agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, □g, or ng of therapeutic agent per ml, dl, or l of blood serum, absorbed into the bloodstream after administration. As used herein, measurable plasma concentrations are typically measured in ng/ml or □g/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound of any of Formula D or the second agent can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of any of Formula (A1-A6), Formula (B1-B6), Formula (C1-C6), or Formula (D1-D6), with one or more pharmaceutical excipients to form a bulk blend composition. When referring to these bulk blend compositions as homogeneous, it is meant that the particles of the compound of any of Formula (A1-A6), Formula (B1-B6), Formula (C1-C6), or Formula (D1-D6), are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound of any of Formula (A1-A6), Formula (B1-B6), Formula (C1-C6), or Formula (D1-D6). In one embodiment, some or all of the particles of the compound of any of Formula (A1-A6), Formula (B1-B6), Formula (C1-C6), or Formula (D1-D6), are coated. In another embodiment, some or all of the particles of the compound of any of Formula (A1-A6), Formula (B1-B6), Formula (C1-C6), or Formula (D1-D6), are microencapsulated. In still another embodiment, the particles of the compound of any of Formula (A1-A6), Formula (B1-B6), Formula (C1-C6), or Formula (D1-D6), are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of any of Formula (A1-A6), Formula (B1-B6), Formula (C1-C6), or Formula (D1-D6), from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocer), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compound of of any of Formula D or the second agent, from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound of any of Formula D or the second agent, described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of any of Formula D or the second agent, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of any of Formula D or the secodn agent, which sufficiently isolate the compound of any of Formula D or the secodn agent, from other non-compatible excipients. Materials compatible with compounds of any of Formula D or the secodn agent, are those that delay the release of the compounds of of any of Formula D or the secodn agent, in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of Formula D or the secodn agent, may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of compounds of any of Formula D or the secodn agent, are microencapsulated prior to being formulated into one of the above forms. In still another embodiment, some or most of the particles are coated prior to being further formulated by using standard coating procedures, such as those described in *Remington's Pharmaceutical Sciences*, 20th Edition (2000).

In other embodiments, the solid dosage formulations of the compounds of any of Formula D or the second agent, are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of Formula D or the secodn agent, described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

(a) Shellac, also called purified lac, a refined product obtained from the resinous secretion of an insect. This coating dissolves in media of pH>7;

(b) Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

(c) Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include compounds of Formula D or the secodn agent, are delivered using a pulsatile dosage form. A pulsatile dosage form is capable of providing one or more immediate release pulses at predetermined time points after a controlled lag time or at specific sites. Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of the compounds of any of Formula D or the secodn agent, described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition to the particles of compounds of Formula (A1-A6), the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, AvicerPH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as) Plasdone®, and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116, 817 and 6,391,452, each of which is specifically incorporated by reference. Formulations that include a compound of any of Formula (A1-A6), Formula (B1-B6), Formula (C1-C6), or Formula (D1-D6), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation, the compounds of any of Formula D or the second agent, described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations that include compounds of any of Formula D or the second agent may be administered using a variety of formulations known in the art. For example, such formulations include, but are not limited to, U.S. Pat. Nos. 4,229,447, 4,596,795, 4,755,386, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of any of Formula D or the second agent, is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound of any of Formula D or the second agent, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation of a compound of any of Formula D or the secodn agent; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of any of Formula D or the second agent. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of any of Formula D or the secodn agent, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Other Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Dosing and Treatment Regimens

Disclosed herein, in certain embodiments, is a method for treating a hematological malignancy in an individual in need thereof, comprising: (a) administering to the individual an amount of an irreversible Btk inhibitor sufficient to mobilize a plurality of cells from the malignancy; and (b) analyzing the mobilized plurality of cells. In some embodiments, the amount of the irreversible Btk inhibitor is sufficient to induce lymphocytosis of a plurality of cells from the malignancy. In some embodiments, the amount of the irreversible Btk inhibitor is from 300 mg/day up to, and including, 1000 mg/day. In some embodiments, the amount of the irreversible Btk inhibitor is from 420 mg/day up to, and including, 840 mg/day. In some embodiments, the amount of the irreversible Btk inhibitor is about 420 mg/day, about 560 mg/day, or about 840 mg/day. In some embodiments, the amount of the irreversible Btk inhibitor is about 420 mg/day. In some embodiments, the $AUC_{0-24}$ of the Btk inhibitor is between about 150 and about 3500 ng*h/mL. In some embodiments, the $AUC_{0-24}$ of the Btk inhibitor is between about 500 and about 1100 ng*h/mL. In some embodiments, the Btk inhibitor is administered orally. In some embodiments, the Btk inhibitor is administered once per day, twice per day, or three times per day. In some embodiments, the Btk inhibitor is administered until disease progression, unacceptable toxicity, or individual choice. In some embodiments, the Btk inhibitor is administered daily until disease progression, unacceptable toxicity, or individual choice. In some embodiments, the Btk inhibitor is administered every other day until disease progression, unacceptable toxicity, or individual choice. In some embodiments, the Btk inhibitor is a maintenance therapy.

The compounds described herein can be used in the preparation of medicaments for the inhibition of Btk or a homolog thereof, or for the treatment of diseases or conditions that would benefit, at least in part, from inhibition of Btk or a homolog thereof, including a patient and/or subject diagnosed with a hematological malignancy. In addition, a method for treating any of the diseases or conditions described herein in a subject in need of such treatment, involves administration of pharmaceutical compositions containing at least one compound of any of Formula (A), Formula (B), Formula (C), or Formula (D), described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic, therapeutic, or maintenance treatment. In some embodiments, compositions containing the compounds described herein are administered for therapeutic applications (e.g., administered to a patient diagnosed with a hematological malignancy). In some embodiments, compositions containing the compounds described herein are administered for therapeutic applications (e.g., dministered to a patient susceptible to or otherwise at risk of developing a hematological malignancy). In some embodiments, compositions containing the compounds described herein are administered to a patient who is in remission as a maintenance therapy.

Amounts of a compound disclosed herein will depend on the use (e.g., therapeutic, prophylactic, or maintenance). Amounts of a compound disclosed herein will depend on severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial). In some embodiments, the amount of the irreversible Btk inhibitor is from 300 mg/day up to, and including, 1000 mg/day. In some embodiments, the amount of the irreversible Btk inhibitor is from 420 mg/day up to, and including, 840 mg/day. In some embodiments, the amount of the Btk inhibitor is from 400 mg/day up to, and including, 860 mg/day. In some embodiments, the amount of the Btk inhibitor is about 360 mg/day. In some embodiments, the amount of the Btk inhibitor is about 420 mg/day. In some embodiments, the amount of the Btk inhibitor is about 560 mg/day. In some embodiments, the amount of the Btk inhibitor is about 840 mg/day. In some embodiments, the amount of the Btk inhibitor is from 2 mg/kg/day up to, and including, 13 mg/kg/day. In some embodiments, the amount of the Btk inhibitor is from 2.5 mg/kg/day up to, and including, 8 mg/kg/day. In some embodiments, the amount of the Btk inhibitor is from 2.5 mg/kg/day up to, and including, 6 mg/kg/day. In some embodiments, the amount of the Btk inhibitor is from 2.5 mg/kg/day up to, and including, 4 mg/kg/day. In some embodiments, the amount of the Btk inhibitor is about 2.5 mg/kg/day. In some embodiments, the amount of the Btk inhibitor is about 8 mg/kg/day.

In some embodiments, a Btk inhibitor disclosed herein is administered daily. In some embodiments, a Btk inhibitor disclosed herein is administered every other day.

In some embodiments, a Btk inhibitor disclosed herein is administered once per day. In some embodiments, a Btk inhibitor disclosed herein is administered twice per day. In some embodiments, a Btk inhibitor disclosed herein is administered here times per day. In some embodiments, a Btk inhibitor disclosed herein is administered times per per day.

In some embodiments, the Btk inhibitor is administered until disease progression, unacceptable toxicity, or individual choice. In some embodiments, the Btk inhibitor is administered daily until disease progression, unacceptable toxicity, or individual choice. In some embodiments, the Btk inhibitor is administered every other day until disease progression, unacceptable toxicity, or individual choice.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, the severity of the disease, the identity (e.g., weight) of the subject or host in need of treatment, but can nevertheless be routinely determined in a manner known in the art according to the particular circumstances surrounding the case, including, e.g., the specific agent being administered, the route of administration, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative. In some embodiments, each unit dosage form comprises 210 mg of a compound disclosed herein. In some embodiments, an individual is administered 1 unit dosage form per day. In some embodiments, an individual is administered 2 unit dosage forms per day. In some embodiments, an individual is administered 3 unit dosage forms per day. In some embodiments, an individual is administered 4 unit dosage forms per day.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Kits/Articles of Manufacture

The present invention also encompasses kits for carrying out the methods of the present invention. For example, the kit can comprise a labeled compound or agent capable of detecting a biomarker described herein, e.g., a biomarker of apoptosis, cellular proliferation or survival, or a Btk-mediated signaling pathway, either at the protein or nucleic acid level, in a biological sample and means for determining the amount of the biomarker in the sample (for example, an antibody or an oligonucleotide probe that binds to RNA encoding a biomarker of interest) following incubation of the sample with a BCLD therapeutic agent of interest. Kits can be packaged to allow for detection of multiple biomarkers of interest by including individual labeled compounds or agents capable of detecting each individual biomarker of interest and means for determining the amount of each biomarker in the sample.

The particular choice of the second agent used will depend upon the diagnosis of the attending physicians and their judgment of the condition of the patient and the appropriate treatment protocol of the Btk inhibitors.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1: Treatment of Non-Hodgkin Lymphoma by Administering a Btk Inhibitor to Induce Pharmaceutical Debulking Two groups of patients with Non-Hodgkin Lymphoma (15 each) are treated with or without a Btk inhibitor followed by administering a second agent (Taxane). Group 1 is subject to the second agent treatment only (Taxane) and Group 2 is subject to a Btk inhibitor treatment for 2 days followed by administering the second agent based on the determined expression or presence of one or more B-cell lymphoproliferative disorder (BCLD) biomarkers from one or more subpopulation of lymphocytes.

Example 2. Determining the Expression or Presence of BCLD after Administering the Btk Inhibitor for the Treatment of Non-Hodgkin Lymphoma Determining the expression or presence of BCLD after administering compound 15 to a patient of Group 1 is used by the known procedures.

Example 3. Use of Taxane for the Treatment of Non-Hodgkin Lymphoma

Following determination of the expression or presence of one or more B-cell lymphoproliferative disorder (BCLD) biomarkers from one or more subpopulation of lymphocytes in the patient, Taxane is used for Group 2 patients.

Example 4: Clinical Example of Determination of BCLDs Using a Btk Inhibitor

A patient with BCLD completes treatment with a Btk inhibitor or another treatment, and appears to be in complete remission. After this treatment is stopped, a short course of the Btk inhibitor is then given. If cells with markers of the malignant cells appear in the peripheral blood, in some embodiments it is an indication for continued treatment or for starting another treatment. One example of the cell subpopulation investigated for in the peripheral blood is cells bearing both the CD5 and CD20 markers, which is typical of CLL/SLL and Mantle Cell Lymphoma. These markers can be detectable by flow cytometry. A further example of cell type is follicular lymphoma, which is characterized by cells with t(14;18) which in other embodiments are detectable by PCR or in situ hybridization in cells harvested from the peripheral blood.

Based on the markers of the malignant cells as determined in the peripheral blood, a suitable second treatment regimen is administered.

Example 5: Pharmaceutical Compositions

The compositions described below are presented with a compound of Formula (D) for illustrative purposes; any of the compounds of any of Formulas (A), (B), (C), or (D) can be used in such pharmaceutical compositions.

Example 5a: Parenteral Composition

To prepare a parenteral pharmaceutical composition suitable for administration by injection, 100 mg of a water-soluble salt of a compound of Formula (D) is dissolved in DMSO and then mixed with 10 mL of 0.9% sterile saline. The mixture is incorporated into a dosage unit form suitable for administration by injection.

Example 5b: Oral Composition

To prepare a pharmaceutical composition for oral delivery, 100 mg of a compound of Formula (D) is mixed with 750 mg of starch. The mixture is incorporated into an oral dosage unit for, such as a hard gelatin capsule, which is suitable for oral administration.

Example 5c: Sublingual (Hard Lozenge) Composition

To prepare a pharmaceutical composition for buccal delivery, such as a hard lozenge, mix 100 mg of a compound of Formula (D), with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 5d: Inhalation Composition

To prepare a pharmaceutical composition for inhalation delivery, 20 mg of a compound of Formula (D) is mixed with 50 mg of anhydrous citric acid and 100 mL of 0.9% sodium chloride solution. The mixture is incorporated into an inhalation delivery unit, such as a nebulizer, which is suitable for inhalation administration.

Example 5e: Rectal Gel Composition

To prepare a pharmaceutical composition for rectal delivery, 100 mg of a compound of Formula (D) is mixed with 2.5 g of methylcellulose (1500 mPa), 100 mg of methylparapen, 5 g of glycerin and 100 mL of purified water. The resulting gel mixture is then incorporated into rectal delivery units, such as syringes, which are suitable for rectal administration.

Example 5f: Topical Gel Composition

To prepare a pharmaceutical topical gel composition, 100 mg of a compound of Formula (D) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 5g: Ophthalmic Solution Composition

To prepare a pharmaceutical opthalmic solution composition, 100 mg of a compound of Formula (D) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 6—Clinical Trial to Determine Efficacy of a Btk Irreversible Inhibitor in CLL and SLL Patients Patients with CLL and/or SLL:

The data provided herein is a pooled analysis of patients with CLL or SLL from two clinical trials of a Btk irreversible inhibitor. The initial trial (Study 04753) was a Phase 1A multi-cohort, first-in-human, dose escalation trial of a Btk irreversible inhibitor in patients with relapsed or refractory B-cell. 56 patients were enrolled between March 2009 and September 2010 and two doses were evaluated, namely oral once-daily dosing of a Btk irreversible inhibitor with a 28-day-on, 7-day-off schedule, and a continuous daily oral dosing schedule. Of the 56 patients enrolled, 16 CLL/SLL patients are included in this pooled analysis.

The second trial (Study 1102) is a Phase 1B/II trial of two once-daily oral doses of a Btk irreversible inhibitor in 2 populations of patients with CLL or SLL; a cohort containing patients with relapsed of refractory disease after at least 2 prior treatment regimens, and a second cohort of elderly patients with treatment-naïve disease. This study began enrollment in May 2010, and has enrolled 56 patients to date. For the purpose of this pooled analysis, 38 patients, with a minimum of 28 days follow-up and 28 patients with on study tumor assessments are included in this analysis. In sum, 56 patients from the two studies are included in this analysis.

The baseline characteristics of patients enrolled to the two studies are summarized here. In study 04753, the median age was 66, there were 11 patients with CLL and 5 patients with SLL. The median # of prior therapies was 3, with a range of 1-10. x % of patients had received prior nucleoside analogues, and x % had received prior anti-CD20 agents.

In study 1102, the median age was 68, 32 patients had CLL and 2 patients had SLL. Of the patients with CLL, 10 had del 17p. 15 patients had bulky disease, defined as a nodal mass>5 cm diameter. In the relapsed/refractory cohort, the median # of prior regimens was ×0.3 Per the eligibility requirements, all patients had received a nucleoside analogue-based regimen. 93% had received prior anti-CD20 agents, 9% alemtuzumab, and 19% bendamustine.

Objectives of the Analysis

The objective of this pooled analysis is to characterize the nature and kinetics of the response to a Btk irreversible inhibitor in CLL. The Btk irreversible inhibitor compound is one of a new class of BCR signaling inhibitors, and, similar to other inhibitors of this pathway, the kinetics of response differ between the peripheral blood and the nodal compartments. The second objective was to summarize the current status of the two studies with respect to best response, patient disposition, and time on treatment. The final objective was the summarization of the adverse event profile of the Btk inhibitor on a larger and more diverse population of patients with CLL or SLL.

Response Criteria

Different response criteria were applied to patients with CLL and SLL respectively in these trials. Though considered biologically similar (or identical) diseases, given the phenotypic differences in presentation, the IW criteria for CLL are based on improvement in circulating lymphocytes, nodal/splenic/marrow-based disease, and normalization of hematologic parameters. In contrast, the NHL criteria used to gauge the lymphomatous presentation of this disease (or SLL) are based only on improvement in lymphadenopathy and organomegaly.

Lymphocyte Count

Figure 5:
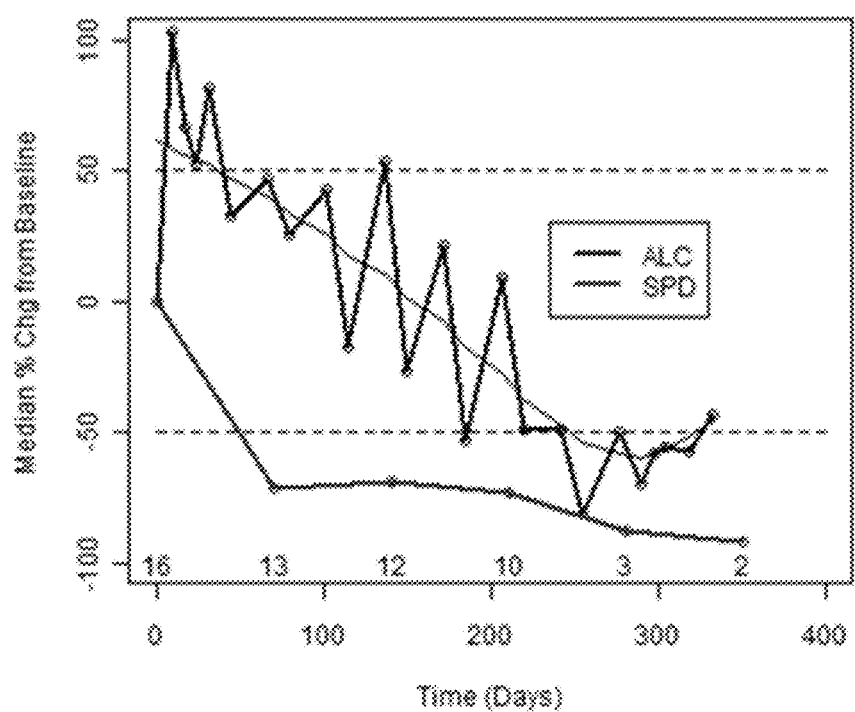
FIG. 5 depicts the effect of an irreversible Btk inhibitor on LN disease burden and lymphocytosis over time in the patients suffering with CLL and/or SLL.

FIG. 5 depicts the change with treatment in the lymphocyte count for a 57 year-old patient with disease relapse following multiple prior therapies and the poor-risk cytogenetic feature del 11q began treatment with a Btk irreversible inhibitor nearly 6 months ago. Typical of the majority of CLL patients treated with a Btk irreversible inhibitor, there was an initial, rapid, and prominent reduction in nodal disease and spleen size, with a corresponding rise in the circulating lymphocyte count, likely a consequence of the inhibitory effects of a Btk irreversible inhibitor on lymphocyte homing to the nodal and splenic compartments. Simultaneous with these changes, patients reported symptomatic improvement consistent with the resolution of bulky disease. Over time, the initial rise in lymphocytes returns to pre-treatment levels in spite of sustained reductions in adenopathy and splenomegaly. Cases such as this seen with a Btk irreversible inhibitor and similar agents, highlights the difficulty in applying standard response criteria to newer agents.

Effect of Treatment on Lymph Node SPD

Figure 6:
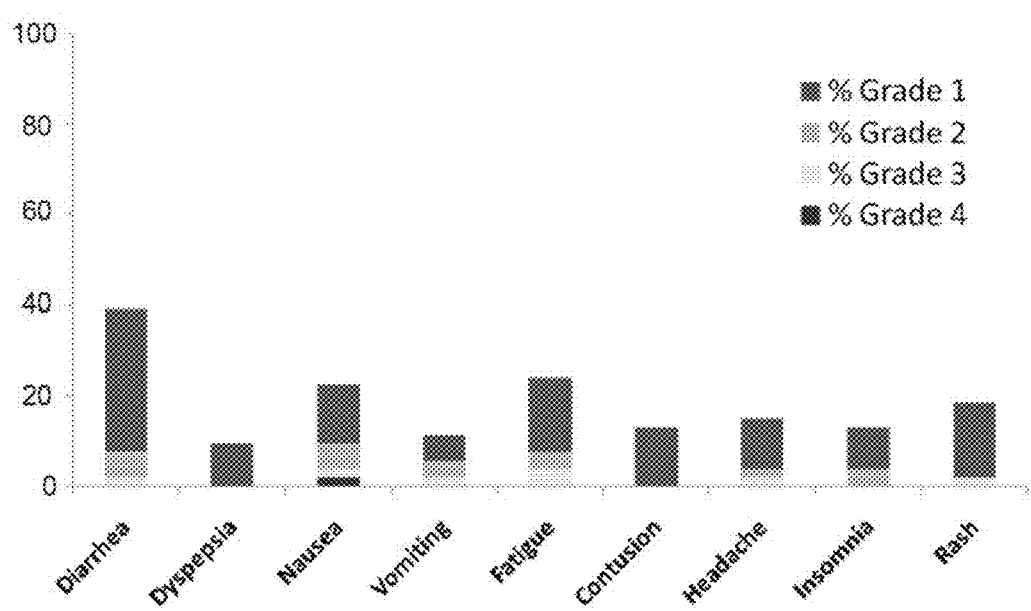
FIG. 6 depicts adverse effects in patients treated with an irreversible Btk inhibitor. Grades 1-4 represent severity of effects with 1 representing very mild to 4 representing extreme discomfort.
Figure 7:
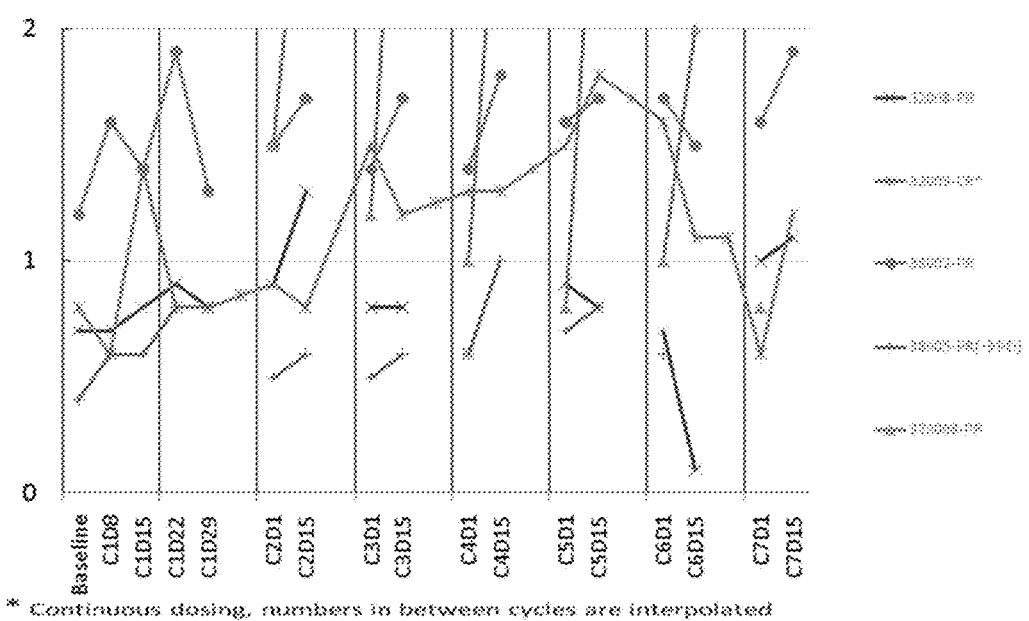
FIG. 7 depicts the absolute lymphocyte count (ALC)/109 L vs. Cycle Day after administering a Btk inhibitor to individuals with follicular lymphoma who achieved complete or partial response (CR/PR). The Y Axis shows the Absolute Lymphocyte Counts (ALC) at each time point by cycle number and day in the X axis. All Patients (except Pt 32009) were treated on schedule of 4 weeks on treatment followed by one week off. Thus, day 1 of each cycle follows one week off drug for these patients. Note the increases of ALC during most cycles of most patients, and the fall of ALC at the beginning of subsequent cycles. This pattern is often blunted in later cycles as patients responded to treatment. Patient 32009 received treatment without interruption and did not show this cyclic pattern, but did show an increase at Cycle 1, day 15, and gradual increases during Cycles 2 to 5.

As shown in FIG. 6, patients treated with a Btk irreversible inhibitor had an immediate and marked nodal response to treatment. 85% of evaluable patients achieved a partial response and even more had some LN shrinkage. 80% of patients with measurable LN disease achieved a 50% reduction in their SPD within 2 cycles of therapy. FIG. 7 shows the remarkable shrinkage in Lymph node post-treatment for the 57 year-old patient described supra.

Change in Lymph Node and Absolute Lymphocyte Count (ALC)

Figure 8:
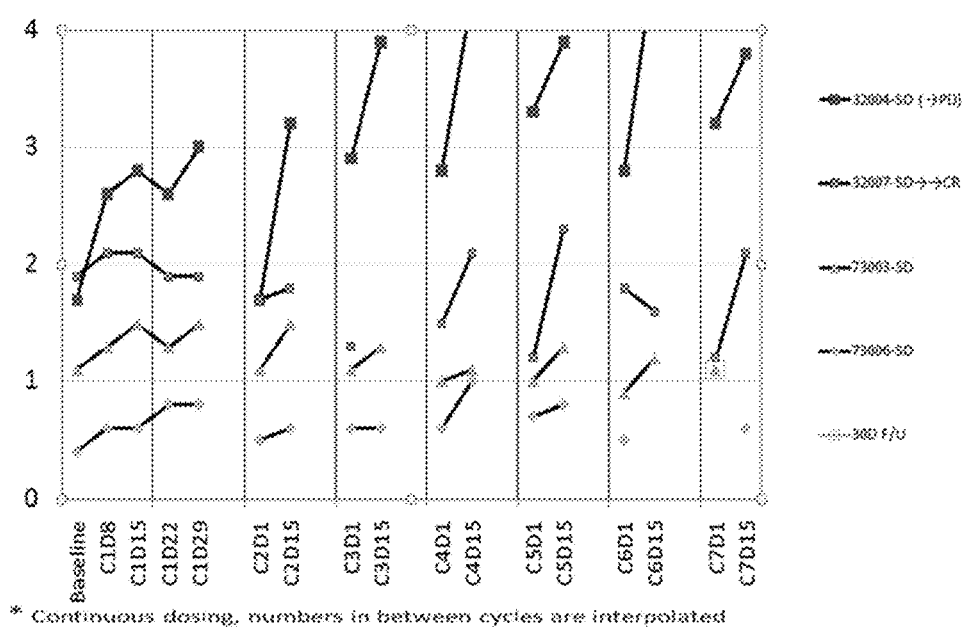
FIG. 8 depicts the absolute lymphocyte count (ALC)/109 L vs. Cycle Day after administering a Btk inhibitor to individuals with follicular lymphoma who had Stable Disease (SD) during treatment. The Y Axis shows the Absolute Lymphocyte Counts (ALC) at each time point by cycle number and day in the X axis. All Patients were treated on schedule of 4 weeks on treatment followed by one week off. Thus, day 1 of each cycle follows one week off drug for these patients. Note the gradual increase of blood ALC mobilization of Patient 32004, who initially was stable but later had Progressive Disease (PD).

FIG. 8 depicts the effect of a Btk irreversible inhibitor on LN disease burden and lymphocytosis over time in the patients from the Phase Ia trial. Summary statistics from the patients with an early lymphocytosis show a similar pattern in the median percent change over time in both ALC and in LN disease burden measured by the SPD. Immediately following treatment, patients develop an early lymphocytosis which decreases with time to pre-treatment or normal levels. There is a sustained decrease in disease burden shown by the LN sum of perpendicular diameters. Thus, with some variability in timing, many patients show a marked decrease in tumor burden in both peripheral blood and in LN disease with sustained treatment.

Adverse Effects

Figure 9:
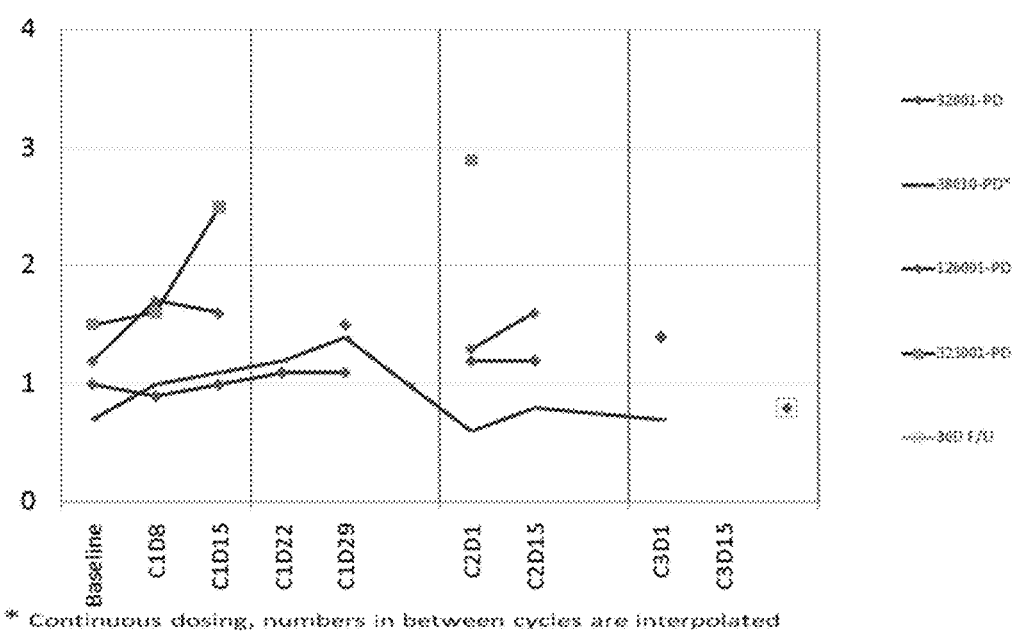
FIG. 9 depicts the absolute lymphocyte count (ALC)/109 L vs. Cycle Day after administering a Btk inhibitor to PD individuals with follicular lymphoma. The Y Axis shows the Absolute Lymphocyte Counts (ALC) at each time point by cycle number and day in the X axis. All Patients except 38010 were treated on schedule of 4 weeks on treatment followed by one week off. Thus, day 1 of each cycle follows one week off drug for these patients. Note lack of mobilization, especially patients 38010 and 32001. Patient 323001 had limited treatment before being taken off study. The lymphocyte response suggests that this patient might had responded if it had been possible to stay on treatment longer.
Figure 10:
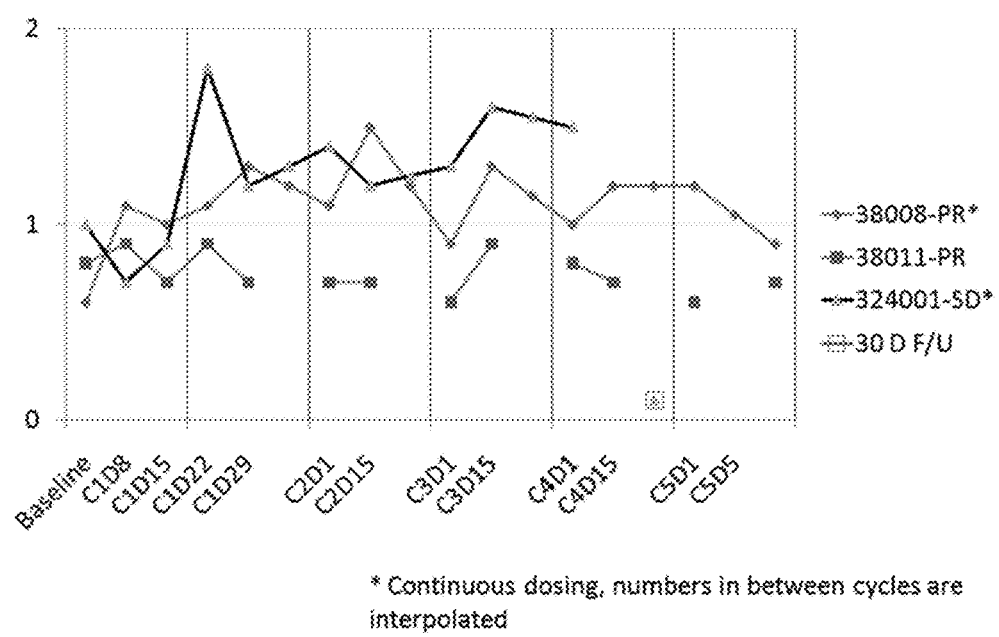
FIG. 10 depicts the absolute lymphocyte count (ALC)/ 109 L vs. Cycle Day after administering a Btk inhibitor to PR and SD individuals with DLBCL. The Y Axis shows the Absolute Lymphocyte Counts (ALC) at each time point by cycle number and day in the X axis. Patient 38011 was treated on schedule of 4 weeks on treatment followed by one week off. Thus, day 1 of each cycle follows one week off drug for this patient. Patients 38008 and 324001 were treated with continuous daily doses.
Figure 11:
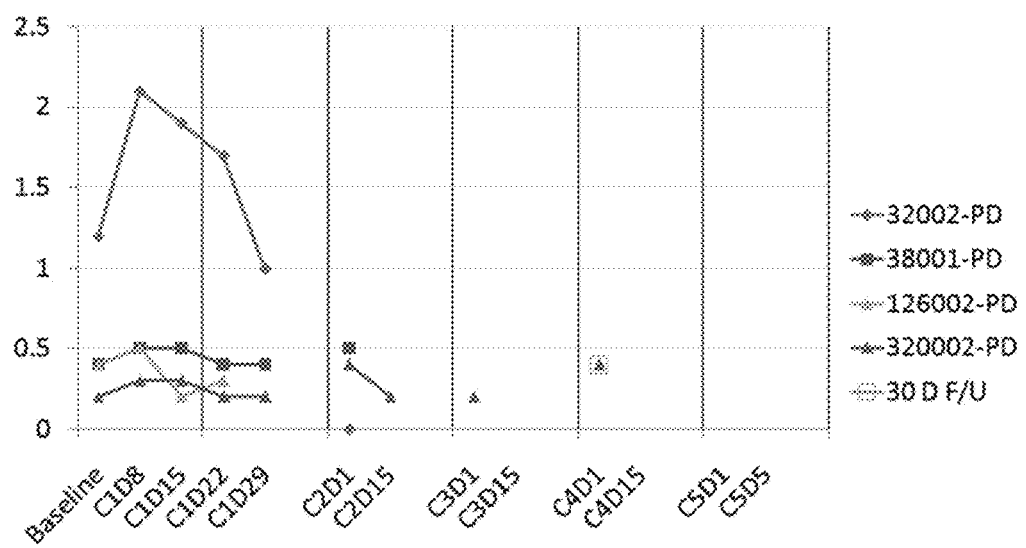
FIG. 11 depicts the absolute lymphocyte count (ALC)/109 L vs. Cycle Day after administering a Btk inhibitor to PD individuals with DLBCL. The Y Axis shows the Absolute Lymphocyte Counts (ALC) at each time point by cycle number and day in the X axis. All Patients were treated on schedule of 4 weeks on treatment followed by one week off. Thus, day 1 of each cycle follows one week off drug for these patients. Note lack of mobilization for 3 of the 4 patients. Patient 32002 received only one cycle of treatment.
Figure 12:
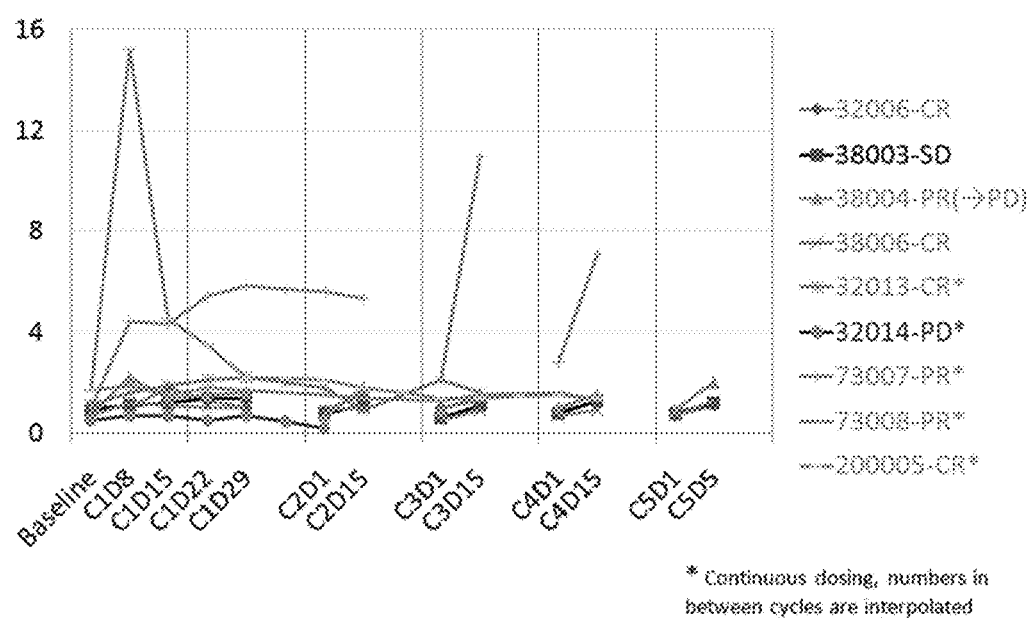
FIG. 12 depicts the absolute lymphocyte count (ALC)/ 109 L vs. Cycle Day after administering a Btk inhibitor to individuals with mantle cell lymphoma. The Y Axis shows the Absolute Lymphocyte Counts (ALC) at each time point by cycle number and day in the X axis. Patients 32006, 38003, and 38004 were treated on schedule of 4 weeks on treatment followed by one week off. Thus, day 1 of each cycle follows one week off drug for these patients. The other patients were treated with continuous daily dosing. Note that the patient with initial PD (32014) failed to show mobilization.
Figure 13:
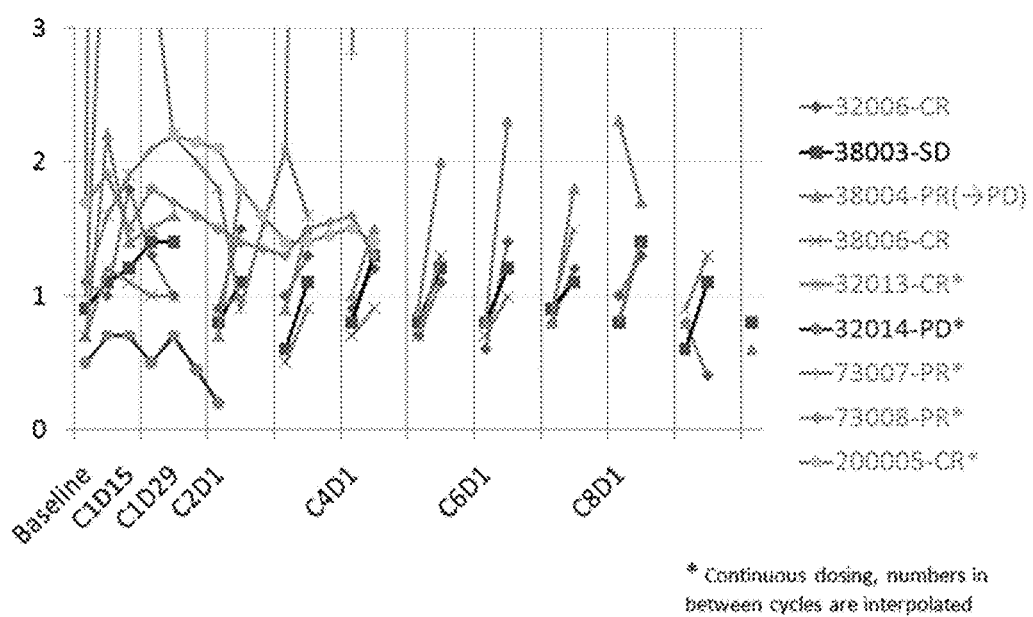
FIG. 13 depicts the absolute lymphocyte count (ALC)/ 109 L vs. Cycle Day for after administering a Btk inhibitor to the individuals with mantle cell lymphoma shown in FIG. 12. The axis has been changed, as compared to FIG. 12, to demonstrate low amplitude fluctuations. Note that all responding patients showed some degree of mobilization.
Figure 14:
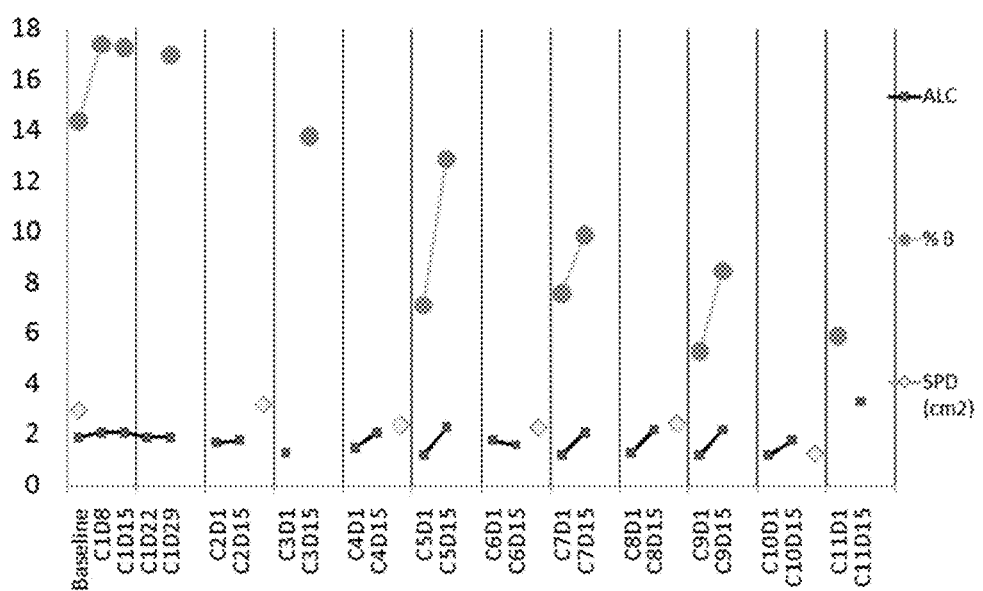
FIG. 14 demonstrates that lymphocyte mobilization, specifically B Cell type, consistent with lymphoma cells, decreases as disease responds. Patient 32007, Cohort 4, had follicular lymphoma, grade 3, which gradually regressed from SD to CR. Although the changes of ALC in this case are not dramatic, the B cell fraction is undergoing characteristic cyclic increases in response to treatment with a Btk inhibitor. Also note the decreasing cycle by cycle magnitude of shifts consistent with cumulative disease control.
Figure 15:
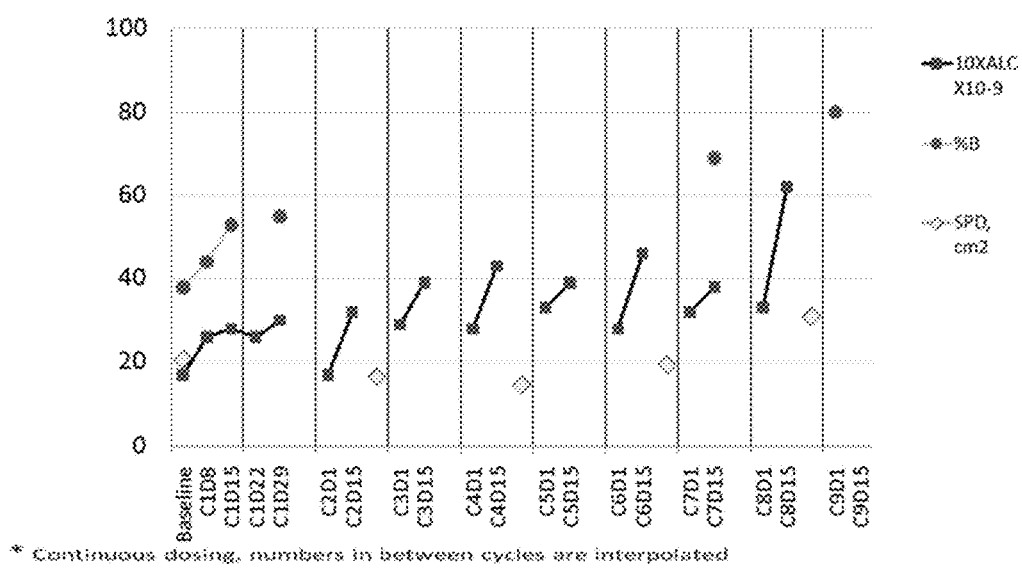
FIG. 15 demonstrates that there is increased B Cell mobilization with disease progression. Patient 32004, Cohort 2, had follicular lymphoma, grade 1, which progressed from SD initially to PD following Cycle 6.
Figure 16:
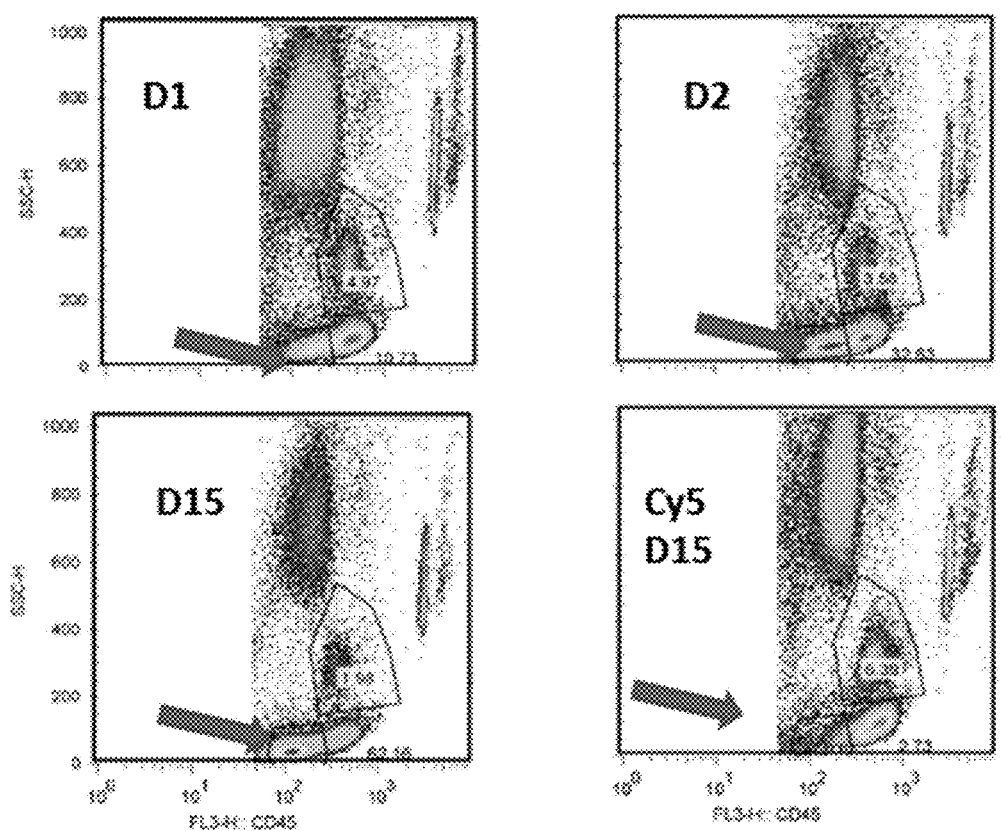
FIG. 16 depicts early mobilization and eventual decrease of a $CD45^{DIM}$ B cell subpopulation in responding mantle cell lymphoma patient 200-005. This subpopulation has a typical MCL immunophenotype ($CD45^{DIM}$) and is different than that of normal lymphocytes.
Figure 17:
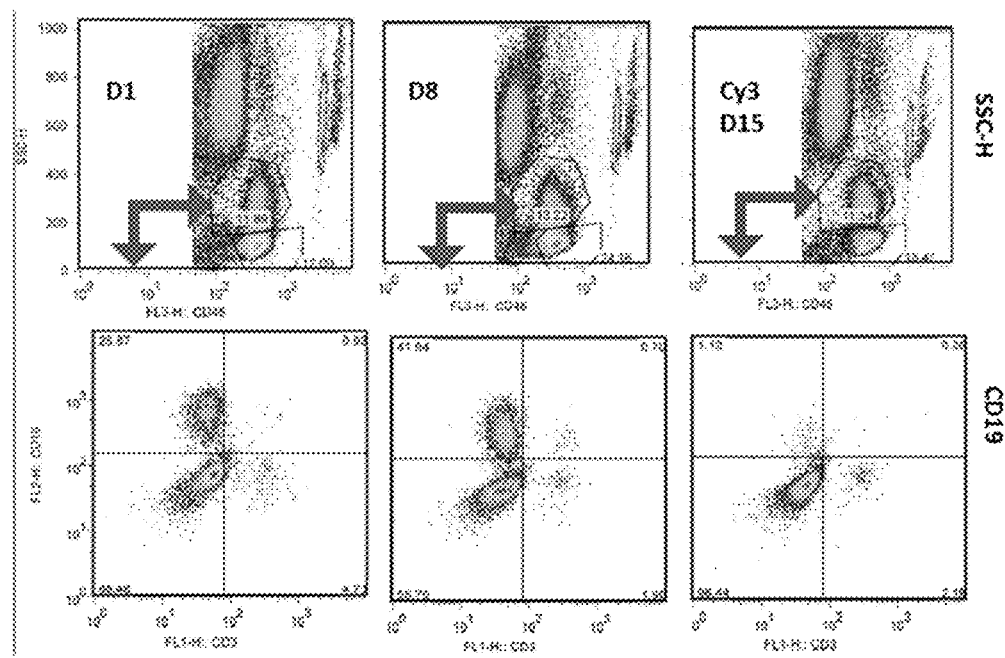
FIG. 17 depicts abnormal high light scatter $CD19^+$ cells mobilizing and then regressing in CR DLBCL Pt 324001. These $CD45^+$ cells with light scatter (SSC-H) in the upper panels were gated upon and their CD3 vs CD19 staining displayed in the lower panels. Here the putative malignant cells were "hidden" in the large MNC window normally defining monocytes. The sequence of mobilization followed by response is similar to other examples.

Adverse effects seen as a side effect of the treatment were monitored as outlined in FIG. 9. The effects were categorized by severity into grades 1-4. Grade 3 or greater events have been very uncommon. The vast majority of events have been mild in severity. Diarrhea, nausea, and fatigue have been the most commonly reported adverse events, with most of the reports occurring early in treatment Thus, the oral Btk inhibitor has marked activity in patients with CLL and SLL including high-risk pts. It provides good disease control with longer follow-up commonly exceeds 6 months. There is no evidence of drug-related myelosuppression or cumulative toxicity.

Example 7 Clinical Trial to Determine Safety and Efficacy of Compounds of Formula (D)

The purpose of this clinical trial is to study the side effects and best dose of a compound of Formula (D) and to determine its efficacy in the treatment of patients diagnosed with recurrent B-cell lymphoma.

Study Design

Cohorts of 6 patients each receive a compound of Formula (D) at 1.25, 2.5, 5.0, 8.3, 12.5, 17.5 mg/kg/d until the MTD is established. In cases where MTD is not reached, dosing levels are increased beyond 17.5 mg/kg/d by 33% increments. Patients receive daily treatment for 28 days followed by a 7 day rest period (one cycle). Tests for Btk occupancy by the drug ("occupancy") are performed on Day 1, 2, 8, 15 and 29 during Cycle 1 and on Day 1 and 15 of Cycles 3, 5, 7, 9, and 11. If ≤1 DLT ("dose-limiting toxicity") is observed in the cohort during Cycle 1, escalation to the next cohort will proceed. Patients are enrolled in the next cohort if four of the six patients enrolled in the cohort completed Cycle 1 without experiencing a DLT, while the remaining two patients are completing evaluation. If ≥2 DLTs are observed during Cycle 1, dosing at that dose and higher is suspended and the MTD is established as the previous cohort. Patients are allowed to continue dosing at the MTD. If ≥2 DLTs are seen at the 5.0 mg/kg/d cohort an additional cohort of 6 patients can be added at 3.75 mg/kg/d.

Upon determination of the MTD, a cohort of 6 patients is enrolled to receive a compound of Formula (D) at the MTD or "preferred occupying dose" continuously for 35 days with no rest period (one cycle).

Study Population

Up to 52 patients with recurrent surface immunoglobulin positive B cell non-Hodgkin's lymphoma according to WHO classification (including small lymphocytic lymphoma/chronic lymphocytic leukemia)

Study Objectives

1. Primary Objectives include:

A. Determine pharmacokinetics (PK) of an orally administered compound of Formula (D).

B. Evaluate tumor response. Patients have screening (i.e., baseline) disease assessments within 30 days before beginning treatment. Patients undergo follow-up disease assessments following specified dosing cycles. Patients without evidence of disease progression on treatment are followed for a maximum of 6 months off treatment for disease progression. At screening, a computed tomography (CT) (with contrast unless contraindicated) and positron-emission tomography (PET) or CT/PET scan of the chest, abdomen, and pelvis are required. At other visits, a CT (with contrast unless contraindicated) scan of the chest, abdomen, and pelvis are obtained. A CT/PET or PET is required to confirm a complete response. Bone marrow biopsy is optional. In patients known to have positive bone marrow before treatment with study drug, a repeat biopsy should be done to confirm a complete response following treatment. All patients are evaluated for response based on International Working Group Revised Response Criteria for Malignant Lymphoma, Guidelines for the diagnosis and treatment of chronic lymphocytic leukemia14, or Uniform Response Criteria in Waldenstrom's Macroglobulinemia.

C. Measure pharmacodynamic (PD) parameters to include drug occupancy of Btk, the target enzyme, and effect on biological markers of B cell function. Specifically, this study examines the pharmacodynamics (PD) of the drug in peripheral blood mononuclear cells (PBMCs) using two PD assays. The first PD assay measures occupancy of the Btk active site by the drug using a specially designed fluorescent probe. The second PD assay measures inhibition of B cell activation by stimulating the PBMCs ex vivo at the BCR with anti-IgM/IgG, and then assaying cell surface expression of the activation marker CD69 by flow cytometry The PD biomarkers are measured in vitro from a blood sample removed from patients 4-6 hours following an oral dose of the drug. These assays determine what drug levels are required to achieve maximal occupancy of Btk and maximal inhibition of BCR signaling. When possible, similar studies are conducted on circulating tumor cells isolated from blood of patients.

2. Secondary Objectives include:

A. To analyze tumor biopsy samples (when possible) for apoptotic biomarker expression analysis.

Inclusion Criteria

To be eligible to participate in this study, a patient must meet the following criteria:

Women and men≥18 years of age

Body weight≥40 kg

Recurrent surface immunoglobulin positive B cell non-Hodgkin's lymphoma (NHL) according to WHO classification, including small lymphocytic lymphoma/chronic lymphocytic leukemia (SLL/CLL) and lymphoplasmacytic lymphoma, including Waldenstrom's Macroglobulinemia (WM)

Measurable disease (for NHL, bidimensional disease≥2 cm diameter in at least one dimension, for CLL≥5000 leukemia cells/mm3, and for WM presence of immunoglobulin M paraprotein with a minimum IgM level≥1000 mg/dL and infiltration of bone marrow by lymphoplasmacytic cells)

Have failed≥1 previous treatment for lymphoma and no standard therapy is available. Patients with diffuse large B cell lymphoma must have failed, refused or be ineligible for autologous stem cell transplant ECOG performance status of ≤1

Ability to swallow oral capsules without difficulty

Willing and able to sign a written informed consent

Exclusion Criteria

A patient meeting any of the following criteria will be excluded from this study:

More than four prior systemic therapies (not counting maintenance rituximab), except for CLL patients. Salvage therapy/conditioning regimen leading up to autologous bone marrow transplantation is considered to be one regimen Prior allogeneic bone marrow transplant Immunotherapy, chemotherapy, radiotherapy or experimental therapy within 4 weeks before first day of study drug dosing Major surgery within 4 weeks before first day of study drug dosing CNS involvement by lymphoma Active opportunistic infection or treatment for opportunistic infection within 4 weeks before first day of study drug dosing Uncontrolled illness including but not limited to: ongoing or active infection, symptomatic congestive heart failure (New York Heart Association Class III or IV heart failure), unstable angina pectoris, cardiac arrhythmia, and psychiatric illness that would limit compliance with study requirements History of myocardial infarction, acute coronary syndromes (including unstable angina), coronary angioplasty and/or stenting within the past 6 months Known HIV infection Hepatitis B sAg or Hepatitis C positive Other medical or psychiatric illness or organ dysfunction which, in the opinion of the investigator, would either compromise the patient's safety or interfere with the evaluation of the safety of the study agent Pregnant or lactating women (female patients of childbearing potential must have a negative serum pregnancy test within 14 days of first day of drug dosing, or, if positive, a pregnancy ruled out by ultrasound)

History of prior cancer<2 years ago, except for basal cell or squamous cell carcinoma of the skin, cervical cancer in situ or other in situ carcinomas Results:

29 pts (12 follicular, 7 CLL/SLL, 4 DLBCL, 4 mantle, 2 marginal) with a median of 3 prior therapies have been enrolled on cohorts 1-4. Therapy was well tolerated with most adverse events<grade 2. One protocol defined DLT (dose delay>7 d due to neutropenia) was observed. 19/22 pts from cohorts 1-3 are evaluable. The ORR is 42%; 1 CR (SLL), 7 PR (4 CLL/SLL, 2 MCL and 1FL). In cohort 2, PD demonstrate complete occupancy of Btk by a compound of Formula (D), with >95% enzyme occupancy 4 hours post dose in all pts. Basophil degranulation, a Btk-dependent cellular process, was completely inhibited up to 24 hrs. T-cell responses were not affected, and no significant depletion of peripheral blood B, T or NK cell counts was observed. Positive correlation ($R2=0.93$) was found between Btk active-site occupancy in PBMCs (mean of Days 1 and 8) and a compound of Formula (D) plasma $AUC0-\infty$ (Day 1) at the 1.25 mg/kg dose.

Example 8: Clinical Example of Diagnosis of BCLDs Using a Btk Inhibitor

A patient with BCLD completes treatment with a Btk inhibitor or another treatment, and appears to be in complete remission. After this treatment is stopped, a short course of the Btk inhibitor is then given. If cells with markers of the malignant cells appear in the peripheral blood, in some embodiments it is an indication for continued treatment or for starting another treatment. One example of the cell subpopulation investigated for in the peripheral blood is cells bearing both the CD5 and CD20 markers, which is typical of CLL/SLL and Mantle Cell Lymphoma. These markers can be detectable by flow cytometry. A further example of cell type is follicular lymphoma, which is characterized by cells with t(14;18) which in other embodiments are detectable by PCR or in situ hybridization in cells harvested from the peripheral blood.

For patients initially starting on treatment an increase of the malignant subpopulation can be an early predictive marker of response or duration of response.

For patients who have previously received treatment and are suspected of progressing based upon changes (for example in a scan) that are non-diagnostic, the BTK test for peripheral blood cell increases could add diagnostic information that enable earlier treatment of relapse. This would be valuable in determining whether to re-start treatment for BCLD or to watch or to pursue an alternative diagnosis.

The test could yield better diagnostic information for patients whose BCLD is suspected to be transforming into a more aggressive cellular form. For example both CLL/SLL and lower grade follicular lymphoma can transform into a higher grade process which may resemble diffuse large B cell lymphoma, and require more aggressive treatment.

Example 9: Patient Selection

Patient selection screens are performed to identify an individual with the ABC subtype of DLBCL. Gene expression profiling is conducted using FFPE biopsy material, using RNA amplified with a Nugen kit and assayed on an Affymetrix U133Plus 2.0 arrays.

Samples are screened for recurrent somatic mutations. This is accomplished by conventional resequencing of candidate genes in the NF-kB and B cell receptor signaling pathways (e.g. CARD11, CD79A, CD79B, MYD88, TNFAIP3) plus p53 by exon amplification and standard dideoxy automated DNA sequencing.

The patient selection screen also identifies patients with ABC DLBCL that are particularly sensitive or resistant to Btk inhibitors. A positive result for a CARD11 mutation indicates that the individual is resistant to Btk inhibitors because CARD11 mutations activate the NF-kB pathway at a step that is downstream of BTK.

Genomic copy number analysis is also required to adequately assess the activity of oncogenic pathways that may be relevant for the response to Btk inhibitors as well as to assess prognosis. In particular, ABC DLBCLs harbor genomic deletions of the TNFAIP3 locus, which encodes A20, a negative regulator of NF-kB. Thus, a full assessment of A20 status requires both resequencing to look for somatic mutations and copy number analysis to look for deletions. In addition, patients are identified with DLBCL tumors that harbor genomic deletions in the INK4a/ARF locus or have trisomy of chromosome 3 because these genomic aberrations are associated with poor prognosis in ABC DLBCL. A single pass high throughput DNA sequencing is performed using the Illumina HiSeq2000 platform to assess genomic copy number globally.

Example 10: PK and Efficacy of a Btk Inhibitor in Individuals with CLL or SLL

A Btk inhibitor was administered to 33 individuals diagnosed with CLL or SLL. Efficacy and PK was determined.

| No. | Dose mg | Patient_ID | Group | Sex | Day 8 AUC0-24 (ng · h/mL) | Cycle | IWG Resp March 2011 |
|---|---|---|---|---|---|---|---|
| 1 | 420 | 073-203 | Naïve | Female | 102 | 7 | PR |
| 2 | 420 | 217-107 | R/R | Male | 120 | 8 | PR |
| 3 | 420 | 217-202 | Naïve | Female | 121 | 7 | SD |
| 4 | 420 | 032-110 | R/R | Male | 155 | 6 | PR |
| 5 | 420 | 217-104 | R/R | Male | 176 | 8 | PR |
| 6 | 420 | 032-201 | Naïve | Male | 177 | 9 | PR |
| 7 | 420 | 217-103 | R/R | Female | 206 | 8 | Nodal |
| 8 | 420 | 032-104 | R/R | Male | 227 | 8 | PR |
| 9 | 420 | 217-102 | R/R | Male | 243 | 9 | Nodal |
| 10 | 420 | 217-106 | R/R | Female | 267 | 8 | Nodal |
| 11 | 420 | 032-109 | R/R | Male | 318 | 7 | Nodal |
| 12 | 420 | 217-110 | R/R | Female | 407 | 7 | Nodal |
| 13 | 420 | 038-101 | R/R | Male | 428 | 7 | PR |
| 14 | 420 | 217-111 | R/R | Male | 473 | 7 | PR |
| 15 | 420 | 217-109 | R/R | Male | 498 | 7 | Nodal |
| 16 | 420 | 032-107 | R/R | Male | 502 | 8 | Nodal |
| 17 | 420 | 073-201 | Naïve | Male | 532 | 2 | SD |
| 18 | 420 | 032-105 | R/R | Male | 534 | 8 | PR |
| 19 | 420 | 217-101 | R/R | Male | 570 | 9 | CR |
| 20 | 420 | 073-101 | R/R | Male | 593 | 4 | PR |
| 21 | 420 | 217-105 | R/R | Female | 594 | 8 | PR |
| 22 | 420 | 032-101 | R/R | Female | 643 | 9 | Nodal |
| 23 | 420 | 073-202 | Naïve | Male | 648 | 9 | PR |
| 24 | 420 | 217-112 | R/R | Female | 653 | 7 | SD |
| 25 | 420 | 217-201 | Naïve | Male | 687 | 9 | PR |
| 26 | 420 | 073-204 | Naïve | Male | 784 | 1 | NE |
| 27 | 420 | 217-108 | R/R | Male | 809 | 1 | PD |
| 28 | 420 | 032-108 | R/R | Male | 907 | 7 | PR |
| 29 | 420 | 032-106 | R/R | Male | 1200 | 8 | Nodal |
| 30 | 420 | 032-102 | R/R | Male | 1210 | 2 | NE |
| 31 | 420 | 217-113 | R/R | Male | 1270 | 4 | Cri |
| 32 | 420 | 032-202 | Naïve | Female | 1670 | 8 | PR |
| 33 | 420 | 038-201 | Naïve | Female | 2000 | 7 | CR |

Example 11: Clinical Trial with Btk Inhibitor

A phase Ib/II clinical trial was performed to study the effects of a Btk inhibitor on individuals with CLL.

Study Type: Interventional

Allocation: Non-Randomized

Endpoint Classification: Safety Study

Intervention Model: Parallel Assignment

Masking: Open Label

Primary Purpose: Treatment

Group I (elderly, naïve, individuals) received 420 mg/day of the Btk inhibitor. Group II (R/R individuals, who had twice been treated with fludara) received 420 mg/day of the Btk inhibitor. Group III (R/R individuals, who had twice been treated with fludara) received 840 mg/day of the Btk inhibitor.

Patient Characteristics

|  | Treatment-Naïve 420 mg (N = 23) | Relapsed/Refractory 420 mg (N = 27) | Relapsed/Refractory 840 mg (N = 33) |
|---|---|---|---|
| Age, y |  |  |  |
| Median: | 71 | 64 | 65 |
| Range: | 66-84 | 40-81 | 44-80 |
| Dx # pts |  |  |  |
| CLL: | 22 (96%) | 26 (96%) | 32 (97%) |
| SLL: | 1 (4%) | 1 (4%) | 1 (3%) |
| Prior Rx, # |  |  |  |
| Median: | 0 | 3 | 5 |
| Range: |  | 2-10 | 2-12 |
| Prior therapy, % |  |  |  |
| Nucleoside analog | 0 (0%) | 27 (100%) | 33 (100%) |
| Rituximab | 0 (0%) | 25 (93%) | 32 (97%) |
| Alkylator | 0 (0%) | 24 (89%) | 27 (82%) |
| Alemtuzumab | 0 (0%) | 5 (19%) | 3 (9%) |
| Bendamustine | 0 (0%) | 8 (30%) | 13 (39%) |
| Ofatumumab | 0 (0%) | 8 (30%) | 10 (30%) |
| Cytopenia at baseline, % |  |  |  |
| ANC <1500/UL | 1 (4%) | 6 (22%) | 17 (52%) |
| HGB <11 g/dL | 7 (30%) | 4 (15%) | 19 (58%) |
| Platelets <100,000/uL | 9 (39%) | 8 (30%) | 22 (67%) |
| Prognostic Markers, %* |  |  |  |
| IgVH unmutated: | 8/16 (50%) | 17/24 (71%) | 18/24 (75%) |
| Del(17p): | 2/17 (12%) | 9/24 (38%) | 10/25 (40%) |
| Del(11q): | 0/17 (0%) | 8/24 (33%) | 12/25 (48%) |
| β Microglobin <3 mg/L | 10/16 (62%) | 14/23 (61%) | 8/25 (32%) |
| β Microglobin ≥3 mg/L | 6/16 (38%) | 9/23 (39%) | 17/25 (68%) |

Tumor assessment was performed every 2 treatment cycles.

Objectives

Describe the characteristics of the antitumor effect of a Btk inhibitor in individuals with CLL/SLL, e.g., reduction in lymphadenopathy/splenomegaly, and kinetics of change in absolute lymphocyte count (ACL).

Summarize the safety profile of the Btk inhibitor.

Inclusion Criteria

FOR TREATMENT-NAIVE GROUP ONLY: Men and women≥65 years of age with confirmed diagnosis of CLL/SLL, who require treatment per NCI or International Working Group guidelines 11-14

FOR RELAPSED/REFRACTORY GROUP ONLY: Men and women≥18 years of age with a confirmed diagnosis of relapsed/refractory CLL/SLL unresponsive to therapy (ie, failed≥2 previous treatments for CLL/SLL and at least 1 regimen had to have had a purine analog [eg, fludarabine] for subjects with CLL)

Body weight≥40 kg

ECOG performance status of ≤2

Agreement to use contraception during the study and for 30 days after the last dose of study drug if sexually active and able to bear children Willing and able to participate in all required evaluations and procedures in this study protocol including swallowing capsules without difficulty Ability to understand the purpose and risks of the study and provide signed and dated informed consent and authorization to use protected health information (in accordance with national and local subject privacy regulations)

Exclusion Criteria

A life-threatening illness, medical condition or organ system dysfunction which, in the investigator's opinion, could compromise the subject's safety, interfere with the absorption or metabolism of Btk inhibitor PO, or put the study outcomes at undue risk Any immunotherapy, chemotherapy, radiotherapy, or experimental therapy within 4 weeks before first dose of study drug (corticosteroids for disease-related symptoms allowed but require 1-week washout before study drug administration)

Central Nervous System (CNS) Involvement by Lymphoma

Major surgery within 4 weeks before first dose of study drug

Creatinine>1.5× institutional upper limit of normal (ULN); total bilirubin>1.5× ULN (unless due to Gilbert's disease); and aspartate aminotransferase (AST) or alanine aminotransferase (ALT)>2.5×ULN unless disease related Concomitant use of medicines known to cause QT prolongation or torsades de pointes Significant screening electrocardiogram (ECG) abnormalities including left bundle branch block, 2nd degree AV block type II, 3rd degree block, bradycardia, and QTc>470 msec Lactating or pregnant Response Criteria NHL IWG criteria 1 were applied to SLL cases without modification The 2008 CLL IWG criteria were applied to CLL cases with the following modifications:
a. An isolated lymphocytosis, in the absence of other parameters meeting the criteria for PD, was not considered PD
b. Patients experiencing a lymphocytosis, but obtaining a PR by other measurable parameters, were classified as "nodal" response until there was a 50% reduction in ALC from baseline in which case they were categorized as PR.
c. Patients with a normal ALC (<5K) at baseline with treatment-related lymphocytosis required normalization to <5K to be categorized as PR.

Results

Subject Disposition

|  | Treatment-Naïve 420 mg (N = 23) | Relapsed/Refractory 420 mg (N = 27) | Relapsed/Refractory 840 mg (N = 33) |
|---|---|---|---|
| Number of subjects | 23 | 27 | 33 |
| Follow-up Median (months) | 6.3 | 7.8 | 4.6 |
| Range | 1.4-9.2 | 0.7-9.5 | 0.3-6.5 |
| Subjects still on study | 21 (91%) | 22 (81%) | 28 (85%) |
| Subject Discontinued | 2 (9%) | 5 (19%) | 5 (15%) |
| Primary Reasons for Discontinuation |  |  |  |
| Disease Progression | 0 (0%) | 2 (7%) | 1 (3%) |
| Death | 0 (0%) | 0 (0%) | 2 (6%) |
| Adverse Event | 1 (4%) | 1 (4%) | 1 (3%) |
| Other | 1 (4%) | 2 (7%) | 1 (3%) |

Best Response

| | Treatment-Naïve 420 mg | Relapsed/Refractory 420 mg |
|---|---|---|
| N | 21 | 27 |
| CR | 1 (5%) | 1 (4%) |
| PR | 13 (62%) | 12 (44%) |
| ORR % | 67% | 48% |
| Nodal | 4 (19%) | 11 (41%) |
| SD | 2 (10%) | 1 (4%) |
| PD | 0 | 1 (4%) |
| NE | 1 (5%) | 1 (4%) |

Best Response by Risk Features

| | | Best Response | |
|---|---|---|---|
| Molecular Risk Feature | N | IWG Response | Nodal Response |
| Overall | 27 | 48% | 41% |
| Del17p | 9 | 44% | 33% |
| Del11q | 8 | 63% | 37% |
| IgVH unmutated | 17 | 53% | 29% |

Figure 18:
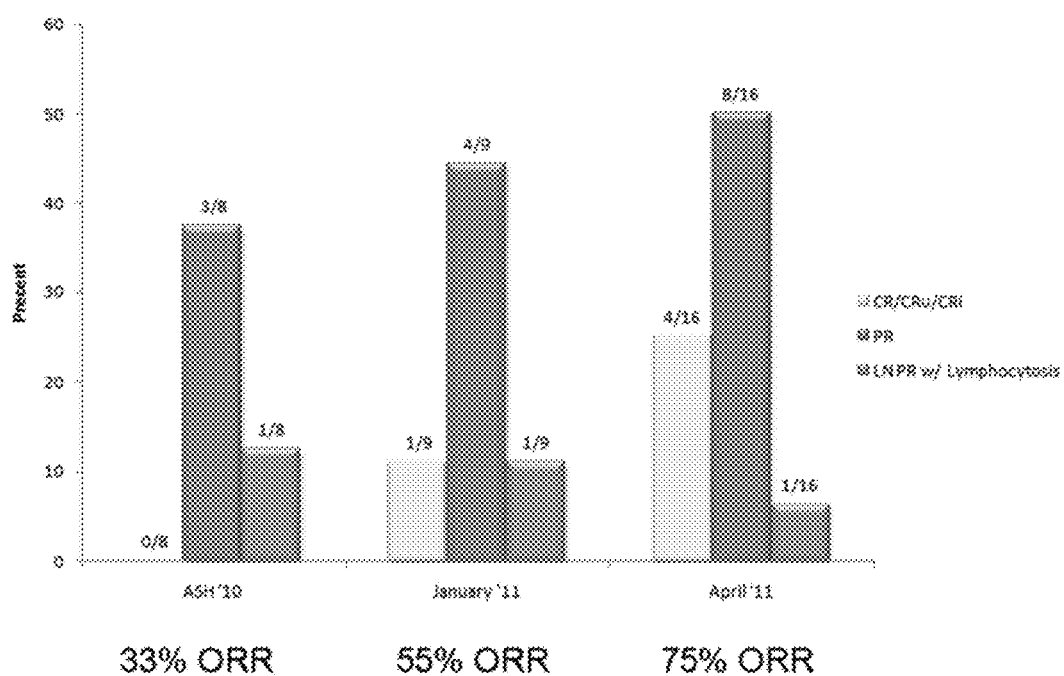
FIG. 18 presents the responses for a clinical trial involving administering a Btk inhibitor to elderly patients with CLL or SLL, who are naïve for drug intervention. Individuals were administered 420 mg/day of a Btk inhibitor.
Figure 19:
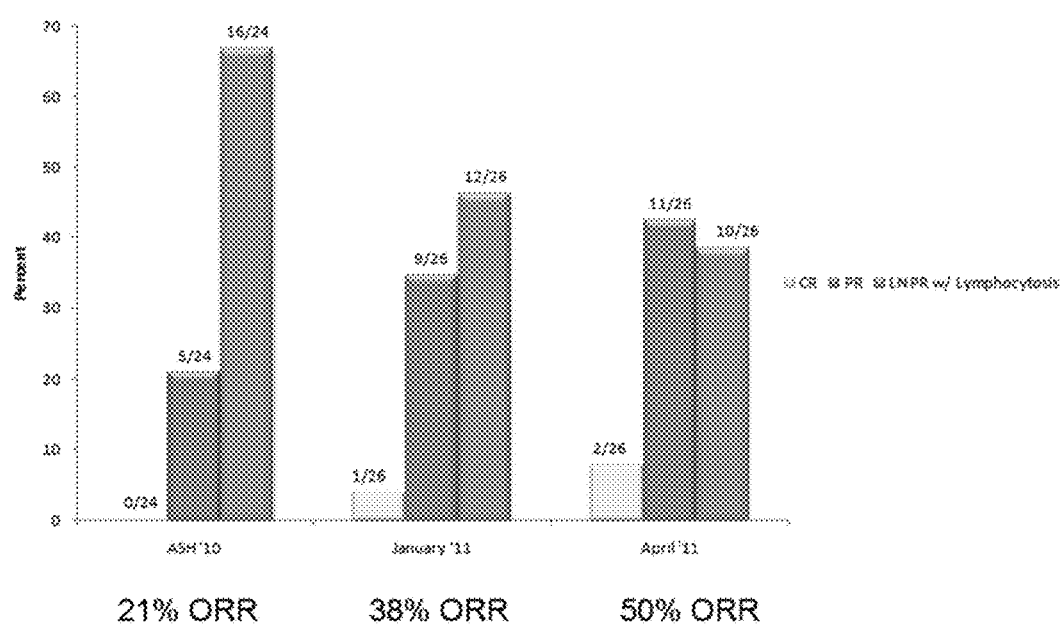
FIG. 19 presents the responses for a clinical trial involving administering a Btk inhibitor to R/R patients with CLL or SLL. Individuals were administered 420 mg/day of a Btk inhibitor.
Figure 20:
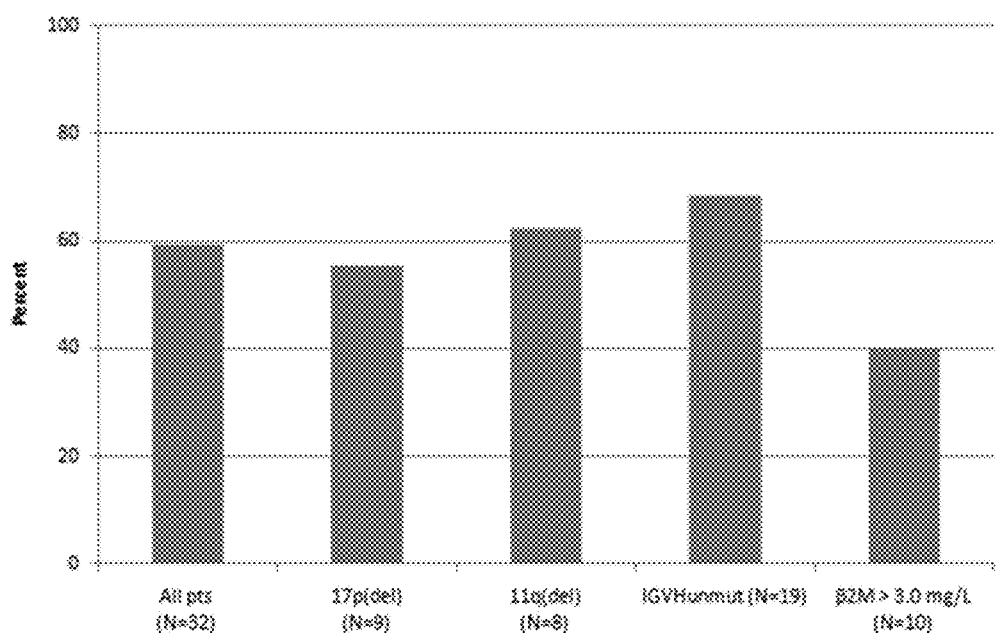
FIG. 20 presents the responses for a clinical trial involving administering a Btk inhibitor to individuals with high risk CLL.
Figure 21:
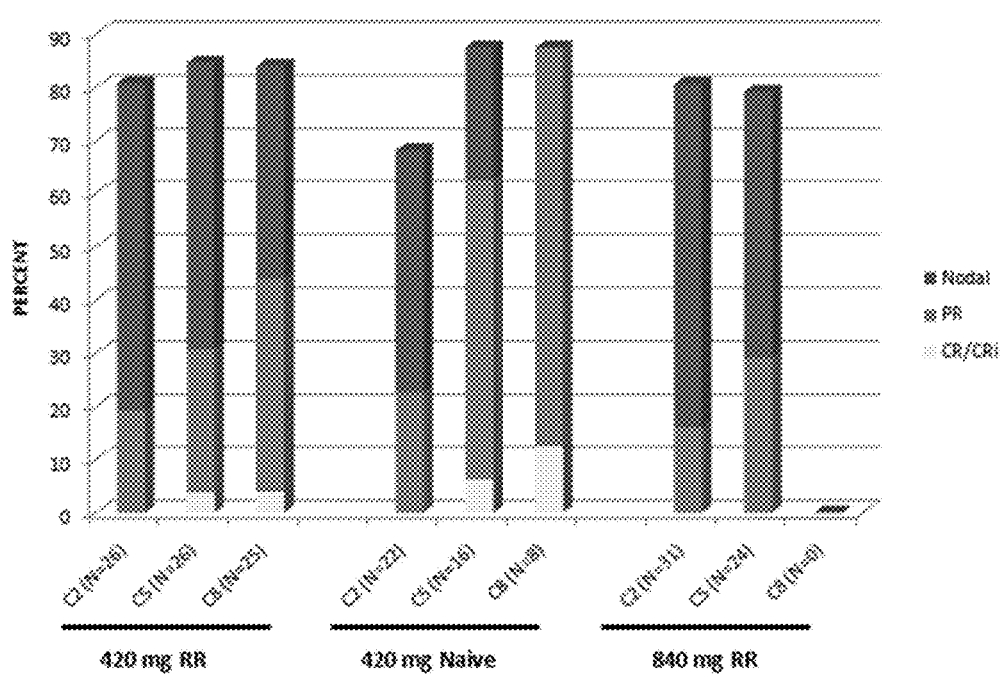
FIG. 21 presents the response over time for a clinical trial involving administering a Btk inhibitor to individuals with CLL or SLL.
Figure 22:
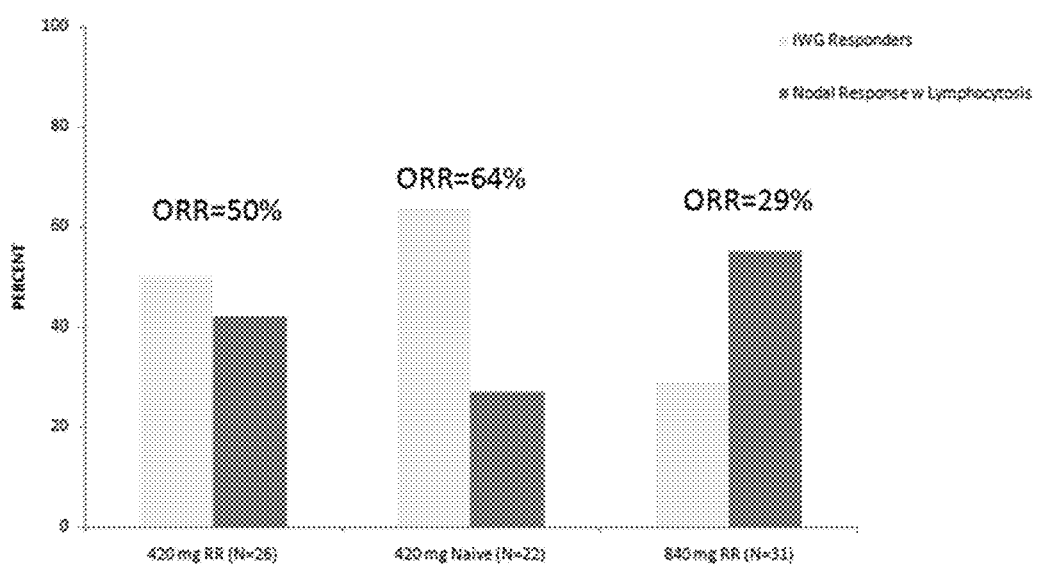
FIG. 22 presents the best responses for all patients in a clinical trial involving administering a Btk inhibitor to individuals with CLL or SLL.
Figure 23:
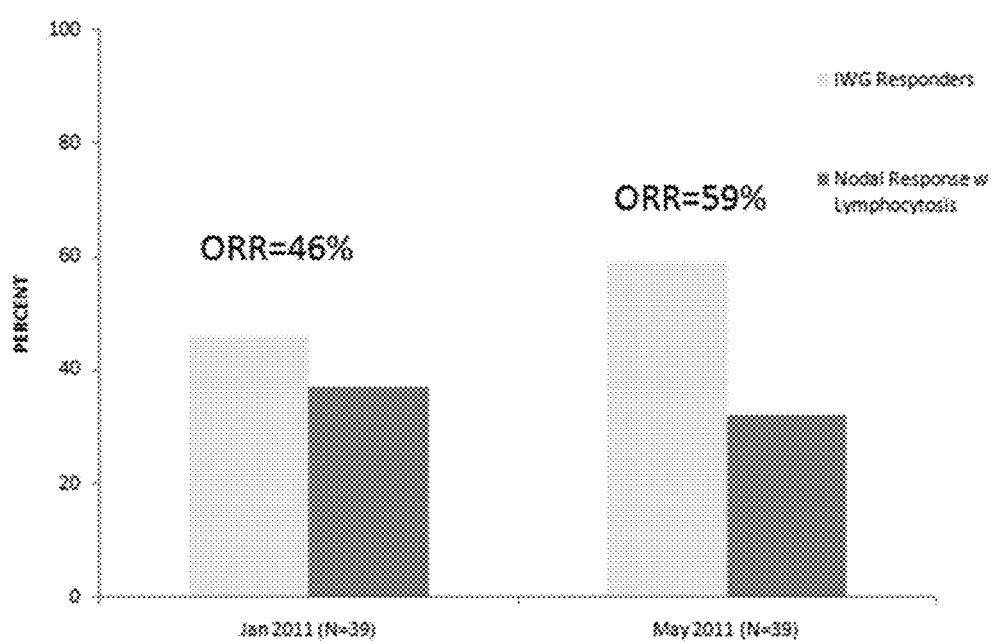
FIG. 23 presents the best responses for abstract patients in a clinical trial involving administering a Btk inhibitor to individuals with CLL or SLL.
Figure 24:
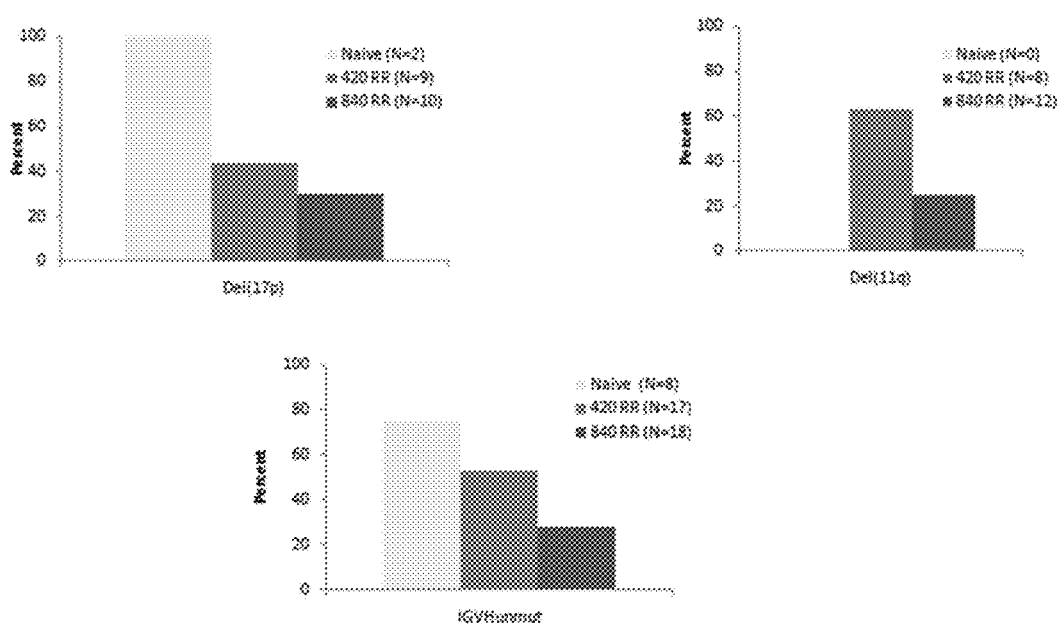
FIG. 24 presents the best response by prognostic factor in CLL or SLL patients involved in a clinical trial involving administering a Btk inhibitor.
Figure 25:
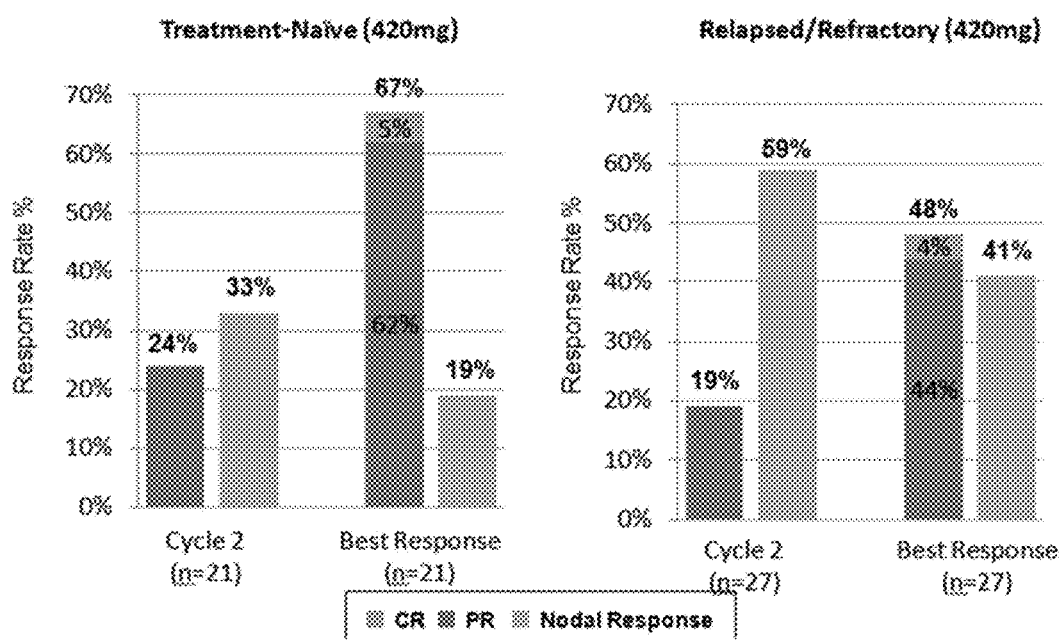
FIG. 25 presents initial (Cycle 2) response assessment and best response (420 mg Cohorts) in CLL or SLL patients involved in a clinical trial involving administering a Btk inhibitor.
Figure 26:
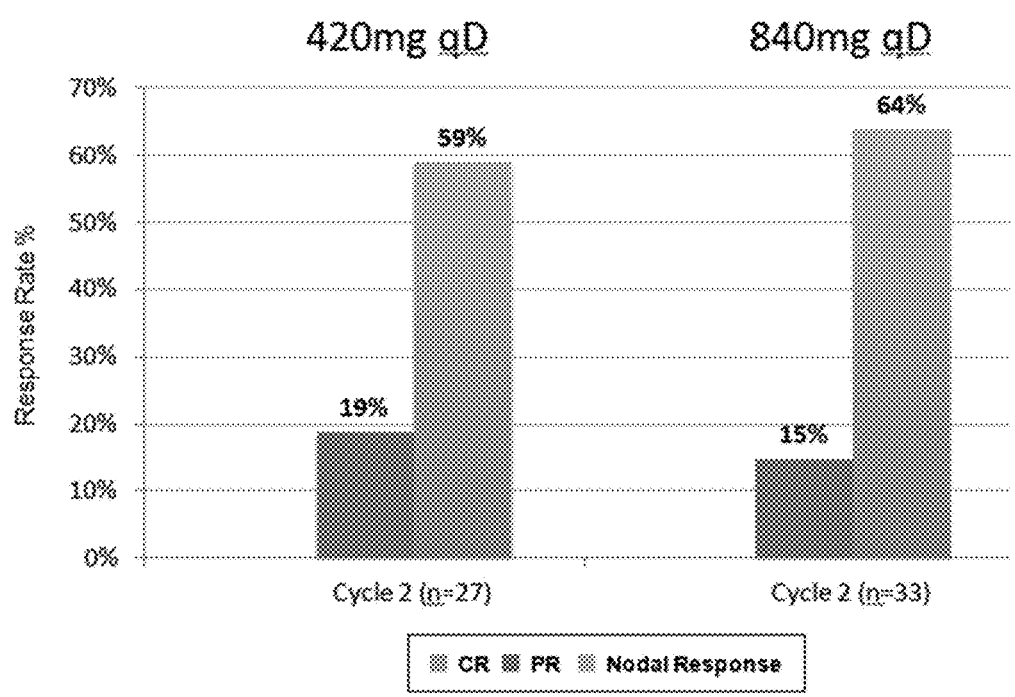
FIG. 26 presents initial (Cycle 2) response assessment by dose in relapsed/refractory CLL or SLL patients involved in a clinical trial involving administering a Btk inhibitor.
Figure 27:
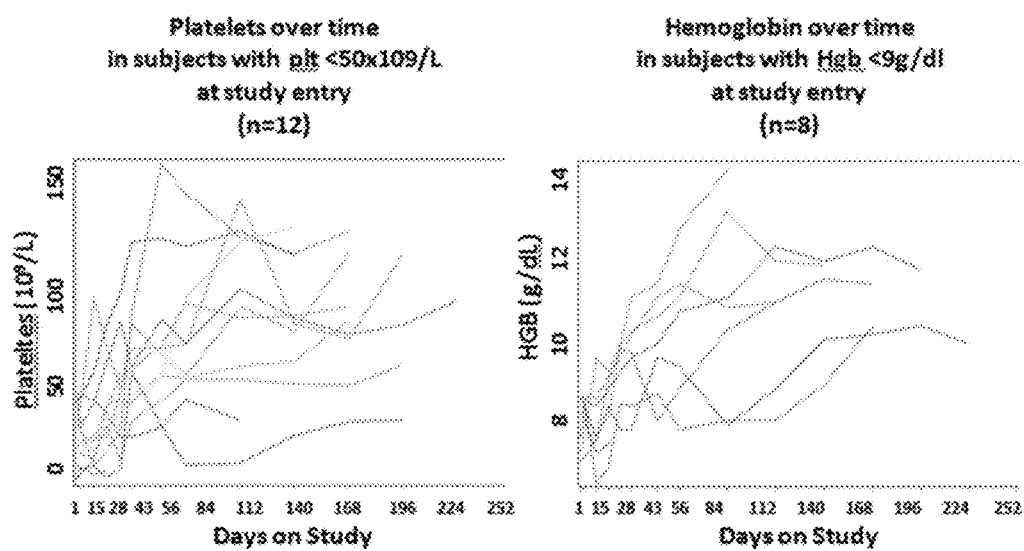
FIG. 27 presents improvements in hematological parameters in CLL or SLL patients involved in a clinical trial involving administering a Btk inhibitor.
Figure 28:
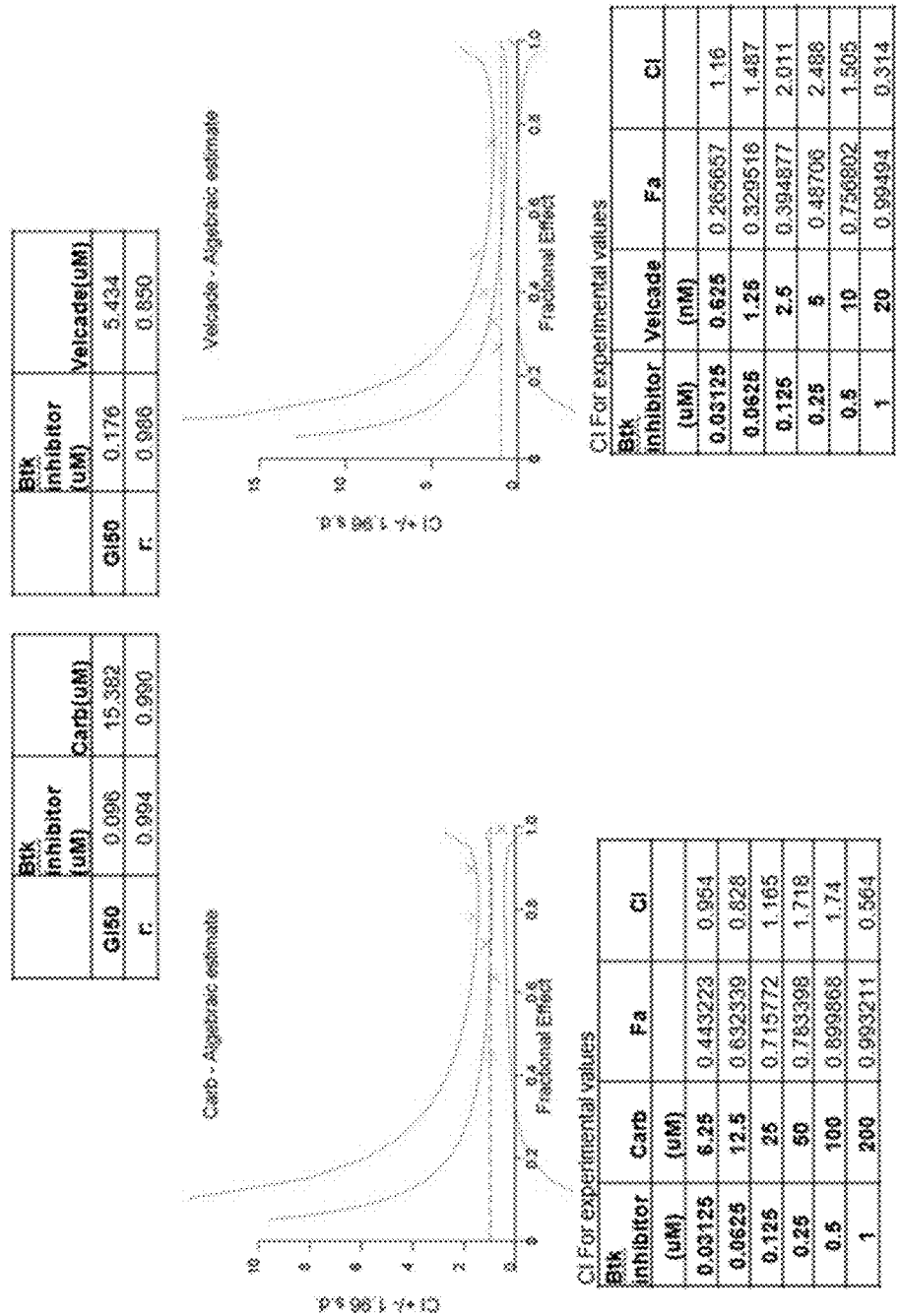
FIG. 28 present data showing the results of a combination of a Btk inhibitor and Carboplatin or Velcade in DoHH2 cells.
Figure 29:
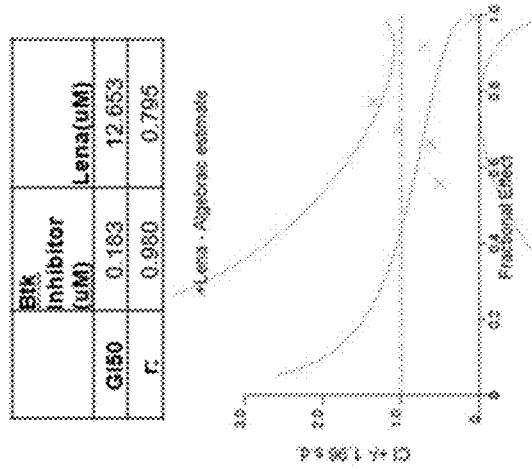
FIG. 29 present data showing the results of a combination of a Btk inhibitor and Dexamethasone or Lenalidomide in DoHH2 cells.
Figure 29:
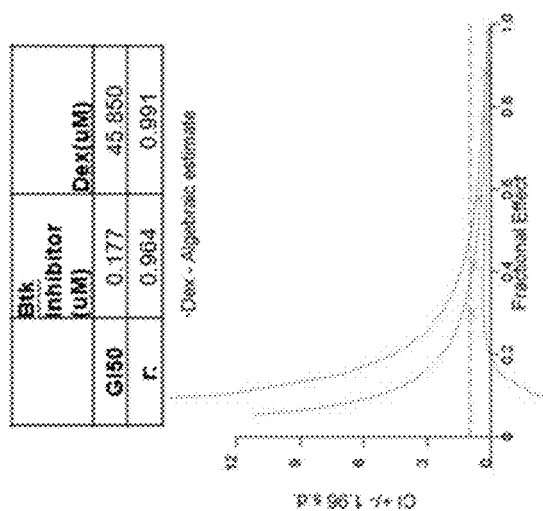
Figure 30:
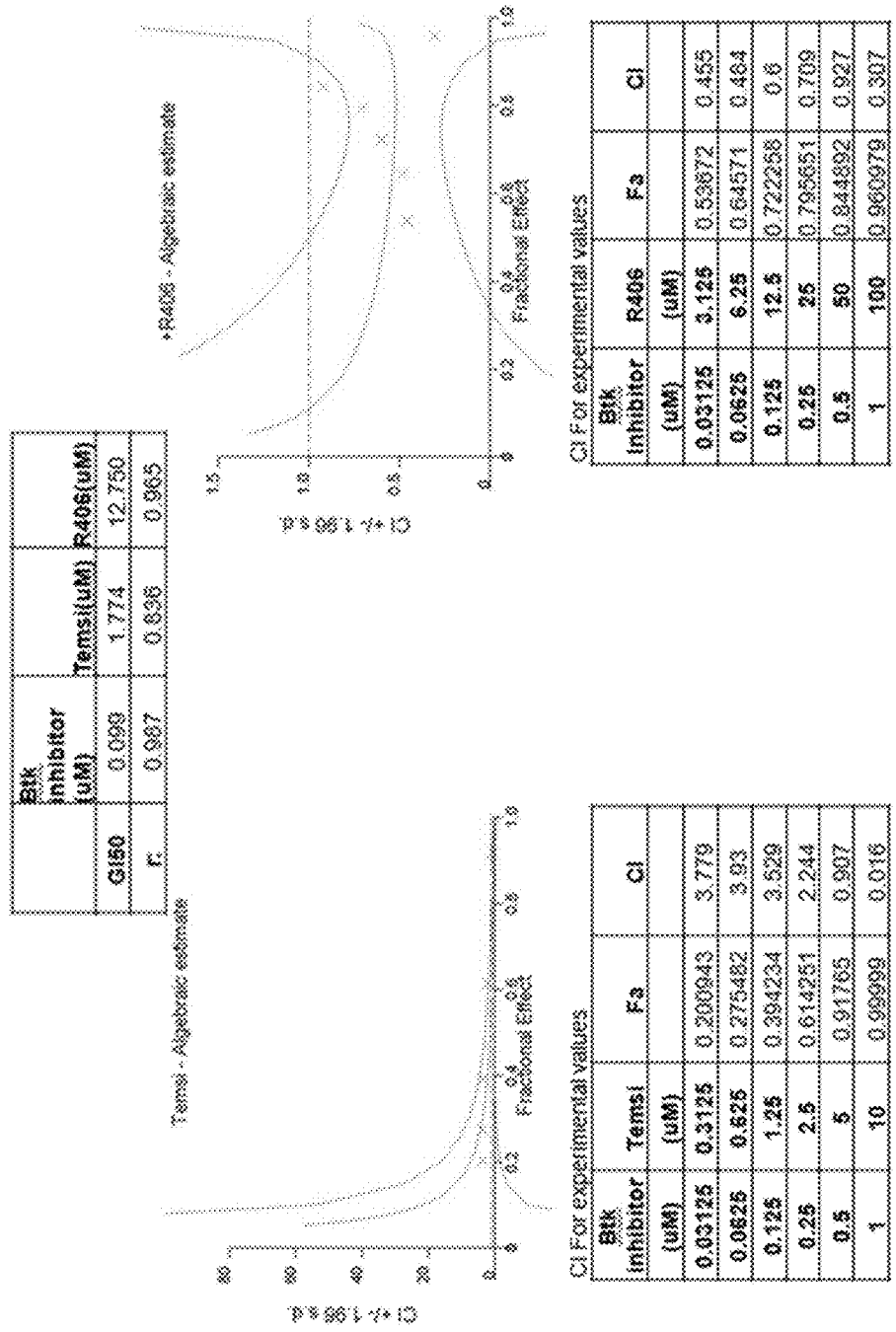
FIG. 30 present data showing the results of a combination of a Btk inhibitor and Temsirolimus or R406 in DoHH2 cells.
Figure 31:
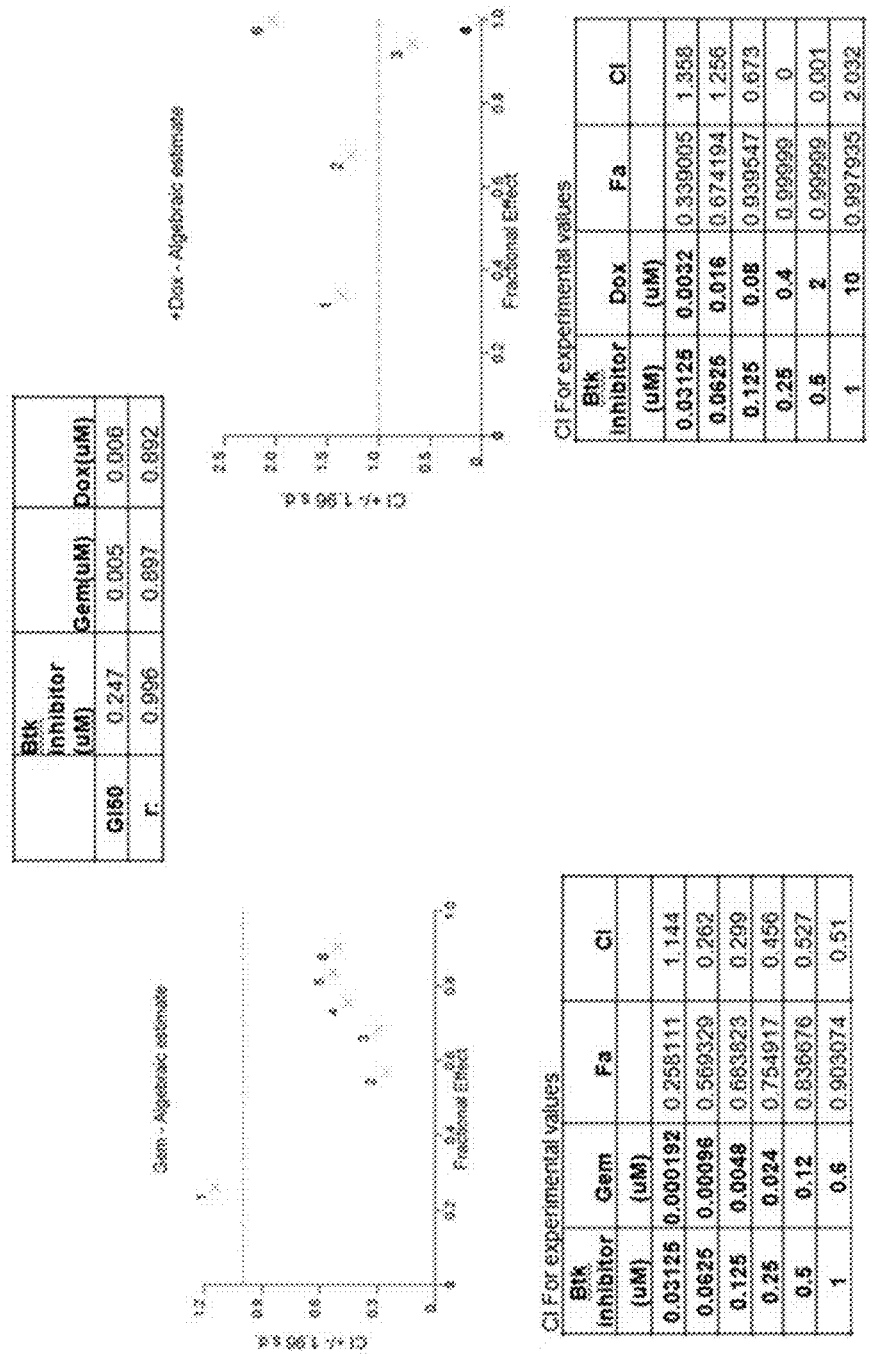
FIG. 31 present data showing the results of a combination of a Btk inhibitor and Gemcitabine or Doxorubicin in DoHH2 cells.
Figure 32:
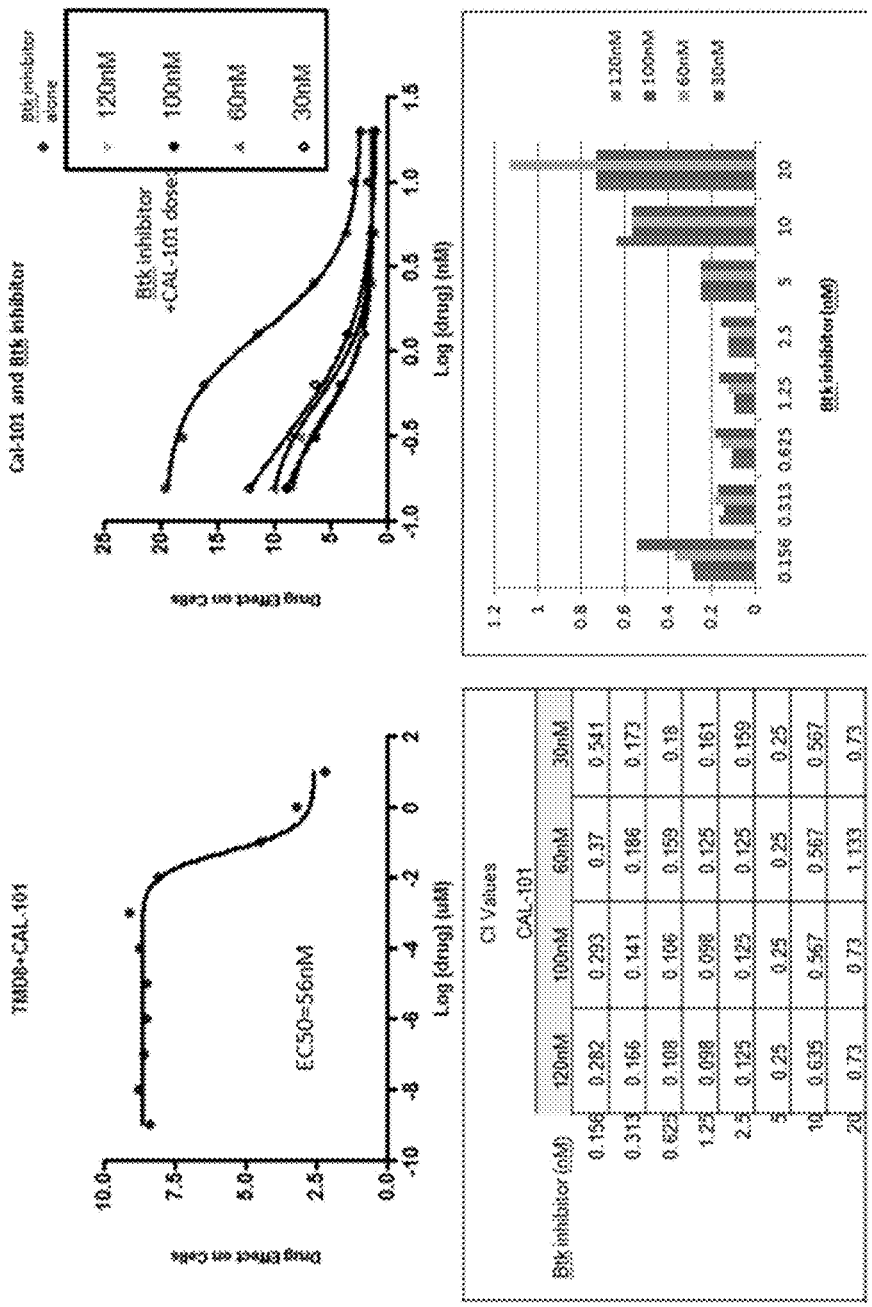
FIG. 32 present data showing the results of a combination of a Btk inhibitor and Cal-101 in TMD8 cells.
Figure 33:
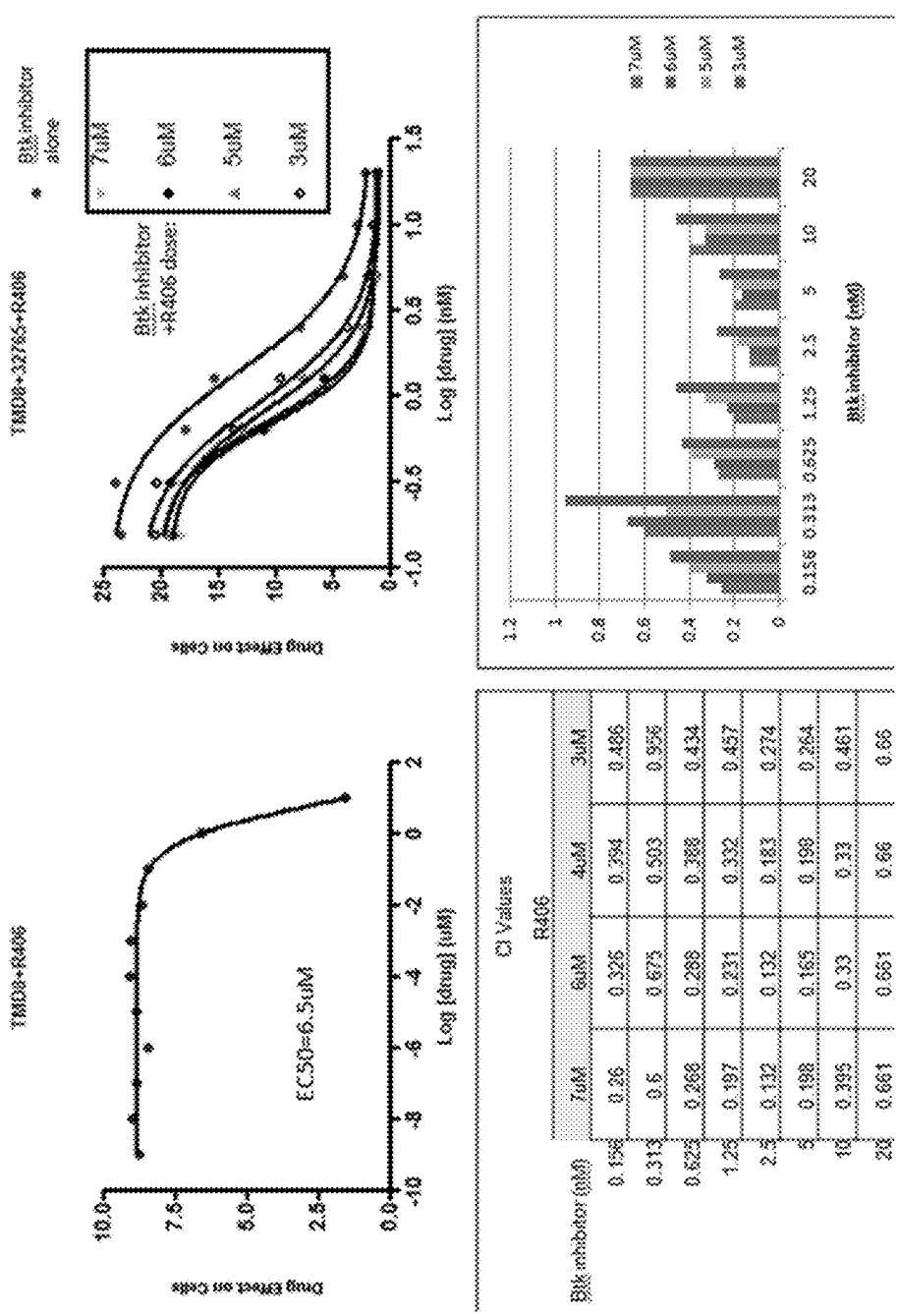
FIG. 33 present data showing the results of a combination of a Btk inhibitor and R406 in TMD8 cells.
Figure 34:
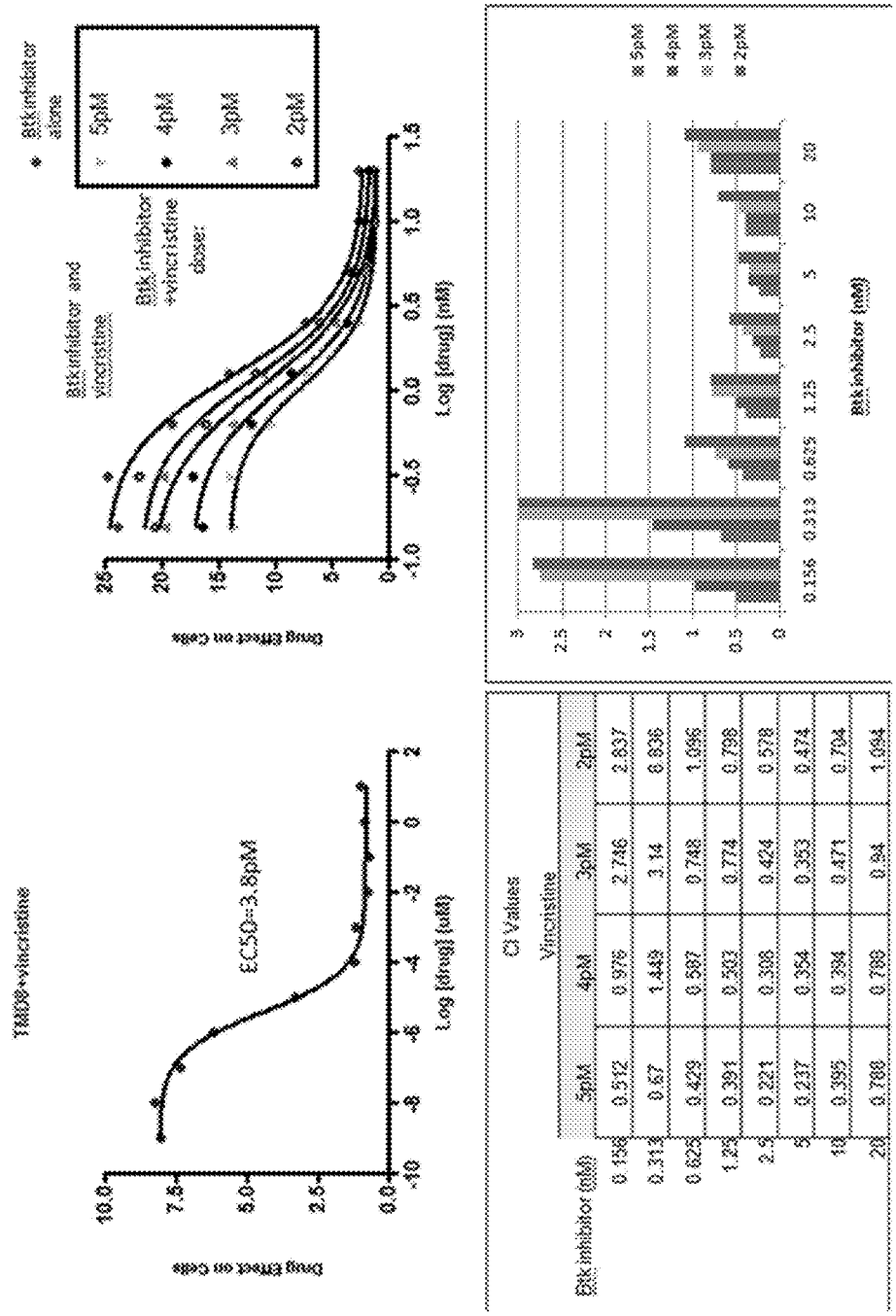
FIG. 34 present data showing the results of a combination of a Btk inhibitor and vincristine in TMD8 cells.
Figure 35:
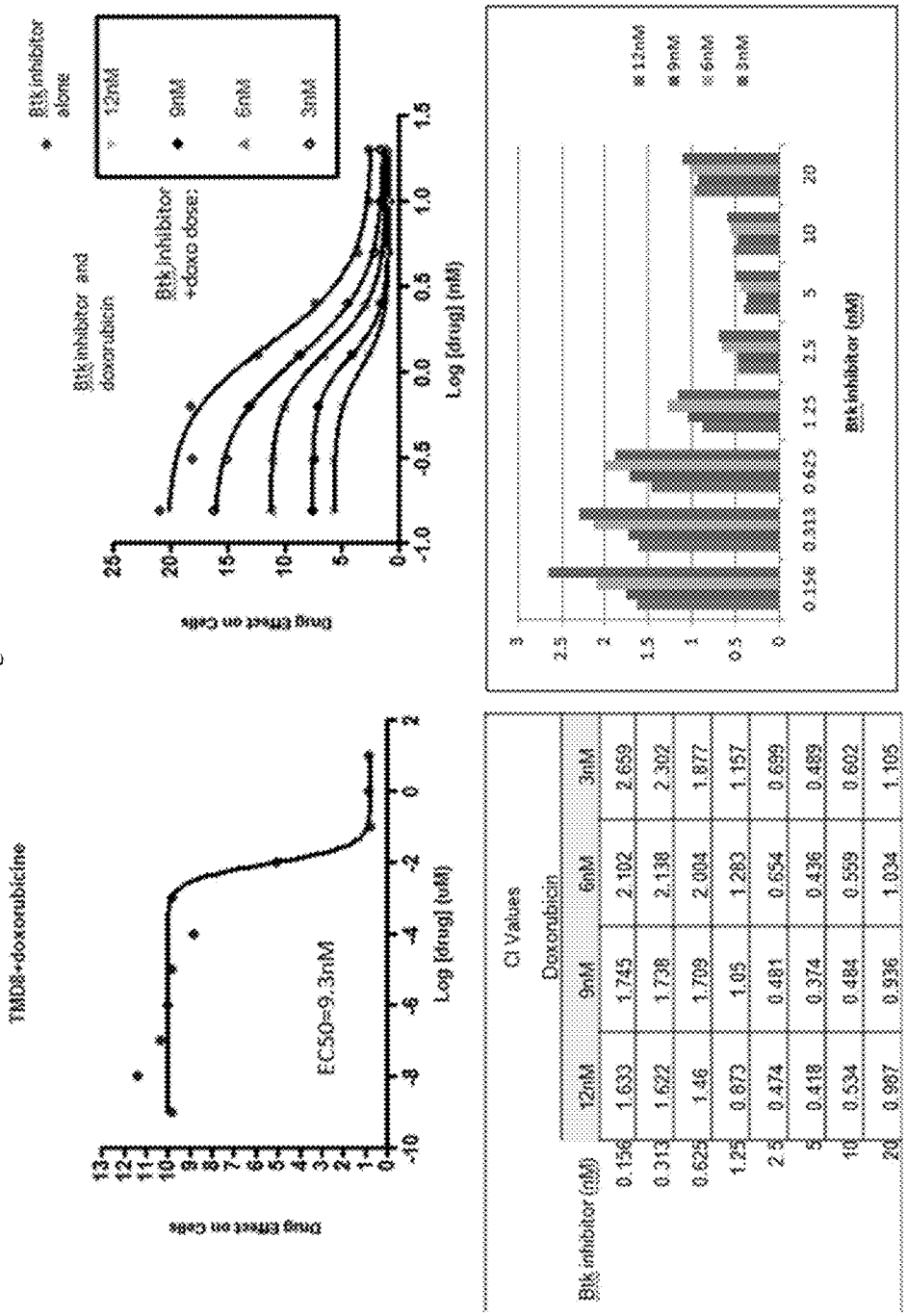
FIG. 35 present data showing the results of a combination of a Btk inhibitor and doxorubicin in TMD8 cells.
Figure 36:
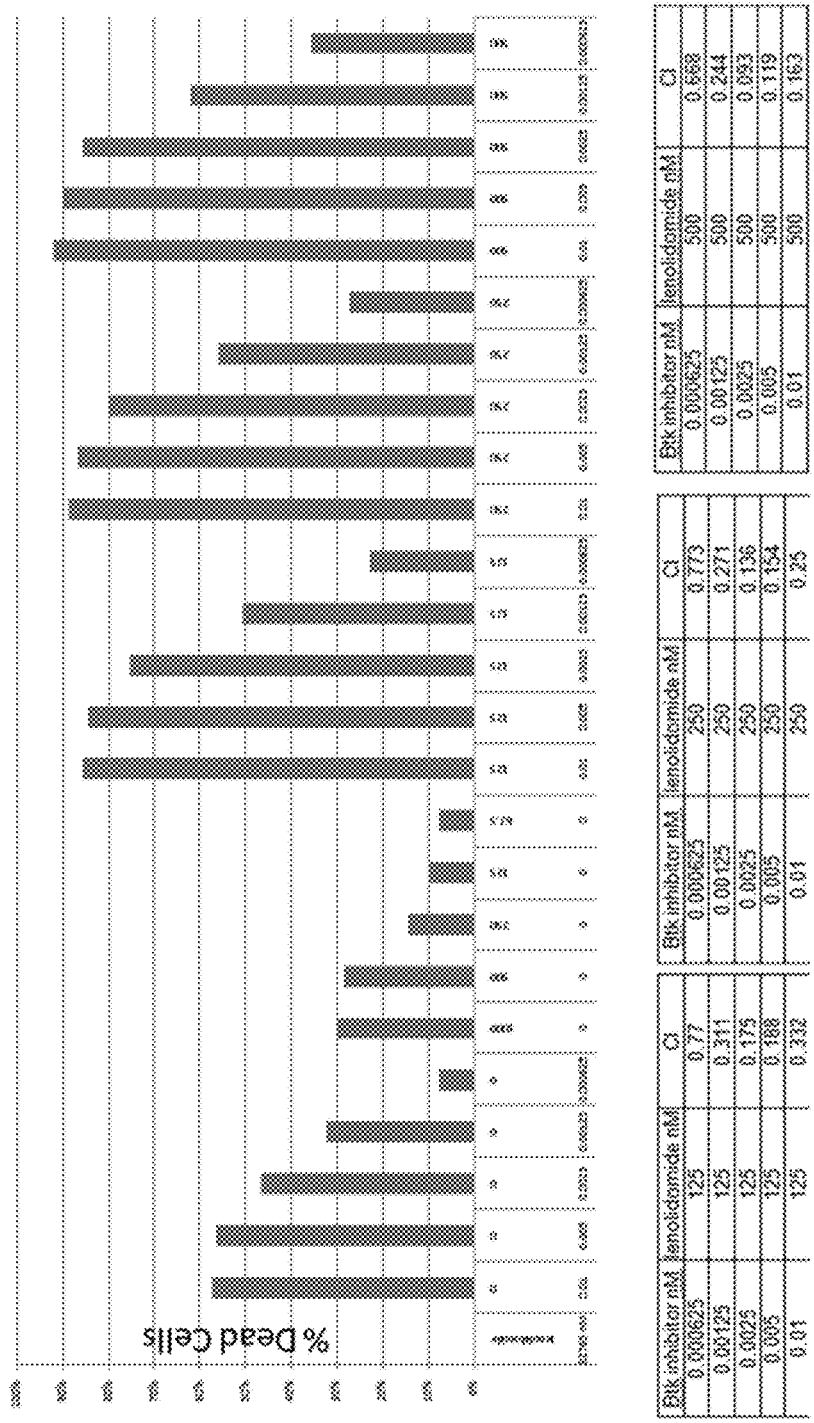
FIG. 36 present data showing the results of a combination of a Btk inhibitor and lenolidomide in TMD8 cells.
Figure 37:
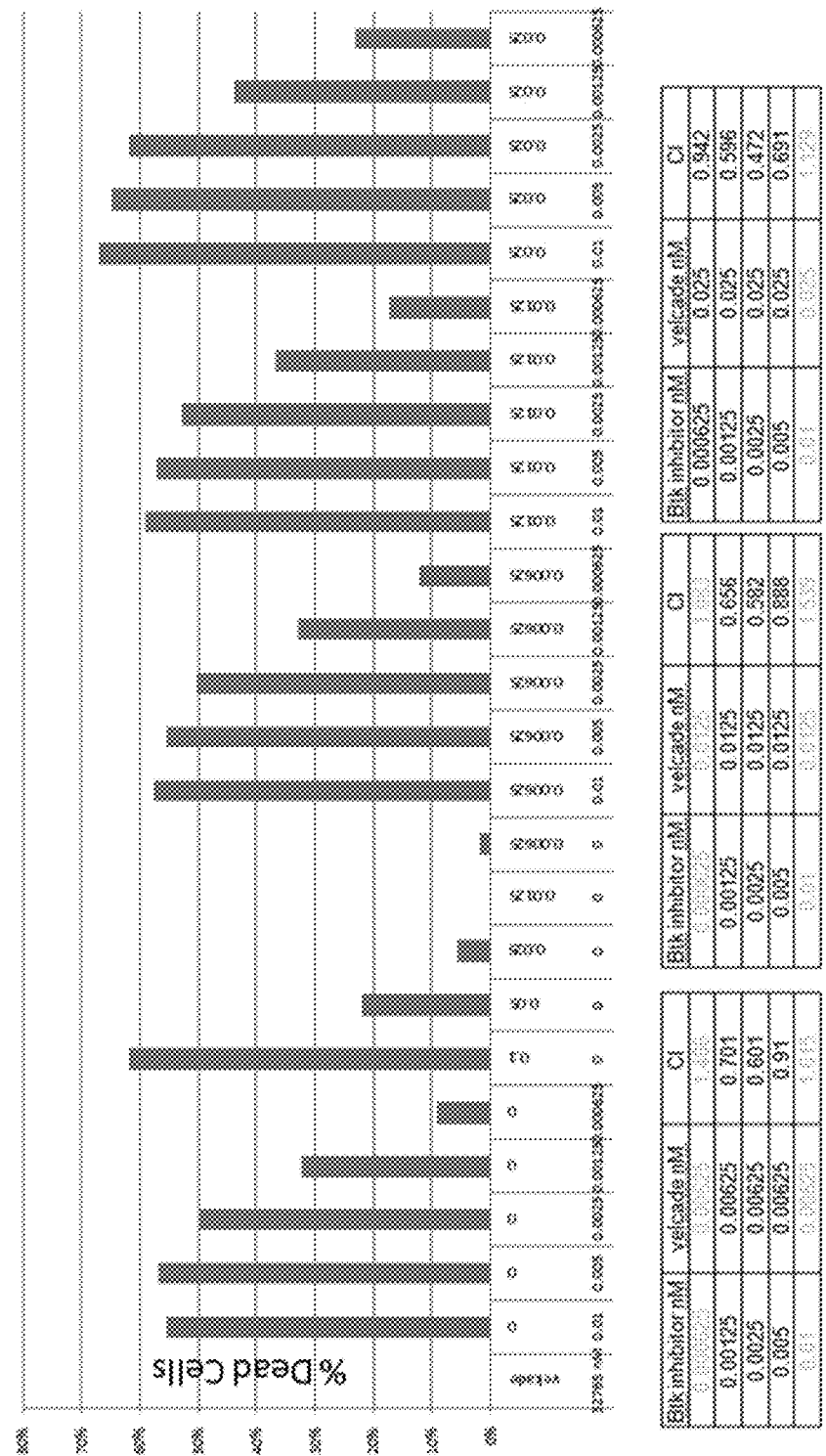
FIG. 37 present data showing the results of a combination of a Btk inhibitor and velcade in TMD8 cells.
Figure 38:
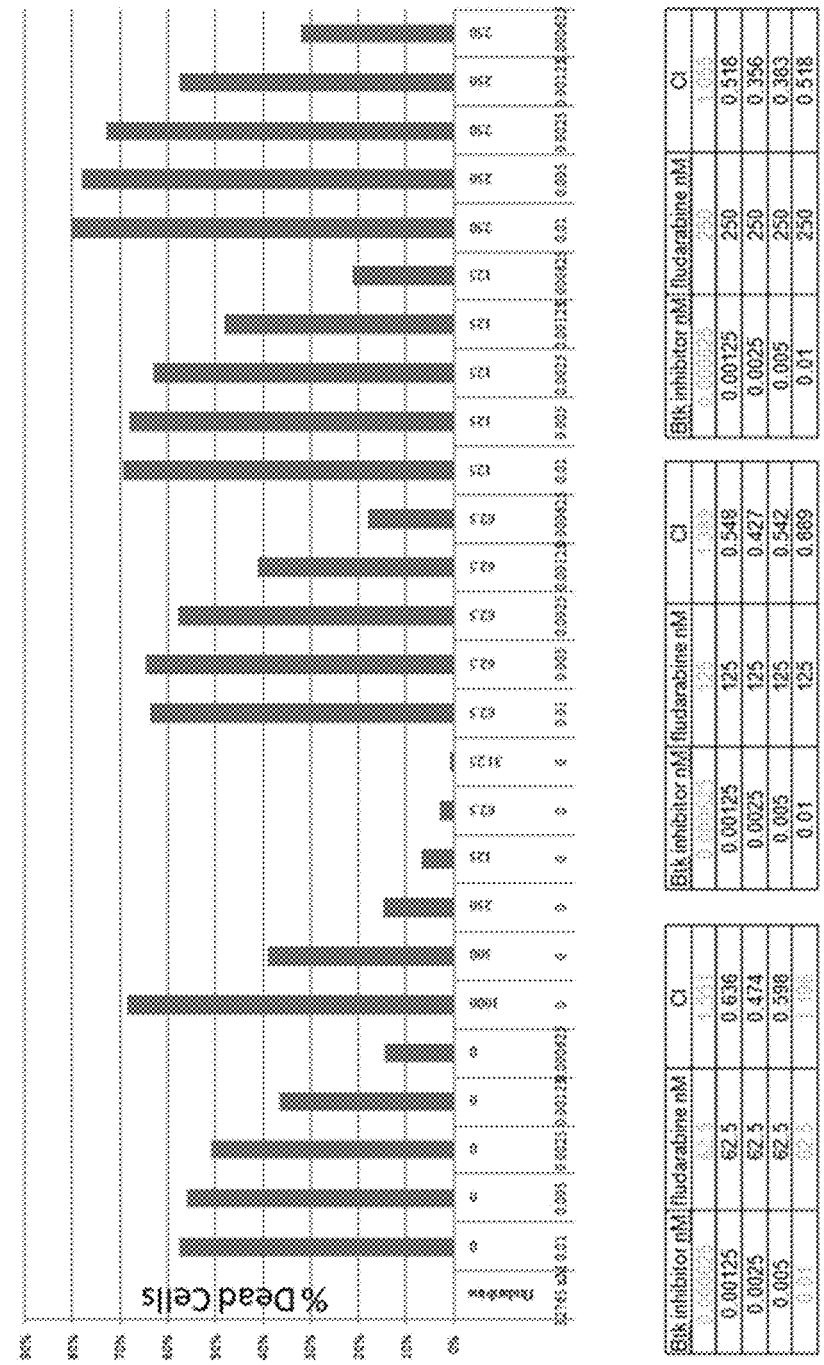
FIG. 38 present data showing the results of a combination of a Btk inhibitor and Fludarabine in TMD8 cells.
Figure 39:
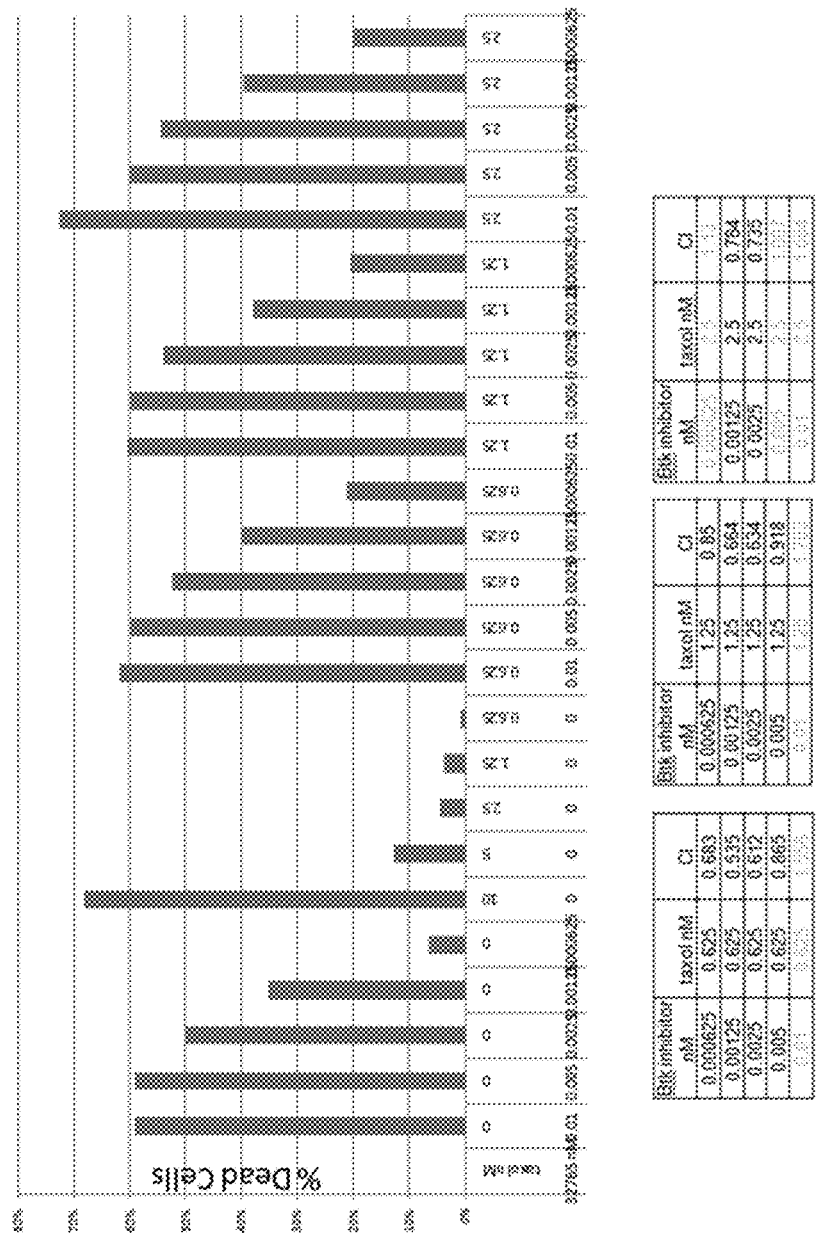
FIG. 39 present data showing the results of a combination of a Btk inhibitor and taxol in TMD8 cells.

Results further summarized in FIGS. 18-27. FIG. 18 presents the responses for the naive, 420 mg/day group. FIG. 19 presents the responses for the R/R, 420 mg/day group. FIG. 20 presents the responses by prognostic factors. FIG. 21 presents responses over time. FIG. 22 presents the best responses for all patients. FIG. 23 presents the best responses for abstract patients. FIG. 24 presents the best response by prognostic factor. FIG. 25 presents initial (Cycle 2) response assessment and best response (420 mg Cohorts). FIG. 26 presents initial (Cycle 2) response assessment by dose: relapsed/refractory. FIG. 27 presents improvements in hematological parameters.

Conclusions

The interim Phase II data confirm that a Btk inhibitor is highly active in both treatment-naïve and relapsed/refractory CLL/SLL patients Class-specific rapid lymph node reduction with concurrent lymphocytosis seen in the majority of patients 2008 CLL IWG objective responses (PR+CR) and nodal responses appear to be durable and independent of high risk genomic features A high proportion (85%) of relapsed or refractory patients are free-of-progression at 6 months (420 mg cohort)

Example 12: Long Term Follow-Up Trial for Individuals Taking Btk Inhibitor

The purpose of this study is to determine the long-term safety of a fixed-dose, daily regimen of Btk inhibitor PO in subjects with B cell lymphoma or chronic lymphocytic leukemia/small lymphocytic leukemia (CLL/SLL).

Study Type: Interventional
Allocation: Non-Randomized
Endpoint Classification: Safety Study
Intervention Model: Single Group Assignment
Masking: Open Label
Primary Purpose: Treatment
Intervention: 420 mg/day of a Btk inhibitor
Applicable conditions: B-cell Chronic Lymphocytic Leukemia; Small Lymphocytic Lymphoma; Diffuse Well-Differentiated Lymphocytic Lymphoma; B Cell Lymphoma; Follicular Lymphoma; Mantle Cell Lymphoma; Non-Hodgkin's Lymphoma; Waldenstrom Macroglobulinemia; Burkitt Lymphoma; B-Cell Diffuse Lymphoma Primary Outcome Measures:
Adverse Events/Safety Tolerability [Time Frame: 30 days after last dose of study drug]–frequency, severity, and relatedness of adverse events Secondary Outcome Measures:
Tumor Response [Time Frame: frequency of tumor assessments done per standard of care]–tumor response will be assessed per established response criteria. This study will capture time to disease progression and duration of response.

Tumor Response [Time Frame: Time to disease progression]–Duration of response as measured by established response criteria for B cell lymphoma and chronic lymphocytic leukemia Inclusion Criteria
Men and women with B cell lymphoma or CLL/small lymphocytic lymphoma (SLL) who had stable disease or response to Btk inhibitor PO for at least 6 months on a prior Btk inhibitor study and want to continue study drug or who had disease progression on PCYC-04753 and want to try a higher dose Eastern Cooperative Oncology Group (ECOG) performance status of ≤2

Agreement to use contraception during the study and for 30 days after the last dose of study drug if sexually active and able to bear children Willing and able to participate in all required evaluations and procedures in this study protocol including swallowing capsules without difficulty Ability to understand the purpose and risks of the study and provide signed and dated informed consent and authorization to use protected health information (in accordance with national and local subject privacy regulations)

Exclusion Criteria
A life-threatening illness, medical condition or organ system dysfunction which, in the investigator's opinion, could compromise the subject's safety, interfere with the absorption or metabolism of Btk inhibitor PO, or put the study outcomes at undue risk Concomitant immunotherapy, chemotherapy, radiotherapy, corticosteroids (at dosages equivalent to prednisone>20 mg/day), or experimental therapy Concomitant use of medicines known to cause QT prolongation or torsades de pointes Central nervous system (CNS) involvement by lymphoma
Creatinine>1.5× institutional upper limit of normal (ULN); total bilirubin>1.5×ULN (unless due to Gilbert's disease); and aspartate aminotransferase (AST) or alanine aminotransferase (ALT)>2.5×ULN unless disease related Lactating or pregnant Example 13: Phase II Study of Btk Inhibitor in R/R MCL The purpose of this study is to: Evaluate the efficacy of Btk inhibitor in relapsed/refractory subjects with MCL who have not had prior bortezomib, and who have had prior bortezomib The secondary objective is to evaluate the safety of a fixed daily dosing regimen of Btk inhibitor capsules in this population.

Study Type: Interventional
Allocation: Non-Randomized

Endpoint Classification: Safety/Efficacy Study
Intervention Model: Parallel Assignment
Masking: Open Label
Primary Purpose: Treatment
Intervention: 560 mg/day of a Btk inhibitor
Primary Outcome Measures
To Measure the Number of Participants with a Response to Study Drug [Time Frame: Participants will be followed until progression of disease or start of another anti-cancer treatment.]
Secondary Outcome Measures
To Measure the Number of Participants with Adverse Events as a Measure of Safety and Tolerability [Time Frame: Participants will be followed until progression of disease or start of another anti-cancer treatment.]
To Measure the Number of Participants Pharmacokinetics to Assist in Determining How the Body Responds to the Study Drug [Time Frame: Procedure to be Performed During the First Month of Receiving Study Drug.]
Patient Reported Outcomes [Time Frame: Participants will be followed until progression of disease or start of another anti-cancer treatment.]
To measure the number of participants reported outcomes in determining the health related quality of life.
Inclusion Criteria:
  Men and women≥18 years of age
  ECOG performance status of ≤2
  Pathologically confirmed MCL, with documentation of either overexpression of cyclin D1 or t(11;14), and measurable disease on cross sectional imaging that is ≥2 cm in the longest diameter and measurable in 2 perpendicular dimensions
  Documented failure to achieve at least partial response (PR) with, or documented disease progression disease after, the most recent treatment regimen
  At least 1, but no more than 5, prior treatment regimens for MCL (Note: Subjects having received ≥2 cycles of prior treatment with bortezomib, either as a single agent or as part of a combination therapy regimen, will be considered to be bortezomib-exposed.)
  Willing and able to participate in all required evaluations and procedures in this study protocol including swallowing capsules without difficulty
  Ability to understand the purpose and risks of the study and provide signed and dated informed consent and authorization to use protected health information (in accordance with national and local subject privacy regulations)
Major Exclusion Criteria:
  Prior chemotherapy within 3 weeks, nitrosoureas within 6 weeks, therapeutic anticancer antibodies within 4 weeks, radio- or toxin-immunoconjugates within 10 weeks, radiation therapy within 3 weeks, or major surgery within 2 weeks of first dose of study drug
  Any life-threatening illness, medical condition or organ system dysfunction which, in the investigator's opinion, could compromise the subject's safety, interfere with the absorption or metabolism of Btk inhibitor capsules, or put the study outcomes at undue risk
  Clinically significant cardiovascular disease such as uncontrolled or symptomatic arrhythmias, congestive heart failure, or myocardial infarction within 6 months of screening, or any Class 3 or 4 cardiac disease as defined by the New York Heart Association Functional Classification
  Malabsorption syndrome, disease significantly affecting gastrointestinal function, or resection of the stomach or small bowel or ulcerative colitis, symptomatic inflammatory bowel disease, or partial or complete bowel obstruction
  Any of the following laboratory abnormalities:
    a. Absolute neutrophil count (ANC)<750 cells/mm3 (0.75×109/L) unless there is documented bone marrow involvement
    b. Platelet count<50,000 cells/mm3 (50×109/L) independent of transfusion support unless there is documented bone marrow involvement
    c. Serum aspartate transaminase (AST/SGOT) or alanine transaminase (ALT/SGPT)>3.0× upper limit of normal (ULN)
    d. Creatinine>2.0×ULN Example 14: Phase II Study of Btk Inhibitor+Ofatumumab in R/R CLL The purpose of this study was to determine the efficacy and safety of a fixed-dose, daily regimen of orally administered Btk inhibitor combined with ofatumumab in subjects with relapsed/refractory CLL/SLL and related diseases
Study Type: Interventional
Allocation: Non-Randomized
Endpoint Classification: Safety Study
Intervention Model: Single Group Assignment
Masking: Open Label
Primary Purpose: Treatment
Intervention: 420 mg/day of a Btk inhibitor, standard dose of ofatumumab
Applicable conditions: B-cell Chronic Lymphocytic Leukemia; Small Lymphocytic Lymphoma; Diffuse Well-Differentiated Lymphocytic Lymphoma; Prolymphocytic Leukemia; Richter's Transformation
Primary Outcome Measures:
  Response and safety of Btk inhibitor [Time Frame: At the end of cycles 1 and 3]
  Response rate as defined by recent guidelines in Chronic Lymphocytic Leukemia
Secondary Outcome Measures:
  Pharmacokinetic/Pharmacodynamic assessments [Time Frame: during 1-2 cycles]
  Pharmacodynamics of Btk inhibitor (ie, drug occupancy of Btk and effect on biological market 1/2) of Btk inhibitor.
  Tumor Response [Time Frame: at the end of Cycles 2, 4 and 6 (28 days for each cycle)]
  Overall response rate as defined by recent guidelines on CLL
Inclusion Criteria:
  Subjects with histologically confirmed chronic lymphocytic leukemia (CLL), small lymphocytic lymphoma (SLL), prolymphocytic leukemia (PLL) as defined by WHO classification of hematopoietic neoplasms, or Richter's transformation arising out of CLL/SLL and satisfying ≥1 of the following conditions:
    Progressive splenomegaly and/or lymphadenopathy identified by physical examination or radiographic studies
    Anemia (<11 g/dL) or thrombocytopenia (<100,000/μL) due to bone marrow involvement
    Presence of unintentional weight loss>10% over the preceding 6 months
    NCI CTCAE Grade 2 or 3 fatigue
    Fevers>100.5 degree or night sweats for >2 weeks without evidence of infection
    Progressive lymphocytosis with an increase of >50% over a 2 month period or an anticipated doubling time of <6 months Need for cytoreduction prior to stem cell transplant Subjects must have failed≥2 prior therapies for CLL including a nucleoside analog or ≥2 prior therapies not including nucleoside analog if there is a contraindication to such therapy >10% expression of CD20 on tumor cells ECOG performance status≤2

Life expectancy≥12 weeks

Subjects must have organ and marrow function as defined below:

Absolute neutrophil count (ANC)≥1000/μL in the absence of bone marrow involvement Platelets≥30,000/μL Total bilirubin≤1.5× institutional upper limit of normal unless due to Gilbert's disease AST(SGOT)≤2.5× institutional upper limit of normal unless due to infiltration of the liver Creatinine≤2.0 mg/dL OR creatinine clearance≥50 mL/min No history of prior anaphylactic reaction to rituximab No history of prior exposure to ofatumumab Age≥18 years Body weight≥40 kg Able to swallow capsules without difficulty and no history of malabsorption syndrome, disease significantly affecting gastrointestinal function, or resection of the stomach or small bowel or ulcerative colitis, symptomatic inflammatory bowel disease, or partial or complete bowel obstruction Exclusion Criteria:

A life-threatening illness, medical condition or organ system dysfunction which, in the investigator's opinion, could compromise the subject's safety, interfere with the absorption or metabolism of Btk inhibitor PO, or put the study outcomes at undue risk Any anticancer immunotherapy, chemotherapy, radiotherapy, or experimental therapy within 4 weeks before first dose of study drug. Corticosteroids for disease-related symptoms are allowed provided 1 week washout occurs.

Active central nervous system (CNS) involvement by lymphoma

Major surgery within 4 weeks before first dose of study drug

Lactating or pregnant

History of prior malignancy, except for adequately treated basal cell or squamous cell skin cancer, in situ cervical cancer, or other cancer from which the subject has been disease free for at least 2 years or which will not limit survival to <2 years History of Grade≥2 toxicity (other than alopecia) continuing from prior anticancer therapy.

Results

6 Patients have been evaluated for DLT through end of cycle 2.0 DLTs occurred in these patients.

4 patients have had end of cycle 3 scans and blood counts. 3 of 4 are responder per IWG criteria. Our response rate is 75% for these pts.

Example 15: Phase II Study of Btk Inhibitor+BR or FCR in R/R CLL

The purpose of this study is to establish the safety of orally administered Btk inhibitor in combination with fludarabine/cyclophosphamide/rituximab (FCR) and bendamustine/rituximab (BR) in patients with chronic lymphocytic leukemia (CLL)/small lymphocytic lymphoma(SLL).

Study Type: Interventional
Allocation: Non-Randomized
Endpoint Classification: Safety Study
Intervention Model: Single Group Assignment
Masking: Open Label
Primary Purpose: Treatment
Intervention: 420 mg/day of a Btk inhibitor, standard FCR or BR regimen
Applicable conditions: B-cell Chronic Lymphocytic Leukemia; Small Lymphocytic Lymphoma; Diffuse Well-differentiated Lymphocytic Lymphoma
Primary Outcome Measures:

To measure the number of participants with prolonged hematologic toxicity [Time Frame: 8 weeks from first dose]

Secondary Outcome Measures:

To measure the number of participants with adverse events as a measure of safety and tolerability [Time Frame: For 30 days after the last dose of Btk inhibitor]

To measure the number of patients who respond to treatment by measuring the increase or decrease of disease in the lymph nodes and/or blood test results [Time Frame: Patients may remain on study until the last subject enrolled completes a maximum of 12 cycles of Btk inhibitor. Any subjects still receiving Btk inhibitor at that time may enroll in a long-term follow-up study to continue to receive Btk inhibitor capsules]

Inclusion Criteria:

Histologically confirmed CLL or SLL and satisfying at least 1 of the following criteria for requiring treatment:

Progressive splenomegaly and/or lymphadenopathy identified by physical examination or radiographic studies Anemia (<11 g/dL) or thrombocytopenia (<100,000/μL) due to bone marrow involvement Presence of unintentional weight loss>10% over the preceding 6 months NCI CTCAE Grade 2 or 3 fatigue Fevers>100.5° or night sweats for >2 weeks without evidence of infection Progressive lymphocytosis with an increase of >50% over a 2 month period or an anticipated doubling time of <6 months 1 to 3 prior treatment regimens for CLL/SLL ECOG performance status of ≤1

≥18 years of age

Willing and able to participate in all required evaluations and procedures in this study protocol including swallowing capsules without difficulty Ability to understand the purpose and risks of the study and provide signed and dated informed consent and authorization to use protected health information (in accordance with national and local subject privacy regulations)

Exclusion Criteria:

Any chemotherapy, therapeutic antineoplastic antibodies (not including radio- or toxin immunoconjugates), radiation therapy, or experimental antineoplastic therapy within 4 weeks of first dose of study drug Radio- or toxin-conjugated antibody therapy within 10 weeks of first dose of study drug Concomitant use of medicines known to cause QT prolongation or torsades de pointes Transformed lymphoma or Richter's transformation Any life-threatening illness, medical condition or organ system dysfunction which, in the investigator's opinion, could compromise the subject's safety, interfere with the absorption or metabolism of Btk inhibitor PO, or put the study outcomes at undue risk Any of the following laboratory abnormalities:
a. Absolute neutrophil count (ANC)<1000 cells/mm3 (1.0×109/L)
b. Platelet count<50,000/mm3 (50×109/L)
c. Serum aspartate transaminase (AST/SGOT) or alanine transaminase (ALT/SGPT)≥3.0× upper limit of normal (ULN)

d. Creatinine>2.0×ULN or creatinine clearance<40 mL/min

Example 16: Phase II Study of Btk Inhibitor in R/R DLBCL

The purpose of this study is to evaluate the efficacy of Btk inhibitor in relapsed/refractory de novo activated B-cell (ABC) and germinal-cell B-Cell (GCB) Diffuse Large B-cell Lymphoma (DLBCL).

Study Type: Interventional
Allocation: Non-Randomized
Endpoint Classification: Safety Study
Intervention Model: Single Group Assignment
Masking: Open Label
Primary Purpose: Treatment
Intervention: 560 mg/day Btk inhibitor Primary Outcome Measures:

To measure the number of patients with a response to study drug [Time Frame: 24 weeks from first dose]

Participants will be followed until progression of disease or start of another anti-cancer treatment.

Secondary Outcome Measures:

To measure the number of patients with adverse events as a measure of safety and tolerability. [Time Frame: For 30 days after the last dose of Btk inhibitor]

Participants will be followed until progression of the disease or start of another anticancer treatment.

To measure the number of participants pharmacokinetics to assist in determining how the body responses to the study drug. [Time Frame: Procedure will be performed during the first month of receiving study drug.]

Inclusion Criteria:

Men and women≥18 years of age.

Eastern Cooperative Oncology Group (ECOG) performance status of ≤2.

Pathologically confirmed de novo DLBCL; subjects must have available archival tissue for central review to be eligible.

Relapsed or refractory disease, defined as either: 1) recurrence of disease after a complete remission (CR), or 2) partial response (PR), stable disease (SD), or progressive disease (PD) at completion of the treatment regimen preceding entry to the study (residual disease):Subjects must have previously received an appropriate first-line treatment regimen. Subjects with suspected residual disease after the treatment regimen directly preceding study enrollment must have biopsy demonstration of residual DLBCL. Subjects who have not received high dose chemotherapy/autologous stem cell transplant (HDT/ASCT) must be ineligible for HDT/ASCT as defined by meeting any of the following criteria: Age≥70 years, Diffuse lung capacity for carbon monoxide (DLCO)<50% by pulmonary function test (PFT), Left ventricular ejection fraction (LVEF)<50% by multiple gated acquisition (MUGA)/echocardiograph (ECHO), Other organ dysfunction or comorbidities precluding the use of HDT/ASCT on the basis of unacceptable risk of treatment-related morbidity, Subject refusal of HDT/ASCT.

Subjects must have ≥1 measurable (>2 cm in longest dimension) disease sites on computed tomography (CT) scan.

Exclusion Criteria:

Transformed DLBCL or DLBCL with coexistent histologies (eg, follicular or mucosa-associated lymphoid tissue [MALT] lymphoma)

Primary mediastinal (thymic) large B-cell lymphoma (PMBL)

Known central nervous system (CNS) lymphoma

Any chemotherapy, external beam radiation therapy, or anticancer antibodies within 3 weeks of the first dose of study drug Radio- or toxin-immunoconjugates within 10 weeks of the first dose of study drug Major surgery within 2 weeks of first dose of study drug Any life-threatening illness, medical condition or organ system dysfunction which, in the investigator's opinion, could compromise the subject's safety, or put the study outcomes at undue risk Clinically significant cardiovascular disease such as uncontrolled or symptomatic arrhythmias, congestive heart failure, or myocardial infarction within 6 months of screening, or any Class 3 or 4 cardiac disease as defined by the New York Heart Association Functional Classification Unable to swallow capsules or malabsorption syndrome, disease significantly affecting gastrointestinal function, or resection of the stomach or small bowel or ulcerative colitis, symptomatic inflammatory bowel disease, or partial or complete bowel obstruction Any of the following laboratory abnormalities:
  a. Absolute neutrophil count (ANC)<750 cells/mm3 (0.75×109/L) unless there is documented bone marrow involvement
  b. Platelet count<50,000 cells/mm3 (50×109/L) independent of transfusion support unless there is documented bone marrow involvement
  c. Serum aspartate transaminase (AST/SGOT) or alanine transaminase (ALT/SGPT)≥3.0 upper limit of normal (ULN)
  d. Creatinine>2.0×ULN Example 17: Assay of Drug Combinations Combinations of a Btk inhibitor and additional cancer treatment agents were assayed using DoHH2 cells.

DOHH2 is a DLBCL (diffuse large B-cell lymphoma) cell line, from a transformed follicular lymphoma patient. It is moderately sensitive to a Btk inhibitor.

The Btk inhibitor was incubated with other cancer drugs for 2 days. Assay was an alamar blue assay.

The combinations were:
  a. Btk inhibitor and Gemicitabine;
  b. Btk inhibitor and Dexamethasone;

c. Btk inhibitor and Lenalinomide;
d. Btk inhibitor and R-406;
e. Btk inhibitor and Temsirolimus;
f. Btk inhibitor and Carboplatin;
g. Btk inhibitor and Bortezomib; and
h. Btk inhibitor and Doxorubicin.
Results are presented in FIGS. 28-31.

Example 18: Assay of Drug Combinations

Combinations of a Btk inhibitor and additional cancer treatment agents were assayed using TMD8 cells.

TMD8 is a NF-kB signalling-dependent ABC-DLBCL cell line. It is sensitive to BTK inhibitors alone at low nanomolar concentrations (GI50~1-3 nM). A Btk inhibitor was incubated with other cancer drugs for 2 days. Assay was an alamar blue assay.

The combinations were:
a. Btk inhibitor and CAL-101;
b. Btk inhibitor and Lenalinomide;
c. Btk inhibitor and R-406;
d. Btk inhibitor and Bortezomib;
e. Btk inhibitor and Vincristine;
f. Btk inhibitor and Taxol;
g. Btk inhibitor and Fludarabine; and
h. Btk inhibitor and Doxorubicin.
Results are presented in FIGS. 32-39.

Example 19: Clinical Trial of Btk Inhibitor in Combination with BR

A clinical trial was performed to determine the effects of combining a Btk inhibitor with BR (bendamustine and rituximab). The Btk inhibitor was administered. Following an increase in the concentration of lymphoid cells in the peripheral blood, BR was administered. Initial results indicated that the combination of the Btk inhibitor and BR resulted in substantially no lymphoid cells in the peripheral blood.

Example 20: Clinical Trial of Btk Inhibitor in Combination with Ofatumumab

A clinical trial was performed to determine the effects of combining a Btk inhibitor with ofatumumab. The Btk inhibitor was administered. Following an increase in the concentration of lymphoid cells in the peripheral blood, ofatumumab was administered. Initial results indicated that the combination of the Btk inhibitor and ofatumumab resulted in a decrease in lymphoid cells in the peripheral blood.

What is claimed is:

1. A method for treating chronic lymphocytic leukemia (CLL)/small lymphocytic lymphoma (SLL) in an individual who has failed at least one prior therapy for chronic lymphocytic leukemia or small lymphocytic lymphoma comprising administering to the individual once per day about 420 mg of an oral dose of an inhibitor of Bruton's tyrosine kinase (Btk) having the structure:

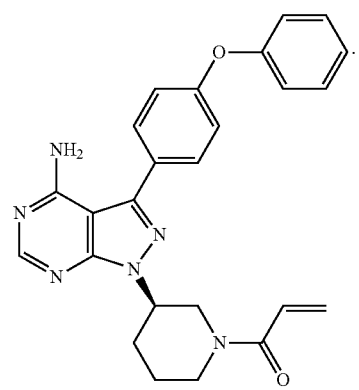 [SMILES: C=CC(=O)N1CCC[C@@H](n2nc(-c3ccc(Oc4ccccc4)cc3)c3c(N)ncnc32)C1]

2. The method of claim 1, wherein the oral dose is a capsule.
3. The method of claim 1, wherein, following administration of the inhibitor, the individual achieves a stable disease, a partial response, or a complete response.
4. The method of claim 1, wherein, following administration of the inhibitor, the individual achieves a partial response or a complete response.
5. The method of claim 1, wherein, following administration of the inhibitor, the individual achieves a complete response.
6. The method of claim 1, wherein, following administration of the inhibitor, the individual does not experience a progressive disease.
7. The method of claim 3, wherein the method is a method of treating chronic lymphocytic leukemia (CLL).
8. The method of claim 3, wherein the method is a method of treating small lymphocytic lymphoma (SLL).
9. The method of claim 1, wherein the individual has nucleic acid deletion in chromosome 17.
10. The method of claim 9, wherein the deletion is in 17p.
11. A method for treating relapsed or refractory chronic lymphocytic leukemia (CLL)/relapsed or refractory small lymphocytic lymphoma (SLL) in an individual comprising

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Btk Peptide Substrate

<400> SEQUENCE: 1

Ala Val Leu Glu Ser Glu Glu Glu Leu Tyr Ser Ser Ala Arg Gln
1               5                   10                  15 administering to the individual in need thereof once per day about 420 mg of an oral dose of an inhibitor of Bruton's tyrosine kinase (Btk) having the structure:

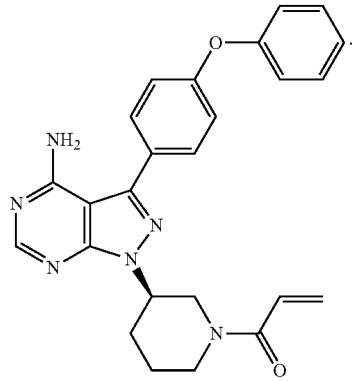 [SMILES: C=CC(=O)N1CCC[C@@H](n2nc(-c3ccc(Oc4ccccc4)cc3)c3c(N)ncnc32)C1]

12. The method of claim 11, wherein the oral dose is a capsule.

13. The method of claim 11, wherein, following administration of the inhibitor, the individual achieves a stable disease, a partial response, or a complete response.

14. The method of claim 11, wherein, following administration of the inhibitor, the individual achieves a partial response or a complete response.

15. The method of claim 11, wherein, following administration of the inhibitor, the individual achieves a complete response.

16. The method of claim 11, wherein, following administration of the inhibitor, the individual does not experience a progressive disease.

17. The method of claim 13, wherein the method is a method of treating relapsed or refractory chronic lymphocytic leukemia (CLL).

18. The method of claim 13, wherein the method is a method of treating relapsed or refractory small lymphocytic lymphoma (SLL).

19. The method of claim 11, wherein the individual has nucleic acid deletion in chromosome 17.

20. The method of claim 19, wherein the deletion is in 17p.

21. A method for treating small lymphocytic lymphoma (SLL) in an individual who has failed at least one prior therapy for small lymphocytic lymphoma comprising administering to the individual once per day about 420 mg of an oral dose of an inhibitor of Bruton's tyrosine kinase (Btk) having the structure:

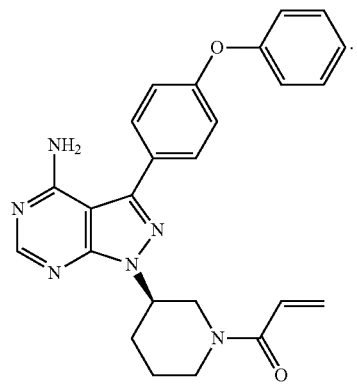 [SMILES: C=CC(=O)N1CCC[C@@H](n2nc(-c3ccc(Oc4ccccc4)cc3)c3c(N)ncnc32)C1]

22. The method of claim 21, wherein, following administration of the inhibitor, the individual achieves a partial response or a complete response.

23. The method of claim 21, wherein, following administration of the inhibitor, the individual achieves a complete response.

24. The method of claim 21, wherein, following administration of the inhibitor, the individual does not experience a progressive disease.

25. The method of claim 21, wherein the individual has nucleic acid deletion in chromosome 17p.

26. A method for treating relapsed or refractory small lymphocytic lymphoma (SLL) in an individual comprising administering to the individual in need thereof once per day about 420 mg of an oral dose of an inhibitor of Bruton's tyrosine kinase (Btk) having the structure:

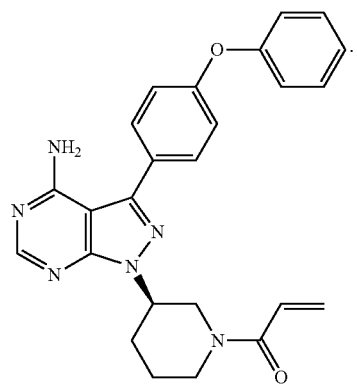 [SMILES: C=CC(=O)N1CCC[C@@H](n2nc(-c3ccc(Oc4ccccc4)cc3)c3c(N)ncnc32)C1]

27. The method of claim 26, wherein, following administration of the inhibitor, the individual achieves a partial response or a complete response.

28. The method of claim 26, wherein, following administration of the inhibitor, the individual achieves a complete response.

29. The method of claim 26, wherein, following administration of the inhibitor, the individual does not experience a progressive disease.

30. The method of claim 26, wherein the individual has nucleic acid deletion in chromosome 17p.

* * * * *

UNITED STATES PATENT AND TRADEMARK OFFICE
CERTIFICATE OF CORRECTION

PATENT NO. : 10,004,746 B2
APPLICATION NO. : 15/659803
DATED : June 26, 2018
INVENTOR(S) : Joseph J. Buggy et al.

Page 1 of 1

It is certified that error appears in the above-identified patent and that said Letters Patent is hereby corrected as shown below:

On page 2, left column, "6,893,636 B2" should appear as follows:
-- 6,893,638 B2 --

Signed and Sealed this
Ninth Day of April, 2019

Andrei Iancu
*Director of the United States Patent and Trademark Office*